(12) United States Patent
Deng et al.

(10) Patent No.: US 9,803,221 B2
(45) Date of Patent: Oct. 31, 2017

(54) ENGINEERING MICROORGANISMS TO INCREASE ETHANOL PRODUCTION BY METABOLIC REDIRECTION

(71) Applicants: Enchi Corporation, Wellesley Hills, MA (US); Dartmouth College, Hanover, NH (US)

(72) Inventors: Yu Deng, West Lebanon, NH (US); Daniel G. Olson, Norwich, VT (US); Johannes Pieter van Dijken, Schiedam (NL); Arthur J. Shaw, IV, Grantham, NH (US); Aaron Argyros, White River Junction, VT (US); Trisha Barrett, Bradford, VT (US); Nicky Caiazza, Rancho Santa Fe, CA (US); Christopher D. Herring, Lebanon, NH (US); Stephen R. Rogers, Hanover, NH (US); Frank Agbogbo, Lebanon, NH (US)

(73) Assignees: Enchi Corporation, Wellesley Hills, MA (US); Dartmouth College, Hanover, NH (US)

( * ) Notice: Subject to any disclaimer, the term of this patent is extended or adjusted under 35 U.S.C. 154(b) by 38 days.

(21) Appl. No.: 14/348,231

(22) PCT Filed: Sep. 28, 2012

(86) PCT No.: PCT/US2012/057952
§ 371 (c)(1),
(2) Date: Jul. 7, 2014

(87) PCT Pub. No.: WO2013/089890
PCT Pub. Date: Jun. 20, 2013

(65) Prior Publication Data
US 2014/0356921 A1    Dec. 4, 2014

Related U.S. Application Data

(60) Provisional application No. 61/542,082, filed on Sep. 30, 2011.

(51) Int. Cl.
*C12P 7/06* (2006.01)
*C12P 7/10* (2006.01)
(Continued)

(52) U.S. Cl.
CPC ............ *C12P 7/065* (2013.01); *C12N 9/0004* (2013.01); *C12N 9/0006* (2013.01);
(Continued)

(58) Field of Classification Search
CPC ..... C12P 7/06; C12P 7/10; C12N 9/02; C12N 9/04; C12N 9/10; C12N 9/12; C12N 9/88
See application file for complete search history.

(56) References Cited

U.S. PATENT DOCUMENTS 7,256,016 B2    8/2007 San et al.
7,709,261 B2    5/2010 San et al.
(Continued)

FOREIGN PATENT DOCUMENTS

WO    WO 2007/110606 A1    10/2007
WO    WO 2008/141174 A2    11/2008
(Continued)

OTHER PUBLICATIONS

Emmerling et al., Altered regulation of pyruvate kinase or co-overexpression of phosphofructokinase increases glycolytic fluxes in resting *Escherichia coli*., Biotechnology and Bioengineering (2000), vol. 67, Issue 5, pp. 623-627.*
(Continued)

*Primary Examiner* — Alexander Kim
(74) *Attorney, Agent, or Firm* — Sterne, Kessler, Goldstein & Fox P.L.L.C.

(57) ABSTRACT

The present invention provides for the manipulation of carbon flux in a recombinant host cell to increase the
(Continued)

formation of desirable products. The invention relates to cellulose-digesting organisms that have been genetically modified to allow the production of ethanol at a high yield by redirecting carbon flux at key steps of central metabolism.

22 Claims, 6 Drawing Sheets

(51) Int. Cl.
  C12N 9/02  (2006.01)
  C12N 9/04  (2006.01)
  C12N 9/10  (2006.01)
  C12N 9/12  (2006.01)
  C12N 9/88  (2006.01)

(52) U.S. Cl.
  CPC ......... *C12N 9/0008* (2013.01); *C12N 9/1029* (2013.01); *C12N 9/1205* (2013.01); *C12N 9/1217* (2013.01); *C12N 9/1294* (2013.01); *C12N 9/88* (2013.01); *C12P 7/10* (2013.01); *Y02E 50/16* (2013.01); *Y02E 50/17* (2013.01)

(56) References Cited

U.S. PATENT DOCUMENTS

| | | | |
|---|---|---|---|
| 2006/0073577 A1* | 4/2006 | Ka-Yiu | ............... C12P 7/40 435/106 |
| 2009/0082600 A1 | 3/2009 | Zhou | |
| 2011/0059485 A1 | 3/2011 | Caiazza et al. | |
| 2011/0171709 A1 | 7/2011 | Bardsley | |
| 2011/0189744 A1 | 8/2011 | Mcbride et al. | |
| 2013/0052646 A1 | 2/2013 | Tripathi et al. | |

FOREIGN PATENT DOCUMENTS

| | | | |
|---|---|---|---|
| WO | WO 2009/098089 | * | 8/2009 |
| WO | WO 2010/056805 | * | 5/2010 |
| WO | WO 2011/019717 A1 | | 2/2011 |
| WO | WO 2011/116358 A2 | | 9/2011 |

OTHER PUBLICATIONS

Chen, Development and application of co-culture for ethanol production by co-fermentation of glucose and xylose: a systematic review. J Ind Microbiol Biotechnol (Epub Nov. 23, 2010), vol. 38(5), pp. 581-597.*
Wendisch et al., Metabolic engineering of *Escherichia coli* and *Corynebacterium glutamicum* for biotechnological production of organic acids and amino acids. Curr Opin Microbiol. (2006), vol. 9(3), pp. 268-274.*
Krebs et al., Coordination of Adenosylmethionine to a Unique Iron Site of the [4Fe—4S] of Pyruvate Formate-Lyase Activating Enzyme: A Mössbauer Spectroscopic Study., J. Am. Chem. Soc. (2002), vol. 124 (6), pp. 912-913.*
Yoshida et al. Enhanced Hydrogen Production from Formic Acid by Formate Hydrogen Lyase-Overexpressing *Escherichia coli* Strains Appl. Environ. Microbiol. (2005), vol. 71(11), pp. 6762-6768.*
Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*

Catalanotti et al., Fermentation metabolism and its evolution in algae., Frontiers in Plant Science (2013), vol. 4, pp. 1-17.*
KEGG Enzyme 1.2.1.2 (last viewed on Jul. 21, 2016).*
Argyros, D.A., et al., "High Ethanol Titers from Cellulose by Using Metabolically Engineered Thermophilic, Anaerobic Microbes," *Applied and Environmental Microbiology* 77(23):8288-8294, American Society for Microbiology, United States (Dec. 2011).
Berríos-Rivera, S.J., et al., "Metabolic Engineering of *Escherichia coli*: Increase of NADH Availability by Overexpressing an $NAD^+$-Dependent Formate Dehydrogenase," *Metabolic Engineering* 4:217-229, Elsevier Science, United States (2002)
Demain, A.L., et al., "Cellulase, Clostridia, and Ethanol," *Microbiology and Molecular Biology Reviews* 69(1):124-154, American Society for Microbiology, United States (2005).
Deng, Y., et al., "Redirecting carbon flux through exogenous pyruvate kinase to achieve high ethanol yields in *Clostridium thermocellum*," *Metabolic Engineering* 15:151-158, Elsevier Inc., United States (Jan. 2013).
Emmerling, M., et al., "Altered Regulation of Pyruvate Kinase or Co-Overexpression of Phosphofructokinase Increases Glycolytic Fluxes in Resting *Escherichia coli*," *Biotechnol Bioeng* 67:623-627, John Wiley & Sons, United States (2000).
Feinberg, L., et al., "Complete Genome Sequence of the Cellulolytic Thermophile *Clostridium thermocellum* DSM1313," *Journal of Bacteriology* 193(11):2906-2907, American Society for Microbiology, United States (Jun. 2011).
Hatrongjit, R. and Packdibamrung, K., "A novel NADP'-dependent formate dehydrogenase from *Burkholderia stabilis* 15516: Screening, purification and characterization," *Enzyme and Microbial Technology* 46:557-561, Elsevier Inc., United States (Jun. 2010).
Lynd, L.R., et al., "Microbial Cellulose Utilization: Fundamentals and Biotechnology," *Microbiology and Molecular Biology Reviews* 66(3):506-577, American Society for Microbiology, United States (2002).
Olson, D.G., et al., "Deletion of the Cel48S cellulase from *Clostridium thermocellum*," *PNAS* 107(41):17727-17732, National Academy of Sciences, United States (Oct. 2010).
Popov, V.O. and Lamzin, V.S., "$NAD^+$-dependent formate dehydrogenase," *Biochem. J.* 301:625-643, Biochemical Society, England (1994).
Roberts, S.B., et al., "Genome-scale metabolic analysis of *Clostridium thermocellum* for bioethanol production," *BMC Systems Biology* 4(31):1-17, BioMed Central Ltd., England (Mar. 2010).
Shanks, R.M.Q., et al.,"*Saccharomyces cerevisiae*-Based Molecular Tool Kit for Manipulation of Genes from Gram-Negative Bacteria," *Applied and Environmental Microbiology* 72(7):5027-5036, American Society for Microbiology, United States (2006).
Sharp, P.M. and Li, W-H., "The codon adaptation index—a measure of directional synonymous codon usage bias, and its potential applications," *Nucleic Acids Research* 15(3):1281-1295, IRL Press Limited, England (1987).
Shaw, A.J., et al., "Metabolic engineering of a thermophilic bacterium to produce ethanol at high yield," *PNAS* 105(37):13769-13774, National Academy of Sciences of the USA, United States (2008).
Tripathi, S.A., et al., "Development of *pyr*F-Based Genetic System for Targeted Gene Deletion in *Clostridium thermocellum* and Creation of a pta Mutant," *Applied and Environmental Microbiology* 76(19):6591-6599, American Society for Microbiology, United States (Oct. 2010).
Van Der Veen, D., et al., "Characterization of *Clostridium thermocellum* strains with disrupted fermentation end-product pathways," *J Ind Microbiol Biotechnol* 40:725-734, Society for Industrial Microbiology and Biotechnology, Springer, England (Jul. 2013).
Wang, S., et al., "$NADP^+$ Reduction with Reduced Ferredoxin and $NADP^+$ Reduction with NADH Are Coupled via an Electron-Bifurcating Enzyme Complex in *Clostridium kluyveri*," *Journal of Bacteriology* 192(19):5115-5123, American Society for Microbiology, United States (Oct. 2010)

(56) References Cited

OTHER PUBLICATIONS

Ziiou, J., et al., "Atypical Glycolysis in *Clostridium thermocellum*," *Applied and Environmental Microbiology* 79(9):3000-3008, American Society for Microbiology, United States (May 2013).
GenBank Accession No. U49975.1, accessed at http://www.ncbi.nlm.nih.gov/nuccore/U49975 on Apr. 2, 2014.
U.S. Appl. No. 61/565,261 inventors Lo, J., et al., filed Nov. 30, 2011.
International Search Report for International Application No. PCT/US2012/057952, European Patent Office, Netherlands, mailed on Nov. 19, 2013.
Welch, M., et al., "Designing Genes for Successful Protein Expression," *Methods in Enzymology* 498:43-66, Elsevier Inc., United States (2011).
Deng, Y., et al., "Corrigendum to 'Redirecting carbon flux through exogenous pyruvate kinase to achieve high ethanol yields in *Clostridium thermocellum*'," *Metabolic Engineering* 22:1-2, Elsevier Inc., United States (2014).

\* cited by examiner

SEQUENCE LISTING

```
<160> NUMBER OF SEQ ID NOS: 71

<210> SEQ ID NO 1
<211> LENGTH: 1752
<212> TYPE: DNA
<213> ORGANISM: Thermoanaerobacterium saccharolyticum
<220> FEATURE:
<221> NAME/KEY: misc_feature
<222> LOCATION: (1)..(1752)
<223> OTHER INFORMATION: pyruvate kinase

<400> SEQUENCE: 1
atgcgtagaa ctaagataat atgcacgatt ggtcctgcca gtgaaaaata tgagatattg      60
```

```
aaagagctta tagaaagcgg tcttaatatt tgcaggttga attttcaca tggggatcat      120 gaagagcatg gaagcagaat agacaatatt ataaagatta gagaagaact taagctgcct      180
attgcaatta tgcttgatac aaagggcct gaaataagga ctggcagatt taaaggcggt      240
gttgcagagc ttaaagaagg ccagacattt acgataacat caaggaaat tgaaggagat      300 aacactattt gttctgtttc atacaagggg cttcctcaag atgtggagag aggttctcgc      360
atattgattg atgacggatt agtatcattg aaagtcaatg acgtaaaagg tgaagatata      420
gtatgcactg tggagaattc tggtacaata ggtgatcaca aggtgtaaa tgtacctggt      480 acaaagctta atttgcctgc cataacgcaa aaagacgtgg atgatataga gtttggaata      540 aaaaaggaa tcgacatgat tgcagcgtct tttgtcagaa aagcagcaga tgtaattgcc      600
ataaggagat tgttagaaga caatgacgct ggccatatac ttatcatatc aaaaattgaa      660
aatcgcgaag gcgtagaaaa tattgacgaa ataatcaaag tctctgatgg cataatggta      720
gcccgcggcg atttgggtgt cgaaattcct atagaggaaa tacctatcgt tcagaaaagg      780
ataattgaaa atgcaacaa agcaggtaaa ccagtagtta ctgctacaca gatgcttgac      840
tctatgataa gaaatccaag gccaacaagg gcagaagtaa cagatgtagc caatgctata      900
ttggatggca ctgatgcgat aatgttgtct ggtgaaacag cgcaaggcaa atatcctgta      960 gaggcttta agacgatgtc aaagatagct gaaagattg agacgtatat aaattacaaa     1020
gaaaatttag ataaaaatgt ggattacaat atttctatga caaatgccat aagccatgct     1080
acgtgcacta ccgcgagaga tataggcgca actgccatta ttcatctac aatatcaggt     1140 tatactgcga gaatggtgtc taagtataga ccgtcagcac ctataatagc agtgacgcca     1200
aacaaagatg ttgcaagaag gcttagcatc gtgtggggtg tacatccatt gatatcacag     1260
gaagtcaatt ctacagatga aatgatagaa gtatcagtaa atacggcttt aaatgaagga     1320
ttaattcgaa atggcgatat tgtagtaata tcggcaggaa tacctgtcgc gactacaggc     1380
acaacaaata tgttgaaggt tcatattgtg ggagatgtaa tagtaaaagg cacaggcata     1440
ggcactaaat ccataagtgg tgttgtttcc atcataagag atccatacaa ggacaaagat     1500
aagttcagag aaggagatat catcgttgct caaaaaactg aaagggatta tatgcctata     1560
attgagaagg cttcagctat cataacagaa gaaggtggac taacgtccca tgctgcaata     1620
gttggattga actatggatt acctgtcatt gtaggctgtg aaggagtaac ttcaaagctt     1680
aaagatggaa tgacggtaac tctcgatact gccagaggat tggtctacaa aggtatagtg     1740
aatataaaat ag                                                        1752
```

<210> SEQ ID NO 2
<211> LENGTH: 583
<212> TYPE: PRT
<213> ORGANISM: Thermoanaerobacterium saccharolyticum
<220> FEATURE:
<221> NAME/KEY: misc_feature
<222> LOCATION: (1)..(583)
<223> OTHER INFORMATION: pyruvate kinase

<400> SEQUENCE: 2

Met Arg Arg Thr Lys Ile Ile Cys Thr Ile Gly Pro Ala Ser Glu Lys
1               5                   10                  15

Tyr Glu Ile Leu Lys Glu Leu Ile Glu Ser Gly Leu Asn Ile Cys Arg
            20                  25                  30

Leu Asn Phe Ser His Gly Asp His Glu Glu His Gly Ser Arg Ile Asp
        35                  40                  45

-continued

```
Asn Ile Ile Lys Ile Arg Glu Glu Leu Lys Leu Pro Ile Ala Ile Met
 50                  55                  60

Leu Asp Thr Lys Gly Pro Glu Ile Arg Thr Gly Arg Phe Lys Gly Gly
 65                  70                  75                  80

Val Ala Glu Leu Lys Glu Gly Gln Thr Phe Thr Ile Thr Ser Arg Glu
                 85                  90                  95

Ile Glu Gly Asp Asn Thr Ile Cys Ser Val Ser Tyr Lys Gly Leu Pro
                100                 105                 110

Gln Asp Val Glu Arg Gly Ser Arg Ile Leu Ile Asp Asp Gly Leu Val
             115                 120                 125

Ser Leu Lys Val Asn Asp Val Lys Gly Glu Asp Ile Val Cys Thr Val
130                 135                 140

Glu Asn Ser Gly Thr Ile Gly Asp His Lys Gly Val Asn Val Pro Gly
145                 150                 155                 160

Thr Lys Leu Asn Leu Pro Ala Ile Thr Gln Lys Asp Val Asp Asp Ile
                165                 170                 175

Glu Phe Gly Ile Lys Lys Gly Ile Asp Met Ile Ala Ala Ser Phe Val
            180                 185                 190

Arg Lys Ala Ala Asp Val Ile Ala Ile Arg Arg Leu Leu Glu Asp Asn
            195                 200                 205

Asp Ala Gly His Ile Leu Ile Ile Ser Lys Ile Glu Asn Arg Glu Gly
210                 215                 220

Val Glu Asn Ile Asp Glu Ile Ile Lys Val Ser Asp Gly Ile Met Val
225                 230                 235                 240

Ala Arg Gly Asp Leu Gly Val Glu Ile Pro Ile Glu Glu Ile Pro Ile
                245                 250                 255

Val Gln Lys Arg Ile Ile Glu Lys Cys Asn Lys Ala Gly Lys Pro Val
            260                 265                 270

Val Thr Ala Thr Gln Met Leu Asp Ser Met Ile Arg Asn Pro Arg Pro
            275                 280                 285

Thr Arg Ala Glu Val Thr Asp Val Ala Asn Ala Ile Leu Asp Gly Thr
290                 295                 300

Asp Ala Ile Met Leu Ser Gly Glu Thr Ala Gln Gly Lys Tyr Pro Val
305                 310                 315                 320

Glu Ala Phe Lys Thr Met Ser Lys Ile Ala Glu Lys Ile Glu Thr Tyr
                325                 330                 335

Ile Asn Tyr Lys Glu Asn Leu Asp Lys Asn Val Asp Tyr Asn Ile Ser
            340                 345                 350

Met Thr Asn Ala Ile Ser His Ala Thr Cys Thr Thr Ala Arg Asp Ile
            355                 360                 365

Gly Ala Thr Ala Ile Ile Thr Ser Thr Ile Ser Gly Tyr Thr Ala Arg
370                 375                 380

Met Val Ser Lys Tyr Arg Pro Ser Ala Pro Ile Ile Ala Val Thr Pro
385                 390                 395                 400

Asn Lys Asp Val Ala Arg Arg Leu Ser Ile Val Trp Gly Val His Pro
                405                 410                 415

Leu Ile Ser Gln Glu Val Asn Ser Thr Asp Glu Met Ile Glu Val Ser
            420                 425                 430

Val Asn Thr Ala Leu Asn Glu Gly Leu Ile Arg Asn Gly Asp Ile Val
            435                 440                 445

Val Ile Ser Ala Gly Ile Pro Val Ala Thr Thr Gly Thr Thr Asn Met
450                 455                 460
```

```
Leu Lys Val His Ile Val Gly Asp Val Ile Val Lys Gly Thr Gly Ile
465                 470                 475                 480

Gly Thr Lys Ser Ile Ser Gly Val Val Ser Ile Ile Arg Asp Pro Tyr
                485                 490                 495

Lys Asp Lys Asp Lys Phe Arg Glu Gly Asp Ile Ile Val Ala Gln Lys
            500                 505                 510

Thr Glu Arg Asp Tyr Met Pro Ile Ile Glu Lys Ala Ser Ala Ile Ile
        515                 520                 525

Thr Glu Glu Gly Gly Leu Thr Ser His Ala Ala Ile Val Gly Leu Asn
    530                 535                 540

Tyr Gly Leu Pro Val Ile Val Gly Cys Glu Gly Val Thr Ser Lys Leu
545                 550                 555                 560

Lys Asp Gly Met Thr Val Thr Leu Asp Thr Ala Arg Gly Leu Val Tyr
                565                 570                 575

Lys Gly Ile Val Asn Ile Lys
            580
```

<210> SEQ ID NO 3
<211> LENGTH: 954
<212> TYPE: DNA
<213> ORGANISM: Clostridium thermocellum
<220> FEATURE:
<221> NAME/KEY: misc_feature
<222> LOCATION: (1)..(954)
<223> OTHER INFORMATION: lactate dehydrogenase

<400> SEQUENCE: 3

```
atgaacaata caaagtaat taaaaaagta accgtagttg gtgcaggctt tgtaggttcc      60
accacagctt atacattgat gctcagcgga cttatatctg aaattgtact gatagacata     120
aatgcaaaaa aagccgacgg agaagtcatg gacttaaatc acggcatgcc ttttgtaagg    180
cccgttgaaa tttatcgtgg tgactacaaa gactgtgccg gatccgacat agtaatcatt    240
accgccggtg ccaaccaaaa agaaggcgaa acgagaatag atcttgttaa agaaacacg     300
gaagtattca aaaatatcat aaatgaaatt gtaaagtaca caacgattg tattcttctg     360
gtagtcacaa atccggtgga tatttaacc tatgtaactt acaaactatc cggattcccg    420
aaaaacaaag taataggttc cggaacggtt ttggacacag ccaggttccg ttatctttta    480
agcgaacatg taaagtgga tgcacgaaat gtacatgctt atattattgg cgaacacggt     540
gacaccgaag ttgcggcctg gagtcttgca atatattgcgg gaattcccat ggatcgctac    600
tgtgacgaat gccatcagtg cgaggagcag atttcccgga ataaaatata tgaaagtgtt    660
aaaaatgcag cttatgaaat catcaggaac aaaggtgcaa cctattatgc cgtagccctt    720
gccgtaagaa gaatcgttga agccattgta agaaatgaaa actccatcct taccgtttca    780
agccttttgg aaggacagta cggacttagc gatgtatgct taagtgttcc gacaatcgtg    840
ggtgtaaacg gtattgagga atattgaac gtgcctttca cgatgaaga aattcagctt     900
ctcagaaagt ccggaaacac tctaaaagaa ataataaaaa cactagatat atga          954
```

<210> SEQ ID NO 4
<211> LENGTH: 317
<212> TYPE: PRT
<213> ORGANISM: Clostridium thermocellum
<220> FEATURE:
<221> NAME/KEY: misc_feature
<222> LOCATION: (1)..(317)
<223> OTHER INFORMATION: lactate dehydrogenase

<400> SEQUENCE: 4

```
Met Asn Asn Asn Lys Val Ile Lys Lys Val Thr Val Gly Ala Gly
1               5                   10                  15

Phe Val Gly Ser Thr Thr Ala Tyr Thr Leu Met Leu Ser Gly Leu Ile
            20                  25                  30

Ser Glu Ile Val Leu Ile Asp Ile Asn Ala Lys Lys Ala Asp Gly Glu
            35                  40                  45

Val Met Asp Leu Asn His Gly Met Pro Phe Val Arg Pro Val Glu Ile
50                  55                  60

Tyr Arg Gly Asp Tyr Lys Asp Cys Ala Gly Ser Asp Ile Val Ile Ile
65                  70                  75                  80

Thr Ala Gly Ala Asn Gln Lys Glu Gly Glu Thr Arg Ile Asp Leu Val
                85                  90                  95

Lys Arg Asn Thr Glu Val Phe Lys Asn Ile Ile Asn Glu Ile Val Lys
                100                 105                 110

Tyr Asn Asn Asp Cys Ile Leu Leu Val Val Thr Asn Pro Val Asp Ile
            115                 120                 125

Leu Thr Tyr Val Thr Tyr Lys Leu Ser Gly Phe Pro Lys Asn Lys Val
            130                 135                 140

Ile Gly Ser Gly Thr Val Leu Asp Thr Ala Arg Phe Arg Tyr Leu Leu
145                 150                 155                 160

Ser Glu His Val Lys Val Asp Ala Arg Asn Val His Ala Tyr Ile Ile
                165                 170                 175

Gly Glu His Gly Asp Thr Glu Val Ala Ala Trp Ser Leu Ala Asn Ile
            180                 185                 190

Ala Gly Ile Pro Met Asp Arg Tyr Cys Asp Glu Cys His Gln Cys Glu
            195                 200                 205

Glu Gln Ile Ser Arg Asn Lys Ile Tyr Glu Ser Val Lys Asn Ala Ala
            210                 215                 220

Tyr Glu Ile Ile Arg Asn Lys Gly Ala Thr Tyr Tyr Ala Val Ala Leu
225                 230                 235                 240

Ala Val Arg Arg Ile Val Glu Ala Ile Val Arg Asn Glu Asn Ser Ile
                245                 250                 255

Leu Thr Val Ser Ser Leu Leu Glu Gly Gln Tyr Gly Leu Ser Asp Val
            260                 265                 270

Cys Leu Ser Val Pro Thr Ile Val Gly Val Asn Gly Ile Glu Glu Ile
            275                 280                 285

Leu Asn Val Pro Phe Asn Asp Glu Glu Ile Gln Leu Leu Arg Lys Ser
            290                 295                 300

Gly Asn Thr Leu Lys Glu Ile Ile Lys Thr Leu Asp Ile
305                 310                 315

<210> SEQ ID NO 5
<211> LENGTH: 1077
<212> TYPE: DNA
<213> ORGANISM: Clostridium thermocellum
<220> FEATURE:
<221> NAME/KEY: misc_feature
<222> LOCATION: (1)..(1077)
<223> OTHER INFORMATION: phosphotransacetylase

<400> SEQUENCE: 5
gtgataatat atagttataa gtattacaaa tacagttttt atgataacag ttttgggatt      60
atgaaaggag aagaatttat gagttttttg gaacaaataa ttgaaagggc gaaatcagac     120
gtaaaaacca tagttttgcc ggaaagtacg gatctgaggg ttattaaagc cgcatccatg     180
```

| | | |
|---|---|---|
| atagtgaaaa agggaattgc aaaggttgta ctgataggca atgaaaagga gattaagagt | 240 | |
| ctggcggggg atattgatct tgaaggagtg atgatagagg attccttaaa ttccgaaaaa | 300 | |
| ttggaggatt atgcaaatac actgtatgag cttagaaaat cgaagggtat gactatagaa | 360 | |
| gccgcaaggg aaacgatcaa agaccctctt tattatggag ttatgatggt aaaaaaaggt | 420 | |
| gaagcggatg gtatggtggc gggtgctgtc aattccactg caaatacttt gagaccggct | 480 | |
| ttgcagatat taaagacggc cccggggaca aaactcgtat catcctttt tgttatggtt | 540 | |
| gtacccaact gtgaatatgg tcataacgga accttttgtat atgccgattg cggcttggtg | 600 | |
| gaaaatccgg atgcagacca gctttctgaa attgcaatat ctgcatccaa atcttttgag | 660 | |
| atgctggttg gagcaaaacc tcaggtggca atgctttctt attcttctta cggcagtgcc | 720 | |
| aaaagtgagc tgaccgaaaa ggtaatcaag gcaacacagc ttgcaaagga aaaagctccc | 780 | |
| caccttgcaa ttgacggaga acttcaggtg gatgccgcca ttgttccgga agtggcaaaa | 840 | |
| tcgaaggcaa agggaagcag tgttgcagga aaggccaatg ttcttatttt cccggatctt | 900 | |
| gatgccggaa atattgcata caagcttaca cagagattgg caaaagctga agcttacggc | 960 | |
| ccgataacac aaggtttggc aagaccggta aatgagctgt cacgaggctg cagtgccgag | 1020 | |
| gatatagtcg gggttgcggc aattactgcg gttcaggctc aatatgtcaa ggcataa | 1077 | |

<210> SEQ ID NO 6
<211> LENGTH: 358
<212> TYPE: PRT
<213> ORGANISM: Clostridium thermocellum
<220> FEATURE:
<221> NAME/KEY: misc_feature
<222> LOCATION: (1)..(358)
<223> OTHER INFORMATION: phosphotransacetylase

<400> SEQUENCE: 6

Val Ile Ile Tyr Ser Tyr Lys Tyr Tyr Lys Tyr Ser Phe Tyr Asp Asn
1               5                   10                  15

Ser Phe Gly Ile Met Lys Gly Glu Glu Phe Met Ser Phe Leu Glu Gln
            20                  25                  30

Ile Ile Glu Arg Ala Lys Ser Asp Val Lys Thr Ile Val Leu Pro Glu
        35                  40                  45

Ser Thr Asp Leu Arg Val Ile Lys Ala Ala Ser Met Ile Val Lys Lys
    50                  55                  60

Gly Ile Ala Lys Val Val Leu Ile Gly Asn Glu Lys Glu Ile Lys Ser
65                  70                  75                  80

Leu Ala Gly Asp Ile Asp Leu Glu Gly Val Met Ile Glu Asp Ser Leu
                85                  90                  95

Asn Ser Glu Lys Leu Glu Asp Tyr Ala Asn Thr Leu Tyr Glu Leu Arg
            100                 105                 110

Lys Ser Lys Gly Met Thr Ile Glu Ala Ala Arg Glu Thr Ile Lys Asp
        115                 120                 125

Pro Leu Tyr Tyr Gly Val Met Met Val Lys Lys Gly Glu Ala Asp Gly
    130                 135                 140

Met Val Ala Gly Ala Val Asn Ser Thr Ala Asn Thr Leu Arg Pro Ala
145                 150                 155                 160

Leu Gln Ile Leu Lys Thr Ala Pro Gly Thr Lys Leu Val Ser Ser Phe
                165                 170                 175

Phe Val Met Val Pro Asn Cys Glu Tyr Gly His Asn Gly Thr Phe
            180                 185                 190

Val Tyr Ala Asp Cys Gly Leu Val Glu Asn Pro Asp Ala Asp Gln Leu

```
              195                 200                 205
Ser Glu Ile Ala Ile Ser Ala Ser Lys Ser Phe Glu Met Leu Val Gly
    210                 215                 220

Ala Lys Pro Gln Val Ala Met Leu Ser Tyr Ser Ser Tyr Gly Ser Ala
225                 230                 235                 240

Lys Ser Glu Leu Thr Glu Lys Val Ile Lys Ala Thr Gln Leu Ala Lys
                245                 250                 255

Glu Lys Ala Pro His Leu Ala Ile Asp Gly Glu Leu Gln Val Asp Ala
            260                 265                 270

Ala Ile Val Pro Glu Val Ala Lys Ser Lys Ala Lys Gly Ser Ser Val
        275                 280                 285

Ala Gly Lys Ala Asn Val Leu Ile Phe Pro Asp Leu Asp Ala Gly Asn
    290                 295                 300

Ile Ala Tyr Lys Leu Thr Gln Arg Leu Ala Lys Ala Glu Ala Tyr Gly
305                 310                 315                 320

Pro Ile Thr Gln Gly Leu Ala Arg Pro Val Asn Glu Leu Ser Arg Gly
                325                 330                 335

Cys Ser Ala Glu Asp Ile Val Gly Val Ala Ala Ile Thr Ala Val Gln
            340                 345                 350

Ala Gln Tyr Val Lys Ala
        355

<210> SEQ ID NO 7
<211> LENGTH: 1200
<212> TYPE: DNA
<213> ORGANISM: Clostridium thermocellum
<220> FEATURE:
<221> NAME/KEY: misc_feature
<222> LOCATION: (1)..(1200)
<223> OTHER INFORMATION: acetate kinase

<400> SEQUENCE: 7
atgaatattt tggttattaa taccggaagc tcatcactaa agtatcagct gattgacatg      60
acaaacgagt ctgtgcttgc aaaaggtgtg tgtgacagaa ttggtcttga acattccttt    120
ttaaagcata caaagaccgg aggggaaacc gtagttatag aaaagacct gtacaatcac     180 aagcttgcca tacaggaggt aatttcggct cttacggatg aaaaaatcgg agtcataaaa    240
agcatgtcgg aaatttctgc cgtcggtcat cgtattgttc acggcggaga gaagtttaag    300
gaatctgcca taattgatga agatgtaatg aaagcaatca gggattgtgt tgaactggct    360
ccgctccaca atccgtcaaa tataatcgga attgaagcct gtaaacagat actgcccgat    420
gtgccgatgg ttgctgtgtt tgacacagct tttcatcaga caatgccaag gcatgcatat    480
atttatgccc tcccttatga gatatatgag aagtataaat tgagaaaata cggattccac    540
ggaacttccc acaaatatgt ggcccacagg gcggctcaga tgctgggcaa acctattgag    600
agcctgaagc tgataacctg ccatcttgga acggagcga gtatttgtgc ggtaaaaggc     660
ggaaaatccg ttgacacctc aatgggattt actcctctgc aggggttgtg catgggtacc    720
agaagcggca atgttgaccc tgcggttata acttatttga tggaaaagga aaaaatgaat    780
attaacgata taacaatttt ccttaacaag aaatcaggtg tgcttggaat ttcaggtgta    840
agcagtgatt tcagagatgt tcaggatgcc gcagaaaagg gagatgacag ggcgcagctg    900
gcattggata ttttctgcta tggtgttagg aaatatattg aaaatatat tgcagtgctg    960 aacggcgttg atgcggtggt attcactgca ggtatcggcg aaaacaatgc ttatataaga   1020
agagaagttt tgaaggatat ggacttttc ggaattaaaa tagatttgga taaaaatgaa   1080
```

```
gtgaaaggca agaagcgga tatcagtgct cccgatgcga agtaaagac tttggttatc    1140 ccgacaaatg aggagcttga gattgcaagg gagactttaa gacttgtaaa aaacttataa   1200

<210> SEQ ID NO 8
<211> LENGTH: 399
<212> TYPE: PRT
<213> ORGANISM: Clostridium thermocellum
<220> FEATURE:
<221> NAME/KEY: misc_feature
<222> LOCATION: (1)..(399)
<223> OTHER INFORMATION: acetate kinase

<400> SEQUENCE: 8

Met Asn Ile Leu Val Ile Asn Thr Gly Ser Ser Leu Lys Tyr Gln
1               5                   10                  15

Leu Ile Asp Met Thr Asn Glu Ser Val Leu Ala Lys Gly Val Cys Asp
                20                  25                  30

Arg Ile Gly Leu Glu His Ser Phe Leu Lys His Thr Lys Thr Gly Gly
            35                  40                  45

Glu Thr Val Val Ile Glu Lys Asp Leu Tyr Asn His Lys Leu Ala Ile
    50                  55                  60

Gln Glu Val Ile Ser Ala Leu Thr Asp Glu Lys Ile Gly Val Ile Lys
65                  70                  75                  80

Ser Met Ser Glu Ile Ser Ala Val Gly His Arg Ile Val His Gly Gly
                85                  90                  95

Glu Lys Phe Lys Glu Ser Ala Ile Ile Asp Glu Asp Val Met Lys Ala
            100                 105                 110

Ile Arg Asp Cys Val Glu Leu Ala Pro Leu His Asn Pro Ser Asn Ile
        115                 120                 125

Ile Gly Ile Glu Ala Cys Lys Gln Ile Leu Pro Asp Val Pro Met Val
    130                 135                 140

Ala Val Phe Asp Thr Ala Phe His Gln Thr Met Pro Arg His Ala Tyr
145                 150                 155                 160

Ile Tyr Ala Leu Pro Tyr Glu Ile Tyr Glu Lys Tyr Lys Leu Arg Lys
                165                 170                 175

Tyr Gly Phe His Gly Thr Ser His Lys Tyr Val Ala His Arg Ala Ala
            180                 185                 190

Gln Met Leu Gly Lys Pro Ile Glu Ser Leu Lys Leu Ile Thr Cys His
        195                 200                 205

Leu Gly Asn Gly Ala Ser Ile Cys Ala Val Lys Gly Gly Lys Ser Val
    210                 215                 220

Asp Thr Ser Met Gly Phe Thr Pro Leu Gln Gly Leu Cys Met Gly Thr
225                 230                 235                 240

Arg Ser Gly Asn Val Asp Pro Ala Val Ile Thr Tyr Leu Met Glu Lys
                245                 250                 255

Glu Lys Met Asn Ile Asn Asp Ile Asn Asn Phe Leu Asn Lys Lys Ser
            260                 265                 270

Gly Val Leu Gly Ile Ser Gly Val Ser Ser Asp Phe Arg Asp Val Gln
        275                 280                 285

Asp Ala Ala Glu Lys Gly Asp Asp Arg Ala Gln Leu Ala Leu Asp Ile
    290                 295                 300

Phe Cys Tyr Gly Val Arg Lys Tyr Ile Gly Lys Tyr Ile Ala Val Leu
305                 310                 315                 320

Asn Gly Val Asp Ala Val Val Phe Thr Ala Gly Ile Gly Glu Asn Asn
                325                 330                 335
```

```
Ala Tyr Ile Arg Arg Glu Val Leu Lys Asp Met Asp Phe Phe Gly Ile
            340                 345                 350

Lys Ile Asp Leu Asp Lys Asn Glu Val Lys Gly Lys Glu Ala Asp Ile
        355                 360                 365

Ser Ala Pro Asp Ala Lys Val Lys Thr Leu Val Ile Pro Thr Asn Glu
    370                 375                 380

Glu Leu Glu Ile Ala Arg Glu Thr Leu Arg Leu Val Lys Asn Leu
385                 390                 395

<210> SEQ ID NO 9
<211> LENGTH: 2652
<212> TYPE: DNA
<213> ORGANISM: Clostridium thermocellum
<220> FEATURE:
<221> NAME/KEY: misc_feature
<222> LOCATION: (1)..(2652)
<223> OTHER INFORMATION: pyruvate-phosphate dikinase

<400> SEQUENCE: 9
atggcaaagt atgtgtattt gtttagtgaa ggcaatgcat caatgagaga cctgcttgga      60
ggaaaaggtg ccaatcttgc agaaatgaca agtttgggac ttccggtacc cagaggtttt     120
accattacca cggaagcttg tacacgctac tatcaagatg aaaagtcat tgccaaggaa      180 atagaagatg aaatatacag aactatggag aagcttgaag agattgtcgg aagaaaattc     240
ggtgacccat caaatccgtt tcttgtttcc gttcgttccg gtgccagagt atcaatgccc     300
ggtatgatgg ataccatatt aaatctcgga cttaatgatg aagttgttgt aggtcttgca     360
aagcttacca ataatgaaag attcgcatat gacagctata aagatttat tcaaatgttc      420 agcgatgttg tcatggaggt ggaaaagtcc aagtttgaag ctattcttga tgctgtgaaa     480
gaagaaaaca actgtgaaaa tgactgcgac ctttctgccg aaaatttaaa ggaagtagtc     540
agaagataca aggagctgtt caagaaagaa aagggatttg attttccgca ggatccgaaa     600
acacagttga tggaagccgt aaaagccgtt ttccgttcat gggaaaatcc aagggctatt     660
gtatatagaa gattaaatga catccccggc gactggggta ctgcagttaa cgttcaggaa     720
atggtttatg gaaatatggg aaatgattcg ggtacgggag ttgcctttac aaggaacccg     780
gctacgggag aaaagaagct ttatggtgaa ttccttatga atgcccaggg agaagacgtt     840
gttgcaggta tcagaactcc ccagtcaatt gaccagctga agaagtaat gcctgatgta     900 tacaatcagt ttgtggagat agccgaaaaa cttgaaagac attatagaga tatgcaggat     960
atggagttta caattgaaag aggaaaactc ttcatgctcc agacaagaaa cggtaaaagg    1020
actgctgcgg ctgcttaaa aatagctgtt gatttggtaa atgagggaat ggtcacaaaa    1080
gaagaagcaa ttttaaaagt cgacccgaaa cagcttgata cactgctcca tccaaatttc    1140
gaaccttcag cgctgaaaaa tgcaaaacct atagcaaagg gattgccggc ttcaccggga    1200
gctgctaccg aaagattta ctttagagcc gaggatgcgg tggaagcggc caaaaacgga    1260 gaaaagaca tcattcttgt aagacttgaa acttcacccg aagatattga gggtatgcat    1320
gtatccaaag gaatacttac aggccgtggt ggaatgacat tcatgctgc agttgttgca    1380 cgcggtatgg gtacttgctg cgttgccggc tgcagtgaaa taagaataaa tgaggaagag    1440
aaatactttg tagataaaaa cggaaagaaa tatgttgagg tgattggat tcccttgac    1500 ggttccacag gtaatgttta tgggaaaag cttcctacag tggagcctga atgaccggc    1560 gactttgcca cacttatgca gtgggccgat gaaatcagaa ctcttaagat tagaaccaat   1620
```

-continued

```
gccgatactc cggctgatgc catccaggca agaaagttcg gtgcggaagg tatcggactt      1680
tgccgtacgg agcatatgtt cttcgattct gacagaattc cggcaatgag agaaatgata      1740
gttgcaagaa ccgaagaaca gagaagaaag ctttggata aactcctgcc gatgcagaga       1800
aaagattttg aagaactgtt tactgcaatg gaaggctatc ctgtgacgat cagattcctg      1860
gatcctccgc ttcatgagtt cctgccccag gaggatgaag acatagaagc cttggcaaaa     1920
gaaatgggaa ttactttcga tgaactgaaa gcaatagtaa ccgggcttca tgagttcaat     1980
cctatgatgg gacacagggg atgccgtctt gcagtcacat atccggaaat tgcggaaatg    2040
cagacgagag cggttattga agctgctatc aacgtgagca ggaagaatat aaaagttgtg    2100
cctgaaatta tgattccgtt ggtaggcgat gtcaaggagc tgaaatatgt caaggacgta    2160
gttgtcagaa cagccaatga attgattgaa aaatccggtg tgaagattga atataaagtc   2220
ggaaccatga tagaaattcc aagggcggcc attactgccg atgaaattgc aaaagaagct    2280
gaattcttct cctttggaac caacgacctg acccagatga cttttggatt cagccgtgac    2340
gatgcaggca agttccttga agaatactac aacaagaaga tatacgagtt cgatcctttt    2400
gcaaaactgg atcaggatgg agtggggaaa ctggttgaaa tggctgcgaa gcttggaaga    2460
caaacaagac cggatattaa gcttggtata tgccgtgaac atggcggaga tccgtcgtcc    2520
attgagttct gccaccaaat tgggctgaac tatgtatcat gctctccgtt ccgtgtgccg    2580
attgcaaggc ttgcagcggc tcaggcaaga gtaaatgaaa taaaaggtac aaaggatttg    2640
ggacagaaat aa                                                        2652
```

<210> SEQ ID NO 10
<211> LENGTH: 883
<212> TYPE: PRT
<213> ORGANISM: Clostridium thermocellum
<220> FEATURE:
<221> NAME/KEY: misc_feature
<222> LOCATION: (1)..(883)
<223> OTHER INFORMATION: pyruvate-phosphate dikinase

<400> SEQUENCE: 10

Met Ala Lys Tyr Val Tyr Leu Phe Ser Glu Gly Asn Ala Ser Met Arg
1               5                   10                  15

Asp Leu Leu Gly Gly Lys Gly Ala Asn Leu Ala Glu Met Thr Ser Leu
                20                  25                  30

Gly Leu Pro Val Pro Arg Gly Phe Thr Ile Thr Glu Ala Cys Thr
            35                  40                  45

Arg Tyr Tyr Gln Asp Gly Lys Val Ile Ala Lys Glu Ile Glu Asp Glu
        50                  55                  60

Ile Tyr Arg Thr Met Glu Lys Leu Glu Glu Ile Val Gly Lys Lys Phe
65                  70                  75                  80

Gly Asp Pro Ser Asn Pro Phe Leu Val Ser Val Arg Ser Gly Ala Arg
                85                  90                  95

Val Ser Met Pro Gly Met Met Asp Thr Ile Leu Asn Leu Gly Leu Asn
            100                 105                 110

Asp Glu Val Val Val Gly Leu Ala Lys Leu Thr Asn Asn Glu Arg Phe
        115                 120                 125

Ala Tyr Asp Ser Tyr Arg Arg Phe Ile Gln Met Phe Ser Asp Val Val
    130                 135                 140

Met Glu Val Glu Lys Ser Lys Phe Glu Ala Ile Leu Asp Ala Val Lys
145                 150                 155                 160

Glu Glu Asn Asn Cys Glu Asn Asp Cys Asp Leu Ser Ala Glu Asn Leu

```
                    165                 170                 175
Lys Glu Val Val Arg Arg Tyr Lys Glu Leu Phe Lys Lys Glu Lys Gly
                180                 185                 190

Phe Asp Phe Pro Gln Asp Pro Lys Thr Gln Leu Met Glu Ala Val Lys
            195                 200                 205

Ala Val Phe Arg Ser Trp Glu Asn Pro Arg Ala Ile Val Tyr Arg Arg
        210                 215                 220

Leu Asn Asp Ile Pro Gly Asp Trp Gly Thr Ala Val Asn Val Gln Glu
225                 230                 235                 240

Met Val Tyr Gly Asn Met Gly Asn Asp Ser Gly Thr Gly Val Ala Phe
                245                 250                 255

Thr Arg Asn Pro Ala Thr Gly Glu Lys Lys Leu Tyr Gly Glu Phe Leu
            260                 265                 270

Met Asn Ala Gln Gly Glu Asp Val Val Ala Gly Ile Arg Thr Pro Gln
        275                 280                 285

Ser Ile Asp Gln Leu Lys Glu Val Met Pro Asp Val Tyr Asn Gln Phe
290                 295                 300

Val Glu Ile Ala Glu Lys Leu Glu Arg His Tyr Arg Asp Met Gln Asp
305                 310                 315                 320

Met Glu Phe Thr Ile Glu Arg Gly Lys Leu Phe Met Leu Gln Thr Arg
                325                 330                 335

Asn Gly Lys Arg Thr Ala Ala Ala Leu Lys Ile Ala Val Asp Leu
            340                 345                 350

Val Asn Glu Gly Met Val Thr Lys Glu Glu Ala Ile Leu Lys Val Asp
        355                 360                 365

Pro Lys Gln Leu Asp Thr Leu Leu His Pro Asn Phe Glu Pro Ser Ala
370                 375                 380

Leu Lys Asn Ala Lys Pro Ile Ala Lys Gly Leu Pro Ala Ser Pro Gly
385                 390                 395                 400

Ala Ala Thr Gly Lys Ile Tyr Phe Arg Ala Glu Asp Ala Val Glu Ala
                405                 410                 415

Ala Lys Asn Gly Glu Lys Asp Ile Ile Leu Val Arg Leu Glu Thr Ser
            420                 425                 430

Pro Glu Asp Ile Glu Gly Met His Val Ser Lys Gly Ile Leu Thr Gly
        435                 440                 445

Arg Gly Gly Met Thr Ser His Ala Ala Val Val Ala Arg Gly Met Gly
450                 455                 460

Thr Cys Cys Val Ala Gly Cys Ser Glu Ile Arg Ile Asn Glu Glu Glu
465                 470                 475                 480

Lys Tyr Phe Val Asp Lys Asn Gly Lys Lys Tyr Val Glu Gly Asp Trp
                485                 490                 495

Ile Ser Leu Asp Gly Ser Thr Gly Asn Val Tyr Gly Glu Lys Leu Pro
            500                 505                 510

Thr Val Glu Pro Glu Met Thr Gly Asp Phe Ala Thr Leu Met Gln Trp
        515                 520                 525

Ala Asp Glu Ile Arg Thr Leu Lys Ile Arg Thr Asn Ala Asp Thr Pro
530                 535                 540

Ala Asp Ala Ile Gln Ala Arg Lys Phe Gly Ala Glu Gly Ile Gly Leu
545                 550                 555                 560

Cys Arg Thr Glu His Met Phe Phe Asp Ser Asp Arg Ile Pro Ala Met
                565                 570                 575

Arg Glu Met Ile Val Ala Arg Thr Glu Glu Gln Arg Arg Lys Ala Leu
            580                 585                 590
```

Asp Lys Leu Leu Pro Met Gln Arg Lys Asp Phe Glu Glu Leu Phe Thr
                595                 600                 605

Ala Met Glu Gly Tyr Pro Val Thr Ile Arg Phe Leu Asp Pro Pro Leu
        610                 615                 620

His Glu Phe Leu Pro Gln Glu Asp Glu Ile Glu Ala Leu Ala Lys
625                 630                 635                 640

Glu Met Gly Ile Thr Phe Asp Glu Leu Lys Ala Ile Val Thr Gly Leu
                645                 650                 655

His Glu Phe Asn Pro Met Met Gly His Arg Gly Cys Arg Leu Ala Val
            660                 665                 670

Thr Tyr Pro Glu Ile Ala Glu Met Gln Thr Arg Ala Val Ile Glu Ala
        675                 680                 685

Ala Ile Asn Val Ser Arg Lys Asn Ile Lys Val Val Pro Glu Ile Met
        690                 695                 700

Ile Pro Leu Val Gly Asp Val Lys Glu Leu Lys Tyr Val Lys Asp Val
705                 710                 715                 720

Val Val Arg Thr Ala Asn Glu Leu Ile Glu Lys Ser Gly Val Lys Ile
                725                 730                 735

Glu Tyr Lys Val Gly Thr Met Ile Glu Ile Pro Arg Ala Ala Ile Thr
            740                 745                 750

Ala Asp Glu Ile Ala Lys Glu Ala Glu Phe Phe Ser Phe Gly Thr Asn
        755                 760                 765

Asp Leu Thr Gln Met Thr Phe Gly Phe Ser Arg Asp Asp Ala Gly Lys
        770                 775                 780

Phe Leu Glu Glu Tyr Tyr Asn Lys Lys Ile Tyr Glu Phe Asp Pro Phe
785                 790                 795                 800

Ala Lys Leu Asp Gln Asp Gly Val Gly Lys Leu Val Glu Met Ala Ala
                805                 810                 815

Lys Leu Gly Arg Gln Thr Arg Pro Asp Ile Lys Leu Gly Ile Cys Gly
            820                 825                 830

Glu His Gly Gly Asp Pro Ser Ser Ile Glu Phe Cys His Gln Ile Gly
        835                 840                 845

Leu Asn Tyr Val Ser Cys Ser Pro Phe Arg Val Pro Ile Ala Arg Leu
        850                 855                 860

Ala Ala Ala Gln Ala Arg Val Asn Glu Ile Lys Gly Thr Lys Asp Leu
865                 870                 875                 880

Gly Gln Lys

<210> SEQ ID NO 11
<211> LENGTH: 2583
<212> TYPE: DNA
<213> ORGANISM: Clostridium thermocellum
<220> FEATURE:
<221> NAME/KEY: misc_feature
<222> LOCATION: (1)..(2583)
<223> OTHER INFORMATION: alternate pyruvate-phosphate dikinase

<400> SEQUENCE: 11
atgccggctt ttgaaagggt tagatcaggt ataccgagtt tggacaaggt tcttgacaac      60
ataagacttg gagataatgt ggtcatacag gtaacttgtt tgaatgattt taaaagaata     120
gtgcatccct ttgtaaatca atccattgag gacaaaagaa atattattta tatccgtttt     180
tccaaccatg aacctttact ggaatacatg gacgggctga aaatttatca gctgaatgcc     240
aatcgagggt tgaggcctt tacggttgag gtccacaata taattgataa ggagggaagg     300

```
gaggcatttt atgtgtttga ttccctttcc gacctgcagg ttgcctggtc cacagacttg      360
atgatgggaa atttcttttg tgtaacctgc ccctatttgt ttgaacttga cactgtggca      420
ttgtttcctg tactgagagg gcatcacgat tttgcaacaa ttgcccgtat tcaggagaca      480
acacagctgt ttattgatgt gtattcggac gaaaaagata cgtttataca tcctattaaa      540
gtttggaacc gctatttgcc tgacatgtat atgccttaca ggctgaatga cgacaacgag      600
ctggaatccc tgaccggcag tgtggatttg gcagattact acaatcttat tcataatgag      660
caaaagaggc acgccgagca gaatattgac agttatgaaa ggttttttcag ggaggccagg      720
gaagcttatt acaggggtga aattacagac tggactctta taaaataac ccgcagcatg        780
atgacccgcg accacagaat ggctgatttg ataagaaaag aattcagtcc tgaggattat       840
ttccatatca agaaagaat gatcggtacc ggaacaattg ggggaaaggc atgtggtatg        900
cttttggcaa gaaaaatggt tgcaaactac ctgcctcagt atgtaaagta tttggagcct      960
caggattcct attatatcgg aactgatatc ttttattcat atatcgtgga aaacaaactc     1020
tggaaattac gtattttaca gcgtaatgac aagtattatt ttgaaaaggc ggaagaactg     1080
aaaaatgcga tatcaaacgg taaattttcc gagcccatta gggcgcaatt cagaagaatg     1140
ctgaactatt tcgacaaat tcctatcatt gtgcgttcga gcagtttcct ggaagacgga      1200
tttggaaatg cttttgcggg aaaatacgag tcgattttct gcgtaaacgc atgcgatccg     1260
gaagaaaggc ttttgcaatt tgaagacgcg gtgcgcaggg tatatgcaag cacgatggac     1320
aggtctgctt tggagtaccg cagacaacgg ggacttgata aaatggacga gcaaatggcg     1380
attttggtgc agcgtgtcag cggaacgaaa tttgacaaat attatatgcc atgtgctgcg     1440
ggagttggtt tttcctatag tgtataccgc tggagtgatg aatttagtgc agatgcggga     1500
cttctgcgtt tggttgcagg tctgggtaca aaggcggtgg acagaacggg tgtcgattat     1560
ccccggctgg taaacctgga taatcctgaa agtaccattt taacgaggtc gagtgataaa     1620
catcgttttt cacagcgaag agtggatgtt attgatttac agaaaaatga agtaagagat     1680
attgatgtaa gtgaactgat tcctgagctt ccggattggt atgtgaatct tgtctgtgag     1740
catgattatg atactgagag aatgttttat gaaagaggac agagacgaaa tgttctttt      1800
gtttcgtgtg acgggattgt taagaaaaga gagcttatga aaatgatgaa agatattctt     1860
tccactcttc aggagcatta cggaaatcct gtggatgtgg aatacacaat taatttcaga     1920
aaggacggag catttaccgt aaatcttctt cagtgcaggc ccatggctgt atgggagagt     1980
actgccaatc gggaaattcc gaatattgaa aaagataaag ttctgtttaa agttaatcag     2040
acttttatgg ggaattccgc agagttgaac attgatgtgg ttgtgtggat tgactcaaaa     2100
aagtatcatg gttatcctta taatcagaaa agctctttgt gcagtgtagt ctctaaaatt     2160
aacaaatatt atgaaggaaa gaataagaaa ctgatgcttg taagcccggg gcgaattggg     2220
acttcatccc ctgaattggg agttccggtt gtgttttcgg atatatccaa ttttaaagtc     2280
ctatgcgagt atgcggatat tgaaattgga tttgttcctg agttgtctta tggcagtcat     2340
atgtttcagg acatagttga aacggaaatg ttttatgtgg cggtaatggg caccgagcga     2400
agcggtaccg aagtatttaa caaagagttt ttcaaaaatg agccttcggt tctgggtaag     2460
attgttcctg aagctgaagc atatgaagat atcatcaaag tatatgaatt tggtgtttca     2520
aaatcactaa gcctctatgc tgattttaag aaaagaactg cagtttgcgg tgtaaattct     2580
taa                                                                    2583
```

<210> SEQ ID NO 12
<211> LENGTH: 860
<212> TYPE: PRT
<213> ORGANISM: Clostridium thermocellum
<220> FEATURE:
<221> NAME/KEY: misc_feature
<222> LOCATION: (1)..(860)
<223> OTHER INFORMATION: alternate pyruvate-phosphate dikinase

<400> SEQUENCE: 12

Met Pro Ala Phe Glu Arg Val Arg Ser Gly Ile Pro Ser Leu Asp Lys
1               5                   10                  15

Val Leu Asp Asn Ile Arg Leu Gly Asp Asn Val Ile Gln Val Thr
            20                  25                  30

Cys Leu Asn Asp Phe Lys Arg Ile Val His Pro Phe Val Asn Gln Ser
            35                  40                  45

Ile Glu Asp Lys Arg Asn Ile Ile Tyr Ile Arg Phe Ser Asn His Glu
    50                  55                  60

Pro Leu Leu Glu Tyr Met Asp Gly Leu Lys Ile Tyr Gln Leu Asn Ala
65                  70                  75                  80

Asn Arg Gly Phe Glu Ala Phe Thr Val Glu Val His Asn Ile Ile Asp
                85                  90                  95

Lys Glu Gly Arg Glu Ala Phe Tyr Val Phe Asp Ser Leu Ser Asp Leu
            100                 105                 110

Gln Val Ala Trp Ser Thr Asp Leu Met Met Gly Asn Phe Phe Cys Val
        115                 120                 125

Thr Cys Pro Tyr Leu Phe Glu Leu Asp Thr Val Ala Leu Phe Pro Val
    130                 135                 140

Leu Arg Gly His His Asp Phe Ala Thr Ile Ala Arg Ile Gln Glu Thr
145                 150                 155                 160

Thr Gln Leu Phe Ile Asp Val Tyr Ser Asp Gly Lys Asp Thr Phe Ile
                165                 170                 175

His Pro Ile Lys Val Trp Asn Arg Tyr Leu Pro Asp Met Tyr Met Pro
            180                 185                 190

Tyr Arg Leu Asn Asp Asp Asn Glu Leu Glu Ser Leu Thr Gly Ser Val
        195                 200                 205

Asp Leu Ala Asp Tyr Tyr Asn Leu Ile His Asn Glu Gln Lys Arg His
    210                 215                 220

Ala Glu Gln Asn Ile Asp Ser Tyr Glu Arg Phe Phe Arg Glu Ala Arg
225                 230                 235                 240

Glu Ala Tyr Tyr Arg Gly Glu Ile Thr Asp Trp Thr Leu Asn Lys Ile
                245                 250                 255

Thr Arg Ser Met Met Thr Arg Asp His Arg Met Ala Asp Leu Ile Arg
            260                 265                 270

Lys Glu Phe Ser Pro Glu Asp Tyr Phe His Ile Lys Glu Arg Met Ile
        275                 280                 285

Gly Thr Gly Thr Ile Gly Gly Lys Ala Cys Gly Met Leu Leu Ala Arg
    290                 295                 300

Lys Met Val Ala Asn Tyr Leu Pro Gln Tyr Val Lys Tyr Leu Glu Pro
305                 310                 315                 320

Gln Asp Ser Tyr Tyr Ile Gly Thr Asp Ile Phe Tyr Ser Tyr Ile Val
                325                 330                 335

Glu Asn Lys Leu Trp Lys Leu Arg Ile Leu Gln Arg Asn Asp Lys Tyr
            340                 345                 350

Tyr Phe Glu Lys Ala Glu Glu Leu Lys Asn Ala Ile Ser Asn Gly Lys
        355                 360                 365

```
Phe Ser Glu Pro Ile Arg Ala Gln Phe Arg Arg Met Leu Asn Tyr Phe
    370                 375                 380

Gly Gln Ile Pro Ile Ile Val Arg Ser Ser Phe Leu Glu Asp Gly
385                 390                 395                 400

Phe Gly Asn Ala Phe Ala Gly Lys Tyr Glu Ser Ile Phe Cys Val Asn
                405                 410                 415

Ala Cys Asp Pro Glu Glu Arg Leu Leu Gln Phe Glu Asp Ala Val Arg
        420                 425                 430

Arg Val Tyr Ala Ser Thr Met Asp Arg Ser Ala Leu Glu Tyr Arg Arg
            435                 440                 445

Gln Arg Gly Leu Asp Lys Met Asp Glu Gln Met Ala Ile Leu Val Gln
450                 455                 460

Arg Val Ser Gly Thr Lys Phe Asp Lys Tyr Tyr Met Pro Cys Ala Ala
465                 470                 475                 480

Gly Val Gly Phe Ser Tyr Ser Val Tyr Arg Trp Ser Asp Glu Phe Ser
                485                 490                 495

Ala Asp Ala Gly Leu Leu Arg Leu Val Ala Gly Leu Gly Thr Lys Ala
            500                 505                 510

Val Asp Arg Thr Gly Val Asp Tyr Pro Arg Leu Val Asn Leu Asp Asn
        515                 520                 525

Pro Glu Ser Thr Ile Leu Thr Arg Ser Ser Asp Lys His Arg Phe Ser
    530                 535                 540

Gln Arg Arg Val Asp Val Ile Asp Leu Gln Lys Asn Glu Val Arg Asp
545                 550                 555                 560

Ile Asp Val Ser Glu Leu Ile Pro Glu Leu Pro Asp Trp Tyr Val Asn
                565                 570                 575

Leu Val Cys Glu His Asp Tyr Asp Thr Glu Arg Met Phe Tyr Glu Arg
            580                 585                 590

Gly Gln Arg Arg Asn Val Leu Phe Val Ser Cys Asp Gly Ile Val Lys
        595                 600                 605

Lys Arg Glu Leu Met Lys Met Met Lys Asp Ile Leu Ser Thr Leu Gln
    610                 615                 620

Glu His Tyr Gly Asn Pro Val Asp Val Glu Tyr Thr Ile Asn Phe Arg
625                 630                 635                 640

Lys Asp Gly Ala Phe Thr Val Asn Leu Leu Gln Cys Arg Pro Met Ala
                645                 650                 655

Val Trp Glu Ser Thr Ala Asn Arg Glu Ile Pro Asn Ile Glu Lys Asp
            660                 665                 670

Lys Val Leu Phe Lys Val Asn Gln Thr Phe Met Gly Asn Ser Ala Glu
        675                 680                 685

Leu Asn Ile Asp Val Val Trp Ile Asp Ser Lys Lys Tyr His Gly
    690                 695                 700

Tyr Pro Tyr Asn Gln Lys Ser Ser Leu Cys Ser Val Val Ser Lys Ile
705                 710                 715                 720

Asn Lys Tyr Tyr Glu Gly Lys Asn Lys Lys Leu Met Leu Val Ser Pro
                725                 730                 735

Gly Arg Ile Gly Thr Ser Ser Pro Glu Leu Gly Val Pro Val Val Phe
            740                 745                 750

Ser Asp Ile Ser Asn Phe Lys Val Leu Cys Glu Tyr Ala Asp Ile Glu
        755                 760                 765

Ile Gly Phe Val Pro Glu Leu Ser Tyr Gly Ser His Met Phe Gln Asp
    770                 775                 780
```

Ile Val Glu Thr Glu Met Phe Tyr Val Ala Val Met Gly Thr Glu Arg
785                 790                 795                 800

Ser Gly Thr Glu Val Phe Asn Lys Glu Phe Phe Lys Asn Glu Pro Ser
            805                 810                 815

Val Leu Gly Lys Ile Val Pro Glu Ala Glu Ala Tyr Glu Asp Ile Ile
            820                 825                 830

Lys Val Tyr Glu Phe Gly Val Ser Lys Ser Leu Ser Leu Tyr Ala Asp
            835                 840                 845

Phe Lys Lys Arg Thr Ala Val Cys Gly Val Asn Ser
        850                 855                 860

<210> SEQ ID NO 13
<211> LENGTH: 1818
<212> TYPE: DNA
<213> ORGANISM: Clostridium thermocellum
<220> FEATURE:
<221> NAME/KEY: misc_feature
<222> LOCATION: (1)..(1818)
<223> OTHER INFORMATION: phosphoenolpyruvate carboxykinase

<400> SEQUENCE: 13

```
atgacatcaa caaacatgac aaaaaacaaa aaactgctgg attgggttaa ggaaatggct      60
gaaatgtgtc agcctgatga aatttattgg tgcgatggtt cggaggaaga aaatgagcgc     120
ttgataaagt tgatggtgga ttcaggtttg gctacgcctt tgaatcctga aaagcgacct     180
ggatgttatc tcttccgcag cgatccgtcc gacgttgccc gtgttgagga cagaactttt     240
attgcatcca aaaccaaaga agatgcagga cctacaaaca actggataga tccggttgag     300
ctcaaggcaa ctatgaaaga gttgtacaag ggttgtatga agggaagaac aatgtatgtt     360
attcctttct ccatgggacc tatcggttca cccatttcaa aaatcggcgt tgaattgacc     420
gacagccctt atgttgttgt taacatgcgc attatgactc gcataggcaa ggctgtgttg     480
gatcagctcg gagaagacgg agattttgta ccttgtctcc actcagtcgg tgctccgctc     540
aaagagggag aaaaggataa aggttggcca tgcgcaccaa tcgaaaagaa atacataagc     600
cacttcccgg aagaaggac tatatggtca tatggttccg gatacggtgg aaatgcgctt     660
ttaggaaaga aatgctttgc acttcgtatt gcatctgtta tggcacgtga cgaaggttgg     720
cttgctgaac acatgcttat ccttcgcata acagaccctg aaggaaacaa gacatatgtt     780
acaggtgctt tcccaagcgc atgcggaaag acgaacctgg ctatgcttat tcctacaatt     840
cccggatgga agttgaaac aatcggtgac gatattgcat ggatgagatt tggaaaagac     900
ggccgtttgt atgctatcaa ccctgaagca ggattctttg tgttgctcc gggtacatcc     960
atggattcaa tccgaacgc aatgcataca attaagaaaa atactatatt tacaaacgtt    1020
gcattgactg atgacggcga tgtttggtgg aaggcatcg gaactgaacc gccggctcat    1080
ctcatagact ggcagggtaa agactggact cctgattccg aactttggc agcacatccc    1140
aacggacgtt ttacagcacc tgcaagtcag tgccctgtaa ttgctcctga tgggaggat    1200
ccggaaggtg tgccgatttc agcaatcctt atcggtggac gccgtccgaa caccattccg    1260
cttgttcatg aaagctttga ctggaaccat ggtgtattca tgggttcaat catgggttct    1320
gaaattacgg ctgccgcaat ttcaaacaaa tcggacagg tacgccgtga cccgtttgct    1380
atgctgcctt tcataggcta caacgtaaat gactatttgc agcactggtt gaacatgggt    1440
accaagactg acccaagcaa gcttcccaag atattctatg taaactggtt ccgcaaggac    1500
agcaacggta atggttgtg gcctggatac ggtgaaaaca gccgtgttct caagtggatt    1560
```

-continued

```
gttgaaagag tcaacggaaa aggtaaagca gtaaagacac ctataggata tatgcctaca    1620
gttgacgcta tcgacacaac cggccttgat gtaagcaaag aggatatgga agaactcttg    1680
agcgttaaca agaacagtg gctccaggaa gttgagtcaa taaaagaaca ttataagtca     1740
tacggagaaa aactgccgaa agaattgtgg gcacaattgg aggctcttga caacgtttg     1800 aaagagtata acggttaa                                                  1818
```

<210> SEQ ID NO 14
<211> LENGTH: 605
<212> TYPE: PRT
<213> ORGANISM: Clostridium thermocellum
<220> FEATURE:
<221> NAME/KEY: misc_feature
<222> LOCATION: (1)..(605)
<223> OTHER INFORMATION: phosphoenolpyruvate carboxykinase

<400> SEQUENCE: 14

```
Met Thr Ser Thr Asn Met Thr Lys Asn Lys Lys Leu Leu Asp Trp Val
 1               5                  10                  15

Lys Glu Met Ala Glu Met Cys Gln Pro Asp Glu Ile Tyr Trp Cys Asp
            20                  25                  30

Gly Ser Glu Glu Glu Asn Glu Arg Leu Ile Lys Leu Met Val Asp Ser
        35                  40                  45

Gly Leu Ala Thr Pro Leu Asn Pro Glu Lys Arg Pro Gly Cys Tyr Leu
    50                  55                  60

Phe Arg Ser Asp Pro Ser Asp Val Ala Arg Val Glu Asp Arg Thr Phe
65                  70                  75                  80

Ile Ala Ser Lys Thr Lys Glu Asp Ala Gly Pro Thr Asn Asn Trp Ile
                85                  90                  95

Asp Pro Val Glu Leu Lys Ala Thr Met Lys Glu Leu Tyr Lys Gly Cys
            100                 105                 110

Met Lys Gly Arg Thr Met Tyr Val Ile Pro Phe Ser Met Gly Pro Ile
        115                 120                 125

Gly Ser Pro Ile Ser Lys Ile Gly Val Glu Leu Thr Asp Ser Pro Tyr
    130                 135                 140

Val Val Val Asn Met Arg Ile Met Thr Arg Ile Gly Lys Ala Val Leu
145                 150                 155                 160

Asp Gln Leu Gly Glu Asp Gly Asp Phe Val Pro Cys Leu His Ser Val
                165                 170                 175

Gly Ala Pro Leu Lys Glu Gly Glu Lys Asp Lys Gly Trp Pro Cys Ala
            180                 185                 190

Pro Ile Glu Lys Lys Tyr Ile Ser His Phe Pro Glu Glu Arg Thr Ile
        195                 200                 205

Trp Ser Tyr Gly Ser Gly Tyr Gly Gly Asn Ala Leu Leu Gly Lys Lys
    210                 215                 220

Cys Phe Ala Leu Arg Ile Ala Ser Val Met Ala Arg Asp Glu Gly Trp
225                 230                 235                 240

Leu Ala Glu His Met Leu Ile Leu Arg Ile Thr Asp Pro Glu Gly Asn
                245                 250                 255

Lys Thr Tyr Val Thr Gly Ala Phe Pro Ser Ala Cys Gly Lys Thr Asn
            260                 265                 270

Leu Ala Met Leu Ile Pro Thr Ile Pro Gly Trp Lys Val Glu Thr Ile
        275                 280                 285

Gly Asp Asp Ile Ala Trp Met Arg Phe Gly Lys Asp Gly Arg Leu Tyr
    290                 295                 300
```

```
Ala Ile Asn Pro Glu Ala Gly Phe Phe Gly Val Ala Pro Gly Thr Ser
305                 310                 315                 320

Met Asp Ser Asn Pro Asn Ala Met His Thr Ile Lys Lys Asn Thr Ile
            325                 330                 335

Phe Thr Asn Val Ala Leu Thr Asp Asp Gly Asp Val Trp Trp Glu Gly
        340                 345                 350

Ile Gly Thr Glu Pro Pro Ala His Leu Ile Asp Trp Gln Gly Lys Asp
    355                 360                 365

Trp Thr Pro Asp Ser Gly Thr Leu Ala Ala His Pro Asn Gly Arg Phe
370                 375                 380

Thr Ala Pro Ala Ser Gln Cys Pro Val Ile Ala Pro Glu Trp Glu Asp
385                 390                 395                 400

Pro Glu Gly Val Pro Ile Ser Ala Ile Leu Ile Gly Gly Arg Arg Pro
                405                 410                 415

Asn Thr Ile Pro Leu Val His Glu Ser Phe Asp Trp Asn His Gly Val
            420                 425                 430

Phe Met Gly Ser Ile Met Gly Ser Glu Ile Thr Ala Ala Ala Ile Ser
        435                 440                 445

Asn Lys Ile Gly Gln Val Arg Arg Asp Pro Phe Ala Met Leu Pro Phe
450                 455                 460

Ile Gly Tyr Asn Val Asn Asp Tyr Leu Gln His Trp Leu Asn Met Gly
465                 470                 475                 480

Thr Lys Thr Asp Pro Ser Lys Leu Pro Lys Ile Phe Tyr Val Asn Trp
                485                 490                 495

Phe Arg Lys Asp Ser Asn Gly Lys Trp Leu Trp Pro Gly Tyr Gly Glu
            500                 505                 510

Asn Ser Arg Val Leu Lys Trp Ile Val Glu Arg Val Asn Gly Lys Gly
        515                 520                 525

Lys Ala Val Lys Thr Pro Ile Gly Tyr Met Pro Thr Val Asp Ala Ile
530                 535                 540

Asp Thr Thr Gly Leu Asp Val Ser Lys Glu Asp Met Glu Glu Leu Leu
545                 550                 555                 560

Ser Val Asn Lys Glu Gln Trp Leu Gln Glu Val Glu Ser Ile Lys Glu
                565                 570                 575

His Tyr Lys Ser Tyr Gly Glu Lys Leu Pro Lys Glu Leu Trp Ala Gln
            580                 585                 590

Leu Glu Ala Leu Glu Gln Arg Leu Lys Glu Tyr Asn Gly
        595                 600                 605

<210> SEQ ID NO 15
<211> LENGTH: 1173
<212> TYPE: DNA
<213> ORGANISM: Clostridium thermocellum
<220> FEATURE:
<221> NAME/KEY: misc_Feature
<222> LOCATION: (1)..(1173)
<223> OTHER INFORMATION: malic enzyme

<400> SEQUENCE: 15
atggattaca gaaagaatc actaaggctt cacggtgagt ggaagggtaa aattgaggtt      60
atacacaagg tacctgtttc aaccaaggaa gagttgtcgc ttgcttatac accgggtgtt    120
gcagaaccat gtcttgcaat tcagaaagat gttaatcttt cttatgaata taagacgt     180 tggaacctgg tagcggttat taccgacggt acggcggttt tagggctcgg agacatagga    240
cctgaagccg gaatgcctgt tatggaaggt aaatgcgtac tcttcaagag gtttggtgat    300
```

```
gtggacgcat tccgctctg tatcaaatca aaagacgtag atgaaattgt aaagacaatc    360
aagctcatct ccggaagctt tggcggtata acctcgaag atatatccgc tccgagatgc    420
tttgaaatag aaagaagact caaagaggaa tgtgacattc aatattcca tgatgaccag    480 cacggtacag ccgttgttac tgttgcagca atgatcaatg cattaaagct tgtcaacaag    540
aaaatcgagg atatagaagt tgttgtaaac ggttcaggtg ctgccggcat agctgtaaca    600
agactgctca tgagtatggg cttaagaaa gttatccttt gcataccaa aggtgcaatt    660 tatgatggaa gagacaactt aaacagtgaa aaagccctga ttgctaaaat ctcgaacctc    720
gagaaaaaga aggtactct tgaagatgta atcaagggag ctgacgtatt catcggtctt    780
tccgttccag gaacagttac aaaggatatg gtaaaatcca tggcaaagga tccgattatc    840
tttgctatgg caaatcctac tcctgaaata atgcctgatg aagcaaaaga agcaggagca    900
aaggtagtgg gtaccggaag atccgacttc ccgaaccaga taaacaacgt tcttgcgttc    960
cccggaatat tcagaggtgc gcttgatgta agagcaagag atatcaatga tgaaatgaag   1020
atagccgctg caaaagcaat agcttctctg gtaagcgatg aagagctcaa tcctgacttc   1080
attcttccgc tcccatttga cccaagagtc ggaaaaacag ttgctgcagc agttgctgaa   1140
gcagcaagaa aaaccggagt tgcaagaata taa                                1173
```

<210> SEQ ID NO 16
<211> LENGTH: 390
<212> TYPE: PRT
<213> ORGANISM: Clostridium thermocellum
<220> FEATURE:
<221> NAME/KEY: misc_feature
<222> LOCATION: (1)..(390)
<223> OTHER INFORMATION: malic enzyme

<400> SEQUENCE: 16

```
Met Asp Tyr Arg Lys Glu Ser Leu Arg Leu His Gly Glu Trp Lys Gly
1               5                   10                  15

Lys Ile Glu Val Ile His Lys Val Pro Val Ser Thr Lys Glu Glu Leu
            20                  25                  30

Ser Leu Ala Tyr Thr Pro Gly Val Ala Glu Pro Cys Leu Ala Ile Gln
        35                  40                  45

Lys Asp Val Asn Leu Ser Tyr Glu Tyr Thr Arg Arg Trp Asn Leu Val
    50                  55                  60

Ala Val Ile Thr Asp Gly Thr Ala Val Leu Gly Leu Gly Asp Ile Gly
65                  70                  75                  80

Pro Glu Ala Gly Met Pro Val Met Glu Gly Lys Cys Val Leu Phe Lys
                85                  90                  95

Arg Phe Gly Asp Val Asp Ala Phe Pro Leu Cys Ile Lys Ser Lys Asp
            100                 105                 110

Val Asp Glu Ile Val Lys Thr Ile Lys Leu Ile Ser Gly Ser Phe Gly
        115                 120                 125

Gly Ile Asn Leu Glu Asp Ile Ser Ala Pro Arg Cys Phe Glu Ile Glu
    130                 135                 140

Arg Arg Leu Lys Glu Glu Cys Asp Ile Pro Ile Phe His Asp Asp Gln
145                 150                 155                 160

His Gly Thr Ala Val Val Thr Val Ala Ala Met Ile Asn Ala Leu Lys
                165                 170                 175

Leu Val Asn Lys Lys Ile Glu Asp Ile Glu Val Val Asn Gly Ser
            180                 185                 190

Gly Ala Ala Gly Ile Ala Val Thr Arg Leu Leu Met Ser Met Gly Leu
```

```
                195                 200                 205
        Lys Lys Val Ile Leu Cys Asp Thr Lys Gly Ala Ile Tyr Asp Gly Arg
            210                 215                 220

Asp Asn Leu Asn Ser Glu Lys Ala Leu Ile Ala Lys Ile Ser Asn Leu
        225                 230                 235                 240

Glu Lys Lys Lys Gly Thr Leu Glu Asp Val Ile Lys Gly Ala Asp Val
                        245                 250                 255

Phe Ile Gly Leu Ser Val Pro Gly Thr Val Thr Lys Asp Met Val Lys
                    260                 265                 270

Ser Met Ala Lys Asp Pro Ile Ile Phe Ala Met Ala Asn Pro Thr Pro
            275                 280                 285

Glu Ile Met Pro Asp Glu Ala Lys Glu Ala Gly Ala Lys Val Val Gly
            290                 295                 300

Thr Gly Arg Ser Asp Phe Pro Asn Gln Ile Asn Val Leu Ala Phe
        305                 310                 315                 320

Pro Gly Ile Phe Arg Gly Ala Leu Asp Val Arg Ala Arg Asp Ile Asn
                        325                 330                 335

Asp Glu Met Lys Ile Ala Ala Ala Lys Ala Ile Ala Ser Leu Val Ser
                    340                 345                 350

Asp Glu Glu Leu Asn Pro Asp Phe Ile Leu Pro Leu Pro Phe Asp Pro
                355                 360                 365

Arg Val Gly Lys Thr Val Ala Ala Val Ala Glu Ala Ala Arg Lys
            370                 375                 380

Thr Gly Val Ala Arg Ile
        385                 390

<210> SEQ ID NO 17
<211> LENGTH: 957
<212> TYPE: DNA
<213> ORGANISM: Clostridium thermocellum
<220> FEATURE:
<221> NAME/KEY: misc_feature
<222> LOCATION: (1)..(957)
<223> OTHER INFORMATION: malate dehydrogenase

<400> SEQUENCE: 17
atggaaatgg taaaaagtag gtcaaaagtt gcaatcattg gtgctggttt tgtaggtgcg     60
tctgcagcct tcacaatggc tttgcggcaa accgcaaatg aacttgttct catcgatgtt    120
ttcaaggaaa aagccatagg cgaggctatg gatattaacc acggtcttcc atttatggga    180
cagatgtcat tgtatgccgg tgattattcc gacgttaaag actgtgatgt atcgtagtc     240 acggccggag ccaacagaaa acctggtgaa cacgtcttg accttgcaaa gaaaaacgtt    300
atgattgcaa agaagtaac tcaaaacatc atgaagtatt acaaccatgg tgtaatactt    360
gtagtatcca atcctgttga cattataact tatatgatcc aaaaatggtc aggcctccct    420
gtgggaaaag ttataggttc aggtaccgta cttgacagta tcagattcag atacttgtta    480
agcgaaaaat tgggcgttga cgtaaagaat gtacacggct acataatagg cgaacacggt    540
gattcacagc ttccgttgtg gagctgcaca catatcgccg gtaaaaatat caacgaatat    600
atcgatgatc cgaaatgcaa tttcacagaa gaagacaaga aaaaaatcgc tgaagatgtt    660
aaaactgcgg gtgcaaccat tatcaagaac aaaggtgcaa catactatgg tattgcagtt    720
tcaatcaaca caatagttga aacactcctt aagaatcaga atacaataag aaccgtagga    780
accgttataa acggcatgta tggaatagaa gatgttgcaa taagccttcc atccatcgta    840
aattccgaag gtgttcagga agttctccaa tttaatctga ctcctgaaga agaagaagct    900
```
ttaagattct cagcggagca ggttaaaaaa gtattgaacg aagttaagaa tttataa    957

<210> SEQ ID NO 18
<211> LENGTH: 318
<212> TYPE: PRT
<213> ORGANISM: Clostridium thermocellum
<220> FEATURE:
<221> NAME/KEY: misc_feature
<222> LOCATION: (1)..(318)
<223> OTHER INFORMATION: malate dehydrogenase

<400> SEQUENCE: 18

Met Glu Met Val Lys Ser Arg Ser Lys Val Ala Ile Ile Gly Ala Gly
1               5                   10                  15

Phe Val Gly Ala Ser Ala Ala Phe Thr Met Ala Leu Arg Gln Thr Ala
                20                  25                  30

Asn Glu Leu Val Leu Ile Asp Val Phe Lys Glu Lys Ala Ile Gly Glu
            35                  40                  45

Ala Met Asp Ile Asn His Gly Leu Pro Phe Met Gly Gln Met Ser Leu
        50                  55                  60

Tyr Ala Gly Asp Tyr Ser Asp Val Lys Asp Cys Asp Val Ile Val Val
65                  70                  75                  80

Thr Ala Gly Ala Asn Arg Lys Pro Gly Glu Thr Arg Leu Asp Leu Ala
                85                  90                  95

Lys Lys Asn Val Met Ile Ala Lys Glu Val Thr Gln Asn Ile Met Lys
            100                 105                 110

Tyr Tyr Asn His Gly Val Ile Leu Val Val Ser Asn Pro Val Asp Ile
        115                 120                 125

Ile Thr Tyr Met Ile Gln Lys Trp Ser Gly Leu Pro Val Gly Lys Val
130                 135                 140

Ile Gly Ser Gly Thr Val Leu Asp Ser Ile Arg Phe Arg Tyr Leu Leu
145                 150                 155                 160

Ser Glu Lys Leu Gly Val Asp Val Lys Asn Val His Gly Tyr Ile Ile
                165                 170                 175

Gly Glu His Gly Asp Ser Gln Leu Pro Leu Trp Ser Cys Thr His Ile
            180                 185                 190

Ala Gly Lys Asn Ile Asn Glu Tyr Ile Asp Asp Pro Lys Cys Asn Phe
        195                 200                 205

Thr Glu Glu Asp Lys Lys Ile Ala Glu Asp Val Lys Thr Ala Gly
    210                 215                 220

Ala Thr Ile Ile Lys Asn Lys Gly Ala Thr Tyr Tyr Gly Ile Ala Val
225                 230                 235                 240

Ser Ile Asn Thr Ile Val Glu Thr Leu Leu Lys Asn Gln Asn Thr Ile
                245                 250                 255

Arg Thr Val Gly Thr Val Ile Asn Gly Met Tyr Gly Ile Glu Asp Val
            260                 265                 270

Ala Ile Ser Leu Pro Ser Ile Val Asn Ser Glu Gly Val Gln Glu Val
        275                 280                 285

Leu Gln Phe Asn Leu Thr Pro Glu Glu Glu Ala Leu Arg Phe Ser
    290                 295                 300

Ala Glu Gln Val Lys Lys Val Leu Asn Glu Val Lys Asn Leu
305                 310                 315

<210> SEQ ID NO 19
<211> LENGTH: 2229
<212> TYPE: DNA

<213> ORGANISM: Clostridium thermocellum
<220> FEATURE:
<221> NAME/KEY: misc_feature
<222> LOCATION: (1)..(2229)
<223> OTHER INFORMATION: pyruvate formate lyase

<400> SEQUENCE: 19

```
atggatgcat ggcgcggatt taataaaggc aactggtgcc aggaaattga cgttcgtgat      60
tttataatta gaaattatac tccttatgaa ggcgatgaaa gctttcttgt aggacctacg     120
gatagaacgc ggaaactttg ggagaaggtt tccgaactgt aaagaaaga acgggagaac      180
ggcggggtat tggatgttga tacccataca atttcaacga ttacgtctca taaacctgga     240
tatatagata agaacttga agttattgtc gggcttcaga cggatgagcc tttaaaaaga     300
gccataatgc cgtttggcgg tatacgtatg gtgattaagg gagccgaagc ttatggccac     360
agtgtggacc ctcaggttgt tgaaatattc acaaagtaca gaaagactca taaccaggga    420
gtttatgatg tatatactcc cgaaatgaga aaagccaaaa aagccgggat tattacagga    480
cttcccgacg catacggcag aggaagaata attggcgatt acagaagggt tgcactttat    540
ggcgttgaca ggctgattgc tgaaaaagag aaagaaatgg caagtcttga aagagattac    600
attgactatg agactgttcg agacagagaa gaaataagcg agcagattaa atctttaaaa    660
caacttaaag aaatggcttt aagttacggt tttgacatat cttgtcctgc aaaggatgcc    720
agagaagcct ttcaatggtt gtattttgca tatcttgcag cagtcaagga acagaacggc    780
gcggcaatga gtattggaag aatttcgact ttccttgaca tatacattga aagggatctc    840
aaagaaggaa aactcacgga ggagttggct caggaactgg ttgaccagct ggttataaag    900
ctgagaattg tgagattttt gagaactcct gagtatgaaa agctcttcag cggagacccc    960
acttgggtaa ccgaaagtat cggaggtatg gcgctggatg aagaacgct ggttacaaaa   1020
tcttcgttca ggtttttgca cactcttttc aacctgggac atgcaccgga gcccaacctt    1080
acagtacttt ggtccgtcaa tcttcccgaa ggctttaaaa agtactgtgc aaaggtatca    1140
attcattcaa gctccatcca gtatgaaagc gacgacataa tgaggaaaca ctggggagac    1200
gattatggaa tagcatgctg tgtttctgct atgagaattg gaaaacagat gcagttcttc    1260
ggtgcaagat gcaatcttgc aaaagctctt ctttacgcta ttaacggcgg aaaggatgaa    1320
atgacgggag aacagattgc tccgatgttt gcaccggtgg aaaccgaata ccttgattac    1380
gaggacgtaa tgaagaggtt tgacatggtg cttgactggg tggcaaggct ttatatgaac    1440
accctcaata taattcacta catgcatgac aaatatgcct atgaggcgct gcagatggca    1500
ttgcatgaca agacgtgtt caggacgatg gcatgcggaa tagccggttt gtctgtggtg    1560
gcagactccc ttagcgcgat aaaatatgca aaggttaaac cgatacgcaa tgaaaacaac    1620
ctcgttgttg actacgaagt tgagggtgat tatcctaaat tcggaaataa cgacgaacgt    1680
gttgatgaaa ttgcagtgca agtagtaaaa atgttcatga caagcttag aaagcaaagg    1740
gcttacagaa gtgccactcc gacccttcc atacttacca taacttcaaa cgtggtatat    1800
ggaaagaaaa ccggaaacac tcctgacggc agaaaagctg agaacccttt ggcgccggga    1860
gcaaatccga tgcatggaag ggatataaac ggagcattgg ctgtactgaa cagtattgcg    1920
aagcttccct atgaatatgc ccaggacggc atttcatata cttctccat aattccaaaa    1980
gctctgggaa gagacgagga aaccagaata aacaatctta atcaatgct tgacggatat    2040
ttcaagcagg gcggccacca cataaatgta atgtgtttg aaaagagac actgttagat    2100
gccatggaac atccggaaaa atatccacaa cttaccataa gagtgtccgg gtatgcagtg    2160
```

```
aactttataa agcttacacg ggagcaacag ctggatgtta ttaacagaac gattcacgga    2220
aagatttaa                                                              2229
```

<210> SEQ ID NO 20
<211> LENGTH: 742
<212> TYPE: PRT
<213> ORGANISM: Clostridium thermocellum
<220> FEATURE:
<221> NAME/KEY: misc_feature
<222> LOCATION: (1)..(742)
<223> OTHER INFORMATION: pyruvate formate lyase

<400> SEQUENCE: 20

```
Met Asp Ala Trp Arg Gly Phe Asn Lys Gly Asn Trp Cys Gln Glu Ile
1               5                   10                  15

Asp Val Arg Asp Phe Ile Ile Arg Asn Tyr Thr Pro Tyr Glu Gly Asp
            20                  25                  30

Glu Ser Phe Leu Val Gly Pro Thr Asp Arg Thr Arg Lys Leu Trp Glu
        35                  40                  45

Lys Val Ser Glu Leu Leu Lys Lys Glu Arg Glu Asn Gly Gly Val Leu
    50                  55                  60

Asp Val Asp Thr His Thr Ile Ser Thr Ile Thr Ser His Lys Pro Gly
65                  70                  75                  80

Tyr Ile Asp Lys Glu Leu Glu Val Ile Val Gly Leu Gln Thr Asp Glu
                85                  90                  95

Pro Leu Lys Arg Ala Ile Met Pro Phe Gly Gly Ile Arg Met Val Ile
            100                 105                 110

Lys Gly Ala Glu Ala Tyr Gly His Ser Val Asp Pro Gln Val Val Glu
        115                 120                 125

Ile Phe Thr Lys Tyr Arg Lys Thr His Asn Gln Gly Val Tyr Asp Val
    130                 135                 140

Tyr Thr Pro Glu Met Arg Lys Ala Lys Lys Ala Gly Ile Ile Thr Gly
145                 150                 155                 160

Leu Pro Asp Ala Tyr Gly Arg Gly Arg Ile Ile Gly Asp Tyr Arg Arg
                165                 170                 175

Val Ala Leu Tyr Gly Val Asp Arg Leu Ile Ala Glu Lys Glu Lys Glu
            180                 185                 190

Met Ala Ser Leu Glu Arg Asp Tyr Ile Asp Tyr Glu Thr Val Arg Asp
        195                 200                 205

Arg Glu Glu Ile Ser Glu Gln Ile Lys Ser Leu Lys Gln Leu Lys Glu
    210                 215                 220

Met Ala Leu Ser Tyr Gly Phe Asp Ile Ser Cys Pro Ala Lys Asp Ala
225                 230                 235                 240

Arg Glu Ala Phe Gln Trp Leu Tyr Phe Ala Tyr Leu Ala Ala Val Lys
                245                 250                 255

Glu Gln Asn Gly Ala Ala Met Ser Ile Gly Arg Ile Ser Thr Phe Leu
            260                 265                 270

Asp Ile Tyr Ile Glu Arg Asp Leu Lys Glu Gly Lys Leu Thr Glu Glu
        275                 280                 285

Leu Ala Gln Glu Leu Val Asp Gln Leu Val Ile Lys Leu Arg Ile Val
    290                 295                 300

Arg Phe Leu Arg Thr Pro Glu Tyr Glu Lys Leu Phe Ser Gly Asp Pro
305                 310                 315                 320

Thr Trp Val Thr Glu Ser Ile Gly Gly Met Ala Leu Asp Gly Arg Thr
                325                 330                 335
```

-continued

Leu Val Thr Lys Ser Ser Phe Arg Phe Leu His Thr Leu Phe Asn Leu
          340             345             350

Gly His Ala Pro Glu Pro Asn Leu Thr Val Leu Trp Ser Val Asn Leu
          355             360             365

Pro Glu Gly Phe Lys Lys Tyr Cys Ala Lys Val Ser Ile His Ser Ser
370             375             380

Ser Ile Gln Tyr Glu Ser Asp Asp Ile Met Arg Lys His Trp Gly Asp
385             390             395             400

Asp Tyr Gly Ile Ala Cys Cys Val Ser Ala Met Arg Ile Gly Lys Gln
              405             410             415

Met Gln Phe Phe Gly Ala Arg Cys Asn Leu Ala Lys Ala Leu Leu Tyr
          420             425             430

Ala Ile Asn Gly Gly Lys Asp Glu Met Thr Gly Glu Gln Ile Ala Pro
          435             440             445

Met Phe Ala Pro Val Glu Thr Glu Tyr Leu Asp Tyr Glu Asp Val Met
          450             455             460

Lys Arg Phe Asp Met Val Leu Asp Trp Val Ala Arg Leu Tyr Met Asn
465             470             475             480

Thr Leu Asn Ile Ile His Tyr Met His Asp Lys Tyr Ala Tyr Glu Ala
              485             490             495

Leu Gln Met Ala Leu His Asp Lys Asp Val Phe Arg Thr Met Ala Cys
          500             505             510

Gly Ile Ala Gly Leu Ser Val Val Ala Asp Ser Leu Ser Ala Ile Lys
          515             520             525

Tyr Ala Lys Val Lys Pro Ile Arg Asn Glu Asn Leu Val Val Asp
          530             535             540

Tyr Glu Val Glu Gly Asp Tyr Pro Lys Phe Gly Asn Asn Asp Glu Arg
545             550             555             560

Val Asp Glu Ile Ala Val Gln Val Val Lys Met Phe Met Asn Lys Leu
              565             570             575

Arg Lys Gln Arg Ala Tyr Arg Ser Ala Thr Pro Thr Leu Ser Ile Leu
          580             585             590

Thr Ile Thr Ser Asn Val Val Tyr Gly Lys Lys Thr Gly Asn Thr Pro
          595             600             605

Asp Gly Arg Lys Ala Gly Glu Pro Leu Ala Pro Gly Ala Asn Pro Met
610             615             620

His Gly Arg Asp Ile Asn Gly Ala Leu Ala Val Leu Asn Ser Ile Ala
625             630             635             640

Lys Leu Pro Tyr Glu Tyr Ala Gln Asp Gly Ile Ser Tyr Thr Phe Ser
          645             650             655

Ile Ile Pro Lys Ala Leu Gly Arg Asp Glu Glu Thr Arg Ile Asn Asn
          660             665             670

Leu Lys Ser Met Leu Asp Gly Tyr Phe Lys Gln Gly His His Ile
          675             680             685

Asn Val Asn Val Phe Glu Lys Glu Thr Leu Leu Asp Ala Met Glu His
          690             695             700

Pro Glu Lys Tyr Pro Gln Leu Thr Ile Arg Val Ser Gly Tyr Ala Val
705             710             715             720

Asn Phe Ile Lys Leu Thr Arg Glu Gln Gln Leu Asp Val Ile Asn Arg
              725             730             735

Thr Ile His Gly Lys Ile
          740

<210> SEQ ID NO 21
<211> LENGTH: 717
<212> TYPE: DNA
<213> ORGANISM: Clostridium thermocellum
<220> FEATURE:
<221> NAME/KEY: misc_feature
<222> LOCATION: (1)..(717)
<223> OTHER INFORMATION: pyruvate formate lyase activating enzyme

<400> SEQUENCE: 21

```
atgacattaa agggcaggat acactcattt gaatcttttg ggacactgga cggaccgggt      60
ataagatttg tggttttcat gcagggctgt cccttgcgtt gtatatattg ccacaacagg     120
gatacctggg atgttaatgc ggggagtgag tacactcccc ggcaagtaat tgatgaaatg     180
atgaaataca tagactatat aaaggtctcc ggaggcggaa taactgttac cggcggggag     240
cctgttctcc aggccgattt tgtggccgag gtgttcagac ttgcaaaaga gcagggagtg     300
catacggcgc tggataccaa tggatttgct gacatagaga aggttgaaag gcttataaaa     360
tacaccgatc ttgtattgct ggatataaag catgcccggg aggataaaca taagataatt     420
accggtgtgt ccaacgaaaa aatcaagcgt tttgcgctgt atctttcgga ccagggagtg     480
cctatctgga taagatatgt ccttgtcccc ggatataccg acgatgaaga tgaccttaaa     540
atggcggctg atttcataaa aaagcttaaa acggtggaaa aaatcgaagt tcttccttat     600
cacaacatgg gagcatacaa atgggaaaaa cttggtcaga aatacatgct tgaaggagta     660
aaggggccga gtgcgcaaga ggtggaaaaa gcaaagagga ttctgtcagg caaataa       717
```

<210> SEQ ID NO 22
<211> LENGTH: 238
<212> TYPE: PRT
<213> ORGANISM: Clostridium thermocellum
<220> FEATURE:
<221> NAME/KEY: misc_feature
<222> LOCATION: (1)..(238)
<223> OTHER INFORMATION: pyruvate formate lyase activating enzyme

<400> SEQUENCE: 22

Met Thr Leu Lys Gly Arg Ile His Ser Phe Glu Ser Phe Gly Thr Leu
1               5                   10                  15

Asp Gly Pro Gly Ile Arg Phe Val Val Phe Met Gln Gly Cys Pro Leu
            20                  25                  30

Arg Cys Ile Tyr Cys His Asn Arg Asp Thr Trp Asp Val Asn Ala Gly
        35                  40                  45

Ser Glu Tyr Thr Pro Arg Gln Val Ile Asp Glu Met Met Lys Tyr Ile
    50                  55                  60

Asp Tyr Ile Lys Val Ser Gly Gly Ile Thr Val Thr Gly Gly Glu
65                  70                  75                  80

Pro Val Leu Gln Ala Asp Phe Val Ala Glu Val Phe Arg Leu Ala Lys
                85                  90                  95

Glu Gln Gly Val His Thr Ala Leu Asp Thr Asn Gly Phe Ala Asp Ile
            100                 105                 110

Glu Lys Val Glu Arg Leu Ile Lys Tyr Thr Asp Leu Val Leu Leu Asp
        115                 120                 125

Ile Lys His Ala Arg Glu Asp Lys His Lys Ile Ile Thr Gly Val Ser
    130                 135                 140

Asn Glu Lys Ile Lys Arg Phe Ala Leu Tyr Leu Ser Asp Gln Gly Val
145                 150                 155                 160

Pro Ile Trp Ile Arg Tyr Val Leu Val Pro Gly Tyr Thr Asp Asp Glu

```
                      165                 170                 175
Asp Asp Leu Lys Met Ala Ala Asp Phe Ile Lys Lys Leu Lys Thr Val
            180                 185                 190

Glu Lys Ile Glu Val Leu Pro Tyr His Asn Met Gly Ala Tyr Lys Trp
        195                 200                 205

Glu Lys Leu Gly Gln Lys Tyr Met Leu Glu Gly Val Lys Gly Pro Ser
    210                 215                 220

Ala Gln Glu Val Glu Lys Ala Lys Arg Ile Leu Ser Gly Lys
225                 230                 235
```

<210> SEQ ID NO 23
<211> LENGTH: 579
<212> TYPE: DNA
<213> ORGANISM: Clostridium thermocellum
<220> FEATURE:
<221> NAME/KEY: misc_feature
<222> LOCATION: (1)..(579)
<223> OTHER INFORMATION: pyruvate ferredoxin oxidoreductase subunit

<400> SEQUENCE: 23

```
atgggcaagg ttgttgaaat cagatggcac gggcgcggcg gacaaggtgc aagactgcg      60 tcgcttctgc tggctgatgc tgcattcaat accggaaaat acatccaggg ttttccggaa    120
tacggtcctg aaagaatggg cgcgccaatt acagcttaca acaggataag tgatgagaaa    180
cttaccattc acagcaatat ttatgaaccg gattatgttg tggttgtaga tgacactctt    240
ttgacatccg ttgatgttac agcaggtttg aaagaggatg gagctattat cgtcaacact    300
ccaaaaactc ctgacgaaat aagacctctt ttaaaaggct acaagggaaa ggtttgcaca    360
attgacgcaa gaaaaatttc cattgaaact ttgggaaaat acttcccgaa caccccaatg    420
cttggtgctg ttgtaaaggt tagcaagata atggacgaag aagaattcct caaggatatg    480
gttgagtcat tcaagcacaa gtttgcgaac aagcctgaag ttgttgaagg caatatcaag    540
gccctggaga ggtcaatgca ggaggtgaaa ggattatga                            579
```

<210> SEQ ID NO 24
<211> LENGTH: 192
<212> TYPE: PRT
<213> ORGANISM: Clostridium thermocellum
<220> FEATURE:
<221> NAME/KEY: misc_feature
<222> LOCATION: (1)..(192)
<223> OTHER INFORMATION: pyruvate ferredoxin oxidoreductase subunit

<400> SEQUENCE: 24

```
Met Gly Lys Val Val Glu Ile Arg Trp His Gly Arg Gly Gly Gln Gly
1               5                   10                  15

Ala Lys Thr Ala Ser Leu Leu Leu Ala Asp Ala Ala Phe Asn Thr Gly
            20                  25                  30

Lys Tyr Ile Gln Gly Phe Pro Glu Tyr Gly Pro Glu Arg Met Gly Ala
        35                  40                  45

Pro Ile Thr Ala Tyr Asn Arg Ile Ser Asp Glu Lys Leu Thr Ile His
    50                  55                  60

Ser Asn Ile Tyr Glu Pro Asp Tyr Val Val Val Asp Asp Thr Leu
65                  70                  75                  80

Leu Thr Ser Val Asp Val Thr Ala Gly Leu Lys Glu Asp Gly Ala Ile
                85                  90                  95

Ile Val Asn Thr Pro Lys Thr Pro Asp Glu Ile Arg Pro Leu Leu Lys
            100                 105                 110
```

Gly Tyr Lys Gly Lys Val Cys Thr Ile Asp Ala Arg Lys Ile Ser Ile
            115                 120                 125

Glu Thr Leu Gly Lys Tyr Phe Pro Asn Thr Pro Met Leu Gly Ala Val
    130                 135                 140

Val Lys Val Ser Lys Ile Met Asp Glu Glu Phe Leu Lys Asp Met
145                 150                 155                 160

Val Glu Ser Phe Lys His Lys Phe Ala Asn Lys Pro Glu Val Val Glu
                165                 170                 175

Gly Asn Ile Lys Ala Leu Glu Arg Ser Met Gln Glu Val Lys Gly Leu
            180                 185                 190

<210> SEQ ID NO 25
<211> LENGTH: 306
<212> TYPE: DNA
<213> ORGANISM: Clostridium thermocellum
<220> FEATURE:
<221> NAME/KEY: misc_feature
<222> LOCATION: (1)..(306)
<223> OTHER INFORMATION: pyruvate ferredoxin oxidoreductase subunit

<400> SEQUENCE: 25
atgagtaaag aattgagaga tgtaaaacct gatgttacct ggaaagagat aacatccggt       60
ggagtgatag attcccctgg aaacgcacat ctttttaaga ccggtgactg gcgttctatg      120
aagccggtgt ggaatgagga aaaatgcaag cagtgtttgc tttgcaaccc ggtatgtcct      180
gattcatcca taatggtaag tgaagaggga aaaatgacag gtatcgatta tgatcactgc      240
aaaggatgtg gcatttgttc aaaggtttgt cctttcaaag ccatagactt tgtagaggaa      300
gtataa                                                                306

<210> SEQ ID NO 26
<211> LENGTH: 101
<212> TYPE: PRT
<213> ORGANISM: Clostridium thermocellum
<220> FEATURE:
<221> NAME/KEY: misc_feature
<222> LOCATION: (1)..(101)
<223> OTHER INFORMATION: pyruvate ferredoxin oxidoreductase subunit

<400> SEQUENCE: 26

Met Ser Lys Glu Leu Arg Asp Val Lys Pro Asp Val Thr Trp Lys Glu
1               5                   10                  15

Ile Thr Ser Gly Gly Val Ile Asp Ser Pro Gly Asn Ala His Leu Phe
            20                  25                  30

Lys Thr Gly Asp Trp Arg Ser Met Lys Pro Val Trp Asn Glu Glu Lys
        35                  40                  45

Cys Lys Gln Cys Leu Leu Cys Asn Pro Val Cys Pro Asp Ser Ser Ile
    50                  55                  60

Met Val Ser Glu Glu Gly Lys Met Thr Gly Ile Asp Tyr Asp His Cys
65                  70                  75                  80

Lys Gly Cys Gly Ile Cys Ser Lys Val Cys Pro Phe Lys Ala Ile Asp
                85                  90                  95

Phe Val Glu Glu Val
            100

<210> SEQ ID NO 27
<211> LENGTH: 1185
<212> TYPE: DNA
<213> ORGANISM: Clostridium thermocellum
<220> FEATURE:
<221> NAME/KEY: misc_feature
<222> LOCATION: (1)..(1185)
<223> OTHER INFORMATION: pyruvate ferredoxin oxidoreductase subunit

<400> SEQUENCE: 27

```
atgggaataa gagaaaggct tagcggtaat gaggcaacgg cgattgccat gagacaaata     60
aatcctgatg tggttgctgc ttttccgata acaccgtcaa cggaaattcc tcaatatttc    120
tcgtcatatg tcgctgacgg acttgtagat acggaatttg ttgctgtgga atcagagcac    180
agtgcaatgt ctgcatgtat aggtgctcag gctgcaggtg caagagcaat gactgccaca    240
tccgcaaacg gtttggcata tatgtgggag ctttgtata tagcggcaag tatgagactt     300
ccgattgtat tggcggctgt aaacagagca ctttcaggtc ctatcaatat ccacaacgac    360
cacagcgata caatgggagc tagggattcg ggatggatcc agttatacag tgaaaacaac    420
caggaggctt atgacaacat gcttatggct cacaggatag gtgagcatcc tgatgtaatg    480
cttcctgtca tggtctgcca ggacggattt attacttctc acgcaataga aatattgaa    540
ctggtggaag atgagaaagt taaggctttt gtaggagaat acaaaccgac tcattatctt    600
ctcgacaggg aaaatccgat ttctgtgggt cctttggatt tgcagatgca ttatttcgag    660
cacaagagac agcaggcaca ggcaatggaa acgccaaaa aggtaattct tgaagtggcg     720
gaagaattct acaagcttac gggaagaaaa tacggatttt ttgaagaata caaaaccgat    780
gatgccgatg ttgccattgt tgttatgaac tccactgccg gtactgtaaa atatgttatc    840
gacgagtaca gggtaaaagg caaaaagtt ggtttgataa aacctagagt attcagacct     900
ttccctgttg atgaactggc acaggctttg tcaaagttta aggcagtggc cgttatggac    960
aaggctgaca gcttcaatgc agccggagga cctttgttta cagaggtaac aagtgcactc   1020
ttcacaaaag gagtatttgg tcctaaggtt attaactata agtttggatt gggtggaaga   1080
gacgttaaag ttgatgatat tgaagttgtt tgtgagaagc ttctggaaat tgcaagtaca   1140
ggcaaggtag actcagtata caattacctt ggtgttagag agtag               1185
```

<210> SEQ ID NO 28
<211> LENGTH: 394
<212> TYPE: PRT
<213> ORGANISM: Clostridium thermocellum
<220> FEATURE:
<221> NAME/KEY: misc_feature
<222> LOCATION: (1)..(394)
<223> OTHER INFORMATION: pyruvate ferredoxin oxidoreductase subunit

<400> SEQUENCE: 28

```
Met Gly Ile Arg Glu Arg Leu Ser Gly Asn Glu Ala Thr Ala Ile Ala
1               5                   10                  15

Met Arg Gln Ile Asn Pro Asp Val Val Ala Ala Phe Pro Ile Thr Pro
            20                  25                  30

Ser Thr Glu Ile Pro Gln Tyr Phe Ser Ser Tyr Val Ala Asp Gly Leu
        35                  40                  45

Val Asp Thr Glu Phe Val Ala Val Glu Ser Glu His Ser Ala Met Ser
    50                  55                  60

Ala Cys Ile Gly Ala Gln Ala Ala Gly Ala Arg Ala Met Thr Ala Thr
65                  70                  75                  80

Ser Ala Asn Gly Leu Ala Tyr Met Trp Glu Ala Leu Tyr Ile Ala Ala
                85                  90                  95

Ser Met Arg Leu Pro Ile Val Leu Ala Ala Val Asn Arg Ala Leu Ser
            100                 105                 110

Gly Pro Ile Asn Ile His Asn Asp His Ser Asp Thr Met Gly Ala Arg
```

```
            115                 120                 125
Asp Ser Gly Trp Ile Gln Leu Tyr Ser Glu Asn Asn Gln Glu Ala Tyr
    130                 135                 140

Asp Asn Met Leu Met Ala His Arg Ile Gly Glu His Pro Asp Val Met
145                 150                 155                 160

Leu Pro Val Met Val Cys Gln Asp Gly Phe Ile Thr Ser His Ala Ile
                165                 170                 175

Glu Asn Ile Glu Leu Val Glu Asp Glu Lys Val Lys Ala Phe Val Gly
            180                 185                 190

Glu Tyr Lys Pro Thr His Tyr Leu Leu Asp Arg Glu Asn Pro Ile Ser
        195                 200                 205

Val Gly Pro Leu Asp Leu Gln Met His Tyr Phe Glu His Lys Arg Gln
    210                 215                 220

Gln Ala Gln Ala Met Glu Asn Ala Lys Lys Val Ile Leu Glu Val Ala
225                 230                 235                 240

Glu Glu Phe Tyr Lys Leu Thr Gly Arg Lys Tyr Gly Phe Phe Glu Glu
                245                 250                 255

Tyr Lys Thr Asp Asp Ala Asp Val Ala Ile Val Val Met Asn Ser Thr
            260                 265                 270

Ala Gly Thr Val Lys Tyr Val Ile Asp Glu Tyr Arg Val Lys Gly Lys
        275                 280                 285

Lys Val Gly Leu Ile Lys Pro Arg Val Phe Arg Pro Phe Pro Val Asp
    290                 295                 300

Glu Leu Ala Gln Ala Leu Ser Lys Phe Lys Ala Val Ala Val Met Asp
305                 310                 315                 320

Lys Ala Asp Ser Phe Asn Ala Ala Gly Gly Pro Leu Phe Thr Glu Val
                325                 330                 335

Thr Ser Ala Leu Phe Thr Lys Gly Val Phe Gly Pro Lys Val Ile Asn
            340                 345                 350

Tyr Lys Phe Gly Leu Gly Gly Arg Asp Val Lys Val Asp Asp Ile Glu
        355                 360                 365

Val Val Cys Glu Lys Leu Leu Glu Ile Ala Ser Thr Gly Lys Val Asp
    370                 375                 380

Ser Val Tyr Asn Tyr Leu Gly Val Arg Glu
385                 390

<210> SEQ ID NO 29
<211> LENGTH: 546
<212> TYPE: DNA
<213> ORGANISM: Clostridium thermocellum
<220> FEATURE:
<221> NAME/KEY: misc_feature
<222> LOCATION: (1)..(546)
<223> OTHER INFORMATION: pyruvate ferredoxin oxidoreductase subunit

<400> SEQUENCE: 29
atgacagaaa taagatggca tggaagagga ggacagggaa gctttaccgc ttcaaaactt      60
cttggggtgt cagttgcttt atatggcgaa aagtatgccc ttgcctttcc ctcctttggg     120
cctgagcgaa gaggcgcccc tgtcctggct tttaccagga ttgacggtaa gaagatttac     180
gaccgcagcg aaatcagaaa atgtgatttt attgtggttt ggatgaaaac cctttttagt     240
gaaagctttt ttgatgattt gaaggaaaat ggaagaatca ttgtaaattc ggccgacaaa     300
gagttttacg caaatatga ttcaagagg ataactgtgg tggatgcgtc ctctgttgct      360
ctggaaatct taggcaaacc tataacaaat accgccatgc ttggcgccct ggttgcagtg     420
```

```
tcggatattg ttgacttgga agcagtagaa aaaggaatgg cagttttttct gaaagggggag    480 cttcttaaga aaatattga agtggttcaa agaaccttcc ttcaatgcag ggaggcggtg       540
tcatga                                                                546
```

<210> SEQ ID NO 30
<211> LENGTH: 181
<212> TYPE: PRT
<213> ORGANISM: Clostridium thermocellum
<220> FEATURE:
<221> NAME/KEY: misc_feature
<222> LOCATION: (1)..(181)
<223> OTHER INFORMATION: pyruvate ferredoxin oxidoreductase subunit
<400> SEQUENCE: 30

```
Met Thr Glu Ile Arg Trp His Gly Arg Gly Gln Gly Ser Phe Thr
1               5                   10                  15

Ala Ser Lys Leu Leu Gly Val Ser Val Ala Leu Tyr Gly Glu Lys Tyr
            20                  25                  30

Ala Leu Ala Phe Pro Ser Phe Gly Pro Glu Arg Arg Gly Ala Pro Val
        35                  40                      45

Leu Ala Phe Thr Arg Ile Asp Gly Lys Lys Ile Tyr Asp Arg Ser Glu
    50                  55                  60

Ile Arg Lys Cys Asp Phe Ile Val Val Leu Asp Glu Thr Leu Phe Ser
65                  70                  75                  80

Glu Ser Phe Phe Asp Asp Leu Lys Glu Asn Gly Arg Ile Ile Val Asn
                85                  90                  95

Ser Ala Asp Lys Glu Phe Tyr Ala Lys Tyr Asp Ser Lys Arg Ile Thr
            100                 105                 110

Val Val Asp Ala Ser Ser Val Ala Leu Glu Ile Leu Gly Lys Pro Ile
        115                 120                 125

Thr Asn Thr Ala Met Leu Gly Ala Leu Val Ala Val Ser Asp Ile Val
    130                 135                 140

Asp Leu Glu Ala Val Glu Lys Gly Met Ala Val Phe Leu Lys Gly Glu
145                 150                 155                 160

Leu Leu Lys Lys Asn Ile Glu Val Val Gln Arg Thr Phe Leu Gln Cys
                165                 170                 175

Arg Glu Ala Val Ser
            180
```

<210> SEQ ID NO 31
<211> LENGTH: 312
<212> TYPE: DNA
<213> ORGANISM: Clostridium thermocellum
<220> FEATURE:
<221> NAME/KEY: misc_feature
<222> LOCATION: (1)..(312)
<223> OTHER INFORMATION: pyruvate ferredoxin oxidoreductase subunit
<400> SEQUENCE: 31

```
atgaacaggc ccgaacttag agagtatgtt aaaccaaagc atattaaaga ttatcctgtg     60
ggtccctgct atacggcagg gtatcttgta accgaaaatt caggttggag aacggaaaag   120
cccgttgtgg aaaatgccgg tgtatcggt tgcttttact gctatctttg ctgcccggaa    180
ggagtaatat tcaaaaaggg gaaggcagtg gatattgact atgcctttg caaggggtgc    240 ggcatatgtg ccagggtttg ccccaaaaaa gcaataaaaa tggtaagaga ggagaaaaac   300
catgggagat aa                                                       312
```

```
<210> SEQ ID NO 32
<211> LENGTH: 103
<212> TYPE: PRT
<213> ORGANISM: Clostridium thermocellum
<220> FEATURE:
<221> NAME/KEY: misc_feature
<222> LOCATION: (1)..(103)
<223> OTHER INFORMATION: pyruvate ferredoxin oxidoreductase subunit

<400> SEQUENCE: 32

Met Asn Arg Pro Glu Leu Arg Glu Tyr Val Lys Pro Lys His Ile Lys
 1               5                  10                  15

Asp Tyr Pro Val Gly Pro Cys Tyr Thr Ala Gly Tyr Leu Val Thr Glu
             20                  25                  30

Asn Ser Gly Trp Arg Thr Glu Lys Pro Val Val Glu Asn Ala Gly Cys
         35                  40                  45

Ile Gly Cys Phe Tyr Cys Tyr Leu Cys Cys Pro Glu Gly Val Ile Phe
     50                  55                  60

Lys Lys Gly Lys Ala Val Asp Ile Asp Tyr Ala Phe Cys Lys Gly Cys
 65                  70                  75                  80

Gly Ile Cys Ala Arg Val Cys Pro Lys Lys Ala Ile Lys Met Val Arg
                 85                  90                  95

Glu Glu Lys Asn His Gly Arg
            100

<210> SEQ ID NO 33
<211> LENGTH: 1188
<212> TYPE: DNA
<213> ORGANISM: Clostridium thermocellum
<220> FEATURE:
<221> NAME/KEY: misc_feature
<222> LOCATION: (1)..(1188)
<223> OTHER INFORMATION: pyruvate ferredoxin oxidoreductase subunit

<400> SEQUENCE: 33
atgggagata aagcgtttct ttcgggaaat gaagcagtgg cggaaggagt gcggcttgca      60
agtccccatg tgattgccgc ttatccgatt actccccaga cggttgtggt ggagcggttg     120
gcggaaatgg tggaggacgg aaggcttaaa gcggaattcc ttcatgtgga gtccgaacat     180
tcggccctgt ctgcatgcat gggagccgcc agtattgggg caagaacttt tacggcaact     240
tcatcccagg gcttttgta tatggctgaa tgccttcatt atgccagcgg agggagattc      300
cccattgtaa tgatgaatgc caaccgttcc cttgcgctac cgtggagtat atacggcgat     360
cacagggatt ccttgtcgca gctggactgc ggctggatac agatatatgt ggaggacgcc     420
caggaaagcc tggatatggt gattcaggct tataaaatag cggaaaatcc aaaggtgctt     480
acaccggtca tgataaatct cgacggattt gtgcttaccc acacttatga gccggtggat     540
attcctttga agaagaagt ggataagttt ctgccgcctt ttgaaacccc atacaaaatg      600
gatttggaaa atcccaagaa catgggtttt agttcttcgc cttcagacaa cacggagttc     660
aaatacctgc agcacaaggc catattggat gcgaaagagg taataaaaga agtggacagt     720
tccttcaaaa aagctttcgg aagaaactat ggaggtcttg ttgacgcata cttgtgcgag     780
gacgcggagt ttatcatgat aagccttggc agcaccacag gaacgtgcag agcggtggtg     840
gatgagctaa ggcgggaagg atttaaagca ggagtgctga aaatacgttt catgcggccg     900
tttcctgaag aggaaatagt agaaattact aagaatgcaa aggctgtggg agtgatagac     960
agggatatat cttttggata tgagggaacg gtctttacca atgtcaactc cgctctttta    1020
aaggcagggg tggatgtgaa gagcgtaaac tttatagccg ggcttggagg acgggatatt    1080
```

```
tccaaagaaa gcatacggga ggcattccat gatttgaggg aagttgctct gggcacttta    1140
aagaagtggt ttaagttttt gagtctgggg gtatctatag atgagtaa                 1188
```

<210> SEQ ID NO 34
<211> LENGTH: 395
<212> TYPE: PRT
<213> ORGANISM: Clostridium thermocellum
<220> FEATURE:
<221> NAME/KEY: misc_feature
<222> LOCATION: (1)..(395)
<223> OTHER INFORMATION: pyruvate ferredoxin oxidoreductase subunit

<400> SEQUENCE: 34

```
Met Gly Asp Lys Ala Phe Leu Ser Gly Asn Glu Ala Val Ala Glu Gly
1               5                   10                  15

Val Arg Leu Ala Ser Pro His Val Ile Ala Ala Tyr Pro Ile Thr Pro
            20                  25                  30

Gln Thr Val Val Val Glu Arg Leu Ala Glu Met Val Glu Asp Gly Arg
        35                  40                  45

Leu Lys Ala Glu Phe Leu His Val Glu Ser Glu His Ser Ala Leu Ser
    50                  55                  60

Ala Cys Met Gly Ala Ala Ser Ile Gly Ala Arg Thr Phe Thr Ala Thr
65                  70                  75                  80

Ser Ser Gln Gly Leu Leu Tyr Met Ala Glu Cys Leu His Tyr Ala Ser
                85                  90                  95

Gly Gly Arg Phe Pro Ile Val Met Met Asn Ala Asn Arg Ser Leu Ala
            100                 105                 110

Leu Pro Trp Ser Ile Tyr Gly Asp His Arg Asp Ser Leu Ser Gln Leu
        115                 120                 125

Asp Cys Gly Trp Ile Gln Ile Tyr Val Glu Asp Ala Gln Glu Ser Leu
    130                 135                 140

Asp Met Val Ile Gln Ala Tyr Lys Ile Ala Glu Asn Pro Lys Val Leu
145                 150                 155                 160

Thr Pro Val Met Ile Asn Leu Asp Gly Phe Val Leu Thr His Thr Tyr
                165                 170                 175

Glu Pro Val Asp Ile Pro Leu Lys Glu Val Asp Lys Phe Leu Pro
            180                 185                 190

Pro Phe Glu Thr Pro Tyr Lys Met Asp Leu Glu Asn Pro Lys Asn Met
        195                 200                 205

Gly Phe Ser Ser Pro Ser Asp Asn Thr Glu Phe Lys Tyr Leu Gln
    210                 215                 220

His Lys Ala Ile Leu Asp Ala Lys Glu Val Ile Lys Glu Val Asp Ser
225                 230                 235                 240

Ser Phe Lys Lys Ala Phe Gly Arg Asn Tyr Gly Gly Leu Val Asp Ala
                245                 250                 255

Tyr Leu Cys Glu Asp Ala Glu Phe Ile Met Ile Ser Leu Gly Ser Thr
            260                 265                 270

Thr Gly Thr Cys Arg Ala Val Val Asp Glu Leu Arg Arg Glu Gly Phe
        275                 280                 285

Lys Ala Gly Val Leu Lys Ile Arg Phe Met Arg Pro Phe Pro Glu Glu
    290                 295                 300

Glu Ile Val Glu Ile Thr Lys Asn Ala Lys Ala Val Gly Val Ile Asp
305                 310                 315                 320

Arg Asp Ile Ser Phe Gly Tyr Glu Gly Thr Val Phe Thr Asn Val Asn
                325                 330                 335
```

```
Ser Ala Leu Leu Lys Ala Gly Val Asp Val Lys Ser Val Asn Phe Ile
            340                 345                 350

Ala Gly Leu Gly Gly Arg Asp Ile Ser Lys Glu Ser Ile Arg Glu Ala
            355                 360                 365

Phe His Asp Leu Arg Glu Val Ala Leu Gly Thr Leu Lys Lys Trp Phe
            370                 375                 380

Lys Phe Leu Ser Leu Gly Val Ser Ile Asp Glu
385                 390                 395
```

<210> SEQ ID NO 35
<211> LENGTH: 906
<212> TYPE: DNA
<213> ORGANISM: Clostridium thermocellum
<220> FEATURE:
<221> NAME/KEY: misc_feature
<222> LOCATION: (1)..(906)
<223> OTHER INFORMATION: pyruvate ferredoxin oxidoreductase subunit

<400> SEQUENCE: 35

| | |
|---|---|
| atgagtaata cgataggaat tgtaaatgcc cgaaatatca ccgacaagga gttttttttac | 60 |
| ggacacaagg catgtgcggg ctgcggcgga agcattgtgg taagacttgt tttaaaggtg | 120 |
| ctgggagaaa ggacgtttac agtaattccg gcaggctgca tgtccgcggt aggttttgtt | 180 |
| taccctcagc tttgttttgc aaccaatgca attatttcaa cctttgcagg aactgcctcc | 240 |
| atgctttcgg gcattgcggc gggagcaaaa gcgttgggc ttaaggacta tcacgttgtg | 300 |
| ggaatcgcag gcgacggcgg gactgcggac ataggtattc aggctttgtc gggagccata | 360 |
| gacagaaggg ataaaattat ctatgtctgc tacgacaatg aagcctacat gaacacggga | 420 |
| atacagaaaa gcggccttac accttatggg gcaaggacta caactactcc ggcgggggaa | 480 |
| aatattcccg ggaccgtgac gcagaagaag aacatgtttg agattgtggc agctcacggt | 540 |
| attgattatg ccgcaactgc aagcataggc tatattcagg attttatgaa caaaattcaa | 600 |
| aaggcttcaa aagtgaacgg gacttcttat atccatgttt ttgccccttg tcccaccggg | 660 |
| tggggaattc cttccgacag tgccgttgac atagccaaag aagcggtgga ttgcggcctt | 720 |
| tggtatcttg ctgagtatga gaataatgag tttactttaa ataaaaaccc taagaatttt | 780 |
| acgccggtgg aggaatacct gaaaaaacag tcccggttta acatctcaa aaagaggac | 840 |
| atagaccgga taattgaagc cagggataaa agtggaaac tgatacgcag tagatggaac | 900 |
| tgctga | 906 |

<210> SEQ ID NO 36
<211> LENGTH: 301
<212> TYPE: PRT
<213> ORGANISM: Clostridium thermocellum
<220> FEATURE:
<221> NAME/KEY: misc_feature
<222> LOCATION: (1)..(301)
<223> OTHER INFORMATION: pyruvate ferredoxin oxidoreductase subunit

<400> SEQUENCE: 36

```
Met Ser Asn Thr Ile Gly Ile Val Asn Ala Arg Asn Ile Thr Asp Lys
1               5                   10                  15

Glu Phe Phe Tyr Gly His Lys Ala Cys Ala Gly Cys Gly Gly Ser Ile
            20                  25                  30

Val Val Arg Leu Val Leu Lys Val Leu Gly Glu Arg Thr Phe Thr Val
            35                  40                  45

Ile Pro Ala Gly Cys Met Ser Ala Val Gly Phe Val Tyr Pro Gln Leu
```

```
            50                  55                  60
Cys Phe Ala Thr Asn Ala Ile Ile Ser Thr Phe Ala Gly Thr Ala Ser
 65                  70                  75                  80

Met Leu Ser Gly Ile Ala Ala Gly Ala Lys Ala Leu Gly Leu Lys Asp
                 85                  90                  95

Tyr His Val Val Gly Ile Ala Gly Asp Gly Gly Thr Ala Asp Ile Gly
                100                 105                 110

Ile Gln Ala Leu Ser Gly Ala Ile Asp Arg Arg Asp Lys Ile Ile Tyr
            115                 120                 125

Val Cys Tyr Asp Asn Glu Ala Tyr Met Asn Thr Gly Ile Gln Lys Ser
        130                 135                 140

Gly Leu Thr Pro Tyr Gly Ala Arg Thr Thr Thr Pro Ala Gly Glu
145                 150                 155                 160

Asn Ile Pro Gly Thr Val Thr Gln Lys Lys Asn Met Phe Glu Ile Val
                165                 170                 175

Ala Ala His Gly Ile Asp Tyr Ala Ala Thr Ala Ser Ile Gly Tyr Ile
            180                 185                 190

Gln Asp Phe Met Asn Lys Ile Gln Lys Ala Ser Lys Val Asn Gly Thr
        195                 200                 205

Ser Tyr Ile His Val Phe Ala Pro Cys Pro Thr Gly Trp Gly Ile Pro
210                 215                 220

Ser Asp Ser Ala Val Asp Ile Ala Lys Glu Ala Val Asp Cys Gly Leu
225                 230                 235                 240

Trp Tyr Leu Ala Glu Tyr Glu Asn Asn Glu Phe Thr Leu Asn Lys Asn
                245                 250                 255

Pro Lys Glu Phe Thr Pro Val Glu Glu Tyr Leu Lys Lys Gln Ser Arg
            260                 265                 270

Phe Lys His Leu Lys Lys Glu Asp Ile Asp Arg Ile Ile Glu Ala Arg
        275                 280                 285

Asp Lys Lys Trp Lys Leu Ile Arg Ser Arg Trp Asn Cys
    290                 295                 300

<210> SEQ ID NO 37
<211> LENGTH: 3528
<212> TYPE: DNA
<213> ORGANISM: Clostridium thermocellum
<220> FEATURE:
<221> NAME/KEY: misc_feature
<222> LOCATION: (1)..(3528)
<223> OTHER INFORMATION: pyruvate ferredoxin oxidoreductase

<400> SEQUENCE: 37
gtgcagaaat tgaaacaat ggatggaaat caggcggctg cgtatgcatc ttacgctttt    60
acggatgttg caacaatata tccgataacg ccgtcatcgc ccatggcgga aactgtggat   120
gaatgggcag cccatggaaa gaaaaacatt tcggacagc cggtcagagt tgtgcagatg   180
cagtccgagg caggtgccgc cggtgcaatg acggttctc ttgcggcagg ggcattgacg   240
accacttata ctgcttccca ggggcttttg ctgatgatcc cgaacctgta caaaatggcg   300
ggagagcttt tgcccggagt attgcatgtt cggcgagag caattgcaac ccatgctttg   360
tccatatttg cgaccacca ggatgtaatg gcttgtcgtc agaccggagt tgcactcctt   420
gcatcatcca atgttcagga agcggcagac ttgggatatg ttgcgcatct ttcggccatt   480
aaatcccggg ttccgtttat ccatttcttt gacggtttca gaacttccca tgaatatcag   540
aagattggac tgattgaata cgatgaactt gcaaagcttg tcgaccataa tgcaataaaa   600
```

```
gaattcaggg acagggcttt aaatcctgaa catcctgttg ccagaggaac ggcgcaaaat    660
ccggatattt atttccaggg aagagaagta cagaataaat tctatgacaa cgttcccgat    720
attgttgcag gctatatgca ggaaataaaa aggattacag gccgcgaata ccgcccgttt    780
gattattacg gggcaaaaga tgcggaatat gtgattgtgg caatgggttc cgtttgcgat    840
accattgatg aaaccattga ctaccttatg gcgaagggag aaaaggtagg ttctgtaaga    900
gtacaccttt acaggccttt ctccgaaaag tacttctttg acgtaattcc aaaaacggtg    960
aagaaaattg cagtgcttga caggactaaa gaacccggag caccgggaga gcctttgtac   1020
cttgatgttt caaaaatgta tctgtcaaaa gaaaacaggc cggttatcgt aggcggaaga   1080
tatggactcg gttcgaagga taccagaccg tcccaaatca tatcagtatt tgagaatttg   1140
aagcaggatg agccgaaaaa caactttaca attggaattg tcgatgatgt gaccaatttg   1200
tctcttccgg aaggggacat aattgagacc acacctcagg ggacaataag ctgcaaattc   1260
tggggcttgg gttccgacgg tacggttgga gcaaacaagt ctgcgataaa gataatagga   1320
gacaatacag acctgtatgt acaaggttat ttctcctatg acagtaaaaa gtcaggtgga   1380
actaccattt cccacttaag attcggtccg aagcctctgc gttccccata tcttgtgtat   1440
aacgctgatt atatcgcctg ccacaacaag tccttcatat acaattatga tattttaaaa   1500
gggcttaaaa agggaggtac tttcgtactt aactgtccgt ggagcgaaga ggagctggac   1560
aaacatcttc ccgcgtcaat gaagagatat attgcaaaca acgacatcaa gttttatata   1620
atagatgctt taaaaattgc ttccgacatt ggacttggca acagaatcaa catggttatg   1680
caatcggcgt ttttcaaact ggcaaatata atccctattg aggatgccgt aaaatatctt   1740
aaagattcaa ttgaaaaaac ttacggcaaa aaaggccaca agatagttga gatgaacaat   1800
gccgctgttg acaagggaca ggaagcatta ataaaggtga atgtgcctga gtcatggaaa   1860
aatgctgttg atgaggaagt gccggttaag aaggaagaac cggagtttgt gaaaaagatt   1920
caaagagtaa tggccagaaa tgaaggcgat gaactgcctg taagcgcatt tttgggaatg   1980
gaggacggca cacatccgtt gggtaccacg gcttatgaaa agcgtggaat tgctccaatg   2040
atccccgaat ggcagattga caaatgtatc cagtgcggac agtgctcctt tgtatgtcct   2100
cacagtacaa tccggttgtt cttgctcaat gatgaagagc taagccgggc accggaaacc   2160
tttacaacca aaaaagctat cggaaaagga tttgaaaact tgcatttccg cgtacaagtt   2220
tctccccttg actgtaccgg atgtggtaat tgtgccgatg tttgtcctac aaaggaaaag   2280
gcattgatca tgaagcctgc ggaagagcaa atagaaaaac aggccgacaa ctgggagttt   2340
gcgatgactg tcacccagaa ggacaatttg ttggaccgca atactttgaa aggaagccag   2400
cttgtaaggc cgcttttgga gtttaacgga gcttgtccgg gatgcggtga gacaccgtat   2460
gtaagacttc ttacccagct tttcggcgag agaatgatga ttgccaacgc aaccggatgt   2520
tcatccatat ggggagcaag ttctccatcc atagcttata ccaccaatgc ggagggcaaa   2580
ggaccggcat gggcaaactc tctgtttgag gataatgcgg agttcggctt tggaatgtat   2640
ttggcggtca agcagataag ggagagactt gccgacctta tgcaaatggc tgtaaattcg   2700
gatattgatg aaaaggttaa aaatgccttc agagaatggc tggacaacaa agatgaggct   2760
gaaggttcaa agacagctac aaagcatata tttgaggcgt tgaaagacta tgattacaaa   2820
ggaaaccgca taattgagga gataatggaa aagaaggatt atctcatcaa gaagtccatc   2880
tggatgatag gtggagacgg atgggcttat gacatcggct atggaggact ggatcaggtt   2940 cttttcctccg gcgaggatgt gaatatactt gtattggata cggaagttta ctccaatacc   3000
```

-continued

```
ggcggtcagt cttcaaaagc aactccgaca gcggctgttg caaagtttgc ggctgcaggt    3060
aagagggtaa ggaaaaaaga tctgggactt atggctatga gttatggtta tgtgtatgtg    3120
gctcagatag ccatgggcgc aaatatgaat cagaccataa agccatggt ggaggcggaa     3180 agctacaaag gaccgtcact tataattgcg tattcgccat gtataagcca tggtatcaaa    3240
acgggtatgg gcacgagcat atttgaagaa aagcgcgctg ttgaagctgg ttactggcat    3300
ttgtacagat acaacccgat gcttaaagag caaggcaaga tccgtttat tctggagtcg     3360 aaagaaccga ccactcctta caaggagttc ctcaagggag aaatcagata ttcacagctt    3420
gcgaatgtat tcccggatgt ggcgggagaa atgtttgacg ctgcggaaag ggatgcaaga    3480
gaacgttatg agacttacaa gagactggca gaacagaaat attcgtaa                 3528
```

<210> SEQ ID NO 38
<211> LENGTH: 1175
<212> TYPE: PRT
<213> ORGANISM: Clostridium thermocellum
<220> FEATURE:
<221> NAME/KEY: misc_feature
<222> LOCATION: (1)..(1175)
<223> OTHER INFORMATION: pyruvate ferredoxin oxidoreductase

<400> SEQUENCE: 38

```
Val Gln Lys Phe Glu Thr Met Asp Gly Asn Gln Ala Ala Ala Tyr Ala
1               5                   10                  15

Ser Tyr Ala Phe Thr Asp Val Ala Thr Ile Tyr Pro Ile Thr Pro Ser
            20                  25                  30

Ser Pro Met Ala Glu Thr Val Asp Glu Trp Ala Ala His Gly Lys Lys
        35                  40                  45

Asn Ile Phe Gly Gln Pro Val Arg Val Val Gln Met Gln Ser Glu Ala
    50                  55                  60

Gly Ala Ala Gly Ala Met His Gly Ser Leu Ala Ala Gly Ala Leu Thr
65                  70                  75                  80

Thr Thr Tyr Thr Ala Ser Gln Gly Leu Leu Leu Met Ile Pro Asn Leu
                85                  90                  95

Tyr Lys Met Ala Gly Glu Leu Leu Pro Gly Val Leu His Val Ser Ala
            100                 105                 110

Arg Ala Ile Ala Thr His Ala Leu Ser Ile Phe Gly Asp His Gln Asp
        115                 120                 125

Val Met Ala Cys Arg Gln Thr Gly Val Ala Leu Leu Ala Ser Ser Asn
    130                 135                 140

Val Gln Glu Ala Ala Asp Leu Gly Tyr Val Ala His Leu Ser Ala Ile
145                 150                 155                 160

Lys Ser Arg Val Pro Phe Ile His Phe Phe Asp Gly Phe Arg Thr Ser
                165                 170                 175

His Glu Tyr Gln Lys Ile Gly Leu Ile Glu Tyr Asp Glu Leu Ala Lys
            180                 185                 190

Leu Val Asp His Asn Ala Ile Lys Glu Phe Arg Asp Arg Ala Leu Asn
        195                 200                 205

Pro Glu His Pro Val Ala Arg Gly Thr Ala Gln Asn Pro Asp Ile Tyr
    210                 215                 220

Phe Gln Gly Arg Glu Val Gln Asn Lys Phe Tyr Asp Asn Val Pro Asp
225                 230                 235                 240

Ile Val Ala Gly Tyr Met Gln Glu Ile Lys Arg Ile Thr Gly Arg Glu
                245                 250                 255
```

-continued

```
Tyr Arg Pro Phe Asp Tyr Gly Ala Lys Asp Ala Glu Tyr Val Ile
            260                 265                 270

Val Ala Met Gly Ser Val Cys Asp Thr Ile Asp Glu Thr Ile Asp Tyr
        275                 280                 285

Leu Met Ala Lys Gly Glu Lys Val Gly Ser Val Arg Val His Leu Tyr
        290                 295                 300

Arg Pro Phe Ser Glu Lys Tyr Phe Phe Asp Val Ile Pro Lys Thr Val
305                 310                 315                 320

Lys Lys Ile Ala Val Leu Asp Arg Thr Lys Glu Pro Gly Ala Pro Gly
                325                 330                 335

Glu Pro Leu Tyr Leu Asp Val Ser Lys Met Tyr Leu Ser Lys Glu Asn
            340                 345                 350

Arg Pro Val Ile Val Gly Gly Arg Tyr Gly Leu Gly Ser Lys Asp Thr
            355                 360                 365

Arg Pro Ser Gln Ile Ile Ser Val Phe Glu Asn Leu Lys Gln Asp Glu
        370                 375                 380

Pro Lys Asn Asn Phe Thr Ile Gly Ile Val Asp Asp Val Thr Asn Leu
385                 390                 395                 400

Ser Leu Pro Glu Gly Asp Ile Ile Glu Thr Thr Pro Gln Gly Thr Ile
                405                 410                 415

Ser Cys Lys Phe Trp Gly Leu Gly Ser Asp Gly Thr Val Gly Ala Asn
            420                 425                 430

Lys Ser Ala Ile Lys Ile Ile Gly Asp Asn Thr Asp Leu Tyr Val Gln
        435                 440                 445

Gly Tyr Phe Ser Tyr Asp Ser Lys Lys Ser Gly Thr Thr Ile Ser
        450                 455                 460

His Leu Arg Phe Gly Pro Lys Pro Leu Arg Ser Pro Tyr Leu Val Tyr
465                 470                 475                 480

Asn Ala Asp Tyr Ile Ala Cys His Asn Lys Ser Phe Ile Tyr Asn Tyr
                485                 490                 495

Asp Ile Leu Lys Gly Leu Lys Lys Gly Gly Thr Phe Val Leu Asn Cys
            500                 505                 510

Pro Trp Ser Glu Glu Glu Leu Asp Lys His Leu Pro Ala Ser Met Lys
            515                 520                 525

Arg Tyr Ile Ala Asn Asn Asp Ile Lys Phe Tyr Ile Ile Asp Ala Leu
530                 535                 540

Lys Ile Ala Ser Asp Ile Gly Leu Gly Asn Arg Ile Asn Met Val Met
545                 550                 555                 560

Gln Ser Ala Phe Phe Lys Leu Ala Asn Ile Ile Pro Ile Glu Asp Ala
                565                 570                 575

Val Lys Tyr Leu Lys Asp Ser Ile Glu Lys Thr Tyr Gly Lys Lys Gly
            580                 585                 590

His Lys Ile Val Glu Met Asn Asn Ala Ala Val Asp Lys Gly Gln Glu
        595                 600                 605

Ala Leu Ile Lys Val Asn Val Pro Glu Ser Trp Lys Asn Ala Val Asp
        610                 615                 620

Glu Glu Val Pro Val Lys Lys Glu Pro Glu Phe Val Lys Lys Ile
625                 630                 635                 640

Gln Arg Val Met Ala Arg Asn Glu Gly Asp Glu Leu Pro Val Ser Ala
                645                 650                 655

Phe Leu Gly Met Glu Asp Gly Thr His Pro Leu Gly Thr Thr Ala Tyr
            660                 665                 670

Glu Lys Arg Gly Ile Ala Pro Met Ile Pro Glu Trp Gln Ile Asp Lys
```

-continued

```
              675                 680                 685
Cys Ile Gln Cys Gly Gln Cys Ser Phe Val Cys Pro His Ser Thr Ile
              690                 695                 700
Arg Leu Phe Leu Leu Asn Asp Glu Glu Leu Ser Arg Ala Pro Glu Thr
705                 710                 715                 720
Phe Thr Thr Lys Lys Ala Ile Gly Lys Gly Phe Glu Asn Leu His Phe
                  725                 730                 735
Arg Val Gln Val Ser Pro Leu Asp Cys Thr Gly Cys Gly Asn Cys Ala
              740                 745                 750
Asp Val Cys Pro Thr Lys Glu Lys Ala Leu Ile Met Lys Pro Ala Glu
              755                 760                 765
Glu Gln Ile Glu Lys Gln Ala Asp Asn Trp Glu Phe Ala Met Thr Val
              770                 775                 780
Thr Gln Lys Asp Asn Leu Leu Asp Arg Asn Thr Leu Lys Gly Ser Gln
785                 790                 795                 800
Leu Val Arg Pro Leu Leu Glu Phe Asn Gly Ala Cys Pro Gly Cys Gly
                  805                 810                 815
Glu Thr Pro Tyr Val Arg Leu Leu Thr Gln Leu Phe Gly Glu Arg Met
              820                 825                 830
Met Ile Ala Asn Ala Thr Gly Cys Ser Ser Ile Trp Gly Ala Ser Ser
              835                 840                 845
Pro Ser Ile Ala Tyr Thr Thr Asn Ala Glu Gly Lys Gly Pro Ala Trp
850                 855                 860
Ala Asn Ser Leu Phe Glu Asp Asn Ala Glu Phe Gly Phe Gly Met Tyr
865                 870                 875                 880
Leu Ala Val Lys Gln Ile Arg Glu Arg Leu Ala Asp Leu Met Gln Met
                  885                 890                 895
Ala Val Asn Ser Asp Ile Asp Glu Lys Val Lys Asn Ala Phe Arg Glu
              900                 905                 910
Trp Leu Asp Asn Lys Asp Glu Ala Glu Gly Ser Lys Thr Ala Thr Lys
              915                 920                 925
His Ile Phe Glu Ala Leu Lys Asp Tyr Asp Tyr Lys Gly Asn Arg Ile
              930                 935                 940
Ile Glu Glu Ile Met Glu Lys Lys Asp Tyr Leu Ile Lys Lys Ser Ile
945                 950                 955                 960
Trp Met Ile Gly Gly Asp Gly Trp Ala Tyr Asp Ile Gly Tyr Gly Gly
                  965                 970                 975
Leu Asp Gln Val Leu Ser Ser Gly Glu Asp Val Asn Ile Leu Val Leu
              980                 985                 990
Asp Thr Glu Val Tyr Ser Asn Thr Gly Gly Gln Ser Ser Lys Ala Thr
              995                 1000                1005
Pro Thr Ala Ala Val Ala Lys Phe Ala Ala Ala Gly Lys Arg Val
              1010                1015                1020
Arg Lys Lys Asp Leu Gly Leu Met Ala Met Ser Tyr Gly Tyr Val
              1025                1030                1035
Tyr Val Ala Gln Ile Ala Met Gly Ala Asn Met Asn Gln Thr Ile
              1040                1045                1050
Lys Ala Met Val Glu Ala Glu Ser Tyr Lys Gly Pro Ser Leu Ile
              1055                1060                1065
Ile Ala Tyr Ser Pro Cys Ile Ser His Gly Ile Lys Thr Gly Met
              1070                1075                1080
Gly Thr Ser Ile Phe Glu Glu Lys Arg Ala Val Glu Ala Gly Tyr
              1085                1090                1095
```

```
Trp His Leu Tyr Arg Tyr Asn Pro Met Leu Lys Glu Gln Gly Lys
    1100            1105            1110

Asn Pro Phe Ile Leu Glu Ser Lys Glu Pro Thr Thr Pro Tyr Lys
    1115            1120            1125

Glu Phe Leu Lys Gly Glu Ile Arg Tyr Ser Gln Leu Ala Asn Val
    1130            1135            1140

Phe Pro Asp Val Ala Gly Glu Met Phe Asp Ala Ala Glu Arg Asp
    1145            1150            1155

Ala Arg Glu Arg Tyr Glu Thr Tyr Lys Arg Leu Ala Glu Gln Lys
    1160            1165            1170

Tyr Ser
    1175

<210> SEQ ID NO 39
<211> LENGTH: 846
<212> TYPE: DNA
<213> ORGANISM: Clostridium thermocellum
<220> FEATURE:
<221> NAME/KEY: misc_feature
<222> LOCATION: (1)..(846)
<223> OTHER INFORMATION: nfnA

<400> SEQUENCE: 39
atgtttaaaa tagttaaaaa gaagattctc aacccacagg ttaagttgat ggaaatatcg      60
gcgccgcacg tagctaaaaa agcagagccg ggacagttca taatcctgag ggtaaatgaa     120
aatggtgaaa gaattcccct cacaatagcc gattttgacc gtgaaaaagg tacggtgaca     180
ataattttc aggaagtggg aaaaaccaca aaactactgg gaactttgga agaaggagac      240
gaattgctgg actttgtcgg acctctgggt aaagcatccc actttgagaa cgtaaaaaaa     300
gcggccgtca ttggaggagg cttgggaacg gcaatagcat atccccaggc caaaaaactt     360
cactccatgg gtgttgaagt ccatacgata gcgggtttca gaaacaaaga cctgataatt     420
cttgaagatg aaatgagagc cgtaagcagc aaactttta taaccaccga tgacggttcc     480
aacggcaata aaggtttcgt aagcgacgta ttaaagaaac ttattgaaga aggaaacaaa     540
tatgatttgg ttgttgccat ggggccgcta attatgatga agttatcag cgagctcaca      600
agaccctacg gcattaaaac cattgtaagc atgaatccgg ttatgattga cggtaccggc     660
atgtgcggag gctgcagggt taccgttggc ggtgaaatca gttcgcatg tgtggacgga      720
cctgattttg acgggcatct ggttgatttt gacgaagcaa tgagaaggca ggcaatgtat     780
aaaaaagaag aatccttggc tttggaaaaa cacaattgca aattgggggt ggagaaaaat     840
gcctaa                                                                846

<210> SEQ ID NO 40
<211> LENGTH: 281
<212> TYPE: PRT
<213> ORGANISM: Clostridium thermocellum
<220> FEATURE:
<221> NAME/KEY: misc_feature
<222> LOCATION: (1)..(281)
<223> OTHER INFORMATION: nfnA

<400> SEQUENCE: 40

Met Phe Lys Ile Val Lys Lys Ile Leu Asn Pro Gln Val Lys Leu
1               5                   10                  15

Met Glu Ile Ser Ala Pro His Val Ala Lys Lys Ala Glu Pro Gly Gln
            20                  25                  30
```

```
Phe Ile Ile Leu Arg Val Asn Glu Asn Gly Glu Arg Ile Pro Leu Thr
             35                  40                  45

Ile Ala Asp Phe Asp Arg Glu Lys Gly Thr Val Thr Ile Ile Phe Gln
 50                  55                  60

Glu Val Gly Lys Thr Thr Lys Leu Leu Gly Thr Leu Glu Glu Gly Asp
 65                  70                  75                  80

Glu Leu Leu Asp Phe Val Gly Pro Leu Gly Lys Ala Ser His Phe Glu
                 85                  90                  95

Asn Val Lys Lys Ala Ala Val Ile Gly Gly Leu Gly Thr Ala Ile
            100                 105                 110

Ala Tyr Pro Gln Ala Lys Lys Leu His Ser Met Gly Val Glu Val His
            115                 120                 125

Thr Ile Ala Gly Phe Arg Asn Lys Asp Leu Ile Ile Leu Glu Asp Glu
130                 135                 140

Met Arg Ala Val Ser Ser Lys Leu Phe Ile Thr Thr Asp Asp Gly Ser
145                 150                 155                 160

Asn Gly Asn Lys Gly Phe Val Ser Asp Val Leu Lys Lys Leu Ile Glu
                165                 170                 175

Glu Gly Asn Lys Tyr Asp Leu Val Val Ala Ile Gly Pro Leu Ile Met
            180                 185                 190

Met Lys Val Ile Ser Glu Leu Thr Arg Pro Tyr Gly Ile Lys Thr Ile
        195                 200                 205

Val Ser Met Asn Pro Val Met Ile Asp Gly Thr Gly Met Cys Gly Gly
        210                 215                 220

Cys Arg Val Thr Val Gly Gly Glu Ile Lys Phe Ala Cys Val Asp Gly
225                 230                 235                 240

Pro Asp Phe Asp Gly His Leu Val Asp Phe Asp Glu Ala Met Arg Arg
                245                 250                 255

Gln Ala Met Tyr Lys Lys Glu Glu Ser Leu Ala Leu Glu Lys His Asn
            260                 265                 270

Cys Lys Leu Gly Val Glu Lys Asn Ala
        275                 280

<210> SEQ ID NO 41
<211> LENGTH: 1395
<212> TYPE: DNA
<213> ORGANISM: Clostridium thermocellum
<220> FEATURE:
<221> NAME/KEY: misc_feature
<222> LOCATION: (1)..(1395)
<223> OTHER INFORMATION: nfnB

<400> SEQUENCE: 41
atgcctaaca tgtcaccgaa aaaagttccc atgccggagc aggacccaaa cgtcagaatc      60
aaaaactttt tggaggttgc tttaggatat accgagcaaa tggcaatgga agaagctcaa     120
aggtgtctta actgcaagca caaaccttgt gtttccggct gtcccgtaaa cgtaaaaatt     180
cctgagtttg tacagcttat cgctcaggga aaatttgaga agcctacaa taaaataaga     240 gaaaccaaca accttccggc aatatgcggc agagtctgtc cgcaggaaaa ccagtgtgaa     300
aagttctgtg taaggggtat aaaaggtgaa cctgttgcca taggaaggct tgaaagattt     360
gcggcggact ggcacatgaa aaacggcacc acttcttatg aaaagcctga aaaaacggc     420 aaaagggtgg cagtaatagg ttcgggacct gcaagcctta cctgtgcaag cgacctggcc     480
aaactcggct acgaagtaac aatcttcgaa gcctttcacg tgcccggcgg agtgttgatg     540
tacggtattc cggaattcag gcttccaaag aaactggttc aggaggaaat tgaaaccata     600
```

```
aagcagctgg gtgtggaaat taaaacaaat atggttatag gaaaggttta ttccattgac      660
gaactcaaag ctgaaggata tgatgccata tttataggct cgggtgccgg attgccttca      720
tttatgaaaa ttcccggaga aaacctcaac ggagtttact cggcaaatga gtttctcaca      780
agaataaacc tcatgaaggc ttatgaattc cccaactgcg atactcccgt gaaagtagga      840
aagaatgtcg ccgttgtggg cggaggaaat gtcgcaatgg acgccgcaag aagcgcaaaa      900
agacttggcg cggaaaacgt ttatatagta tacaggcgtt cggaagcgga aatgcccgca      960
agacttgaag aaattcatca cgcaaaggaa gaggaatttt tgttcaaatt ccttacaaac     1020
cccacaagaa ttcttggcac cgacgacggc tgggtcaaag catggagtg catagagatg     1080 gagctgggcg aacctgatga atccggaaga agaagacccg tgccaaagcc gggatccgaa     1140
catgtaattg atgttgaaac ggttattatc gccatcggcc aaactccaaa tccgttaatt     1200
gcctcaacaa ccccggggct ggccactcaa aaatggggcg gaattattgt cgatgaaaac     1260
accggcgcca ccaacataga aggtgtatat gccggcggag atgcggtaac cggtgccgca     1320
accgtcattc ttgcaatggg agcaggcaaa aaagccgcaa aggcaattga cgaatatctt     1380
aaaaacaaaa aatag                                                     1395

<210> SEQ ID NO 42
<211> LENGTH: 464
<212> TYPE: PRT
<213> ORGANISM: Clostridium thermocellum
<220> FEATURE:
<221> NAME/KEY: misc_feature
<222> LOCATION: (1)..(464)
<223> OTHER INFORMATION: nfnB

<400> SEQUENCE: 42

Met Pro Asn Met Ser Pro Lys Lys Val Pro Met Pro Glu Gln Asp Pro
1               5                   10                  15

Asn Val Arg Ile Lys Asn Phe Leu Glu Val Ala Leu Gly Tyr Thr Glu
            20                  25                  30

Gln Met Ala Met Glu Glu Ala Gln Arg Cys Leu Asn Cys Lys His Lys
        35                  40                  45

Pro Cys Val Ser Gly Cys Pro Val Asn Val Lys Ile Pro Glu Phe Val
    50                  55                  60

Gln Leu Ile Ala Gln Gly Lys Phe Glu Lys Ala Tyr Asn Lys Ile Arg
65                  70                  75                  80

Glu Thr Asn Asn Leu Pro Ala Ile Cys Gly Arg Val Cys Pro Gln Glu
                85                  90                  95

Asn Gln Cys Glu Lys Phe Cys Val Arg Gly Ile Lys Gly Glu Pro Val
            100                 105                 110

Ala Ile Gly Arg Leu Glu Arg Phe Ala Ala Asp Trp His Met Lys Asn
        115                 120                 125

Gly Thr Thr Ser Tyr Glu Lys Pro Glu Lys Asn Gly Lys Arg Val Ala
    130                 135                 140

Val Ile Gly Ser Gly Pro Ala Ser Leu Thr Cys Ala Ser Asp Leu Ala
145                 150                 155                 160

Lys Leu Gly Tyr Glu Val Thr Ile Phe Glu Ala Phe His Val Pro Gly
                165                 170                 175

Gly Val Leu Met Tyr Gly Ile Pro Glu Phe Arg Leu Pro Lys Lys Leu
            180                 185                 190

Val Gln Glu Glu Ile Glu Thr Ile Lys Gln Leu Gly Val Glu Ile Lys
        195                 200                 205
```

| | | | | | | | | | | | |
|---|---|---|---|---|---|---|---|---|---|---|---|
|Thr|Asn|Met|Val|Ile|Gly|Lys|Val|Tyr|Ser|Ile|Asp|Glu|Leu|Lys|Ala|
| |210| | | |215| | | |220| | |

Thr Asn Met Val Ile Gly Lys Val Tyr Ser Ile Asp Glu Leu Lys Ala
     210                 215                 220

Glu Gly Tyr Asp Ala Ile Phe Ile Gly Ser Gly Ala Gly Leu Pro Ser
225                 230                 235                 240

Phe Met Lys Ile Pro Gly Glu Asn Leu Asn Gly Val Tyr Ser Ala Asn
                245                 250                 255

Glu Phe Leu Thr Arg Ile Asn Leu Met Lys Ala Tyr Glu Phe Pro Asn
             260                 265                 270

Cys Asp Thr Pro Val Lys Val Gly Lys Asn Val Ala Val Val Gly Gly
             275                 280                 285

Gly Asn Val Ala Met Asp Ala Ala Arg Ser Ala Lys Arg Leu Gly Ala
     290                 295                 300

Glu Asn Val Tyr Ile Val Tyr Arg Arg Ser Glu Ala Glu Met Pro Ala
305                 310                 315                 320

Arg Leu Glu Glu Ile His His Ala Lys Glu Glu Gly Ile Leu Phe Lys
                325                 330                 335

Phe Leu Thr Asn Pro Thr Arg Ile Leu Gly Thr Asp Asp Gly Trp Val
                340                 345                 350

Lys Gly Met Glu Cys Ile Glu Met Glu Leu Gly Glu Pro Asp Glu Ser
                355                 360                 365

Gly Arg Arg Arg Pro Val Pro Lys Pro Gly Ser Glu His Val Ile Asp
370                 375                 380

Val Glu Thr Val Ile Ile Ala Ile Gly Gln Thr Pro Asn Pro Leu Ile
385                 390                 395                 400

Ala Ser Thr Thr Pro Gly Leu Ala Thr Gln Lys Trp Gly Gly Ile Ile
                405                 410                 415

Val Asp Glu Asn Thr Gly Ala Thr Asn Ile Glu Gly Val Tyr Ala Gly
                420                 425                 430

Gly Asp Ala Val Thr Gly Ala Ala Thr Val Ile Leu Ala Met Gly Ala
                435                 440                 445

Gly Lys Lys Ala Ala Lys Ala Ile Asp Glu Tyr Leu Lys Asn Lys Lys
     450                 455                 460

<210> SEQ ID NO 43
<211> LENGTH: 1197
<212> TYPE: DNA
<213> ORGANISM: Methylacidiphilum infernorum
<220> FEATURE:
<221> NAME/KEY: misc_feature
<222> LOCATION: (1)..(1197)
<223> OTHER INFORMATION: v4 formate dehydrogenase

<400> SEQUENCE: 43

| | | |
|---|---|---|
|atggcaaaag ttctttgtgt tctttatccc gatcctgtcg atggctatcc gaagtcttat|60|
|atccgtgatt cgattcctaa aatcgaatcg tatcctggag acaaaccgt tcccaatccc|120|
|aagggaatag actttgttcc cggcgaactt ttaggttcag tctccggggg tttaggccta|180|
|agaaagtacc ttgaaagcct tggtcatgag ttcatcgtca cctcggacaa agatgggcca|240|
|aactccgttt tgaaaaagaa cttcccgac gctgatgtcg ttatatccca gcccttttgg|300|
|cccgcctacc ttacccccgga aagaatcaag aaagctaaaa acttaaagtt ggctataaca|360|
|gcgggcatag ggtcagatca cgtggatatc caagctgcaa ttgaagcggg aataaccgta|420|
|gccgagatta cctattcgaa tagcatcagt gtagccgaac atgtggtaat gatgattcta|480|
|tcccttgtga gaaattatct cccttctcat gaatgggcgg ttaaggggg atggaatatt|540|

-continued

```
gccgattgtg ctgtcagagc ctatgatcta gagggaatgc atgttggaac agtggctgca      600
ggaagaatcg gtcttgcggt gctaagaagg ttaaaacctt ttgatgttca tcttcattat      660
accgatacgc accggctgcc cgccgaaatt gaaagggagc ttggagtgac ctatcatccc      720
gatgtttatg acatggttcc ccactgtgat gtcattacca ttaattgtcc tttgcatcct      780
tctactgaac atcttttttaa cgaccggctt ttcgagaagt gcaaacgggg aaccttcctt      840
gtgaatacgg ccaggggaaa gatctgcgat cgtgacgctc tggtaagggc cgtgcaaagt      900
ggaaaaattg ctgcctatgc cggagatgtt tggtttcctc aacctcctcc tgccgaccat      960
ccttggagga ccatgcccta acgggatg accctcact attctggaac aacgctttcg     1020
gctcaagccc gatatgccgc ggggaccaga gaaatcctcg aatgcttttt cgaaggccgt     1080
cccattcgcg aggaatatct catcgtcaaa gggggaaaac tggccggaac aggagcccac     1140
tcttataccg tgggaagcac cactaaggga gtcgaagaag cattgaaaag tgcctag        1197
```

<210> SEQ ID NO 44
<211> LENGTH: 398
<212> TYPE: PRT
<213> ORGANISM: Methylacidiphilum infernorum
<220> FEATURE:
<221> NAME/KEY: misc_feature
<222> LOCATION: (1)..(398)
<223> OTHER INFORMATION: v4 formate dehydrogenase

<400> SEQUENCE: 44

```
Met Ala Lys Val Leu Cys Val Leu Tyr Pro Asp Pro Val Asp Gly Tyr
1               5                   10                  15

Pro Lys Ser Tyr Ile Arg Asp Ser Ile Pro Lys Ile Glu Ser Tyr Pro
            20                  25                  30

Gly Gly Gln Thr Val Pro Asn Pro Lys Gly Ile Asp Phe Val Pro Gly
        35                  40                  45

Glu Leu Leu Gly Ser Val Ser Gly Gly Leu Gly Leu Arg Lys Tyr Leu
    50                  55                  60

Glu Ser Leu Gly His Glu Phe Ile Val Thr Ser Asp Lys Asp Gly Pro
65                  70                  75                  80

Asn Ser Val Phe Glu Lys Glu Leu Pro Asp Ala Asp Val Ile Ser
                85                  90                  95

Gln Pro Phe Trp Pro Ala Tyr Leu Thr Pro Glu Arg Ile Lys Lys Ala
            100                 105                 110

Lys Asn Leu Lys Leu Ala Ile Thr Ala Gly Ile Gly Ser Asp His Val
        115                 120                 125

Asp Ile Gln Ala Ala Ile Glu Ala Gly Ile Thr Val Ala Glu Ile Thr
    130                 135                 140

Tyr Ser Asn Ser Ile Ser Val Ala Glu His Val Val Met Met Ile Leu
145                 150                 155                 160

Ser Leu Val Arg Asn Tyr Leu Pro Ser His Glu Trp Ala Val Lys Gly
                165                 170                 175

Gly Trp Asn Ile Ala Asp Cys Ala Val Arg Ala Tyr Asp Leu Glu Gly
            180                 185                 190

Met His Val Gly Thr Val Ala Ala Gly Arg Ile Gly Leu Ala Val Leu
        195                 200                 205

Arg Arg Leu Lys Pro Phe Asp Val His Leu His Tyr Thr Asp Thr His
    210                 215                 220

Arg Leu Pro Ala Glu Ile Glu Arg Glu Leu Gly Val Thr Tyr His Pro
225                 230                 235                 240
```

```
Asp Val Tyr Asp Met Val Pro His Cys Asp Val Ile Thr Ile Asn Cys
            245                 250                 255

Pro Leu His Pro Ser Thr Glu His Leu Phe Asn Asp Arg Leu Phe Glu
        260                 265                 270

Lys Cys Lys Arg Gly Thr Phe Leu Val Asn Thr Ala Arg Gly Lys Ile
            275                 280                 285

Cys Asp Arg Asp Ala Leu Val Arg Ala Val Gln Ser Gly Lys Ile Ala
    290                 295                 300

Ala Tyr Ala Gly Asp Val Trp Phe Pro Gln Pro Pro Ala Asp His
305                 310                 315                 320

Pro Trp Arg Thr Met Pro Tyr Asn Gly Met Thr Pro His Tyr Ser Gly
                325                 330                 335

Thr Thr Leu Ser Ala Gln Ala Arg Tyr Ala Ala Gly Thr Arg Glu Ile
            340                 345                 350

Leu Glu Cys Phe Phe Glu Gly Arg Pro Ile Arg Glu Glu Tyr Leu Ile
            355                 360                 365

Val Lys Gly Gly Lys Leu Ala Gly Thr Gly Ala His Ser Tyr Thr Val
    370                 375                 380

Gly Ser Thr Thr Lys Gly Val Glu Glu Ala Leu Lys Ser Ala
385                 390                 395
```

<210> SEQ ID NO 45
<211> LENGTH: 1095
<212> TYPE: DNA
<213> ORGANISM: Candida boidinii
<220> FEATURE:
<221> NAME/KEY: misc_feature
<222> LOCATION: (1)..(1095)
<223> OTHER INFORMATION: fdh3 gene for NAD-dependent formate
       dehydrogenase

<400> SEQUENCE: 45

| | | |
|---|---|---|
| atgaagattg tcttagttct ttatgatgct ggtaagcacg ctgctgatga agaaaaatta | 60 |
| tatggttgta ctgaaaataa attaggtatt gccaattggt taaaagatca aggtcatgaa | 120 |
| ctaattacta cttctgataa agaaggtgaa acaagcgaat tggataaaca tatcccagat | 180 |
| gctgatatta tcatcaccac tcctttccat cctgcttata tcactaagga aagacttgac | 240 |
| aaggctaaga acttaaaatt agtcgttgtc gctggtgttg ttctgatca cattgattta | 300 |
| gattatatta atcaaacagg taagaaaatc tcagtcctgg aagttacagg ttctaatgtt | 360 |
| gtctctgttg ctgaacacgt tgtcatgacc atgcttgtct tggttagaaa tttcgttcca | 420 |
| gcacatgaac aaattattaa ccacgattgg gaggttgctg ctatcgctaa ggatgcttac | 480 |
| gatatcgaag gtaaaactat cgctaccatt ggtgctggta gaattggtta cagagtcttg | 540 |
| gaaagattac tcccatttaa tccaaaagaa ttattatact acgattatca agctttacca | 600 |
| aaagaagctg aagaaaaagt tggtgctaga agagttgaaa atattgaaga attagttgct | 660 |
| caagctgata tcgttacagt taatgctcca ttacacgcag gtacaaaagg tttaattaat | 720 |
| aaggaattat tatctaaatt taaaaaaggt gcttggttag tcaataccgc aagaggtgct | 780 |
| atttgtgttg ctgaagatgt tgcagcagct ttagaatctg gtcaattaag aggttacggt | 840 |
| ggtgatgttt ggttcccaca accagctcca aaggatcacc catggagaga tatgagaaat | 900 |
| aaatatggtg ctggtaatgc catgactcct cactactctg gtactacttt agacgctcaa | 960 |
| acaagatacg ctgaaggtac taaaaatatt ttggaatcat tctttaccgg taaatttgat | 1020 |
| tacagaccac aagatattat cttattaaat ggggaatacg ttactaaagc ttacggtaaa | 1080 | cacgataaga aatag                                              1095

<210> SEQ ID NO 46
<211> LENGTH: 364
<212> TYPE: PRT
<213> ORGANISM: Candida boidinii
<220> FEATURE:
<221> NAME/KEY: misc_feature
<222> LOCATION: (1)..(364)
<223> OTHER INFORMATION: fdh3 gene for NAD-dependent formate
      dehydrogenase

<400> SEQUENCE: 46

Met Lys Ile Val Leu Val Leu Tyr Asp Ala Gly Lys His Ala Ala Asp
 1               5                  10                  15

Glu Glu Lys Leu Tyr Gly Cys Thr Glu Asn Lys Leu Gly Ile Ala Asn
            20                  25                  30

Trp Leu Lys Asp Gln Gly His Glu Leu Ile Thr Thr Ser Asp Lys Glu
        35                  40                  45

Gly Glu Thr Ser Glu Leu Asp Lys His Ile Pro Asp Ala Asp Ile Ile
    50                  55                  60

Ile Thr Thr Pro Phe His Pro Ala Tyr Ile Thr Lys Glu Arg Leu Asp
65                  70                  75                  80

Lys Ala Lys Asn Leu Lys Leu Val Val Ala Gly Val Gly Ser Asp
                85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
        115                 120                 125

Met Thr Met Leu Val Leu Val Arg Asn Phe Val Pro Ala His Glu Gln
    130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Leu Pro Phe Asn Pro Lys Glu Leu Leu
            180                 185                 190

Tyr Tyr Asp Tyr Gln Ala Leu Pro Lys Glu Ala Glu Lys Val Gly
        195                 200                 205

Ala Arg Arg Val Glu Asn Ile Glu Glu Leu Val Ala Gln Ala Asp Ile
    210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Cys Val Ala Glu Asp Val Ala Ala Ala Leu Glu
            260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Glu Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu 340                 345                 350
Tyr Val Thr Lys Ala Tyr Gly Lys His Asp Lys Lys
        355                 360

<210> SEQ ID NO 47
<211> LENGTH: 1206
<212> TYPE: DNA
<213> ORGANISM: Thiobacillus sp.
<220> FEATURE:
<221> NAME/KEY: misc_feature
<222> LOCATION: (1)..(1206)
<223> OTHER INFORMATION: KNK65MA formate dehydrogenase

<400> SEQUENCE: 47

```
atggcgaaaa tactttgcgt tctctatgat gatccggtcg acggctatcc gaagacctat      60
gcgcgcgacg atctgccgaa gatcgaccac tatccgggcg gcagaccct gccgacgccg     120
aaggcgatcg acttcacccc cggccagctt ctcggctcgg tctccggcga gctgggcctg     180
cgcaaatatc tcgaagccaa cggccacacc ttcgtcgtca cctccgacaa ggacggcccg     240
gattcggtgt tcgagaagga gctcgtcgac gccgacgtgg tgatctccca gcccttctgg     300
ccggcctatc tgacacctga gcgcatcgcc aaggcgaaga acctgaagct ggcgctcacc     360
gccggcatcg gctccgatca cgtcgatctt cagtcggcga tcgaccgcgg catcaccgtg     420
gccgaagtca cctactgcaa ctcgatcagc gtcgccgagc atgtggtgat gatgatcctc     480
ggcctggtgc gcaactacat tccctcgcat gactgggcgc gcaagggcgg ctggaacata     540
gccgactgcg tggagcactc ctacgacctc gagggcatga ccgtcggctc cgttgccgcc     600
ggccgcatcg gcctcgccgt gctgcgccgc ctcgcgccct cgacgtgaa gctgcactac     660
accgaccgcc accgcctgcc ggaagcggtc gagaaggagt tgggcctggt ctggcacgac     720
acccgcgagg acatgtaccc acattgcgac gtggtcacgc tcaacgtgcc gctgcatccc     780
gagacggagc acatgatcaa tgacgagacg ctgaagctgt tcaagcgcgg cgcctatatc     840
gtcaacaccg cccgcggcaa gctcgccgac cgcgacgcca tcgtgcgtgc gatcgagagc     900
gggcagctcg ccggctatgc tggcgacgtg tggttcccgc agccggcgcc gaaggatcac     960
ccctggcgca ccatgaagtg gaaggcatg acgccgcaca tttccggcac ctcgctctcc    1020
gcccaggcgc gctatgcggc gggcacgcgc gagatcctcg aatgcttctt cgaaggtcgg    1080
ccgatccgcg acgagtacct gatcgtgcag ggcggcgcac tcgccggcac gggggcgcat    1140
tcctactcca agggcaatgc gaccggcggc tcggaagagg ccgcgaagtt caagaaggcc    1200
ggctga                                                               1206
```

<210> SEQ ID NO 48
<211> LENGTH: 401
<212> TYPE: PRT
<213> ORGANISM: Thiobacillus sp.
<220> FEATURE:
<221> NAME/KEY: misc_feature
<222> LOCATION: (1)..(401)
<223> OTHER INFORMATION: KNK65MA formate dehydrogenase

<400> SEQUENCE: 48

Met Ala Lys Ile Leu Cys Val Leu Tyr Asp Asp Pro Val Asp Gly Tyr
1               5                   10                  15

Pro Lys Thr Tyr Ala Arg Asp Asp Leu Pro Lys Ile Asp His Tyr Pro
            20                  25                  30

Gly Gly Gln Thr Leu Pro Thr Pro Lys Ala Ile Asp Phe Thr Pro Gly
        35                  40                  45

```
Gln Leu Leu Gly Ser Val Ser Gly Glu Leu Gly Leu Arg Lys Tyr Leu
 50                  55                  60

Glu Ala Asn Gly His Thr Phe Val Val Thr Ser Asp Lys Asp Gly Pro
 65                  70                  75                  80

Asp Ser Val Phe Glu Lys Glu Leu Val Asp Ala Asp Val Ile Ser
                 85                  90                  95

Gln Pro Phe Trp Pro Ala Tyr Leu Thr Pro Glu Arg Ile Ala Lys Ala
                100                 105                 110

Lys Asn Leu Lys Leu Ala Leu Thr Ala Gly Ile Gly Ser Asp His Val
                115                 120                 125

Asp Leu Gln Ser Ala Ile Asp Arg Gly Ile Thr Val Ala Glu Val Thr
130                 135                 140

Tyr Cys Asn Ser Ile Ser Val Ala Glu His Val Val Met Met Ile Leu
145                 150                 155                 160

Gly Leu Val Arg Asn Tyr Ile Pro Ser His Asp Trp Ala Arg Lys Gly
                165                 170                 175

Gly Trp Asn Ile Ala Asp Cys Val Glu His Ser Tyr Asp Leu Glu Gly
                180                 185                 190

Met Thr Val Gly Ser Val Ala Ala Gly Arg Ile Gly Leu Ala Val Leu
                195                 200                 205

Arg Arg Leu Ala Pro Phe Asp Val Lys Leu His Tyr Thr Asp Arg His
210                 215                 220

Arg Leu Pro Glu Ala Val Glu Lys Glu Leu Gly Leu Val Trp His Asp
225                 230                 235                 240

Thr Arg Glu Asp Met Tyr Pro His Cys Asp Val Val Thr Leu Asn Val
                245                 250                 255

Pro Leu His Pro Glu Thr Glu His Met Ile Asn Asp Glu Thr Leu Lys
                260                 265                 270

Leu Phe Lys Arg Gly Ala Tyr Ile Val Asn Thr Ala Arg Gly Lys Leu
                275                 280                 285

Ala Asp Arg Asp Ala Ile Val Arg Ala Ile Glu Ser Gly Gln Leu Ala
290                 295                 300

Gly Tyr Ala Gly Asp Val Trp Phe Pro Gln Pro Ala Pro Lys Asp His
305                 310                 315                 320

Pro Trp Arg Thr Met Lys Trp Glu Gly Met Thr Pro His Ile Ser Gly
                325                 330                 335

Thr Ser Leu Ser Ala Gln Ala Arg Tyr Ala Ala Gly Thr Arg Glu Ile
                340                 345                 350

Leu Glu Cys Phe Phe Glu Gly Arg Pro Ile Arg Asp Glu Tyr Leu Ile
                355                 360                 365

Val Gln Gly Gly Ala Leu Ala Gly Thr Gly Ala His Ser Tyr Ser Lys
                370                 375                 380

Gly Asn Ala Thr Gly Gly Ser Glu Glu Ala Ala Lys Phe Lys Lys Ala
385                 390                 395                 400

Gly

<210> SEQ ID NO 49
<211> LENGTH: 341
<212> TYPE: PRT
<213> ORGANISM: Staphylococcus aureus
<220> FEATURE:
<221> NAME/KEY: misc_feature
<222> LOCATION: (1)..(341)
<223> OTHER INFORMATION: formate dehydrogenase NAD-dependent
```

<400> SEQUENCE: 49

Met Lys Ile Val Ala Leu Phe Pro Glu Ala Val Glu Gly Gln Glu Asn
1               5                   10                  15

Gln Leu Leu Asn Thr Lys Lys Ala Leu Gly Leu Lys Thr Phe Leu Glu
            20                  25                  30

Glu Arg Gly His Glu Phe Ile Ile Leu Ala Asp Asn Gly Glu Asp Leu
        35                  40                  45

Asp Lys His Leu Pro Asp Met Asp Val Ile Ile Ser Ala Pro Phe Tyr
    50                  55                  60

Pro Ala Tyr Met Thr Arg Glu Arg Ile Glu Lys Ala Pro Asn Leu Lys
65                  70                  75                  80

Leu Ala Ile Thr Ala Gly Val Gly Ser Asp His Val Asp Leu Ala Ala
                85                  90                  95

Ala Ser Glu His Asn Ile Gly Val Val Glu Val Thr Gly Ser Asn Thr
            100                 105                 110

Val Ser Val Ala Glu His Ala Val Met Asp Leu Leu Ile Leu Leu Arg
        115                 120                 125

Asn Tyr Glu Glu Gly His Arg Gln Ser Val Glu Gly Glu Trp Asn Leu
    130                 135                 140

Ser Gln Val Gly Asn His Ala His Glu Leu Gln His Lys Thr Ile Gly
145                 150                 155                 160

Ile Phe Gly Phe Gly Arg Ile Gly Gln Leu Val Ala Glu Arg Leu Ala
                165                 170                 175

Pro Phe Asn Val Thr Leu Gln His Tyr Asp Pro Ile Asn Gln Gln Asp
            180                 185                 190

His Lys Leu Ser Lys Phe Val Ser Phe Asp Glu Leu Val Ser Thr Ser
    195                 200                 205

Asp Ala Ile Thr Ile His Ala Pro Leu Thr Pro Glu Thr Asp Asn Leu
210                 215                 220

Phe Asp Lys Asp Val Leu Ser Arg Met Lys Lys His Ser Tyr Leu Val
225                 230                 235                 240

Asn Thr Ala Arg Gly Lys Ile Val Asn Arg Asp Ala Leu Val Glu Ala
                245                 250                 255

Leu Ala Ser Glu His Leu Gln Gly Tyr Ala Gly Asp Val Trp Tyr Pro
            260                 265                 270

Gln Pro Ala Pro Ala Asp His Pro Trp Arg Thr Met Pro Arg Asn Ala
    275                 280                 285

Met Thr Val His Tyr Ser Gly Met Thr Leu Glu Ala Gln Lys Arg Ile
290                 295                 300

Glu Asp Gly Val Lys Asp Ile Leu Glu Arg Phe Phe Asn His Glu Pro
305                 310                 315                 320

Phe Gln Asp Lys Asp Ile Ile Val Ala Ser Gly Arg Ile Ala Ser Lys
                325                 330                 335

Ser Tyr Thr Ala Lys
            340

<210> SEQ ID NO 50
<211> LENGTH: 386
<212> TYPE: PRT
<213> ORGANISM: Burkholderia stablis
<220> FEATURE:
<221> NAME/KEY: misc_feature
<222> LOCATION: (1)..(386)
<223> OTHER INFORMATION: formate dehydrogenase

<400> SEQUENCE: 50

```
Met Ala Thr Val Leu Cys Val Leu Tyr Pro Asp Pro Val Asp Gly Tyr
1               5                   10                  15

Pro Pro His Tyr Val Arg Asp Thr Ile Pro Val Ile Thr Arg Tyr Ala
            20                  25                  30

Asp Gly Gln Thr Ala Pro Thr Pro Ala Gly Pro Pro Gly Phe Arg Pro
        35                  40                  45

Gly Glu Leu Val Gly Ser Val Ser Gly Ala Leu Gly Leu Arg Gly Tyr
    50                  55                  60

Leu Glu Ala His Gly His Thr Leu Ile Val Thr Ser Asp Lys Asp Gly
65              70                  75                  80

Pro Asp Ser Glu Phe Glu Arg Arg Leu Pro Asp Ala Asp Val Val Ile
                85                  90                  95

Ser Gln Pro Phe Trp Pro Ala Tyr Leu Thr Ala Glu Arg Ile Ala Arg
            100                 105                 110

Ala Pro Lys Leu Arg Leu Ala Leu Thr Ala Gly Ile Gly Ser Asp His
        115                 120                 125

Val Asp Leu Asp Ala Ala Ala Arg Ala His Ile Thr Val Ala Glu Val
130                 135                 140

Thr Gly Ser Asn Ser Ile Ser Val Ala Glu His Val Val Met Thr Thr
145                 150                 155                 160

Leu Ala Leu Val Arg Asn Tyr Leu Pro Ser His Ala Ile Ala Gln Gln
                165                 170                 175

Gly Gly Trp Asn Ile Ala Asp Cys Val Ser Arg Ser Tyr Asp Val Glu
            180                 185                 190

Gly Met His Phe Gly Thr Val Gly Ala Gly Arg Ile Gly Leu Ala Val
        195                 200                 205

Leu Arg Arg Leu Lys Pro Phe Gly Leu His Leu His Tyr Thr Gln Arg
210                 215                 220

His Arg Leu Asp Ala Ala Ile Glu Gln Glu Leu Gly Leu Thr Tyr His
225                 230                 235                 240

Ala Asp Pro Ala Ser Leu Ala Ala Val Asp Ile Val Asn Leu Gln
                245                 250                 255

Ile Pro Leu Tyr Pro Ser Thr Glu His Leu Phe Asp Ala Ala Met Ile
            260                 265                 270

Ala Arg Met Lys Arg Gly Ala Tyr Leu Ile Asn Thr Ala Arg Ala Lys
        275                 280                 285

Leu Val Asp Arg Asp Ala Val Val Arg Ala Val Thr Ser Gly His Leu
    290                 295                 300

Ala Gly Tyr Gly Gly Asp Val Trp Phe Pro Gln Pro Ala Pro Ala Asp
305                 310                 315                 320

His Pro Trp Arg Ala Met Pro Phe Asn Gly Met Thr Pro His Ile Ser
                325                 330                 335

Gly Thr Ser Leu Ser Ala Gln Ala Arg Tyr Ala Ala Gly Thr Leu Glu
            340                 345                 350

Ile Leu Gln Cys Trp Phe Asp Gly Arg Pro Ile Arg Asn Glu Tyr Leu
        355                 360                 365

Ile Val Asp Gly Gly Thr Leu Ala Gly Thr Gly Ala Gln Ser Tyr Arg
    370                 375                 380

Leu Thr
385

<210> SEQ ID NO 51
<211> LENGTH: 933
```

<212> TYPE: DNA
<213> ORGANISM: Clostridium cellulolyticum
<220> FEATURE:
<221> NAME/KEY: misc_feature
<222> LOCATION: (1)..(933)
<223> OTHER INFORMATION: malate dehydrogenase

<400> SEQUENCE: 51

| | | | | | |
|---|---|---|---|---|---|
| atgggtttta | aagttgcgat | cataggagca | ggatttgttg | gagcatcagc | tgcgtatgcg | 60 |
| atgtctataa | acaacttggt | ttctgaattg | gtattaattg | atgtaaataa | agagaaggct | 120 |
| tatggtgaag | cacttgatat | cagccatggc | ttatcattct | caggaaatat | gacagtttat | 180 |
| tccggcgact | attctgatgt | taaggattgt | gatgttatag | ttgtaactgc | aggggcagca | 240 |
| agaaaaccgg | gagaaactcg | tttggacctt | gctaaaaaga | atactatgat | catgaagagc | 300 |
| atagttactg | atataatgaa | gtactacaat | aagggtgtta | ttgtaagtgt | atcaaatcct | 360 |
| gttgatgtat | ggcatatatg | gacacaaaag | tggtcaggat | tgcctgcaaa | taaagttata | 420 |
| ggatcaggaa | cagttcttga | cagtgcaaga | ctgagaactc | atatcagtca | ggcattggat | 480 |
| gtagacattg | ctaacgttca | cggttatatt | gttggtgaac | atggtgattc | tcagttgcca | 540 |
| ttatggagtg | caacacatat | agcaggagta | caatttgacg | actatgtaaa | agctactggc | 600 |
| ttaaatgttg | ataaggaagc | tcttttcaat | gaagttaagg | tagcaggtgc | aactattatt | 660 |
| aagaacaagg | gagcaactta | ctacggtata | gctctttcaa | ttaacagaat | agttgaatca | 720 |
| atcctgaagg | acttcaatac | tattatgcct | gttggtacag | ttcttgacgg | acagtacgga | 780 |
| ttaaaggatg | ttttattaaa | cgttcctacg | atagttggcg | aaacggagc | tgaaaaagtt | 840 |
| cttgaagtga | acattacaga | tgcagaatta | caactttga | agcattcagc | tgaacaggtt | 900 |
| agggcagtta | ttaacgaagt | taaagacata | taa | | | 933 |

<210> SEQ ID NO 52
<211> LENGTH: 310
<212> TYPE: PRT
<213> ORGANISM: Clostridium cellulolyticum
<220> FEATURE:
<221> NAME/KEY: misc_feature
<222> LOCATION: (1)..(310)
<223> OTHER INFORMATION: malate dehydrogenase

<400> SEQUENCE: 52

Met Gly Phe Lys Val Ala Ile Ile Gly Ala Gly Phe Val Gly Ala Ser
1               5                   10                  15

Ala Ala Tyr Ala Met Ser Ile Asn Asn Leu Val Ser Glu Leu Val Leu
            20                  25                  30

Ile Asp Val Asn Lys Glu Lys Ala Tyr Gly Glu Ala Leu Asp Ile Ser
        35                  40                  45

His Gly Leu Ser Phe Ser Gly Asn Met Thr Val Tyr Ser Gly Asp Tyr
    50                  55                  60

Ser Asp Val Lys Asp Cys Asp Val Ile Val Val Thr Ala Gly Ala Ala
65                  70                  75                  80

Arg Lys Pro Gly Glu Thr Arg Leu Asp Leu Ala Lys Lys Asn Thr Met
                85                  90                  95

Ile Met Lys Ser Ile Val Thr Asp Ile Met Lys Tyr Tyr Asn Lys Gly
            100                 105                 110

Val Ile Val Ser Val Ser Asn Pro Val Asp Val Leu Ala Tyr Met Thr
        115                 120                 125

Gln Lys Trp Ser Gly Leu Pro Ala Asn Lys Val Ile Gly Ser Gly Thr
    130                 135                 140

```
Val Leu Asp Ser Ala Arg Leu Arg Thr His Ile Ser Gln Ala Leu Asp
145                 150                 155                 160

Val Asp Ile Ala Asn Val His Gly Tyr Ile Val Gly Glu His Gly Asp
                165                 170                 175

Ser Gln Leu Pro Leu Trp Ser Ala Thr His Ile Ala Gly Val Gln Phe
            180                 185                 190

Asp Asp Tyr Val Lys Ala Thr Gly Leu Asn Val Asp Lys Glu Ala Leu
            195                 200                 205

Phe Asn Glu Val Lys Val Ala Gly Ala Thr Ile Ile Lys Asn Lys Gly
    210                 215                 220

Ala Thr Tyr Tyr Gly Ile Ala Leu Ser Ile Asn Arg Ile Val Glu Ser
225                 230                 235                 240

Ile Leu Lys Asp Phe Asn Thr Ile Met Pro Val Gly Thr Val Leu Asp
                245                 250                 255

Gly Gln Tyr Gly Leu Lys Asp Val Leu Leu Asn Val Pro Thr Ile Val
            260                 265                 270

Gly Gly Asn Gly Ala Glu Lys Val Leu Glu Val Asn Ile Thr Asp Ala
            275                 280                 285

Glu Leu Gln Leu Leu Lys His Ser Ala Glu Gln Val Arg Ala Val Ile
    290                 295                 300

Asn Glu Val Lys Asp Ile
305                 310

<210> SEQ ID NO 53
<211> LENGTH: 951
<212> TYPE: DNA
<213> ORGANISM: Clostridium cellulolyticum
<220> FEATURE:
<221> NAME/KEY: misc_feature
<222> LOCATION: (1)..(951)
<223> OTHER INFORMATION: lactate dehydrogenase

<400> SEQUENCE: 53
atgaaaaata atctataaa taaaatagta attgtaggta cgggttttgt cggttcaaca      60
actgcctata ctttaatggt cagcggacta gtttccgaga ttgtacttat tgaccgtaac    120
acaagcaaag ccgaaggaga ggcaatggat atgaatcacg gtatgccctt tgtaagacct    180
gtcagaatat acaaaggtga ttatcctgat tgcaaaggtg ctgatattgt tgtaataaca    240
ggtggagcaa accagaagcc cggtgaaacc agaattgacc ttgtaaataa aaatactgaa    300 gttttaaag acattgttgg aaatatcatt aaatacaata cagactgtat tttacttgtt    360
gttacaaacc cggttgatat cttaacctat gtaacataca aattatccgg atttcccaaa    420
aacagagtta taggctccgg aacagttctt gatactgcac gtttcaaata tatgcttggt    480
gaacacatgg gagttgaccc aagaaacgtt catgcttata taatcggtga acatggagat    540
acagaggtac ctacatggag tctggcatcc atagccggga taccgatgga tgcttattgc    600
aaggaatgta atcctgtga tgctgaaaac tttaagagtg aaactttga caaagtaaaa    660 aatgcagctt atgaaattat tgatagaaaa aatgcaacct actacgccgt tgctcttgca    720
gtaagaagaa ttgtagaggc tatcgttcgt aatgaaaact ccatattgac ggtatcaagc    780
ctattcgaag gagaatacgg cctcaatgac atatgtctca gtattcccag ccaggtaaat    840
tcggagggtg tttcaaggat tttgaatatt cctctgagca gtgaggaaac aggtttactt    900
aataaatctg cccaggcctt gaaacaggtt atcagtgggc tgaatttata a              951
```

<210> SEQ ID NO 54
<211> LENGTH: 316
<212> TYPE: PRT
<213> ORGANISM: Clostridium cellulolyticum
<220> FEATURE:
<221> NAME/KEY: misc_feature
<222> LOCATION: (1)..(316)
<223> OTHER INFORMATION: lactate dehydrogenase

<400> SEQUENCE: 54

Met Lys Asn Lys Ser Ile Asn Lys Ile Val Ile Val Gly Thr Gly Phe
1               5                   10                  15

Val Gly Ser Thr Thr Ala Tyr Thr Leu Met Val Ser Gly Leu Val Ser
            20                  25                  30

Glu Ile Val Leu Ile Asp Arg Asn Thr Ser Lys Ala Glu Gly Glu Ala
        35                  40                  45

Met Asp Met Asn His Gly Met Pro Phe Val Arg Pro Val Arg Ile Tyr
    50                  55                  60

Lys Gly Asp Tyr Pro Asp Cys Lys Gly Ala Asp Ile Val Val Ile Thr
65                  70                  75                  80

Gly Gly Ala Asn Gln Lys Pro Gly Glu Thr Arg Ile Asp Leu Val Asn
                85                  90                  95

Lys Asn Thr Glu Val Phe Lys Asp Ile Val Gly Asn Ile Ile Lys Tyr
            100                 105                 110

Asn Thr Asp Cys Ile Leu Leu Val Val Thr Asn Pro Val Asp Ile Leu
        115                 120                 125

Thr Tyr Val Thr Tyr Lys Leu Ser Gly Phe Pro Lys Asn Arg Val Ile
    130                 135                 140

Gly Ser Gly Thr Val Leu Asp Thr Ala Arg Phe Lys Tyr Met Leu Gly
145                 150                 155                 160

Glu His Met Gly Val Asp Pro Arg Asn Val His Ala Tyr Ile Ile Gly
                165                 170                 175

Glu His Gly Asp Thr Glu Val Pro Thr Trp Ser Leu Ala Ser Ile Ala
            180                 185                 190

Gly Ile Pro Met Asp Ala Tyr Cys Lys Glu Cys Lys Ser Cys Asp Ala
        195                 200                 205

Glu Asn Phe Lys Ser Glu Thr Phe Asp Lys Val Lys Asn Ala Ala Tyr
    210                 215                 220

Glu Ile Ile Asp Arg Lys Asn Ala Thr Tyr Tyr Ala Val Ala Leu Ala
225                 230                 235                 240

Val Arg Arg Ile Val Glu Ala Ile Val Arg Asn Glu Asn Ser Ile Leu
                245                 250                 255

Thr Val Ser Ser Leu Phe Glu Gly Glu Tyr Gly Leu Asn Asp Ile Cys
            260                 265                 270

Leu Ser Ile Pro Ser Gln Val Asn Ser Glu Gly Val Ser Arg Ile Leu
        275                 280                 285

Asn Ile Pro Leu Ser Ser Glu Glu Thr Gly Leu Leu Asn Lys Ser Ala
    290                 295                 300

Gln Ala Leu Lys Gln Val Ile Ser Gly Leu Asn Leu
305                 310                 315

<210> SEQ ID NO 55
<211> LENGTH: 2940
<212> TYPE: DNA
<213> ORGANISM: Thermoanaerobacterium saccharolyticum
<220> FEATURE:
<221> NAME/KEY: misc_feature
<222> LOCATION: (1)..(2940)

<223> OTHER INFORMATION: plasmid pMU2106

<400> SEQUENCE: 55

```
ttgaaaaaaa atgtagacaa taacgacggc tactgtgaag ttatggttcc taattcagaa        60
gctcaggatg cacagaatat tattattgaa tatggtcttt aattacccct tataagggggg      120
acttttaata aaatgggaca tataatgacc cggttggtaa ggaggatata ttatgagaac       180
aataggagtt ttaacaagtg gtggagatgc accaggcatg aatgctgcca taagggcagt      240
ggtaagatgc ggcatatata acgggctgac agtaaaaggc atcatgagag gctatcaggg      300
gcttatagac gacgagatag aagacatgac attgtcatca gtaggtgaca taattcaaag      360
aggcggtaca atacttcgta cagccagaag tgcagaattt aaaacaaaag aaggaagagc      420
caaggctgca gaggtattga aaaagcacaa tattgaaggg cttgtggtca taggcggaga      480
tggctctttt agaggtgcac agcttttaag taatgaacat ggtgttaata cgatcggtat      540
tccaggcact atcgacaatg acataccgtg tacagattat acaatcggtt ttgatacagc      600
ttgcaatacg gctatagatg ccatcaacaa gattagagac acggcaacgt cacacgaaag      660
agcaaatatc atagaggtaa tgggaagaaa tgctgggtac atagcgcttt atgcaggact      720
tgctggagga gcagagatta taataatacc ggaagtcaag tttgacatag atgaagtgtg      780
cgaaaaaatt tcgtacggca taagagggg caagctgcat cacataattg tactggcaga      840
aggtgtaatg agcggtctgg agttatcaaa gatgattcaa gagagacttc ctaagcttga      900
tttaaggcat acgactttgg gccacataca aaggggtggc gcgcctactg tcatggacag      960
agttatcgca agccaaatgg gatcaagagc tgtagagctt ctgttagaaa acaaatctca     1020
aaggataata agcataagaa ataaccagat tgtggatgat gatatagaca ctgctttggc     1080
aatgaaaaaa gagtttaatt taagcttta tgaactcagc aaaatattat caatttaagg     1140
agtgaagata tgcgtagaac taagataata tgcacgattg gtcctgccag tgaaaaatat     1200
gagatattga aagagcttat agaaagcggt cttaatattt gcaggttgaa ttttccacat     1260
ggggatcatg aagagcatgg aagcagaata gacaatatta taaagattag agaagaactt     1320
aagctgccta ttgcaattat gcttgataca aaagggcctg aaataaggac tggcagattt     1380
aaaggcggtg ttgcagagct taaagaaggc cagacattta cgataacatc aagggaaatt     1440
gaaggagata acactatttg ttctgtttca tacaagggc ttcctcaaga tgtggagaga     1500
ggttctcgca tattgattga tgacggatta gtatcattga aagtcaatga cgtaaaaggt     1560
gaagatatag tatgcactgt ggagaattct ggtacaatag gtgatcacaa aggtgtaaat     1620
gtacctggta caaagcttaa tttgcctgcc ataacgcaaa aagacgtgga tgatatagag     1680
tttggaataa aaaaggaat cgacatgatt gcagcgtctt ttgtcagaaa agcagcagat     1740
gtaattgcca taggagatt gttagaagac aatgacgctg ccatatact tatcatatca     1800
aaaattgaaa atcgcgaagg cgtagaaaat attgacgaaa taatcaaagt ctctgatggc     1860
ataatggtag cccgcggcga tttgggtgtc gaaattccta tagaggaaat acctatcgtt     1920
cagaaaagga taattgaaaa atgcaacaaa gcaggtaaac cagtagttac tgctacacag     1980
atgcttgact ctatgataag aaatccaagg ccaacaaggg cagaagtaac agatgtagcc     2040
aatgctatat tggatggcac tgatgcgata atgttgtctg gtgaaacagc gcaaggcaaa     2100
tatcctgtag aggcttttaa gacgatgtca aagatagctg aaaagattga gacgtatata     2160
aattacaaag aaaatttaga taaaatgtg gattacaata tttctatgac aaatgccata     2220
agccatgcta cgtgcactac cgcgagagat ataggcgcaa ctgccattat tacatctaca     2280
```

```
atatcaggtt atactgcgag aatggtgtct aagtatagac cgtcagcacc tataatagca    2340
gtgacgccaa acaaagatgt tgcaagaagg cttagcatcg tgtggggtgt acatccattg    2400
atatcacagg aagtcaattc tacagatgaa atgatagaag tatcagtaaa tacggcttta    2460
aatgaaggat taattcgaaa tggcgatatt gtagtaatat cggcaggaat acctgtcgcg    2520
actacaggca caacaaatat gttgaaggtt catattgtgg gagatgtaat agtaaaaggc    2580
acaggcatag gcactaaatc cataagtggt gttgtttcca tcataagaga tccatacaag    2640
gacaaagata agttcagaga aggagatatc atcgttgctc aaaaaactga aagggattat    2700
atgcctataa ttgagaaggc ttcagctatc ataacagaag aaggtggact aacgtcccat    2760
gctgcaatag ttggattgaa ctatggatta cctgtcattg taggctgtga aggagtaact    2820
tcaaagctta aagatggaat gacggtaact ctcgatactg ccagaggatt ggtctacaaa    2880
ggtatagtga atataaaata ggacaggaag tcatcttctt gtctttattt ttttgaggtg    2940

<210> SEQ ID NO 56
<211> LENGTH: 6227
<212> TYPE: DNA
<213> ORGANISM: Clostridium thermocellum
<220> FEATURE:
<221> NAME/KEY: misc_feature
<222> LOCATION: (1)..(6227)
<223> OTHER INFORMATION: plasmid insert for integration of the pyruvate
      kinase gene into the chromosome of C.thermocellum strain 1313 at
      the ldh locus
<220> FEATURE:
<221> NAME/KEY: misc_feature
<222> LOCATION: (1)..(770)
<223> OTHER INFORMATION: ldh_flank1 upstream of native ldh gene
<220> FEATURE:
<221> NAME/KEY: promoter
<222> LOCATION: (771)..(1298)
<223> OTHER INFORMATION: gapDH_promoter C.thermocellum sequence upstream
      of gapD gene
<220> FEATURE:
<221> NAME/KEY: misc_feature
<222> LOCATION: (2636)..(3405)
<223> OTHER INFORMATION: ldh_flank1 upstream of native ldh gene
<220> FEATURE:
<221> NAME/KEY: misc_feature
<222> LOCATION: (3406)..(3585)
<223> OTHER INFORMATION: C.thermocellum enolase promoter
<220> FEATURE:
<221> NAME/KEY: misc_feature
<222> LOCATION: (5336)..(6224)
<223> OTHER INFORMATION: ldh_flank2 downstream of native ldh gene

<400> SEQUENCE: 56
tgacactatc ctgtatcctg attttttccgc aaggtaagga ataacggtat catcaagcat     60
cggcatcatc tccggcggag gaccgggaag cattaccaca atctttccct tatcttcaat    120
aatgcagccc ggggctgtgc cgctgttatt ctcaaccact gtgcacccctt ccggaagata   180 tgcctgcttg acattattgt ccgtcatttt tcggtttatc ctggtaaaaa aagttttaat   240
cctctcaagg ctttcttcgt gtaaaacaag cttttttcccc aaaacttccg caacagtctc   300
ctttgtaagg tcatcctgcg tggggccgag tcctccggtc ataataacaa ggtcgcacct   360
ttccaaagct gcaagaagac attttttcag ccgaacggaa ttgtccccca ccacactgtg   420
ataatacaca ttcacaccaa tgtcattgag ccttttggat atatactggg cattggtatt   480
tgctatctgc cccattaaaa gctcggttcc aaccgctaat atctccgcat tcatattgaa   540
agacccctta aatttaaact ttttgtaact tattatatca attagtgtta taaaataaaa   600
gggaaaaaga attaaaatca aaggtttcaa gagcagccgt atcacccgta aagtttcag   660
```

```
ccgattcaac cttttacac ataaaactt caaaaattga tgacttacaa ttatcaagta    720
ggatataata ttactaatgc taaacagtta ttgataaagg aggaaggaat gtatttcttt    780
tccgaaagag aggaaaagat tctaaagagt tttggaaata ctgatgaata ttgtgtgcag    840
agtacaattc tatggacaag aaaagaggct tgtcaaaac tttttcgtct gggaatgagg     900
atggatttta aaaagctgga tactttggag gacgaggtgg ttttcagga aacaaacagg     960 gcgcgtctgt tttcttttat atgcaataat tactgtatct ctctggcatt gccaggtttt   1020
aataaagatt aaaattattg actagaaata aaaaaattgt ccataatatt aatggacaaa   1080
aaaacaaaga attcatcaa aggaagataa aaatactttg ttaaaaaatt aattattttt    1140
tatctaaact attgaaaatg aaaataaaat aatataaaat gaatcatagt gcaagagata   1200
cttgccagag gatgaatatt ttactgcatt catgctttat ggcagctaat agaggcatta   1260
aattaaattt taatttacaa taggaggcga tattaatgat gaactttaat aaaattgatt   1320
tagacaattg gaagagaaaa gagatatta atcattatt gaaccaacaa acgactttta    1380
gtataaccac agaaattgat attagtgttt taccgaaa cataaaacaa gaaggatata    1440
aattttaccc tgcatttatt ttcttagtga caagggtgat aaactcaaat acagcttta    1500 gaactggtta caatagcgac ggagagttag gttattggga taagttagag ccactttata   1560 caattttga tggtgtatct aaaacattct ctggtatttg gactcctgta aagaatgact    1620
tcaaagagtt ttatgattta tacctttctg atgtagagaa atataatggt tcggggaaat   1680
tgtttcccaa aacacctata cctgaaaatg ctttttctct ttctattatt ccatggactt   1740
catttactgg gtttaactta aatatcaata ataatagtaa ttaccttcta cccattatta   1800
cagcaggaaa attcattaat aaaggtaatt caatatattt accgctatct ttacaggtac   1860
atcattctgt ttgtgatggt tatcatgcag gattgtttat gaactctatt caggaattgt   1920
cagataggcc taatgactgg cttttataaa caagattaag gaggaaattt gatggaaaat   1980
ttatcaaaag acatcgatga aattttgatc acagaagaag aacttaagga aaagataaaa   2040
gagcttggga ggcaaatcac aaaagactac aaagggaaaa atttgatgtt ggtaggagtt   2100
ttaaaaggtg ctttaatgtt tatggctgat ttgtcaagac acatagattt gcctttatca   2160 cttgattta tggctgtttc cagctatgga agctcaactc attcatcagg aatagtaaag    2220
ataatcaaag atcttgatat aagcatagaa ggcaaagatg ttctgattgt ggaagacata   2280
attgacagcg gtttgacttt gtcttactta agggaaactt tacttggaag gaagccaaaa   2340
agcctgaaaa tatgcacaat attagacaaa ccggagagaa gagaagcatc tgtaaaagtc   2400
gattatgtag gatttaagat acctgataag tttgtcgtgg ttatggatt ggactttgat    2460 gaaaagtaca ggaaccttcc ttttataggc gttttgaaac ctgaaatgta cagctaaaat   2520
ttgttttttt atatggtata tgttattata aattaagtga tacggctttg aagggagggc   2580
catatttgaa taaaacgatc agaggtatcg ttatatggat actgataatt atcgctgaca   2640
ctatcctgta tcctgatttt tccgcaaggt aaggaataac ggtatcatca agcatcggca   2700
tcatctccgg cggaggaccg ggaagcatta ccacaatctt tcccttatct tcaataatgc   2760
agcccggggc tgtgccgctg ttattctcaa ccactgtgca cccttccgga agatatgcct   2820
gcttgacatt attgtccgtc attttcggt ttatcctggt aaaaaaagtt ttaatcctct    2880
caaggctttc ttcgtgtaaa acaagctttt tccccaaaac ttccgcaaca gtctcctttg   2940
taaggtcatc ctgcgtgggg ccgagtcctc cggtcataat aacaaggtcg cacctttcca   3000
```

```
aagctgcaag aagacatttt ttcagccgaa cggaattgtc ccccaccaca ctgtgataat    3060
acacattcac accaatgtca ttgagccttt tggatatata ctgggcattg gtatttgcta    3120
tctgccccat taaaagctcg gttccaaccg ctaatatctc cgcattcata ttgaaagacc    3180
ccttaaattt aaacttttg taacttatta tatcaattag tgttataaaa taaaagggaa    3240
aaagaattaa aatcaaaggt ttcaagagca gccgtatcac ccgtaaaagt ttcagccgat    3300
tcaacctttt tacacataaa actttcaaaa attgatgact tacaattatc aagtaggata    3360
taatattact aatgctaaac agttattgat aaaggaggaa ggaatggaaa tattaaaatg    3420
gaaatgttga aaaatgttt taagatgggt cattatggat aaaatatact atggttttgc    3480
aataaatgct ttctattaat tggactttgt ggtaatatgg tagaaggatg cagtgttaat    3540
tttttaacat ataaaaataa gctatatgaa gggagaatgg agaatgcgta gaactaagat    3600
aatatgcacg attggtcctg ccagtgaaaa atatgagata ttgaaagagc ttatagaaag    3660
cggtcttaat atttgcaggt tgaatttttc acatggggat catgaagagc atggaagcag    3720
aatagacaat attataaaga ttagagaaga acttaagctg cctattgcaa ttatgcttga    3780
tacaaaaggg cctgaaataa ggactggcag atttaaaggc ggtgttgcag agcttaaaga    3840
aggccagaca tttacgataa catcaaggga aattgaagga gataacacta tttgttctgt    3900
ttcatacaag gggcttcctc aagatgtgga gagaggttct cgcatattga ttgatgacgg    3960
attagtatca ttgaaagtca atgacgtaaa aggtgaagat atagtatgca ctgtggagaa    4020
ttctggtaca ataggtgatc acaaaggtgt aaatgtacct ggtacaaagc ttaatttgcc    4080
tgccataacg caaaaagacg tggatgatat agagtttgga ataaaaaaag gaatcgacat    4140
gattgcagcg tcttttgtca gaaaagcagc agatgtaatt gccataagga gattgttaga    4200
agacaatgac gctggccata tacttatcat atcaaaaatt gaaaatcgcg aaggcgtaga    4260
aaatattgac gaaataatca aagtctctga tggcataatg gtagcccgcg gcgatttggg    4320
tgtcgaaatt cctatagagg aaataccata cgttcagaaa aggataattg aaaaatgcaa    4380
caaagcaggt aaaccagtag ttactgctac acagatgctt gactctatga taagaaatcc    4440
aaggccaaca agggcagaag taacagatgt agccaatgct atattggatg cactgatgc    4500 gataatgttg tctggtgaaa cagcgcaagg caaatatcct gtagaggctt ttaagacgat    4560
gtcaaagata gctgaaaaga ttgagacgta tataaattac aaagaaaatt tagataaaaa    4620
tgtggattac aatatttcta tgacaaatgc cataagccat gctacgtgca ctaccgcgag    4680
agatataggc gcaactgcca ttattacatc tacaatatca ggttatactg cgagaatggt    4740
gtctaagtat agaccgtcag cacctataat agcagtgacg ccaaacaaag atgttgcaag    4800
aaggcttagc atcgtgtggg gtgtacatcc attgatatca caggaagtca attctacaga    4860
tgaaatgata gaagtatcag taaatacggc tttaaatgaa ggattaattc gaaatggcga    4920
tattgtagta atatcggcag gaatacctgt cgcgactaca ggcacaacaa atatgttgaa    4980
ggttcatatt gtgggagatg taatagtaaa aggcacaggc ataggcacta atccataag    5040 tggtgttgtt tccatcataa gagatccata caaggacaaa gataagttca gagaaggaga    5100
tatcatcgtt gctcaaaaaa ctgaaaggga ttatatgcct ataattgaga aggcttcagc    5160
tatcataaca gaagaaggtg gactaacgtc ccatgctgca atagttggat tgaactatgg    5220
attacctgtc attgtaggct gtgaaggagt aacttcaaag cttaaagatg gaatgacggt    5280
aactctcgat actgccagag gattggtcta caaaggtata gtgaatataa aatagaagtt    5340
ctcctttcct tttatgaaaa ggagaacttt cattattgat aaatatataa actagtatat    5400
```

-continued

| | |
|---|---|
| aattttaata taaaacctat tttacataat ggaaattatc tatcggggga ggaaatatga | 5460 |
| acaattcagt ggaaatttta aataaaatcg tgtcaaatat tgaaaaagtc attgttggaa | 5520 |
| aaaagaaagc tatcgagttg atattaatat cacttatttg cgatggacat gttttgattg | 5580 |
| aagatgtccc cggtgtcgga aaaccagta ttgtatcatc tcttgcaaag tcggtaaatg | 5640 |
| cttcttttaa aagaatacag tttacaccgg atattcttcc ttcagacatt acaggattta | 5700 |
| cgatgtacaa tcagaaagaa ggtaaattcg aatatcatcc cggaagcatt atgagccaga | 5760 |
| taatacttgc ggatgaaata aaccgaacat ctccaaaaac ccaggcaagc cttcttgaag | 5820 |
| caatggaaga aaaacaggtg accgttgacg gtgtgacata caatcttcca aggccttta | 5880 |
| tggtactggc aactcaaaat cccgtggagt atctcggcac ctatcctctt cccgaagctc | 5940 |
| agctggacag ttttttatg aaagtttcca taggttatcc tgaaaagttt gaagaatccg | 6000 |
| aaatactgtc aagatttcac gacgaaaacc ccttggaaac cttaaaacct gtggcggaca | 6060 |
| gcagcgatat actgaatatt caaagcgagg ttaaaaaagt ttatgttgac aggtccatca | 6120 |
| acaactacat agtggatata gtaagccgga caagattcca ttcggaaata agtctgggtt | 6180 |
| caagtccaag aggttctctt tctctataca gagcctccca ggcatgg | 6227 |

<210> SEQ ID NO 57
<211> LENGTH: 1930
<212> TYPE: DNA
<213> ORGANISM: Thermoanaerobacterium saccharolyticum
<220> FEATURE:
<221> NAME/KEY: Misc_Feature
<222> LOCATION: (1)..(1930)
<223> OTHER INFORMATION: nucleotide sequence for expression of pyruvate
     kinase

<400> SEQUENCE: 57

| | |
|---|---|
| ggaaatatta aaatggaaat gttgaaaaaa tgttttaaga tgggtcatta tggataaaat | 60 |
| atactatggt tttgcaataa atgctttcta ttaattggac tttgtggtaa tatggtagaa | 120 |
| ggatgcagtg ttaattttt aacatataaa aataagctat atgaagggag aatggagaat | 180 |
| gcgtagaact aagataatat gcacgattgg tcctgccagt gaaaaatatg agatattgaa | 240 |
| agagcttata gaaagcggtc ttaatatttg caggttgaat ttttcacatg gggatcatga | 300 |
| agagcatgga agcagaatag acaatattat aaagattaga gaagaactta agctgcctat | 360 |
| tgcaattatg cttgatacaa aagggcctga aataaggact ggcagattta aaggcggtgt | 420 |
| tgcagagctt aaagaaggcc agacatttac gataacatca agggaaattg aaggagataa | 480 |
| cactatttgt tctgtttcat acaaggggct tcctcaagat gtggagagag gttctcgcat | 540 |
| attgattgat gacggattag tatcattgaa agtcaatgac gtaaaaggtg aagatatagt | 600 |
| atgcactgtg gagaattctg gtacaatagg tgatcacaaa ggtgtaaatg tacctggtac | 660 |
| aaagcttaat ttgcctgcca taacgcaaaa agacgtggat gatatagagt ttggaataaa | 720 |
| aaaaggaatc gacatgattg cagcgtcttt tgtcagaaaa gcagcagatg taattgccat | 780 |
| aaggagattg ttagaagaca tgacgctgg ccatatactt atcatatcaa aaattgaaaa | 840 |
| tcgcgaaggc gtagaaaata ttgacgaaat aatcaaagtc tctgatggca taatggtagc | 900 |
| ccgcggcgat ttgggtgtcg aaattcctat agaggaaata cctatcgttc agaaaaggat | 960 |
| aattgaaaaa tgcaacaaag caggtaaacc agtagttact gctacacaga tgcttgactc | 1020 |
| tatgataaga aatccaaggc caacaagggc agaagtaaca gatgtagcca atgctatatt | 1080 |
| ggatggcact gatgcgataa tgttgtctgg tgaaacagcg caaggcaaat atcctgtaga | 1140 |

-continued

```
ggcttttaag acgatgtcaa agatagctga aaagattgag acgtatataa attacaaaga    1200
aaatttagat aaaaatgtgg attacaatat ttctatgaca aatgccataa gccatgctac    1260
gtgcactacc gcgagagata taggcgcaac tgccattatt acatctacaa tatcaggtta    1320
tactgcgaga atggtgtcta agtatagacc gtcagcacct ataatagcag tgacgccaaa    1380
caaagatgtt gcaagaaggc ttagcatcgt gtggggtgta catccattga tatcacagga    1440
agtcaattct acagatgaaa tgatagaagt atcagtaaat acggctttaa atgaaggatt    1500
aattcgaaat ggcgatattg tagtaatatc ggcaggaata cctgtcgcga ctacaggcac    1560
aacaaatatg ttgaaggttc atattgtggg agatgtaata gtaaaaggca caggcatagg    1620
cactaaatcc ataagtggtg ttgtttccat cataagagat ccatacaagg acaaagataa    1680
gttcagagaa ggagatatca tcgttgctca aaaaactgaa agggattata tgcctataat    1740
tgagaaggct tcagctatca taacagaaga aggtggacta acgtcccatg ctgcaatagt    1800
tggattgaac tatggattac ctgtcattgt aggctgtgaa ggagtaactt caaagcttaa    1860
agatggaatg acggtaactc tcgatactgc cagaggattg gtctacaaag gtatagtgaa    1920
tataaaatag                                                          1930
```

<210> SEQ ID NO 58
<211> LENGTH: 3508
<212> TYPE: DNA
<213> ORGANISM: Clostridium thermocellum
<220> FEATURE:
<221> NAME/KEY: misc_feature
<222> LOCATION: (1)..(3508)
<223> OTHER INFORMATION: plasmid insert for changing the start codon of
      the gene for PEPCK in C.thermocellum strain DSM1313
<220> FEATURE:
<221> NAME/KEY: misc_feature
<222> LOCATION: (1)..(578)
<223> OTHER INFORMATION: pepck flank1 upstream of C.thermocellum gene
      for PEPCK
<220> FEATURE:
<221> NAME/KEY: promoter
<222> LOCATION: (596)..(1243)
<223> OTHER INFORMATION: gapD_promoter DNA upstream of gapD gene from
      C.thermocellum
<220> FEATURE:
<221> NAME/KEY: misc_feature
<222> LOCATION: (2526)..(3508)
<223> OTHER INFORMATION: pepck flank2 924 bp upstream of PEPCK from
      C.thermocellum plus 60 bp of coding region
<220> FEATURE:
<221> NAME/KEY: misc_feature
<222> LOCATION: (3372)..(3372)
<223> OTHER INFORMATION: deleted in strain YD01
<220> FEATURE:
<221> NAME/KEY: misc_feature
<222> LOCATION: (3449)..(3449)
<223> OTHER INFORMATION: pepck start codon changed to GTG

<400> SEQUENCE: 58

```
tcagacattt gccacgaaca tttctatatc cttgactgag acaaagtaat ttttggatt      60 ttcagggtct atatataccg gaagactggt aatacccttt tcgtgtatta taggttcggg    120
atcaaaccag atattgtcgc tggtaaaaaa gtaaacaat cctgtgtcgg gatctttcca    180
cttgcaggta ataacatatg ggtgcttact gtttactgta tagcttgtgt tcaaagtgat    240
ttcactaatg tctgcgtata ctgtccggcc ggtttccaac aaccgtttgc gaagtctgaa    300
tttcttaaac tgtgatgcgg taaagctaat tccaatgata aaaaatacca atccgattcc    360
aaccaaaaag agatcatcga agacgaaacc catggtttta acgtgcctcg gcttatttgg    420
```

| | |
|---|---|
| gtcataatag acggtgattt tcctgcctac atacatcaaa ggggagtgtg caataatttc | 480 |
| gtagtattct tctccttcca cggaatattt tattaccact tcgtaatgtt tatcaccgtc | 540 |
| aaagtcgcgg taggacttta tatcggtaac aacagcggga tcctcgcgag gccggccagt | 600 |
| attctgacat gggtgtatca ataacccatg cgtttccgta ttgtatcgga atggtttcgg | 660 |
| acagggcggt gggaatagac atggaaaaga ttttttttgcc cgaggatgca ttgataaagt | 720 |
| atttcttttc cgaaagagag gaaaagattc taaagagttt tggaaatact gatgaatatt | 780 |
| gtgtgcagag tacaattcta tggacaagaa aagaggcttt gtcaaaactt tttcgtctgg | 840 |
| gaatgaggat ggattttaaa aagctggata ctttggagga cgaggtggtt tttcaggaaa | 900 |
| caaacagggc gcgtctgttt tcttttatat gcaataatta ctgtatctct ctggcattgc | 960 |
| caggttttaa taaagattaa aattattgac tagaaataaa aaaattgtcc ataatattaa | 1020 |
| tggacaaaaa aacaaagaat tacatcaaag gaagataaaa atactttgtt aaaaaattaa | 1080 |
| ttatttttta tctaaactat tgaaaatgaa aataaaataa tataaaatga atcatagtgc | 1140 |
| aagagatact tgccagagga tgaatatttt actgcattca tgctttatgg cagctaatag | 1200 |
| aggcattaaa ttaaatttta atttacaata ggaggcgata ttaatgaact ttaataaaat | 1260 |
| tgatttagac aattggaaga gaaaagagat atttaatcat tatttgaacc aacaaacgac | 1320 |
| ttttagtata accacagaaa ttgatattag tgttttatac cgaaacataa aacaagaagg | 1380 |
| atataaattt taccctgcat ttattttctt agtgacaagg gtgataaact caaatacagc | 1440 |
| ttttagaact ggttacaata gcgacggaga gttaggttat tgggataagt tagagccact | 1500 |
| ttatacaatt tttgatggtg tatctaaaac attctctggt atttggactc ctgtaaagaa | 1560 |
| tgacttcaaa gagttttatg atttatacct ttctgatgta gagaaatata atggttcggg | 1620 |
| gaaattgttt cccaaaacac ctatacctga aaatgctttt tctctttcta ttattccatg | 1680 |
| gacttcattt actgggttta acttaaatat caataataat agtaattacc ttctacccat | 1740 |
| tattacagca ggaaaattca ttaataaagg taattcaata tatttaccgc tatctttaca | 1800 |
| ggtacatcat tctgtttgtg atggttatca tgcaggattg tttatgaact ctattcagga | 1860 |
| attgtcagat aggcctaatg actggctttt ataataaagg aggtcgacgt catggaaaat | 1920 |
| ttatcaaaag acatcgatga aattttgatc acagaagaag aacttaagga aaagataaaa | 1980 |
| gagcttggga ggcaaatcac aaaagactac aaagggaaaa atttgatgtt ggtaggagtt | 2040 |
| ttaaaaggtg ctttaatgtt tatggctgat tgtcaagac acatagattt gcctttatca | 2100 |
| cttgatttta tggctgtttc cagctatgga agctcaactc attcatcagg aatagtaaag | 2160 |
| ataatcaaag atcttgatat aagcatagaa ggcaaagatg ttctgattgt ggaagacata | 2220 |
| attgacagcg gtttgacttt gtcttactta agggaaactt tacttggaag gaagccaaaa | 2280 |
| agcctgaaaa tatgcacaat attagacaaa ccggagagaa gagaagcatc tgtaaaagtc | 2340 |
| gattatgtag gatttaagat acctgataag tttgtcgtgg gttatggatt ggactttgat | 2400 |
| gaaaagtaca ggaaccttcc ttttataggc gttttgaaac ctgaaatgta cagctaagcc | 2460 |
| cgggcctcga gaaaacaaaa ggctcagtcg gaagactggg ccttttgttt tggtaccgaa | 2520 |
| ttcggtccac ttgcaggtaa taacatatgg gtgcttactg tttactgtat agcttgtgtt | 2580 |
| caaagtgatt tcactaatgt ctgcgtatac tgtccggccg gtttccaaca accgtttgcg | 2640 |
| aagtctgaat tcttaaaact gtgatgcggt aaagctaatt ccaatgataa aaaataccaa | 2700 |
| tccgattcca accaaaaaga gatcatcgaa gacgaaaccc atggttttaa cgtgcctcgg | 2760 |
| cttatttggg tcataataga cggtgatttt cctgcctaca tacatcaaag gggagtgtgc | 2820 |

```
aataatttcg tagtattctt ctccttccac ggaatatttt attaccactt cgtaatgttt      2880
atcaccgtca aagtcgcggt aggactttat atcggtaaca acagcggtgg ttctggcggc      2940
attgcttata aaattgtaat gagaaaggaa aaaagttacg ccgattaaaa tgggaatcag      3000
acctgctgcg gtaaaaacaa ttcccagaat caacacaaca ttttttttca ttattaattt      3060
tatcctccca tataaattgt ttacatttac aaagttattc tatcacaaaa aaagatgtgt      3120
aaaaactata tattaggcaa agtacggtgt ataaaaacaa taataaagca caataatttc      3180
catatgtaat gttgtatgca tataaatgca taaaaatcag atgaattttt gtagaacaaa      3240
acctgcaaaa aacccaaaaa gatttgttga tattttgacg gttttgtgtt agtatgttag      3300
tgaaaaaatt aactaattgc tcgggaagaa aaaatatcca gagtatttt agttttactt       3360 atattgcaaa aatgcaacaa caaaaatgca acaacacaca atgtaatatc ataaaaaaat      3420
aataatatag ttggaaggag aatttctggt gacatcaaca acatgacaa aaaacaaaaa       3480 actgctggat tgggttaagg aaatggct                                         3508
```

<210> SEQ ID NO 59
<211> LENGTH: 2018
<212> TYPE: DNA
<213> ORGANISM: Clostridium thermocellum
<220> FEATURE:
<221> NAME/KEY: misc_feature
<222> LOCATION: (1)..(2018)
<223> OTHER INFORMATION: modified gene for PEPCK and its promoter from
      C.thermocellum strain DSM1313
<220> FEATURE:
<221> NAME/KEY: misc_feature
<222> LOCATION: (1)..(200)
<223> OTHER INFORMATION: DNA sequence from upstream of pepck
<220> FEATURE:
<221> NAME/KEY: misc_feature
<222> LOCATION: (124)..(124)
<223> OTHER INFORMATION: deleted in strain YD01
<220> FEATURE:
<221> NAME/KEY: misc_feature
<222> LOCATION: (201)..(201)
<223> OTHER INFORMATION: pepck start codon changed to GTG

<400> SEQUENCE: 59

```
aaaacccaaa aagatttgtt gatattttga cggttttgtg ttagtatgtt agtgaaaaaa       60
ttaactaatt gctcgggaag aaaaaatatc cagagtattt ttagttttac ttatattgca      120
aaaatgcaac aacaaaaatg caaacaacac aaatgtaata tcataaaaaa ataataatat      180
agttggaagg agaatttctg gtgacatcaa caaacatgac aaaaaacaaa aaactgctgg      240
attgggttaa ggaaatggct gaaatgtgtc agcctgatga aatttattgg tgcgatggtt      300
cggaggaaga aaatgagcgc ttgataaagt tgatggtgga ttcaggtttg gctacgcctt      360
tgaatcctga aaagcgacct ggatgttatc tcttccgcag cgatccgtcc gacgttgccc      420
gtgttgagga cagaactttt attgcatcca aaaccaaaga agatgcagga cctacaaaca      480
actggataga tccggttgag ctcaaggcaa ctatgaaaga gttgtacaag ggttgtatga      540
agggaagaac aatgtatgtt attcctttct ccatgggacc tatcggttca cccatttcaa      600
aaatcggcgt tgaattgacc gacagcccct atgttgttgt taacatgcgc attatgactc      660
gcataggcaa ggctgtgttg gatcagctcg gagaagacgg agattttgta ccttgtctcc      720
actcagtcgg tgctccgctc aaagagggag aaaaggataa aggttggcca tgcgcaccaa      780
tcgaaaagaa atacataagc cacttccccgg aagaaaggac tatatggtca tatggttccg      840
gatacggtgg aaatgcgctt ttaggaaaga aatgctttgc acttcgtatt gcatctgtta      900
```

```
tggcacgtga cgaaggttgg cttgctgaac acatgcttat ccttcgcata acagaccctg    960
aaggaaacaa gacatatgtt acaggtgctt tcccaagcgc atgcggaaag acgaacctgg    1020
ctatgcttat tcctacaatt cccggatgga agttgaaac aatcggtgac gatattgcat     1080
ggatgagatt tggaaaagac ggccgtttgt atgctatcaa ccctgaagca ggattctttg    1140
gtgttgctcc gggtacatcc atggattcaa atccgaacgc aatgcataca attaagaaaa    1200
atactatatt tacaaacgtt gcattgactg atgacggcga tgtttggtgg gaaggcatcg    1260
gaactgaacc gccggctcat ctcatagact ggcagggtaa agactggact cctgattccg    1320
gaactttggc agcacatccc aacgacgtt ttacagcacc tgcaagtcag tgccctgtaa     1380
ttgctcctga atgggaggat ccggaaggtg tgccgatttc agcaatcctt atcggtggac    1440
gccgtccgaa caccattccg cttgttcatg aaagctttga ctggaaccat ggtgtattca    1500
tgggttcaat catgggttct gaaattacgg ctgccgcaat tcaaacaaa atcggacagg     1560 tacgccgtga cccgtttgct atgctgcctt tcataggcta aacgtaaat gactatttgc     1620 agcactggtt gaacatgggt accaagactg acccaagcaa gcttcccaag atattctatg    1680
taaactggtt ccgcaaggac agcaacggta aatggttgtg gcctggatac ggtgaaaaca    1740
gccgtgttct caagtggatt gttgaaagag tcaacggaaa aggtaaagca gtaaagacac    1800
ctataggata tatgcctaca gttgacgcta tcgacacaac cggccttgat gtaagcaaag    1860
aggatatgga agaactcttg agcgttaaca aagaacagtg gctccaggaa gttgagtcaa    1920
taaaagaaca ttataagtca tacggagaaa aactgccgaa agaattgtgg gcacaattgg    1980
aggctcttga caacgtttg aaagagtata acggttaa                             2018
```

<210> SEQ ID NO 60
<211> LENGTH: 605
<212> TYPE: PRT
<213> ORGANISM: Clostridium thermocellum
<220> FEATURE:
<221> NAME/KEY: Misc_Feature
<222> LOCATION: (1)..(605)
<223> OTHER INFORMATION: protein sequence of C.thermocellum pepck with
      modified start codon

<400> SEQUENCE: 60

```
Val Thr Ser Thr Asn Met Thr Lys Asn Lys Lys Leu Leu Asp Trp Val
1               5                   10                  15

Lys Glu Met Ala Glu Met Cys Gln Pro Asp Glu Ile Tyr Trp Cys Asp
            20                  25                  30

Gly Ser Glu Glu Asn Glu Arg Leu Ile Lys Leu Met Val Asp Ser
        35                  40                  45

Gly Leu Ala Thr Pro Leu Asn Pro Glu Lys Arg Pro Gly Cys Tyr Leu
    50                  55                  60

Phe Arg Ser Asp Pro Ser Asp Val Ala Arg Val Glu Asp Arg Thr Phe
65                  70                  75                  80

Ile Ala Ser Lys Thr Lys Glu Asp Ala Gly Pro Thr Asn Asn Trp Ile
                85                  90                  95

Asp Pro Val Glu Leu Lys Ala Thr Met Lys Glu Leu Tyr Lys Gly Cys
            100                 105                 110

Met Lys Gly Arg Thr Met Tyr Val Ile Pro Phe Ser Met Gly Pro Ile
        115                 120                 125

Gly Ser Pro Ile Ser Lys Ile Gly Val Glu Leu Thr Asp Ser Pro Tyr
    130                 135                 140
```

```
Val Val Val Asn Met Arg Ile Met Thr Arg Ile Gly Lys Ala Val Leu
145                 150                 155                 160

Asp Gln Leu Gly Glu Asp Gly Asp Phe Val Pro Cys Leu His Ser Val
            165                 170                 175

Gly Ala Pro Leu Lys Glu Gly Lys Asp Lys Gly Trp Pro Cys Ala
            180                 185                 190

Pro Ile Glu Lys Lys Tyr Ile Ser His Phe Pro Glu Arg Thr Ile
            195                 200                 205

Trp Ser Tyr Gly Ser Gly Tyr Gly Gly Asn Ala Leu Leu Gly Lys Lys
            210                 215                 220

Cys Phe Ala Leu Arg Ile Ala Ser Val Met Ala Arg Asp Glu Gly Trp
225                 230                 235                 240

Leu Ala Glu His Met Leu Ile Leu Arg Ile Thr Asp Pro Gly Asn
            245                 250                 255

Lys Thr Tyr Val Thr Gly Ala Phe Pro Ser Ala Cys Gly Lys Thr Asn
            260                 265                 270

Leu Ala Met Leu Ile Pro Thr Ile Pro Gly Trp Lys Val Glu Thr Ile
            275                 280                 285

Gly Asp Asp Ile Ala Trp Met Arg Phe Gly Lys Asp Gly Arg Leu Tyr
290                 295                 300

Ala Ile Asn Pro Glu Ala Gly Phe Phe Gly Val Ala Pro Gly Thr Ser
305                 310                 315                 320

Met Asp Ser Asn Pro Asn Ala Met His Thr Ile Lys Lys Asn Thr Ile
                325                 330                 335

Phe Thr Asn Val Ala Leu Thr Asp Asp Gly Asp Val Trp Trp Glu Gly
            340                 345                 350

Ile Gly Thr Glu Pro Pro Ala His Leu Ile Asp Trp Gln Gly Lys Asp
            355                 360                 365

Trp Thr Pro Asp Ser Gly Thr Leu Ala Ala His Pro Asn Gly Arg Phe
            370                 375                 380

Thr Ala Pro Ala Ser Gln Cys Pro Val Ile Ala Pro Glu Trp Glu Asp
385                 390                 395                 400

Pro Glu Gly Val Pro Ile Ser Ala Ile Leu Ile Gly Gly Arg Arg Pro
                405                 410                 415

Asn Thr Ile Pro Leu Val His Glu Ser Phe Asp Trp Asn His Gly Val
            420                 425                 430

Phe Met Gly Ser Ile Met Gly Ser Glu Ile Thr Ala Ala Ala Ile Ser
            435                 440                 445

Asn Lys Ile Gly Gln Val Arg Arg Asp Pro Phe Ala Met Leu Pro Phe
450                 455                 460

Ile Gly Tyr Asn Val Asn Asp Tyr Leu Gln His Trp Leu Asn Met Gly
465                 470                 475                 480

Thr Lys Thr Asp Pro Ser Lys Leu Pro Lys Ile Phe Tyr Val Asn Trp
            485                 490                 495

Phe Arg Lys Asp Ser Asn Gly Lys Trp Leu Trp Pro Gly Tyr Gly Glu
            500                 505                 510

Asn Ser Arg Val Leu Lys Trp Ile Val Glu Arg Val Asn Gly Lys Gly
            515                 520                 525

Lys Ala Val Lys Thr Pro Ile Gly Tyr Met Pro Thr Val Asp Ala Ile
            530                 535                 540

Asp Thr Thr Gly Leu Asp Val Ser Lys Glu Asp Met Glu Glu Leu Leu
545                 550                 555                 560

Ser Val Asn Lys Glu Gln Trp Leu Gln Glu Val Glu Ser Ile Lys Glu
```

|   |   |   |
|---|---|---|
| 565 | 570 | 575 |

His Tyr Lys Ser Tyr Gly Glu Lys Leu Pro Lys Glu Leu Trp Ala Gln
    580                 585                 590

Leu Glu Ala Leu Glu Gln Arg Leu Lys Glu Tyr Asn Gly
    595                 600             605

```
<210> SEQ ID NO 61
<211> LENGTH: 3734
<212> TYPE: DNA
<213> ORGANISM: Clostridium thermocellum
<220> FEATURE:
<221> NAME/KEY: misc_feature
<222> LOCATION: (1)..(3734)
<223> OTHER INFORMATION: plasmid insert for deletion of the gene for
      malic enzyme and part of the the gene for malate dehydrogenase
      from C.thermocellum strain DSM1313
<220> FEATURE:
<221> NAME/KEY: misc_feature
<222> LOCATION: (1)..(605)
<223> OTHER INFORMATION: fragment1 internal fragment of gene for malic
      enzyme from C.thermocellum
<220> FEATURE:
<221> NAME/KEY: promoter
<222> LOCATION: (623)..(1270)
<223> OTHER INFORMATION: gapD_promoter sequence upstream of gapD gene
      from C.thermocellum
<220> FEATURE:
<221> NAME/KEY: misc_feature
<222> LOCATION: (2553)..(3254)
<223> OTHER INFORMATION: mae_upstream_flank sequence upstream of malic
      enzyme gene from C.thermocellum
<220> FEATURE:
<221> NAME/KEY: misc_feature
<222> LOCATION: (3255)..(3734)
<223> OTHER INFORMATION: mae_downstream_flank seq downstream of malic
      enzyme gene from C.thermocellum
```

<400> SEQUENCE: 61

| | | | | | |
|---|---|---|---|---|---|
| ggtacagccg | ttgttactgt | tgcagcaatg | atcaatgcat | taaagcttgt | caacaagaaa |    60 |
| atcgaggata | tagaagttgt | tgtaaacggt | tcaggtgctg | ccggcatagc | tgtaacaaga |   120 |
| ctgctcatga | gtatggggct | taagaaagtt | atcctttgcg | ataccaaagg | tgcaatttat |   180 |
| gatggaagag | acaacttaaa | cagtgaaaaa | gccctgattg | ctaaaatctc | gaacctcgag |   240 |
| aaaaagaaag | gtactcttga | agatgtaatc | aagggagctg | acgtattcat | cggtctttcc |   300 |
| gttccaggaa | cagttacaaa | ggatatggta | aaatccatgg | caaaggatcc | gattatcttt |   360 |
| gctatggcaa | atcctactcc | tgaaataatg | cctgatgaag | caaagaagc | aggagcaaag |   420 |
| gtagtgggta | ccggaagatc | cgacttcccg | aaccagataa | acaacgttct | tgcgttcccc |   480 |
| ggaatattca | gaggtgcgct | tgatgtaaga | gcaagagata | tcaatgatga | aatgaagata |   540 |
| gccgctgcaa | aagcaatagc | ttctctggta | agcgatgaag | agctcaatcc | tgacttcatt |   600 |
| cttccgatcc | tcgcgaggcc | ggccagtatt | ctgacatggg | tgtatcaata | acccatgcgt |   660 |
| ttccgtattg | tatcggaatg | gtttcggaca | gggcggtggg | aatagacatg | aaaagattt |   720 |
| ttttgcccga | ggatgcattg | ataaagtatt | tcttttccga | aagagaggaa | aagattctaa |   780 |
| agagttttgg | aaatactgat | gaatattgtg | tgcagagtac | aattctatgg | acaagaaaag |   840 |
| aggctttgtc | aaaactttt | cgtctgggaa | tgaggatgga | ttttaaaaag | ctggatactt |   900 |
| tggaggacga | ggtggttttt | caggaaacaa | acagggcgcg | tctgttttct | tttatatgca |   960 |
| ataattactg | tatctctctg | gcattgccag | gttttaataa | agattaaaat | tattgactag |  1020 |
| aaataaaaaa | attgtccata | atattaatgg | acaaaaaaac | aaagaattac | atcaaaggaa |  1080 |
| gataaaaata | ctttgttaaa | aaattaatta | tttttatct | aaactattga | aaatgaaaat |  1140 |

```
aaaataatat aaaatgaatc atagtgcaag agatacttgc cagaggatga atattttact    1200
gcattcatgc tttatggcag ctaatagagg cattaaatta aattttaatt tacaatagga    1260
ggcgatatta atgaacttta ataaaattga tttagacaat tggaagagaa aagagatatt    1320
taatcattat ttgaaccaac aaacgactttt tagtataacc acagaaattg atattagtgt    1380
tttataccga aacataaaac aagaaggata taaattttac cctgcattta ttttcttagt    1440
gacaagggtg ataaactcaa atacagcttt tagaactggt tacaatagcg acggagagtt    1500
aggttattgg gataagttag agccacttta tacaattttt gatggtgtat ctaaaacatt    1560
ctctggtatt tggactcctg taaagaatga cttcaaagag ttttatgatt tatacctttc    1620
tgatgtagag aaatataatg gttcggggaa attgtttccc aaaacaccta tacctgaaaa    1680 tgcttttttct ctttctatta ttccatggac ttcattact gggtttaact taaatatcaa     1740
taataatagt aattaccttc tacccattat tacagcagga aaaattcatta ataaaggtaa    1800 ttcaatatat ttaccgctat ctttacaggt acatcattct gtttgtgatg ttatcatgc     1860 aggattgttt atgaactcta ttcaggaatt gtcagatagg cctaatgact ggcttttata    1920 ataaggagg tcgacgtcat ggaaaattta tcaaaagaca tcgatgaaat tttgatcaca     1980
gaagaagaac ttaaggaaaa gataaaagag cttgggaggc aaatcacaaa agactacaaa    2040
gggaaaaatt tgatgttggt aggagtttta aaaggtgctt taatgtttat ggctgatttg    2100
tcaagacaca tagatttgcc tttatcactt gattttatgg ctgtttccag ctatggaagc    2160
tcaactcatt catcaggaat agtaaagata atcaaagatc ttgatataag catagaaggc    2220
aaagatgttc tgattgtgga agacataatt gacagcggtt tgactttgtc ttacttaagg    2280
gaaactttac ttggaaggaa gccaaaaagc ctgaaaatat gcacaatatt agacaaaccg    2340
gagagaagag aagcatctgt aaaagtcgat tatgtaggat ttaagatacc tgataagttt    2400
gtcgtgggtt atggattgga ctttgatgaa aagtacagga accttccttt tataggcgtt    2460
ttgaaacctg aaatgtacag ctaagcccgg gcctcgagaa aacaaaaggc tcagtcggaa    2520
gactgggcct tttgttttgg taccgaattc ggtaggcgag gctatggata ttaaccacgg    2580
tcttccattt atgggacaga tgtcattgta tgccggtgat tattccgacg ttaaagactg    2640
tgatgttatc gtagtcacgg ccggagccaa cagaaaacct ggtgaaacac gtcttgacct    2700
tgcaaagaaa aacgttatga ttgcaaaaga agtaactcaa aacatcatga agtattacaa    2760
ccatggtgta atacttgtag tatccaatcc tgttgacatt ataacttata tgatccaaaa    2820
atggtcaggc ctccctgtgg gaaaagttat aggttcaggt accgtacttg acagtatcag    2880
attcagatac ttgttaagcg aaaaattggg cgttgacgta aagaatgtac acggctacat    2940
aataggcgaa cacggtgatt cacagcttcc gttgtggagc tgcacacata tcgccggtaa    3000
aaatatcaac gaatatatcg atgatccgaa atgcaatttc acagaagaag acaagaaaaa    3060
aatcgctgaa gatgttaaaa ctgcgggtgc aaccattatc aagaacaaag gtgcaacata    3120
ctatggtatt gcagtttcaa tcaacacaat agttgaaaca ctccttaaga atcagaatac    3180
aataagaacc gtaggaaccg ttataaacgg catgtatgga atagaagatg ttgcaataag    3240
ccttccatcc atcgaactaa aatcaagata tatgatacta aataaaaaa gacaggcaaa     3300 ggttttactc ctttacctgt cttttttatt taatctcctt tttaaaacct cttttctttt    3360
ggttatcgaa tatccaaaat atcccaatgt cttttcaaa gaccagtatt ctccatggga     3420
atagcatata agatccgctt tctccatgca cagcctccct ttcttgtcaa taagggattc    3480
```

```
atccacactt acggcttcaa tctgtgctat gaacatgtca tgagagccca attcaattat    3540
atccttcacc gtgcattcaa tattcacagg actttccttt atcattggta catccactac    3600
agaggccttc tcctgtgtca gcttgagaac ttcaaactta tcaacatccc tgccggactt    3660
tacaccgcaa aaatcagcgg caaatgccag ctttctggtt gtaagattta ttacaaactg    3720 tccttttttcc ttta                                                     3734
```

<210> SEQ ID NO 62
<211> LENGTH: 1344
<212> TYPE: DNA
<213> ORGANISM: Clostridium thermocellum
<220> FEATURE:
<221> NAME/KEY: Misc_Feature
<222> LOCATION: (1)..(1344)
<223> OTHER INFORMATION: sequence eliminated from C.thermocellum strain
      DSM1313 in the creation of strain YDO2
<220> FEATURE:
<221> NAME/KEY: misc_feature
<222> LOCATION: (1)..(119)
<223> OTHER INFORMATION: end of malate dehydrogenase gene
<220> FEATURE:
<221> NAME/KEY: gene
<222> LOCATION: (172)..(1344)
<223> OTHER INFORMATION: Clo1313_1879

<400> SEQUENCE: 62

```
taaattccga aggtgttcag gaagttctcc aatttaatct gactcctgaa gaagaagaag      60
ctttaagatt ctcagcggag caggttaaaa aagtattgaa cgaagttaag aatttataat     120
tgtgcattaa tatcgcagat atttaataat ataatttgga ggtagaatca aatggattac     180
agaaaagaat cactaaggct tcacggtgag tggaagggta aaattgaggt tatacacaag     240
gtacctgttt caaccaagga agagttgtcg cttgcttata caccgggtgt tgcagaacca     300
tgtcttgcaa ttcagaaaga tgttaatctt tcttatgaat atacaagacg ttggaacctg     360
gtagcggtta ttaccgacgg tacggcggtt ttagggctcg gagacatagg acctgaagcc     420
ggaatgcctg ttatggaagg taaatgcgta ctcttcaaga ggtttggtga tgtggacgca     480
tttccgctct gtatcaaatc aaaagacgta gatgaaattg taaagacaat caagctcatc     540
tccggaagct ttggcggtat aaacctcgaa gatatatccg ctccgagatg ctttgaaata     600
gaaagaagac tcaaagagga atgtgacatt ccaatattcc atgatgacca gcacggtaca     660
gccgttgtta ctgttgcagc aatgatcaat gcattaaagc ttgtcaacaa gaaaatcgag     720
gatatagaag ttgttgtaaa cggttcaggt gctgccggca tagctgtaac aagactgctc     780
atgagtatgg ggcttaagaa agttatcctt tgcgatacca aaggtgcaat ttatgatgga     840
agagacaact taaacagtga aaaagccctg attgctaaaa tctcgaacct cgagaaaaag     900
aaaggtactc ttgaagatgt aatcaaggga gctgacgtat tcatcggtct ttccgttcca     960
ggaacagtta caaaggatat ggtaaaatcc atggcaaagg atccgattat ctttgctatg    1020
gcaaatccta ctcctgaaat aatgcctgat gaagcaaaag aagcaggagc aaaggtagtg    1080
ggtaccggaa gatccgactt cccgaaccag ataaacaacg ttcttgcgtt ccccggaata    1140
ttcagaggtg cgcttgatgt aagagcaaga gatatcaatg atgaaatgaa gatagccgct    1200
gcaaaagcaa tagcttctct ggtaagcgat gaagagctca atcctgactt cattcttccg    1260
ctcccatttg acccaagagt cggaaaaaca gttgctgcag cagttgctga agcagcaaga    1320
aaaaccggag ttgcaagaat ataa                                          1344
```

<210> SEQ ID NO 63

<211> LENGTH: 3474
<212> TYPE: DNA
<213> ORGANISM: Clostridium thermocellum
<220> FEATURE:
<221> NAME/KEY: Misc_Feature
<222> LOCATION: (1)..(3474)
<223> OTHER INFORMATION: plasmid insert for deletion of the ppdk gene from C.thermocellum strain 1313
<220> FEATURE:
<221> NAME/KEY: misc_feature
<222> LOCATION: (1)..(549)
<223> OTHER INFORMATION: ppdk_internal internal fragment of ppdk gene from C.thermocellum
<220> FEATURE:
<221> NAME/KEY: promoter
<222> LOCATION: (550)..(1077)
<223> OTHER INFORMATION: gapD_promoter sequence upstream of gapD gene from C.thermocellum
<220> FEATURE:
<221> NAME/KEY: misc_feature
<222> LOCATION: (1078)..(1728)
<223> OTHER INFORMATION: chlormaphenicol acetyl transferase
<220> FEATURE:
<221> NAME/KEY: misc_feature
<222> LOCATION: (1744)..(2298)
<223> OTHER INFORMATION: hypoxanthine phosporibosyl transferase from T.saccharolyticum
<220> FEATURE:
<221> NAME/KEY: misc_feature
<222> LOCATION: (2433)..(2954)
<223> OTHER INFORMATION: ppdk_upstream 460 bp upstream of ppdk and 60 bp of coding sequence
<220> FEATURE:
<221> NAME/KEY: misc_feature
<222> LOCATION: (2955)..(3474)
<223> OTHER INFORMATION: ppdk_downstream 100 bp of the 3'end of ppdk and 400 bp downstream

<400> SEQUENCE: 63

```
tcagcgatgt tgtcatggag gtggaaaagt ccaagtttga agctattctt gatgctgtga      60
aagaagaaaa caactgtgaa atgactgcg  acctttctgc cgaaaattta aggaagtag      120
tcagaagata caaggagctg ttcaagaaag aaaagggatt tgattttccg caggatccga     180
aaacacagtt gatggaagcc gtaaaagccg ttttccgttc atgggaaaat ccaagggcta     240
ttgtatatag aagattaaat gacatccccg gcgactgggg tactgcagtt aacgttcagg     300
aaatggttta tggaaatatg ggaaatgatt cgggtacggg agttgccttt acaaggaacc     360
cggctacggg agaaaagaag ctttatggtg aattccttat gaatgcccag ggagaagacg     420
ttgttgcagg tatcagaact ccccagtcaa ttgaccagct gaaagaagta atgcctgatg     480
tatacaatca gtttgtggag atagccgaaa aacttgaaag acattataga gatatgcagg     540
atatggagtg tatttctttt ccgaaagaga ggaaaagatt ctaaagagtt ttggaaatac     600
tgatgaatat tgtgtgcaga gtacaattct atggacaaga aaagaggctt tgtcaaaact     660
ttttcgtctg ggaatgagga tggatttttaa aaagctggat actttggagg acgaggtggt     720
ttttcaggaa acaaacaggg cgcgtctgtt ttcttttata tgcaataatt actgtatctc     780
tctggcattg ccaggtttta ataaagatta aaattattga ctagaaataa aaaaattgtc     840
cataatatta atggacaaaa aaacaaagaa ttacatcaaa ggaagataaa aatactttgt     900
taaaaaatta attattttt  atctaaacta ttgaaaatga aaataaaata atataaaatg     960
aatcatagtg caagagatac ttgccagagg atgaatattt tactgcattc atgctttatg    1020
gcagctaata gaggcattaa attaaatttt aatttacaat aggaggcgat attaatgatg    1080
aactttaata aaattgattt agacaattgg aagagaaaag atatttaa  tcattatttg    1140
aaccaacaaa cgacttttag tataaccaca gaaattgata ttagtgtttt ataccgaaac    1200
```

```
ataaaacaag aaggatataa attttaccct gcatttattt tcttagtgac aagggtgata    1260
aactcaaata cagcttttag aactggttac aatagcgacg gagagttagg ttattgggat    1320
aagttagagc cactttatac aattttttgat ggtgtatcta aaacattctc tggtatttgg   1380
actcctgtaa agaatgactt caaagagttt tatgatttat accttctga tgtagagaaa     1440 tataatggtt cggggaaatt gtttcccaaa acacctatac ctgaaaatgc tttttctctt    1500
tctattattc catggacttc atttactggg tttaacttaa atatcaataa taatagtaat    1560
taccttctac ccattattac agcaggaaaa ttcattaata aggtaattc aatatattta     1620 ccgctatctt tacaggtaca tcattctgtt tgtgatggtt atcatgcagg attgtttatg    1680
aactctattc aggaattgtc agataggcct aatgactggc ttttataaag ggaggaagga    1740
tgtatgataa atcaaattaa agaaattttg gttaccagag aggaacttaa aaacaacgct    1800
aaagagttgg gaaagaggat tccagtgac tatgaaggaa aagagcttgt cctgataggg     1860
gtgttaaaag gaggagtggt attttttgcc gacttaataa gggaaataac catacccatt    1920
gatgtggatt tcatatcggt gtcaagttac ggcaattcca ccaaatcatc ggggttgtg     1980 cgtataataa aagacatcga tatagatata accaacaagc atgtccttat cgttgaagac    2040
ttggtggata caggtcttac gctgcattat ctgaaaagca tgtttgaagc cagaggaccc    2100
aaagatgtaa aatatgcac cgcccttgac aaaccgtcaa ggagaaaggt tgatttggaa     2160
atagattata aggtatcac ataccggat aagtttgtgg tgggctatgg attggattat      2220
gcggaaaaat acagaaatct cccggatgtg tgcgtgctgg attcgtctgt ttatacggac    2280
aaagaagata tggactaaaa aatatacaaa ggtttcttgt gtttttaata ccgttatgtt    2340
aatataatgt aatatatatt ttataataat atgtatgaga gatagtgttt tgctatattg    2400
ctataaagaa tgaggaggga actagttgaa gctgcttgcg atcctaagtc ttcatagtga    2460
aagtcgccac gggcagccga aaagaggat gtaacaatga agcattgaca tgaagcgata     2520
acaagggaaa atttatatta attcaatgtt attatataac aaaattgtga ttttgtaaag    2580
atgtttaatc tgcttcaa acgttgtatg aaattatatt tttttgggta atttataaat      2640
atgtgtccaa gaaattttt ctaaaaagaa aaattttttt gaacttgagg gttacaaaaa     2700
ggaatattgc atattttagc aaaaataata atgaaaaata ctattattat gttataattt    2760
taaatgagtt ggtatgaatt tattcctgac aagtctttt tcaaacttca agcgcttatt    2820
taggaaagta tttgcgttta tatgctttcc tacatacata aagaaaaaat aaataaatgg    2880
gaggtttttt tatggcaaag tatgtgtatt tgtttagtga aggcaatgca tcaatgagag    2940
acctgcttgg aggagtatca tgctctccgt tccgtgtgcc gattgcaagg cttgcagcgg    3000
ctcaggcaag agtaaatgaa ataaaaggta caaggatttt gggacagaaa taataaggac    3060
agaaataata aaaaataat aaatagcaaa aggtatatat taacacccta tcatgtaaaa     3120
gtggtagggt gtttttttaa atacatattt tttatgaata ttaaaagctt aagaagtgtt    3180
tggtagcagg aaaaagcaat aacaaaaata ttaaaaaata tttgactcaa tctcaagcat    3240 ttttttacgtt tttttgcctg acgggggaag aattttttacg cttttgctgg gactgttttt   3300
ttaccttgcc aagtatatat aaaataaatt aataaaagtt gttataaaca gtttatctaa    3360
aaatagggaa agtcagcttc cttatcttaa gaccttttga gatttacatt gaatgataga    3420
aatgttataa tttatttgta ttctgtcaat tttaacgtcc aggttgcatg gctt          3474
```

<210> SEQ ID NO 64

<211> LENGTH: 2490
<212> TYPE: DNA
<213> ORGANISM: Clostridium thermocellum
<220> FEATURE:
<221> NAME/KEY: Misc_Feature
<222> LOCATION: (1)..(2490)
<223> OTHER INFORMATION: DNA sequence deleted from the ppdk gene in
      C.thermocellum to make strain M1631

<400> SEQUENCE: 64

| | | | | | |
|---|---|---|---|---|---|
| aaaggtgcca | atcttgcaga | aatgacaagt | ttgggacttc | cggtacccag | aggttttacc | 60 |
| attaccacgg | aagcttgtac | acgctactat | caagatggaa | aagtcattgc | caaggaaata | 120 |
| gaagatgaaa | tatacagaac | tatggagaag | cttgaagaga | ttgtcgggaa | gaaattcggt | 180 |
| gacccatcaa | atccgtttct | tgtttccgtt | cgttccggtg | ccagagtatc | aatgcccggt | 240 |
| atgatggata | ccatattaaa | tctcggactt | aatgatgaag | ttgttgtagg | tcttgcaaag | 300 |
| cttaccaata | tgaaagatt | cgcatatgac | agctatagaa | gatttattca | aatgttcagc | 360 |
| gatgttgtca | tggaggtgga | aaagtccaag | tttgaagcta | ttcttgatgc | tgtgaaagaa | 420 |
| gaaaacaact | gtgaaaatga | ctgcgacctt | tctgccgaaa | atttaaagga | agtagtcaga | 480 |
| agatacaagg | agctgttcaa | gaagaaaag | ggatttgatt | ttccgcagga | tccgaaaaca | 540 |
| cagttgatgg | aagccgtaaa | agccgttttc | cgttcatggg | aaaatccaag | ggctattgta | 600 |
| tatagaagat | taaatgacat | ccccggcgac | tggggtactg | cagttaacgt | tcaggaaatg | 660 |
| gtttatggaa | atatgggaaa | tgattcgggt | acgggagttg | cctttacaag | gaacccggct | 720 |
| acgggagaaa | agaagcttta | tggtgaattc | cttatgaatg | cccagggaga | agacgttgtt | 780 |
| gcaggtatca | gaactcccca | gtcaattgac | cagctgaaag | aagtaatgcc | tgatgtatac | 840 |
| aatcagtttg | tggagatagc | cgaaaaactt | gaaagacatt | atagagatat | gcaggatatg | 900 |
| gagtttacaa | ttgaaagagg | aaaactcttc | atgctccaga | caagaaacgg | taaaaggact | 960 |
| gctgcggctg | ctttaaaaat | agctgttgat | ttggtaaatg | agggaatggt | cacaaaagaa | 1020 |
| gaagcaattt | taaaagtcga | cccgaaacag | cttgatacac | tgctccatcc | aaatttcgaa | 1080 |
| ccttcagcgc | tgaaaaatgc | aaaacctata | gcaagggat | tgccggcttc | accgggagct | 1140 |
| gctaccggaa | agatttactt | tagagccgag | gatgcggtgg | aagcggccaa | aaacggagaa | 1200 |
| aaagacatca | ttcttgtaag | acttgaaact | tcacccgaag | atattgaggg | tatgcatgta | 1260 |
| tccaaaggaa | tacttacagg | ccgtggtgga | atgacatctc | atgctgcagt | tgttgcacgc | 1320 |
| ggtatgggta | cttgctgcgt | tgccggctgc | agtgaaataa | gaataaatga | ggaagagaaa | 1380 |
| tactttgtag | ataaaaacgg | aaagaaatat | gttgagggtg | attggatttc | ccttgacggt | 1440 |
| tccacaggta | atgtttatgg | ggaaaagctt | cctacagtgg | agcctgaaat | gaccggcgac | 1500 |
| tttgccacac | ttatgcagtg | ggccgatgaa | atcagaactc | ttaagattag | aaccaatgcc | 1560 |
| gatactccgg | ctgatgccat | ccaggcaaga | aagttcggtg | cggaaggtat | cggactttgc | 1620 |
| cgtacggagc | atatgttctt | cgattctgac | agaattccgg | caatgagaga | atgatagtt | 1680 |
| gcaagaaccg | aagaacagag | aagaaaggct | ttggataaac | tcctgccgat | gcagagaaaa | 1740 |
| gattttgaag | aactgtttac | tgcaatggaa | ggctatcctg | tgacgatcag | attcctggat | 1800 |
| cctccgcttc | atgagttcct | gccccaggag | gatgaagaca | tagaagcctt | ggcaaaagaa | 1860 |
| atgggaatta | ctttcgatga | actgaaagca | atagtaaccg | ggcttcatga | gttcaatcct | 1920 |
| atgatgggac | acagggatg | ccgtcttgca | gtcacatatc | cggaaattgc | ggaaatgcag | 1980 |
| acgagagcgg | ttattgaagc | tgctatcaac | gtgagcagga | agaatataaa | agttgtgcct | 2040 |

| | |
|---|---:|
| gaaattatga ttccgttggt aggcgatgtc aaggagctga atatgtcaa ggacgtagtt | 2100 |
| gtcagaacag ccaatgaatt gattgaaaaa tccggtgtga agattgaata taaagtcgga | 2160 |
| accatgatag aaattccaag ggcggccatt actgccgatg aaattgcaaa agaagctgaa | 2220 |
| ttcttctcct ttggaaccaa cgacctgacc cagatgactt ttggattcag ccgtgacgat | 2280 |
| gcaggcaagt tccttgaaga atactacaac aagaagatat acgagttcga tccttttgca | 2340 |
| aaactggatc aggatggagt ggggaaactg gttgaaatgg ctgcgaagct tggaagacaa | 2400 |
| acaagaccgg atattaagct tggtatatgc ggtgaacatg gcggagatcc gtcgtccatt | 2460 |
| gagttctgcc accaaattgg gctgaactat | 2490 |

<210> SEQ ID NO 65
<211> LENGTH: 8961
<212> TYPE: DNA
<213> ORGANISM: Artificial Sequence
<220> FEATURE:
<223> OTHER INFORMATION: plasmid pYD10

<400> SEQUENCE: 65

| | |
|---|---:|
| ttaccaatgc ttaatcagtg aggcacctat ctcagcgatc tgtctatttc gttcatccat | 60 |
| agttgcctga ctccccgtcg tgtagataac tacgatacgg gagggcttac catctggccc | 120 |
| cagtgctgca atgataccgc gagacccacg ctcaccggct ccagatttat cagcaataaa | 180 |
| ccagccagcc ggaagggccg agcgcagaag tggtcctgca actttatccg cctccatcca | 240 |
| gtctattaat tgttgccggg aagctagagt aagtagttcg ccagttaata gtttgcgcaa | 300 |
| cgttgttgcc attgctgcag gcatcgtggt gtcacgctcg tcgtttggta tggcttcatt | 360 |
| cagctccggt tcccaacgat caaggcgagt tacatgatcc cccatgttgt gcaaaaaagc | 420 |
| ggttagctcc ttcggtcctc cgatcgttgt cagaagtaag ttggccgcag tgttatcact | 480 |
| catggttatg gcagcactgc ataattctct tactgtcatg ccatccgtaa gatgcttttc | 540 |
| tgtgactggt gagtactcaa ccaagtcatt ctgagaatag tgtatgcggc gaccgagttg | 600 |
| ctcttgcccg gcgtcaacac gggataatac cgcgccacat agcagaactt taaaagtgct | 660 |
| catcattgga aaacgttctt cggggcgaaa actctcaagg atcttaccgc tgttgagatc | 720 |
| cagttcgatg taacccactc gtgcacccaa ctgatcttca gcatctttta ctttcaccag | 780 |
| cgtttctggg tgagcaaaaa caggaaggca aaatgccgca aaaaagggaa taagggcgac | 840 |
| acggaaatgt tgaatactca tactcttcct ttttcaatat tattgaagca tttatcaggg | 900 |
| ttattgtctc atgagcggat acatatttga atgtatttag aaaaataaac aaaagagttt | 960 |
| gtagaaacgc aaaaaggcca tccgtcagga tggccttctg cttaatttga tgcctggcag | 1020 |
| tttatgcgg gcgtcctgcc cgccaccctc cgggccgttg cttcgcaacg ttcaaatccg | 1080 |
| ctcccggcgg atttgtccta ctcaggagag cgttcaccga caaacaacag ataaaacgaa | 1140 |
| aggcccagtc tttcgactga gcctttcgtt ttatttgatg cctggcagtt ccctactctc | 1200 |
| gcatgggag accccacact accatcggcg ctacggcgtt tcacttctga gttcggcatg | 1260 |
| gggtcaggtg gaccaccgc gctactgccg ccaggcaaat tctgttttat cagaccgctt | 1320 |
| ctgcgttctg atttaatctg tatcaggctg aaaatcttct ctcatccgcc aaaacagcca | 1380 |
| agctttaatt actgtatctc tctggcattg ccaggtttta ataaagatta aaattattga | 1440 |
| ctagaaataa aaaaattgtc cataatatta atgacaaaa aaacaaagaa ttacatcaaa | 1500 |
| ggaagataaa aatactttgt taaaaaatta attatttttt atctaaacta ttgaaaatga | 1560 |
| aaataaaata atataaaatg aatcatagtg caagagatac ttgccagagg atgaatattt | 1620 |

```
tactgcattc atgctttatg gcagctaata gaggcattaa attaaatttt aatttacaat    1680
aggaggcgat attaatgcag tcattcaagc gaatttcctg ttgaaatgct tgaaaaactg    1740
atacaatcac ctgaaatgta gagatttatt gttaataaat taacacggag gtgtttatta    1800
tggcaacgac aaaaacggaa ttagacgttc agaagcagat agatctactt gtgtcaagag    1860
cacaagaggc tcagaaaaaa ttcatgtctt acacgcaaga gcaaatcgac gcaatagtta    1920
aggcaatggc tttagcaggc gttgacaaac acgtagagct ggcaaagatg gcgtacgaag    1980
agacaaaaat gggtgtatac gaagataaga taacaaaaaa tctcttcgca acagagtacg    2040
tgtaccacga cataaaaaat gaaaagactg taggaatcat aaacgagaac atagaagaaa    2100
actacatgga agtggcagaa ccgataggcg taattgccgg tgtcacacct gtcacaaacc    2160
caacatctac cacgatgttt aaatgcttaa tatccataaa gacgcgaaat cctataatat    2220
tcagcttcca tccaaaggca ataaagtgca gcatcgcagc agccaaagtg atgtatgaag    2280
ctgcactaaa ggcaggcgca cctgaaggat gcataggatg gatagaaacg ccatcaattg    2340
aggccacaca gcttctcatg acacatccag gcgtatcgct gatccttgca acgggcggtg    2400
caggaatggt aaaagcggca tacagctcag gaaaaccggc attaggcgta ggtcctggca    2460
atgtgccatg ctacatcgaa aaatcagcaa acataaagag ggctgtatcg gatctcatac    2520
taagcaagac atttgacaat ggagtaatat gcgcatcaga gcaggccgta ataatagacg    2580
aggaaatagc agatgaagtc aaaaagctta tgaaagaata cggctgctac ttcttaaaca    2640
aagatgaaat aaagaagctt gagaaatttg caattgatga gcaaagctgc gccatgagcc    2700
ctgcagtggt aggtcagcca gcggcgaaga ttgctgaaat ggcaggcttc aaagtccccg    2760
aaggcacaaa gatattagtg gcagagtacg aaggagtagg tccaaaatat cctctatcaa    2820
gggagaaact aagcccgatt cttgcttgct acaccgtcaa agactacaat gaaggaatca    2880
aaaagtgcga ggaaatgact gaattcggag gtttaggcca ctctgctgta atacactctg    2940
aaaatcaaaa cgtcataaat gaatttgcaa ggcgagtccg cacaggaaga cttatcgtaa    3000
attcaccatc atcacaggga gcaataggag atatatacaa tacaaacacg ccatcactta    3060
cattaggctg tggttctatg ggaagaaact caacgacaga caatgtaagc gtcaagaacc    3120
ttttgaatat taagcgtgtc gtgataagga aggatagaat gaaatggttc aagattccac    3180
cgaagattta ctttgaaagc gggtcactcc agtacctgtg caaagtcaaa agaaaaaaag    3240
cgtttatcgt cacagatcca ttcatggtta agcttggctt cgtagacaaa gtgacatatc    3300
aattagacaa agcaaacatc gaatacgaaa tattctcaga agtagagcca gatccatctg    3360
ttgacacagt catgaacggc gtaaaaataa tgaattcgta caatcctgac ttaataatcg    3420
ctgtaggcgg tggctctgca atagacgcag caaagggaat gtggcttttc tacgaatatc    3480
ctgatacaga gtttgaaaca ttgaggctta aatttgcaga catcagaaaa agggcattta    3540
agttcccaga acttggcaaa aaagcgctat tcatcgcaat accgacaaca agcggcacag    3600
gctcagaagt gacagcattt gccgtaataa ccgacaaaaa gagaaacatc aagtatccac    3660
tggcagacta cgaacttaca cctgacatag ccataataga tcctgacctt acaaagactg    3720
taccgccatc tgtaacagca gacacaggca tggatgtgct gacacacgcc atagaagcat    3780
acgtatcagt aatggcatca gactacacag atgcactggc ggaaaaggct ataaagatcg    3840
tatttgaata cctgccaagg gcttataaaa acggcaatga tgaagaagcc cgcgaaaaga    3900
tgcacaatgc ttcctgcatg gctggtatgg cattcacaaa tgcattctta ggaataaacc    3960
```

```
acagcatggc acacatactg ggcggaaagt tccacatacc acacggaaga gcaaatgcaa    4020
tacttctgcc gtatgtaata aggtacaatg cagaaaaacc tacaaagttt gtggcattcc    4080
cacaatacga atatccaaaa gcagcagaaa gatatgcgga aatcgccaaa ttcttaggac    4140
tgcctgcttc aactgttgaa gaaggcgtag aaagcttaat agaagctata agaaacctca    4200
tgaaagagct taacattccg cttacactta agacgccgg catcaacaaa gaacagtttg    4260
aaaaagaaat agaggaaatg tcagacatcg ccttcaacga tcagtgcaca gggacaaacc    4320
cgagaatgcc tctcacaaaa gaaattgcag agatctacag aaaagcatac ggtgcatagc    4380
ttaagactgg tttaaaataa acaggaaaac ttaagaaaac gggaaactat ttcctgttga    4440
gaatgtgaaa ttaaatgata aaaagtgata taatagggtc aggcgtacag aagcctgacc    4500
tttttgcaaa attgttttat tggcgcggcg tatatataca gcatatatac aatgtaaatt    4560
tatacaatca aattgttgat acaatcgaat tatgcggcta aaaatttgct gagctcgaat    4620
tcgctagccc aaaaaacgg gtatggaaa acagtagaga gttgcgataa aaagcgtcag    4680
gtaggatccg ctaatcttat ggataaaaat gctatgcat agcaaagtgt gacgccgtgc    4740
aaataatcaa tgtggacttt tctgccgtga ttatagacac ttttgttacg cgttttttgtc    4800 atggctttgg tcccgctttg ttacagaatg cttttaataa gcggggttac cggtttggtt    4860
agcgagaaga gccagtaaaa gacgcagtga cggcaatgtc tgatgcaata tggacaattg    4920
gtttcttctc tgaatggcgg gagtatgaaa agtatggctg aagcgcaaaa tgatcccctg    4980
ctgccgggat actcgtttaa tgcccatctg gtggcgggtt taacgccgat tgaggccaac    5040
ggttatctcg atttttttat cgaccgaccg ctgggaatga aaggttatat tctcaatctc    5100
accattcgcg gtcaggggt ggtgaaaaat cagggacgag aatttgtttg ccgaccgggt    5160
gatattttgc tgttcccgcc aggagagatt catcactacg gtcgtcatcc ggaggctcgc    5220
gaatggtatc accagtgggt ttactttcgt ccgcgcgcct actggcatga atggcttaac    5280
tggccgtcaa tatttgccaa tacgggttc tttcgcccgg atgaagcgca ccagccgcat    5340
ttcagcgacc tgtttgggca aatcattaac gccgggcaag gggaagggcg ctattcggag    5400
ctgctggcga taaatctgct tgagcaattg ttactgcggc gcatggaagc gattaacgag    5460
tcgctccatc caccgatgga taatcgggta cgcgaggctt gtcagtacat cagcgatcac    5520
ctggcagaca gcaattttga tatcgccagc gtcgcacagc atgtttgctt gtcgccgtcg    5580
cgtctgtcac atcttttccg ccagcagtta gggattagcg tcttaagctg gcgcgaggac    5640
caacgtatca gccaggcgaa gctgcttttg agcaccaccc ggatgcctat cgccaccgtc    5700
ggtcgcaatg ttggttttga cgatcaactc tatttctcgc gggtatttaa aaaatgcacc    5760
ggggccagcc cgagcgagtt ccgtgccggt tgtgaagaaa aagtgaatga tgtagccgtc    5820
aagttgtcat aattggtaac gaatcagaca attgacggct gacggagta gcatagggtt    5880 tgcagaatcc ctgcttcgtc catttgacag gcacattatg catcgatgat aagctgtcaa    5940
acatgagcag atcctctacg ccggacgcat cgtggccggc atcaccggcg ccacaggtgc    6000
ggttgctggc gcctatatcg ccgacatcac cgatgggaa gatcgggctc gccacttcgg    6060
gctcatgagc ctagaaatat tttatctgat taataagatg atcttcttga gatcgttttg    6120
gtctgcgcgt aatctcttgc tctgaaaacg aaaaaaccgc cttgcagggc ggttttttcga    6180 aggttctctg agctaccaac tctttgaacc gaggtaactg gcttggagga gcgcagtcac    6240
caaaacttgt cctttcagtt tagccttaac cggcgcatga cttcaagact aactcctcta    6300
aatcaattac cagtggctgc tgccagtggt gcttttgcat gtctttccgg gttggactca    6360
```

```
agacgatagt taccggataa ggcgcagcgg tcggactgaa cgggggttc  gtgcatacag    6420 tccagcttgg agcgaactgc ctacccggaa ctgagtgtca ggcgtggaat gagacaaacg    6480
cggccataac agcggaatga caccggtaaa ccgaaaggca ggaacaggag agcgcacgag    6540
ggagccgcca gggggaaacg cctggtatct ttatagtcct gtcgggtttc gccaccactg    6600
atttgagcgt cagatttcgt gatgcttgtc aggggggcgg agcctatgga aaaacggctt    6660
tgccgcggcc ctctcacttc cctgttaagt atcttcctgg catcttccag gaaatctccg    6720
ccccgttcgt aagccatttc cgctcgccgc agtcgaacga ccgagcgtag cgagtcagtg    6780
agcgaggaag cggaatatat cctgtatcac atattctgct gacgcaccgg tgcagccttt    6840
tttctcctgc cacatgaagc acttcactga caccctcatc agtgccaaca tagtaagcca    6900
gtatacaaat gagtgctttt tttgcgtttt gagcgtagcg aaaaacgagt tcttttctatt    6960 cttgatacat atagaaataa cgtcattttt attttagttg ctgaaaggtg cgttgaagtg    7020
ttggtatgta tgtgttttaa agtattgaaa acccttaaaa ttggttgcac agaaaaaccc    7080
catctgttaa agttataagt gaccaaacaa ataactaaat gatgggggt  ttcttttaat    7140 attatgtgtc ctaatagtag catttattca gatgaaaaat caagggtttt agtggacaag    7200
acaaaaagtg gaaaagtgag accatggaga gaaagaaaa  tcgctaatgt tgattacttt    7260
gaacttctgc atattcttga atttaaaaag gctgaaagag taaagattg  tgctgaaata    7320 ttagagtata aacaaaatcg tgaaacaggc gaaagaaagt tgtatcgagt gtggttttgt    7380
aaatccaggc tttgtccaat gtgcaactgg aggagagcaa tgaacatgg  cattcagtca    7440 caaaaggttg ttgctgaagt tattaaacaa agccaacag  ttcgttggtt gtttctcaca    7500
ttaacagtta aaaatgttta tgatggcgaa gaattaaata agagtttgtc agatatggct    7560
caaggatttc gccgaatgat gcaatataaa aaaattaata aaaatcttgt tggttttatg    7620
cgtgcaacgg aagtgacaat aaataataaa gataattctt ataatcagca catgcatgta    7680
ttggtatgtg tggaaccaac ttatttttaag aatacagaaa actacgtgaa tcaaaaacaa    7740
tggattcaat tttggaaaaa ggcaatgaaa ttagactatg atccaaatgt aaaagttcaa    7800
atgattcgac cgaaaaataa atataaatcg gatatacaat cggcaattga cgaaactgca    7860
aaatatcctg taaaggatac ggattttatg accgatgatg aagaaaagaa tttgaaacgt    7920
ttgtctgatt tggaggaagg tttacaccgt aaaaggttaa tctcctatgg tggtttgtta    7980
aaagaaatac ataaaaaatt aaaccttgat gacacagaag aaggcgattt gattcataca    8040
gatgatgacg aaaaagccga tgaagatgga ttttctatta ttgcaatgtg gaattgggaa    8100
cggaaaaatt attttattaa agagtagttc aacaaacggg attgacttt  aaaaaaggat    8160 tgattctaat gaagaaagca gacaagtaag cctcctaaat tcactttaga taaaaattta    8220
ggaggcatat caaatgaact ttaataaaat tgatttagac aattggaaga gaaagagat     8280 atttaatcat tatttgaacc aacaaacgac ttttagtata accacagaaa ttgatattag    8340
tgttttatac cgaaacataa aacaagaagg atataaattt taccctgcat ttatttctt     8400 agtgacaagg gtgataaact caaatacagc ttttagaact ggttacaata gcgacggaga    8460
gttaggttat tgggataagt tagagccact ttatacaatt tttgatggtg tatctaaaac    8520
attctctggt attttggactc ctgtaaagaa tgacttcaaa gagttttatg atttatacct    8580
ttctgatgta gagaaatata atggttcggg gaaattgttc cccaaaacac ctatacctga    8640
aaatgctttt tctctttcta ttattccatg gacttcattt actgggttta acttaaatat    8700
```

| | |
|---|---|
| caataataat agtaattacc ttctacccat tattacagca ggaaaattca ttaataaagg | 8760 |
| taattcaata tatttaccgc tatcttaca ggtacatcat tctgtttgtg atggttatca | 8820 |
| tgcaggattg tttatgaact ctattcagga attgtcagat aggcctaatg actggctttt | 8880 |
| ataatatgag ataatgccga ctgtactttt tacagtcggt tttctaatgt cactagggct | 8940 |
| cgcctttggg aagtttgaag g | 8961 |

<210> SEQ ID NO 66
<211> LENGTH: 9876
<212> TYPE: DNA
<213> ORGANISM: Artificial Sequence
<220> FEATURE:
<223> OTHER INFORMATION: plasmid pMU1817

<400> SEQUENCE: 66

| | |
|---|---|
| ggggtctgac gctcagtgga acgaaaactc acgttaaggg attttggtca tgagattatc | 60 |
| aaaaaggatc ttcacctaga tcctttaaa ttaaaaatga gtttaaat caatctaaag | 120 |
| tatatatgag taaacttggt ctgacagtta ccaatgctta atcagtgagg cacctatctc | 180 |
| agcgatctgt caattcgcgg ccgccgaaaa gtgggtaata actgatataa ttaaattgaa | 240 |
| gctctaattt gtgagtttag tatacatgca tttacttata atacagtttt ttagttttgc | 300 |
| tggccgcatc ttctcaaata tgcttcccag cctgcttttc tgtaacgttc accctctacc | 360 |
| ttagcatccc ttccctttgc aaatagtcct cttccaacaa taataatgtc agatcctgta | 420 |
| gagaccacat catccacggt tctatactgt tgacccaatg cgtctccctt gtcatctaaa | 480 |
| cccacaccgg gtgtcataat caaccaatcg taaccttcat ctcttccacc catgtctctt | 540 |
| tgagcaataa agccgataac aaaatctttg tcgctcttcg caatgtcaac agtacccta | 600 |
| gtatattctc cagtagatag ggagcccttg catgacaatt ctgctaacat caaaaggcct | 660 |
| ctaggttcct ttgttacttc ttctgccgcc tgcttcaaac cgctaacaat acctgggccc | 720 |
| accacaccgt gtgcattcgt aatgtctgcc cattctgcta ttctgtatac acccgcagag | 780 |
| tactgcaatt tgactgtatt accaatgtca gcaaattttc tgtcttcgaa gagtaaaaaa | 840 |
| ttgtacttgg cggataatgc ctttagcggc ttaactgtgc cctccatgga aaatcagtc | 900 |
| aagatatcca catgtgtttt tagtaaacaa attttgggac ctaatgcttc aactaactcc | 960 |
| agtaattcct tggtggtacg aacatccaat gaagcacaca gtttgtttg cttttcgtgc | 1020 |
| atgatattaa atagcttggc agcaacagga ctaggatgag tagcagcacg ttccttatat | 1080 |
| gtagctttcg acatgattta tcttcgtttc ctgcaggttt ttgttctgtg cagttgggtt | 1140 |
| aagaatactg ggcaatttca tgtttcttca acactacata tgcgtatata taccaatcta | 1200 |
| agtctgtgct ccttccttcg ttcttccttc tgttcggaga ttaccgaatc aaaaaaattt | 1260 |
| caaagaaacc gaaatcaaaa aaagaataa aaaaaaatg atgaattgaa ttgaaaagct | 1320 |
| agcttatcga tgggtccttt tcatcacgtg ctataaaaat aattataatt taaattttt | 1380 |
| aatataaata tataaattaa aaatagaaag taaaaaaaga aattaaagaa aaatagttt | 1440 |
| ttgttttccg aagatgtaaa agactctagg gggatcgcca acaaatacta ccttttatct | 1500 |
| tgctcttcct gctctcaggt attaatgccg aattgtttca tcttgtctgt gtagaagacc | 1560 |
| acacacgaaa atcctgtgat tttacatttt acttatcgtt aatcgaatgt atatctattt | 1620 |
| aatctgcttt tcttgtctaa taatatata tgtaaagtac gctttttgtt gaatttttt | 1680 |
| aaaccttgt ttattttttt ttcttcattc cgtaactctt ctaccttctt tatttacttt | 1740 |
| ctaaaatcca aatacaaaac ataaaaataa ataaacacag agtaaattcc caaattattc | 1800 |

```
catcattaaa agatacgagg cgcgtgtaag ttacaggcaa gcgatcgcgg ccgcggtacc    1860
cggggatcct ctagagtcga cctgcagtgt catctcccct ttctgcggca tcctgaacat    1920
ctctgaaatc actgcttaca cctgaaattc aagcacacc tgatttcttg ttaaggaaat     1980
tgtttatatc gttaatattc attttttcct tttccatcaa ataagttata accgcagggt    2040
caacattgcc gcttctggta cccatgcaca acccctgcag aggagtaaat cccattgagg    2100
tgtcaacgga ttttccgcct tttaccgcac aaatacttgc tccgtttcca agatggcagg    2160
ttatcagctt caggctctca ataggtttgc ccagcatctg agccgccctg tgggccacat    2220
atttgtggga agttccgtgg aatccgtatt ttctcaattt atacttctca tatatctcat    2280
aagggagggc ataaatatat gcatgccttg gcattgtctg atgaaaagct gtgtcaaaca    2340
cagcaaccat cggcacatcg ggcagtatct gtttacaggc ttcaattccg attatatttg    2400
acggattgtg gagcggagcc agttcaacac aatccctgat tgctttcatt acatcttcat    2460
caattatggc agattcctta aacttctctc cgccgtgaac aatacgatga ccgacggcag    2520
aaatttccga catgcttttt atgactccga ttttttcatc cgtaagagcc gaaattacct    2580
cctgtatggc aagcttgtga ttgtacaggt cttttttctat aactacggtt tccctccgg    2640
tctttgtatg ctttaaaaag gaatgttcaa gaccaattct gtcacacaca ccttttgcaa    2700
gcacagactc gtttgtcatg tcaatcagct gatactttag tgatgagctt ccggtattaa    2760
taaccaaaat attcatttca aaaactcact cccgtcttgt tttttttaat tttcctattc    2820
ctaaacttcg ataaacagat gttttttatta aacgctgcgc aacaccttct tcaatgtccg    2880
gttttaacag aatttatgcc ttgacatatt gagcctgaac cggcggcttt aataaccctc    2940
agatccgtac tttccggcaa aactatggtt tttacgtctg atttcgccct ttcaattatt    3000
tgttccaaaa aactcataaa ttcttctcct ttcataatcc caaaactgtt atcataaaaa    3060
ctgtatttgt aatacttata actatatatt atcaccaggt aataataccct actcactata    3120
aacagctatt ttactgggtt ccaagcaact ctaattatat acaaaatgtt ttttgtatac    3180
aacaccctcc ttatcttttt ttcggcttta gccataaaata acggcaagta actccaaaat    3240
acaggatatt tcatgctttt agaaactttt tattagtctt cttaattatt cagattttgt    3300
ggcaattaaa ctttgcagct cctccaaata gttgtccagc tcctcttctt taagattgct    3360
gagatatgac aatctgtaat ttttagcctt tttggccatc tctagcgcac tctccgtcat    3420
tcccaaatct ttcaaaacac agctatagtt atagtatgcc tcaggaaaat ttggattaag    3480
acctataagc tttcgatata tttcctcggc ctttttaatg ttaccgattt tgtaataggt    3540
atagcctaaa ttgtcaagta tgacaggatc agagctgtta tactcatacg cctccttatt    3600
gaaatttaaa gctttgttca tatccccgtc cagaataaga agatatccga gacttccgta    3660
tatggttgta ttcttatagt ttgaaaacac atcctccagc attttttatgc catctttcaa    3720
ctgtcccttt ttccaaagca ccaatgcata gttggacttt gcctggcgat aattatcagt    3780
atccatataa cgatacctct gatcgtttta ttcaaatatg gccctccctt caaagccgta    3840
tcacttaatt tataataaca tataccatat aaaaaaacaa attttagctg tacatttcag    3900
gtttcaaaac gcctataaaa ggaaggttcc tgtactttc atcaaagtcc aatccataac    3960
ccacgacaaa cttatcaggt atcttaaatc ctacataatc gacttttaca gatgcttctc    4020
ttctctccgg tttgtctaat attgtgcata ttttcaggct ttttggcttc cttccaagta    4080
aagtttccct taagtaagac aaagtcaaac cgctgtcaat tatgtcttcc acaatcagaa    4140
```

-continued

```
catctttgcc ttctatgctt atatcaagat ctttgattat ctttactatt cctgatgaat    4200
gagttgagct tccatagctg gaaacagcca taaaatcaag tgataaaggc aaatctatgt    4260
gtcttgacaa atcagccata acattaaag caccttttaa aactcctacc aacatcaaat    4320
ttttcccttt gtagtctttt gtgatttgcc tcccaagctc ttttatcttt tccttaagtt    4380
cttcttctgt gatcaaaatt tcatcgatgt cttttgataa attttccatc aaatttcctc    4440
cttaatcttg tttataaaag ccagtcatta ggcctatctg acaattcctg aatagagttc    4500
ataaacaatc ctgcatgata accatcacaa acagaatgat gtacctgtaa agatagcggt    4560
aaatatattg aattaccttt attaatgaat tttcctgctg taataatggg tagaaggtaa    4620
ttactattat tattgatatt taagttaaac ccagtaaatg aagtccatgg aataatagaa    4680
agagaaaaag cattttcagg tataggtgtt ttgggaaaca atttccccga accattatat    4740
ttctctacat cagaaaggta taaatcataa aactctttga agtcattctt tacaggagtc    4800
caaataccag agaatgtttt agatacacca tcaaaaattg tataaagtgg ctctaactta    4860
tcccaataac ctaactctcc gtcgctattg taaccagttc taaaagctgt atttgagttt    4920
atcacccttg tcactaagaa aataaatgca gggtaaaatt tatatccttc ttgttttatg    4980
tttcggtata aaacactaat atcaatttct gtggttatac taaaagtcgt ttgttggttc    5040
aaataatgat taaatatctc ttttctcttc caattgtcta aatcaatttt attaaagttc    5100
atcattaata tcgcctccta ttgtaaatta aaatttaatt taatgcctct attagctgcc    5160
ataaagcatg aatgcagtaa aatattcatc ctctggcaag tatctcttgc actatgattc    5220
attttatatt attttatttt cattttcaat agtttagata aaaataatt aattttttaa    5280
caaagtattt ttatcttcct ttgatgtaat tcttttgtttt tttgtccatt aatattatgg    5340
acaatttttt tatttctagt caataatttt aatcttatt aaaacctggc aatgccagag    5400
agatacagta attattgcat ataaagaaa acagacgcgc cctgtttgtt tcctgaaaaa    5460
ccacctcgtc ctccaaagta tccagctttt taaaatccat cctcattccc agacgaaaaa    5520
gttttgacaa agcctctttt cttgtccata gaattgtact ctgcacacaa tattcatcag    5580
tatttccaaa actcttttaga atcttttcct ctctttcgga aaagaaatac caatggcggc    5640
atccacctga agttctccgt caattgcaag gtggggagct ttttcctttg caagctgtgt    5700
tgccttgatt acctttttcgg tcagctcact tttggcactg ccgtaagaag aataagaaag    5760
cattgccacc tgaggttttg ctccaaccag catctcaaaa gatttggatg cagatattgc    5820
aatttcagaa agctggtctg catccggatt ttccaccaag ccgcaatcgg catatacaaa    5880
ggttccgtta tgaccatatt cacagttggg tacaaccata acaaaaaagg atgatacgag    5940
ttttgtcccc ggggccgtct ttaatatctg caaagccggt ctcaaagtat ttgcagtgga    6000
attgacagca cccgccacca taccatccgc ttcaccttt tttaccatca taactccata    6060
ataaagaggg tctttgatcg tttcccttgc ggcttctata gtcataccct tcgattttct    6120
aagctcatac agtgtatttg cataatcctc caattttcg gaatttaagg aatcctctat    6180
catcactcct tcaagatcaa tatccccgc cagactctta atctccttt cattgcctat    6240
cagtacaacc tttgcaattc ccttaagtcc gcgggacttc atggcacttt ctacaccttg    6300
cttcataaga ctcctttgct ccaaccatta atgggatc gtcgtaattg gcaggcttcc    6360
catttataag cctttgcgtg cgagtagcag gattgccaca cttcatgcat atagcagtaa    6420
gcttatcgac aaattcagct atggccatca attctggagt cggaccaaat ggttcacctc    6480
taaagtccat gtcaagccct gcacatatga ctcttttccc gctatcggca atctctttta    6540
```

```
cgatgtcgac tatttcagaa tcaaaaaatt gaacttcatc tatagcaaat acatccgtat   6600
cttcttcagc ataagccaat atgtcagaag cctttactat ggcaatggcg tgcatgttgt   6660
cgccgttatg agatacgact ttgtctatgg aatacctatc gtctatagcc ggtttgaaaa   6720
cctgaacttt ttgcctggca atcttagctc tctttatcct tcttataagt tcctcacttt   6780
ttccactgaa catgggacca gttacaactt ctatgtaccc gtggtcttta ggcccataca   6840
tctttcgtcc tccttaaaat tttcgtttat ttgtttttta tttagtgtgc ctaaaagcac   6900
catcttatac attcgtacct tatatctctt atcttgtatc tcttacctca tatctcttat   6960
tattaactac cgaagtatat tttcataacg gaatcttatg acttatttt ctgactgccg   7020 ttttaccata cggttaattt atacggaaac agctaatcta accttgctga aggcatgttt   7080
accaaaatat tatatctact ttaccatatt aattcaagtg gtcattttga tattttacgc   7140
caaaattttt agcgttcctt tacttgataa tttatccaaa aaccttcatt cgtcaaaaca   7200
attatgatat aattaattta tgatatgatt aattaatatt tacggataac taatcatttc   7260
aatgcaatag atcaacatgc aaatcaatat ccaccttact ccgaacattt tgcaccaacg   7320
aatgcccagc actatatccc ggcaagcaat ataacgtcta taatttttta tgataacgat   7380
aaaattaaat tttatgaaag gggtaaaagc atgagaaaaa tagctgtatt gttaattact   7440
ttgacgttct tagtcacgac tcttgatatg cctcctaaat ttttatctaa agtgaattta   7500
ggaggcttac ttgtctgctt tcttcattag aatcaatcct ttttaaaag tcaatcccgt   7560 ttgttgaact actctttaat aaaataattt ttccgttccc aattccacat tgcaataata   7620
gaaaatccat cttcatcggc ttttcgtca tcatctgtat gaatcaaatc gccttcttct   7680
gtgtcatcaa ggtttaattt tttatgtatt tcttttaaca aaccaccata ggagattaac   7740
cttttacggt gtaaaccttc ctccaaatca gacaaacgtt tcaaattctt ttcttcatca   7800
tcggtcataa aatccgtatc ctttacagga tattttgcag tttcgtcaat tgccgattgt   7860
atatccgatt tatatttatt tttcggtcga atcatttgaa cttttacatt tggatcatag   7920
tctaatttca ttgccttttt ccaaaattga atccattgtt tttgattcac gtagttttct   7980
gtattcttaa aataagttgg ttccacacat accaatacag gcatgtgctg attataagaa   8040
ttatctttat tatttattgt cacttccgtt gcacgcataa aaccaacaag attttatta   8100 atttttttat attgcatcat tcggcgaaat ccttgagcca tatctgacaa actcttattt   8160
aattcttcgc catcataaac attttttaact gttaatgtga gaaacaacca acgaactgtt   8220
ggcttttgtt taataacttc agcaacaacc ttttgtgact gaatgccatg tttcattgct   8280
ctcctccagt tgcacattgg acaaagcctg gatttacaaa accacactcg atacaacttt   8340
ctttcgcctg tttcacgatt ttgtttatac tctaatattt cagcacaatc ttttactctt   8400 tcagccttt taaattcaag aatatgcaga agttcaaagt aatcaacatt agcgattttc   8460
ttttctctcc atggtctcac ttttccactt tttgtcttgt ccactaaaac ccttgatttt   8520
tcatctgaat aaatgctact attaggacac ataatattaa aagaaacccc catctattta   8580
gttatttgtt tggtcactta aactttaac agatggggtt tttctgtgca accaatttta   8640
agggttttca atactttaaa acacatacat accaacactt caacgcacct ttcagcaact   8700
aaaataaaaa tgacgttatt tctatatgta tcaagaatag aaagaactcg ttttcgcta   8760 cgctcaaaac gcaaaaaag cactcattcg agtgcttttt cttatcgctc caaatcatgc   8820 gatttttcc tctttgcttt tctttgctca cgaagttctc gatcacgctg caaaacatct   8880
```

```
tgaagcgaaa aagtattctt cttttcttcc gatcgctcat gctgacgcac gaaaagccct    8940
ctaggcgcat aggaacaact cctaaatgca tgtgagggt tttctcgtcc atgtgaacag     9000
tcgcatacgc aatattttgt ttcccatact gcattaatga atcggccaac gcgcggggag    9060
aggcggtttg cgtattgggc gctcttccgc ttcctcgctc actgactcgc tgcgctcggt    9120
cgttcggctg cggcgagcgg tatcagctca ctcaaaggcg gtaatacggt tatccacaga    9180
atcaggggat aacgcaggaa agaacatgtg agcaaaggc cagcaaaagg ccaggaaccg     9240
taaaaaggcc gcgttgctgg cgttttccaa taggctccgc ccccctgacg agcatcacaa    9300
aaatcgacgc tcaagtcaga ggtggcgaaa cccgacagga ctataaagat accaggcgtt    9360
tccccctgga agctccctcg tgcgctctcc tgttccgacc ctgccgctta ccggatacct    9420
gtccgccttt ctcccttcgg gaagcgtggc gctttctcat agctcacgct gtaggtatct    9480
cagttcggtg taggtcgttc gctccaagct gggctgtgtg cacgaacccc ccgttcagcc    9540
cgaccgctgc gccttatccg gtaactatcg tcttgagtcc aacccggtaa gacacgactt    9600
atcgccactg gcagcagcca ctggtaacag gattagcaga gcgaggtatg taggcggtgc    9660
tacagagttc ttgaagtggt ggcctaacta cggctacact agaagaacag tatttggtat    9720
ctgcgctctg ctgaagccag ttaccttcgg aaaaagagtt ggtagctctt gatccggcaa    9780
acaaaccacc gctggtagcg gtggtttttt tgtttgcaag cagcagatta cgcgcagaaa    9840
aaaaggatct caagaagatc ctttgatctt ttctac                              9876
```

<210> SEQ ID NO 67
<211> LENGTH: 2580
<212> TYPE: DNA
<213> ORGANISM: Thermoanaerobacterium saccharolyticum
<220> FEATURE:
<221> NAME/KEY: misc_feature
<222> LOCATION: (1)..(2580)
<223> OTHER INFORMATION: bifunctional acetaldehyde-alcohol dehydrogenase
      from T.saccharolyticum strain ALK2

<400> SEQUENCE: 67

```
atggcaacga caaaaacgga attagacgtt cagaagcaga tagatctact tgtgtcaaga     60
gcacaagagg ctcagaaaaa attcatgtct tacacgcaag agcaaatcga cgcaatagtt    120
aaggcaatgg ctttagcagg cgttgacaaa cacgtagagc tggcaaagat ggcgtacgaa    180
gagacaaaaa tgggtgtata cgaagataag ataacaaaaa atctcttcgc aacagagtac    240
gtgtaccacg acataaaaaa tgaaaagact gtaggaatca taaacgagaa catagaagaa    300
aactacatgg aagtggcaga accgataggc gtaattgccg tgtcacacc tgtcacaaac    360 ccaacatcta ccacgatgtt taaatgctta atatccataa agacgcgaaa tcctataata    420
ttcagcttcc atccaaaggc aataaagtgc agcatcgcag cagccaaagt gatgtatgaa    480
gctgcactaa aggcaggcgc acctgaagga tgcataggat ggatagaaac gccatcaatt    540
gaggccacac agcttctcat gacacatcca ggcgtatcgc tgatccttgc aacgggcggt    600
gcaggaatgg taaaagcggc atacagctca ggaaaaccgg cattaggcgt aggtcctggc    660
aatgtgccat gctacatcga aaaatcagca aacataaaga gggctgtatc ggatctcata    720
ctaagcaaga catttgacaa tggagtaata tgcgcatcag gcaggccgt aataatagac    780 gaggaaatag cagatgaagt caaaaagctt atgaaagaat acggctgcta cttcttaaac    840
aaagatgaaa taagaagct tgagaaattt gcaattgatg agcaaagctg cgccatgagc    900
cctgcagtgg taggtcagcc agcggcgaag attgctgaaa tggcaggctt caaagtcccc    960
```

```
gaaggcacaa agatattagt ggcagagtac gaaggagtag gtccaaaata tcctctatca   1020
agggagaaac taagcccgat tcttgcttgc tacaccgtca aagactacaa tgaaggaatc   1080
aaaaagtgcg aggaaatgac tgaattcgga ggtttaggcc actctgctgt aatacactct   1140
gaaaatcaaa acgtcataaa tgaatttgca aggcgagtcc gcacaggaag acttatcgta   1200
aattcaccat catcacaggg agcaatagga gatatataca atacaaacac gccatcactt   1260
acattaggct gtggttctat gggaagaaac tcaacgacag acaatgtaag cgtcaagaac   1320
cttttgaata ttaagcgtgt cgtgataagg aatgatagaa tgaaatggtt caagattcca   1380
ccgaagattt actttgaaag cgggtcactc cagtacctgt gcaaagtcaa agaaaaaaaa   1440
gcgtttatcg tcacagatcc attcatggtt aagcttggct tcgtagacaa agtgacatat   1500
caattagaca aagcaaacat cgaatacgaa atattctcag aagtagagcc agatccatct   1560
gttgacacag tcatgaacgg cgtaaaaata atgaattcgt acaatcctga cttaataatc   1620
gctgtaggcg gtggctctgc aatagacgca gcaaagggaa tgtggctttt ctacgaatat   1680
cctgatacag agtttgaaac attgaggctt aaatttgcag acatcagaaa aagggcattt   1740
aagttcccag aacttggcaa aaaagcgcta ttcatcgcaa taccgacaac aagcggcaca   1800
ggctcagaag tgacagcatt tgccgtaata accgacaaaa agaaacat caagtatcca   1860 ctggcagact acgaacttac acctgacata gccataatag atcctgaccct tacaaagact   1920 gtaccgccat ctgtaacagc agacacaggc atggatgtgc tgacacacgc catagaagca   1980
tacgtatcag taatggcatc agactacaca gatgcactgg cggaaaaggc tataaagatc   2040
gtatttgaat acctgccaag ggcttataaa acggcaatg atgaagaagc ccgcgaaaag   2100
atgcacaatg cttcctgcat ggctggtatg gcattcacaa atgcattctt aggaataaac   2160
cacagcatgg cacacatact gggcggaaag ttccacatac cacacggaag agcaaatgca   2220
atacttctgc cgtatgtaat aaggtacaat gcagaaaaac ctacaaagtt tgtggcattc   2280
ccacaatacg aatatccaaa agcagcagaa agatatgcgg aaatcgccaa attcttagga   2340
ctgcctgctt caactgttga agaaggcgta gaaagcttaa tagaagctat aaagaacctc   2400
atgaaagagc ttaacattcc gcttacactt aaagacgccg gcatcaacaa agaacagttt   2460 gaaaagaaa tagaggaaat gtcagacatc gccttcaacg atcagtgcac agggacaaac   2520
ccgagaatgc ctctcacaaa agaaattgca gagatctaca gaaaagcata cggtgcatag   2580
```

<210> SEQ ID NO 68
<211> LENGTH: 859
<212> TYPE: PRT
<213> ORGANISM: Thermoanaerobacterium saccharolyticum
<220> FEATURE:
<221> NAME/KEY: MISC_FEATURE
<222> LOCATION: (1)..(859)
<223> OTHER INFORMATION: bifunctional acetaldehyde-alcohol dehydrogenase
      from T.saccharolyticum strain ALK2

<400> SEQUENCE: 68

Met Ala Thr Thr Lys Thr Glu Leu Asp Val Gln Lys Gln Ile Asp Leu
1               5                   10                  15

Leu Val Ser Arg Ala Gln Glu Ala Gln Lys Lys Phe Met Ser Tyr Thr
            20                  25                  30

Gln Glu Gln Ile Asp Ala Ile Val Lys Ala Met Ala Leu Ala Gly Val
        35                  40                  45

Asp Lys His Val Glu Leu Ala Lys Met Ala Tyr Glu Glu Thr Lys Met
    50                  55                  60

```
Gly Val Tyr Glu Asp Lys Ile Thr Lys Asn Leu Phe Ala Thr Glu Tyr
 65                  70                  75                  80

Val Tyr His Asp Ile Lys Asn Glu Lys Thr Val Gly Ile Ile Asn Glu
                 85                  90                  95

Asn Ile Glu Glu Asn Tyr Met Glu Val Ala Glu Pro Ile Gly Val Ile
                100                 105                 110

Ala Gly Val Thr Pro Val Thr Asn Pro Thr Ser Thr Thr Met Phe Lys
            115                 120                 125

Cys Leu Ile Ser Ile Lys Thr Arg Asn Pro Ile Ile Phe Ser Phe His
130                 135                 140

Pro Lys Ala Ile Lys Cys Ser Ile Ala Ala Lys Val Met Tyr Glu
145                 150                 155                 160

Ala Ala Leu Lys Ala Gly Ala Pro Glu Gly Cys Ile Gly Trp Ile Glu
                165                 170                 175

Thr Pro Ser Ile Glu Ala Thr Gln Leu Leu Met Thr His Pro Gly Val
            180                 185                 190

Ser Leu Ile Leu Ala Thr Gly Gly Ala Gly Met Val Lys Ala Ala Tyr
    195                 200                 205

Ser Ser Gly Lys Pro Ala Leu Gly Val Gly Pro Gly Asn Val Pro Cys
210                 215                 220

Tyr Ile Glu Lys Ser Ala Asn Ile Lys Arg Ala Val Ser Asp Leu Ile
225                 230                 235                 240

Leu Ser Lys Thr Phe Asp Asn Gly Val Ile Cys Ala Ser Glu Gln Ala
                245                 250                 255

Val Ile Ile Asp Glu Glu Ile Ala Asp Glu Val Lys Lys Leu Met Lys
            260                 265                 270

Glu Tyr Gly Cys Tyr Phe Leu Asn Lys Asp Glu Ile Lys Lys Leu Glu
        275                 280                 285

Lys Phe Ala Ile Asp Glu Gln Ser Cys Ala Met Ser Pro Ala Val Val
290                 295                 300

Gly Gln Pro Ala Ala Lys Ile Ala Glu Met Ala Gly Phe Lys Val Pro
305                 310                 315                 320

Glu Gly Thr Lys Ile Leu Val Ala Glu Tyr Glu Gly Val Gly Pro Lys
                325                 330                 335

Tyr Pro Leu Ser Arg Glu Lys Leu Ser Pro Ile Leu Ala Cys Tyr Thr
            340                 345                 350

Val Lys Asp Tyr Asn Glu Gly Ile Lys Lys Cys Glu Met Thr Glu
    355                 360                 365

Phe Gly Gly Leu Gly His Ser Ala Val Ile His Ser Glu Asn Gln Asn
370                 375                 380

Val Ile Asn Glu Phe Ala Arg Arg Val Arg Thr Gly Arg Leu Ile Val
385                 390                 395                 400

Asn Ser Pro Ser Ser Gln Gly Ala Ile Gly Asp Ile Tyr Asn Thr Asn
                405                 410                 415

Thr Pro Ser Leu Thr Leu Gly Cys Gly Ser Met Gly Arg Asn Ser Thr
            420                 425                 430

Thr Asp Asn Val Ser Val Lys Asn Leu Leu Asn Ile Lys Arg Val Val
    435                 440                 445

Ile Arg Asn Asp Arg Met Lys Trp Phe Lys Ile Pro Pro Lys Ile Tyr
450                 455                 460

Phe Glu Ser Gly Ser Leu Gln Tyr Leu Cys Lys Val Lys Arg Lys Lys
465                 470                 475                 480

Ala Phe Ile Val Thr Asp Pro Phe Met Val Lys Leu Gly Phe Val Asp
```

```
                485                 490                 495
Lys Val Thr Tyr Gln Leu Asp Lys Ala Asn Ile Glu Tyr Glu Ile Phe
                500                 505                 510

Ser Glu Val Glu Pro Asp Pro Ser Val Asp Thr Val Met Asn Gly Val
                515                 520                 525

Lys Ile Met Asn Ser Tyr Asn Pro Asp Leu Ile Ile Ala Val Gly Gly
            530                 535                 540

Gly Ser Ala Ile Asp Ala Ala Lys Gly Met Trp Leu Phe Tyr Glu Tyr
545                 550                 555                 560

Pro Asp Thr Glu Phe Glu Thr Leu Arg Leu Lys Phe Ala Asp Ile Arg
                565                 570                 575

Lys Arg Ala Phe Lys Phe Pro Glu Leu Gly Lys Lys Ala Leu Phe Ile
                580                 585                 590

Ala Ile Pro Thr Thr Ser Gly Thr Gly Ser Glu Val Thr Ala Phe Ala
                595                 600                 605

Val Ile Thr Asp Lys Lys Arg Asn Ile Lys Tyr Pro Leu Ala Asp Tyr
610                 615                 620

Glu Leu Thr Pro Asp Ile Ala Ile Ile Asp Pro Asp Leu Thr Lys Thr
625                 630                 635                 640

Val Pro Pro Ser Val Thr Ala Asp Thr Gly Met Asp Val Leu Thr His
                645                 650                 655

Ala Ile Glu Ala Tyr Val Ser Val Met Ala Ser Asp Tyr Thr Asp Ala
                660                 665                 670

Leu Ala Glu Lys Ala Ile Lys Ile Val Phe Glu Tyr Leu Pro Arg Ala
                675                 680                 685

Tyr Lys Asn Gly Asn Asp Glu Glu Ala Arg Glu Lys Met His Asn Ala
                690                 695                 700

Ser Cys Met Ala Gly Met Ala Phe Thr Asn Ala Phe Leu Gly Ile Asn
705                 710                 715                 720

His Ser Met Ala His Ile Leu Gly Gly Lys Phe His Ile Pro His Gly
                725                 730                 735

Arg Ala Asn Ala Ile Leu Leu Pro Tyr Val Ile Arg Tyr Asn Ala Glu
                740                 745                 750

Lys Pro Thr Lys Phe Val Ala Phe Pro Gln Tyr Glu Tyr Pro Lys Ala
                755                 760                 765

Ala Glu Arg Tyr Ala Glu Ile Ala Lys Phe Leu Gly Leu Pro Ala Ser
                770                 775                 780

Thr Val Glu Glu Gly Val Glu Ser Leu Ile Glu Ala Ile Lys Asn Leu
785                 790                 795                 800

Met Lys Glu Leu Asn Ile Pro Leu Thr Leu Lys Asp Ala Gly Ile Asn
                805                 810                 815

Lys Glu Gln Phe Glu Lys Glu Ile Glu Met Ser Asp Ile Ala Phe
                820                 825                 830

Asn Asp Gln Cys Thr Gly Thr Asn Pro Arg Met Pro Leu Thr Lys Glu
                835                 840                 845

Ile Ala Glu Ile Tyr Arg Lys Ala Tyr Gly Ala
850                 855

<210> SEQ ID NO 69
<211> LENGTH: 12114
<212> TYPE: DNA
<213> ORGANISM: Artificial Sequence
<220> FEATURE:
<223> OTHER INFORMATION: plasmid pJLO7
```

<400> SEQUENCE: 69

```
gggtaataac tgatataatt aaattgaagc tctaatttgt gagtttagta tacatgcatt      60
tacttataat acagtttttt agttttgctg gccgcatctt ctcaaatatg cttcccagcc     120
tgcttttctg taacgttcac cctctacctt agcatccctt cccttttgcaa atagtcctct   180
tccaacaata ataatgtcag atcctgtaga gaccacatca tccacggttc tatactgttg    240
acccaatgcg tctcccttgt catctaaacc cacaccgggt gtcataatca accaatcgta    300
accttcatct cttccaccca tgtctctttg agcaataaag ccgataacaa aatctttgtc    360
gctcttcgca atgtcaacag tacccttagt atattctcca gtagataggg agcccttgca    420
tgacaattct gctaacatca aaaggcctct aggttccttt gttacttctt ctgccgcctg    480
cttcaaaccg ctaacaatac ctgggcccac cacaccgtgt gcattcgtaa tgtctgccca    540
ttctgctatt ctgtatacac ccgcagagta ctgcaatttg actgtattac caatgtcagc    600
aaatttctg tcttcgaaga gtaaaaaatt gtacttggcg gataatgcct ttagcggctt      660
aactgtgccc tccatggaaa aatcagtcaa gatatccaca tgtgttttta gtaaacaaat    720
tttgggacct aatgcttcaa ctaactccag taattccttg gtggtacgaa catccaatga    780
agcacacaag tttgtttgct tttcgtgcat gatattaaat agcttggcag caacaggact    840
aggatgagta gcagcacgtt ccttatatgt agctttcgac atgatttatc ttcgtttcct    900
gcaggttttt gttctgtgca gttgggttaa gaatactggg caatttcatg tttcttcaac    960
actacatatg cgtatatata ccaatctaag tctgtgctcc ttccttcgtt cttccttctg   1020
ttcggagatt accgaatcaa aaaatttca aagaaaccga aatcaaaaaa aagaataaaa     1080
aaaaaatgat gaattgaatt gaaaagctag cttatcgatg ggtccttttc atcacgtgct   1140
ataaaaataa ttataatta aatttttttaa tataaatata taaattaaaa atagaaagta   1200
aaaaagaaa ttaagaaaa aatagttttt gttttccgaa gatgtaaaag actctagggg      1260
gatcgccaac aaatactacc ttttatcttg ctcttcctgc tctcaggtat taatgccgaa   1320
tgtttcatc ttgtctgtgt agaagaccac acacgaaaat cctgtgattt tacatttttac    1380
ttatcgttaa tcgaatgtat atctatttaa tctgcttttc ttgtctaata aatatatatg   1440
taaagtacgc tttttgttga aattttttaa accttttgttt atttttttttt cttcattccg   1500
taactcttct accttcttta tttactttct aaaatccaaa tacaaaacat aaaaataaat   1560
aaacacagag taaattccca aattattcca tcattaaaag atacgaggcg cgtgtaagtt   1620
acaggcaagc gatccgtccg ccggcgaacg tggcgagaaa ggaagggaag aaagcgaaag   1680
gagcgggggc tagggcggtg ggaagtgtag gggtcacgct gggcgtaacc accacacccg   1740
ccgcgcttaa tggggcgcta cagggcgcgt ggggatgatc cactagtaag cttggatcca   1800
atatgtttgc acgagcttaa agaggaagac atatatttca ataaggaagt aaacataccc   1860
ggaattacgg ttgttgatga aatatgtggc agcttggagg caacccttat tgatgtttcc   1920
gcagattgct ttagtataga ggattttaca aaggtaccgg acaaaagcaa ggttcagttt   1980
tttgattatg acaggctgaa agagggaata tacttaagaa acagaagaga cggtgatgtt   2040
ttcaggcccc gtaactcaaa cggcaccaaa aaactcaagg agttttttat tgacaataaa   2100
atcccaagag aaacaagaaa tcaaatacag ttaatttcaa cacgtaaaga aattgtatgg   2160
ataataggtt acaaaatcag tgataaattt aaagtaactg aaaatactaa aatcatactg   2220
aaattatcct atgataactc gcactgaacc aatcaaaatt ctaaaaaccg gcatattggt   2280
gttaagtgaa agacgacggc agggaaatat taaaatggaa atgttgaaaa aatgttttaa   2340
```

```
gatgggtcat tatggataaa atatactatg gttttgcaat aaatgctttc tattaattgg    2400
actttgtggt aatatggtag aaggatgcag tgttaatttt ttaacatata aaaataagct    2460
atatgaaggg agaatggaga tgaacaatag acaacccctt tctgtgatct tgttttttgc    2520
aaatgctatt ttatcacaag agatttctct agttcttttt tacttaaaaa aaccctacga    2580
aattttaaac tatgtcgaat aaattattga taatttttaa ctatgtgcta ttatattatt    2640
gcaaaaaatt taacaatcat cgcgtaagct agttttcaca ttaatgactt acccagtatt    2700
ttaggaggtg tttaatgatg aaaggttttg caatgctcag tatcggtaaa gttggctgga    2760
ttgagaagga aaagcctgct cctggcccat ttgatgctat tgtaagacct ctagctgtgg    2820
ccccttgcac ttcggacatt cataccgttt ttgaaggcgc cattggcgaa agacataaca    2880
tgatactcgg tcacgaagct gtaggtgaag tagttgaagt aggtagtgag gtaaaagatt    2940
ttaaacctgg tgatcgcgtt gttgtgccag ctattacccc tgattggcgg acctctgaag    3000
tacaaagagg atatcaccag cactccggtg gaatgctggc aggctggaaa ttttcgaatg    3060
taaaagatgg tgttttttggt gaattttttc atgtgaatga tgctgatatg aatttagcac    3120
atctgcctaa agaaattcca ttggaagctg cagttatgat tcccgatatg atgaccactg    3180
gttttcacgg agctgaactg gcagatatag aattaggtgc gacggtagca gttttgggta    3240
ttggcccagt aggtcttatg gcagtcgctg gtgccaaatt gcgtggagcc ggaagaatta    3300
ttgccgtagg cagtagacca gttgtgtag atgctgcaaa atactatgga gctactgata    3360
ttgtaaacta taaagatggt cctatcgaaa gtcagattat gaatctaact gaaggcaaag    3420
gtgtcgatgc tgccatcatc gctggaggaa atgctgacat tatggctaca gcagttaaga    3480
ttgttaaacc tggtggcacc atcgctaatg taaattattt tggcgaagga gaggttttgc    3540
ctgttcctcg tcttgaatgg ggttgcggca tggctcataa aactataaaa ggcgggctat    3600
gccccggtgg acgtctaaga atggaaagac tgattgacct tgttttttat aagcgtgtcg    3660
atccttctaa gctcgtcact cacgttttcc ggggatttga caatattgaa aaagccttta    3720
tgttgatgaa agacaaacca aaagacctaa tcaaacctgt tgtaatatta gcataaaaat    3780
ggggacttag tcccccattt ttatgctaat aaggctaaat acactggttt ttttatatga    3840
cacatcggcc agtaaactct tggtaaaaaa ataacaaaaa atagttattt tcttaacatt    3900
tttacgccat taacacttga taacatcatc gaagaagtaa ataaacaact attaaataaa    3960
agaagaagga ggattatcat gttcaaaatt ttagaaaaaa gagaattggc accttccatc    4020
aagttgtttg taatagaggc accactagta gccaaaaaag caaggccagg ccaattcgtt    4080
atgctaagga taaagaagg aggagaaaga attctgagaa gatatggact aaaaaatata    4140
caaaggtttc ttgtgttttt aataccgtta tgttaatata atgtaatata tattttataa    4200
taatatgtat gagagatagt gttttgctat attgctataa agaatgagga gggaactagt    4260
tgaaatattt taaaaatata agcttttata tagtgctgtt tgtgatgttg ctggcttttc    4320
tggtcatagt gcaaagccgg cctgttgaaa aggaacaaaa gtattcccag cttataagcg    4380
atattcacaa cggtaaggtt caggaaatta tactggaaga caataaagcc acggtaaaat    4440
ataaagaaga gggacagagg gaccagtttg tttatatacc cgatgttgaa gtgttcatga    4500
atgagataaa cgaccttatc agagaaggag agcttgagtt tcgaagcaag gttccttatt    4560
cgccgccgtg gtggatttct atattgccta ctttggtaat tatagttgtg tttgtgctgt    4620
tctgggtgtt cttcctccag cagtctcagg gcggcggaag cagagtaatg tcttttggaa    4680
```

```
atcgcgaggc cggccagtat tctgacatgg gtgtatcaat aacccatgcg tttccgtatt    4740
gtatcggaat ggtttcggac agggcggtgg aatagacact ggaaaagatt tttttgcccg    4800
aggatgcatt gataaagtat ttcttttccg aaagagagga aaagattcta aagagtttg    4860
gaaatactga tgaatattgt gtgcagagta caattctatg gacaagaaaa gaggctttgt    4920
caaaactttt tcgtctggga atgaggatgg attttaaaaa gctggatact tggaggacg    4980
aggtggtttt tcaggaaaca aacagggcgc gtctgttttc ttttatatgc aataattact    5040
gtatctctct ggcattgcca ggttttaata aagattaaaa ttattgacta gaaataaaaa    5100
aattgtccat aatattaatg gacaaaaaaa caagaattaa catcaaagga agataaaaat    5160
actttgttaa aaaattaatt attttttatc taaactattg aaaatgaaaa taaaataata    5220
taaaatgaat catagtgcaa gagatacttg ccagaggatg aatattttac tgcattcatg    5280
ctttatggca gctaatagag gcattaaatt aaattttaat ttacaatagg aggcgatatt    5340
aatgaacttt aataaaattg atttagacaa ttggaagaga aaagagatat ttaatcatta    5400
tttgaaccaa caaacgactt ttagtataac cacagaaatt gatattagtg ttttataccg    5460
aaacataaaa caagaaggat ataaatttta ccctgcattt attttcttag tgacaagggt    5520
gataaactca aatacagctt ttagaactgg ttacaatagc gacggagagt taggttattg    5580
ggataagtta gagccacttt atacaatttt tgatggtgta tctaaaacat tctctggtat    5640
ttggactcct gtaaagaatg acttcaaaga gttttatgat ttatacctt ctgatgtaga    5700
gaaatataat ggttcgggga aattgtttcc caaaacacct atacctgaaa atgcttttc    5760
tctttctatt attccatgga cttcatttac tgggtttaac ttaaatatca ataataatag    5820
taattacctt ctacccatta ttacagcagg aaaattcatt aataaggta attcaatata    5880
tttaccgcta tctttacagg tacatcattc tgtttgtgat ggttatcatg caggattgtt    5940
tatgaactct attcaggaat tgtcagatag gcctaatgac tggctttat aataaaggag    6000
gtcgacgtca tggaaaattt atcaaaagac atcgatgaaa ttttgatcac agaagaagaa    6060
cttaaggaaa agataaaaga gcttgggagg caaatcacaa aagactacaa agggaaaaat    6120
ttgatgttgg taggagtttt aaaaggtgct taatgtttta tggctgattt gtcaagacac    6180
atagatttgc ctttatcact tgatttatg gctgtttcca gctatggaag ctcaactcat    6240
tcatcaggaa tagtaaagat aatcaaagat cttgatataa gcatagaagg caaagatgtt    6300
ctgattgtgg aagacataat tgacagcggt ttgactttgt cttacttaag ggaaacttta    6360
cttgaaggaa agccaaaaag cctgaaaata tgcacaatat tagacaaacc ggagagaaga    6420
gaagcatctg taaagtcga ttatgtagga tttaagatac ctgataagtt tgtcgtgggt    6480
tatgattggg actttgatga aaagtacagg aaccttcctt ttataggcgt tttgaaacct    6540
gaaatgtaca gctaagcccg ggcctcgaga aaacaaaagg ctcagtcgga agactgggcc    6600
ttttgttttg gtaccagaag atatggacta aaaaatatac aaaggtttct tgtgttttta    6660
ataccgttat gttaatataa tgtaatatat attttataat aatatgtatg agagatagtg    6720
ttttgctata ttgctataaa gaatgaggag ggaactagtt gaaatatttt aaaaatataa    6780
gcttttatat agtgctgttt gtgatgttgc tggcttttct ggtcatagtg caaagccggc    6840
ctgttgaaaa ggaacaaaag tattcccagc ttataagcga tattcacaac ggtaaggttc    6900
aggaaattat actggaagac aataaagcca cggtaaaata taagaagag ggacagaggg    6960
accagtttgt ttatataccc gatgttgaag tgttcatgaa tgagataaac gaccttatca    7020
gagaaggaga gcttgagttt cgaagcaagg ttccttattc gccgccgtgg tggatttcta    7080
```

```
tattgcctac tttggtaatt atagttgtgt ttgtgctgtt ctgggtgttc ttcctccagc    7140
agtctcaggg cggcggaagc agagtaatgt cttttggaaa gaattcggcg cgcctcagcg    7200
tttaaacccg ctgatcctag agggccgcat catgtaatta gttatgtcac gcttacattc    7260
acgccctccc cccacatccg ctctaaccga aaaggaagga gttagacaac ctgaagtcta    7320
ggtccctatt tatttttta tagttatgtt agtattaaga acgttattta tatttcaaat     7380
ttttctttt tttctgtaca gacgcgtgta cgcatgtaac attatactga aaaccttgct     7440
tgagaaggtt ttgggacgct cgaaggcttt aatttgcaag ctgcggccct gcattaatga    7500
atcggccaac gcgcggggag aggcggtttg cgtattgggc gctcttccgc ttcctcgctc    7560
actgactcgc tgcgctcggt cgttcggctg cggcgagcgg tatcagctca ctcaaaggcg    7620
gtaatacggt tatccacaga atcagggggat aacgcaggaa agaacatgtg agcaaaaggc   7680
cagcaaaagc ccaggaaccg taaaaaggcc gcgttgctgg cgttttccca taggctccgc    7740
cccccctgacg agcatcacaa aaatcgacgc tcaagtcaga ggtggcgaaa cccgacagga   7800
ctataaagat accaggcgtt ccccctgga agctccctcg tgcgctctcc tgttccgacc     7860
ctgccgctta ccggatacct gtccgccttt ctcccttcgg gaagcgtggc gctttctcat    7920
agctcacgct gtaggtatct cagttcggtg taggtcgttc gctccaagct gggctgtgtg    7980
cacgaaccc ccgttcagcc cgaccgctgc gccttatccg gtaactatcg tcttgagtcc     8040
aacccggtaa gacacgactt atcgccactg gcagcagcca ctggtaacag gattagcaga    8100
gcgaggtatg taggcggtgc tacagagttc ttgaagtggt ggcctaacta cggctacact    8160
agaaggacag tatttggtat ctgcgctctg ctgaagccag ttaccttcgg aaaaagagtt    8220
ggtagctctt gatccggcaa acaaaccacc gctggtagcg gtggtttttt tgtttgcaag    8280
cagcagatta cgcgcagaaa aaaggatct caagaagatc ctttgatctt ttctacgggg     8340
tctgacgctc agtggaacga aaactcacgt taagggattt tggtcatgaa aaatccgct     8400
taagtccgcg ggacttcatg gcactttcta caccttgctt cataagactc ctttgctcca    8460
accattataa tgggatcgtc gtaattggca ggcttcccat ttataagcct ttgcgtgcga    8520
gtagcaggat tgccacactt catgcatata gcagtaagct tatcgacaaa ttcagctatg    8580
gccatcaatt ctggagtcgg accaaatggt tcacctctaa agtccatgtc aagccctgca    8640
catatgactc ttttcccgct atcggcaatc tcttttacga tgtcgactat ttcagaatca    8700
aaaaattgaa cttcatctat agcaaataca tccgtatctt cttcagcata agccaatatg    8760
tcagaagcct ttactatggc aatggcgtgc atgttgtcgc cgttatgaga tacgactttg    8820
tctatggaat acctatcgtc tatagccggt ttgaaaacct gaacttttg cctggcaatc     8880
ttagctctct ttatccttct tataagttcc tcactttttc cactgaacat gggaccagtt    8940
acaacttcta tgtacccgtg gtctttaggc ccatacatct ttcgtcctcc ttaaaatttt    9000
cgtttatttg ttttttattt agtgtgccta aaagcaccat cttatacatt cgtacccttat   9060
atctcttatc ttgtatctct tacctcatat ctcttattat taactaccga agtatatttt    9120
cataacggaa tcttatgact tatttttctg actgccgttt taccatacgg ttaatttata    9180
cggaaacagc taatctaacc ttgctgaagg catgttttacc aaaatattat atctacttta   9240
ccatattaat tcaagtggtc atttttgatat tttacgccaa aatttttagc gttcctttac   9300
ttgataattt atccaaaaac cttcattcgt caaaacaatt atgatataat taatttatga    9360
tatgattaat taatatttac ggataactaa tcatttcaat gcaatagatc aacatgcaaa    9420
```

```
tcaatatcca ccttactccg aacattttgc accaacgaat gcccagcact atatcccggc    9480
aagcaatata acgtctataa tttttttatga taacgataaa attaaatttt atgaaagggg   9540
taaaagcatg agaaaaatag ctgtattgtt aattactttg acgttcttag tcacgactcg    9600
aatttaggag gcttacttgt ctgctttctt cattagaatc aatccttttt taaaagtcaa    9660
tcccgtttgt tgaactactc tttaataaaa taattttttcc gttcccaatt ccacattgca   9720
ataatagaaa atccatcttc atcggctttt tcgtcatcat ctgtatgaat caaatcgcct    9780
tcttctgtgt catcaaggtt taatttttta tgtatttctt ttaacaaacc accataggag    9840 attaacctttt tacggtgtaa accttcctcc aaatcagaca aacgtttcaa attctttttct 9900 tcatcatcgg tcataaaatc cgtatccttt acaggatatt ttgcagtttc gtcaattgcc    9960
gattgtatat ccgatttata tttatttttc ggtcgaatca tttgaacttt tacatttgga   10020
tcatagtcta atttcattgc cttttttccaa aattgaatcc attgttttg attcacgtag    10080 tttttctgtat tcttaaaata agttggttcc acacatacca atacatgcat gtgctgatta  10140
taagaattat ctttattatt tattgtcact tccgttgcac gcataaaacc aacaagattt    10200
ttattaattt ttttatattg catcattcgg cgaaatcctt gagccatatc tgacaaactc   10260
ttatttaatt cttcgccatc ataaacattt ttaactgtta atgtgagaaa caaccaacga   10320
actgttggct tttgtttaat aacttcagca acaaccttttt gtgactgaat gccatgtttc   10380
attgctctcc tccagttgca cattggacaa agcctggatt tacaaaacca cactcgatac   10440
aactttcttt cgcctgtttc acgattttgt ttatactcta atatttcagc acaatctttt   10500 actcttcag ccttttttaaa ttcaagaata tgcagaagtt caaagtaatc aacattagcg   10560 atttttctttt ctctccatgg tctcacttttt ccacttttttg tcttgtccac taaaaccctt   10620 gattttttcat ctgaataaat gctactatta ggacacataa tattaaaaga aaccccccatc  10680 tatttagtta tttgtttggt cacttataac tttaacagat ggggttttttc tgtgcaacca   10740 atttttaaggg ttttcaatac tttaaaaacac atacatacca acacttcaac gcacctttca  10800
gcaactaaaa taaaaatgac gttatttcta tatgtatcaa gaatagaaag aactcgtttt   10860
tcgctacgct caaaacgcaa aaaaagcact cattcgagtg ctttttctta tcgctccaaa    10920
tcatgcgatt ttttcctctt tgcttttcttt tgctcacgaa gttctcgatc acgctgcaaa   10980
acatcttgaa gcgaaaaagt attcttcttt tcttccgatc gctcatgctg acgcacgaaa   11040
agccctctag gcgcatagga acaactccta aatgcatgtg aggggttttttc tcgtccatgt  11100 gaacagtcgc atacgcaata ttttgttttcc catagcggcc gcgattatca aaaaggatct   11160
tcacctagat cctttttaaat taaaaatgaa gttttaaatc aatctaaagt atatatgagt   11220
aaacttggtc tgacagttac caatgcttaa tcagtgaggc acctatctca gcgatctgtc   11280
tatttcgttc atccatagtt gcctgactcc ccgtcgtgta gataactacg atacgggagc    11340
gcttaccatc tggccccagt gctgcaatga taccgcgaga cccacgctca ccggctccag   11400
atttatcagc aataaaccag ccagccggaa gggccgagcg cagaagtggt cctgcaactt    11460
tatccgcctc catccagtct attaattgtt gccgggaagc tagagtaagt agttcgccag   11520
ttaatagttt gcgcaacgtt gttggcattg ctacaggcat cgtggtgtca ctctcgtcgt    11580
ttggtatggc ttcattcagc tccggttccc aacgatcaag gcgagttaca tgatccccca   11640
tgttgtgcaa aaaagcggtt agctccttcg gtcctccgat cgttgtcaga agtaagttgg   11700
ccgcagtgtt atcactcatg gttatggcag cactgcataa ttctcttact gtcatgccat   11760
ccgtaagatg cttttctgtg actggtgagt actcaaccaa gtcattctga aatagtgta     11820
```

```
tgcggcgacc gagttgctct tgcccggcgt caatacggga taatagtgta tcacatagca    11880
gaactttaaa agtgctcatc attggaaaac gttcttcggg gcgaaaactc tcaaggatct    11940
taccgctgtt gagatccagt tcgatgtaac ccactcgtgc acccaactga tcttcagcat    12000 cttttactt caccagcgtt tctgggtgag caaaaacagg aaggcaaaat gccgcaaaaa     12060
agggaataag ggcgacacgg aaatgttgaa tactcatact cttccttttt caat          12114
```

<210> SEQ ID NO 70
<211> LENGTH: 25
<212> TYPE: DNA
<213> ORGANISM: Artificial sequence
<220> FEATURE:
<223> OTHER INFORMATION: Primer X09712

<400> SEQUENCE: 70
cctcatttga taattgcctc ctcat                                          25

<210> SEQ ID NO 71
<211> LENGTH: 29
<212> TYPE: DNA
<213> ORGANISM: Artificial sequence
<220> FEATURE:
<223> OTHER INFORMATION: Primer X09713

<400> SEQUENCE: 71
atcgcatttt gccgttatgt gccattgaa                                      29

ENGINEERING MICROORGANISMS TO INCREASE ETHANOL PRODUCTION BY METABOLIC REDIRECTION

CROSS-REFERENCE TO RELATED APPLICATIONS

This application is the National Stage of International Application Number PCT/US2012/057952, filed Sep. 28, 2012, which claims the benefit of U.S. Provisional Application No. 61/542,082, filed Sep. 30, 2011, which are incorporated by reference herein.

STATEMENT REGARDING FEDERALLY-SPONSORED RESEARCH AND DEVELOPMENT

This invention was funded, in part, by the United States government under a Department of Energy Biomass Program award # DE-FC36-07G017057. This invention was also funded, in part, by the BioEnergy Science Center (BESC) under the DOE Office of Science through award number DE-POS2-06ER64304. The U.S. Government has certain rights in this invention.

REFERENCE TO SEQUENCE LISTING SUBMITTED ELECTRONICALLY VIA EFS-WEB

The content of the electronically submitted sequence listing (Name: 2608_0640001_CORRECTED_Sequence-Listing_ascii.txt; 253,390 bytes; and Date of Creation: May 12,2014)is herein incorporated by reference in its entirety.

BACKGROUND OF THE INVENTION

Fuel and energy production have emerged as one of the great challenges of the 21$^{st}$ century, and solving these problems touches upon an arena of issues that range from security to poverty to the environment. New approaches to providing for the world's energy needs are required to address these mounting concerns.

Among forms of plant biomass, lignocellulosic biomass ("biomass") is particularly well-suited for energy applications because of its large-scale availability, low cost, and environmentally benign production. In particular, many energy production and utilization cycles based on cellulosic biomass have very low greenhouse gas emissions on a life-cycle basis. The primary obstacle impeding the more widespread production of energy from biomass feedstocks is the general absence of low-cost technology for overcoming the recalcitrance of these materials to conversion into useful products. Lignocellulosic biomass contains carbohydrate fractions (e.g., cellulose and hemicellulose) that can be converted into ethanol or other end-products including lactic acid and acetic acid. In order to convert these fractions, the cellulose or hemicellulose must ultimately be converted or hydrolyzed into monosaccharides. This hydrolysis has historically proven to be problematic.

Cellulose digesting anaerobic bacteria are of great potential utility because they can be used to produce ethanol or other fuels from abundant substrates such as forestry, municipal and agricultural waste. However, it has been challenging to realize this potential utility because of difficulty in the genetic manipulation of these organisms and lack of understanding of their metabolic biochemistry. Genome sequence data and recent advances in biotechnological tools for genetic modification of *Clostridium thermocellum* and other similar organisms have made it possible to make progress in this area, but the great complexity of metabolism makes it difficult to achieve efficiently a desired outcome such as near theoretical ethanol yield from cellulosic substrates.

Many microorganisms can metabolize glucose, cellulose or cellodextrins anaerobically, but they vary in the pathways utilized and the products generated. It has been demonstrated in genetically modified *Thermoanaerobacterium saccharolyticum* that glucose and cellobiose can be fermented to ethanol at very close to theoretical yield, but similar genetic manipulations in *Clostridium thermocellum* have not had the same outcome. Argyros, D A, Tripathi S A, Barrett T F, Rogers S R, Feinberg L F, Olson D G, Foden J M, Miller B B, Lynd L R, Hogsett D A, Caiazza N C, High ethanol titers from cellulose using metabolically engineered thermophilic, anaerobic microbes. *Appl. Env. Microbiol.* 2011. 77(23):8288-94.

*Clostridium thermocellum* has both cellulolytic and ethanologenic fermentation capabilities and can directly convert a cellulose-based substrate into ethanol. However, *C. thermocellum* possesses a branched carbon utilization pathway that generates products other than ethanol and is not as amenable to manipulation for ethanol production as that of *T. saccharolyticum*. This is exemplified more clearly when the carbon utilization pathways from the two organisms are compared. In homoethanologenic *T. saccharolyticum*, the carbon atoms from glucose flow down a linear central metabolic pathway to ethanol (FIG. 1A). In *C. thermocellum*, a different set of enzymes is present and thus the carbon utilization pathway (FIG. 1B) is different than in *T. saccharolyticum*. This difference in the carbon-utilization pathways in these organisms makes it infeasible to produce ethanol at theoretical yield with the same modifications.

The invention relates to cellulose-digesting organisms that have been genetically modified to allow the production of ethanol at a high yield by redirecting carbon flux at key steps of central metabolism. Redirection means altering the flux of carbon from the normally prevailing routes to alternate routes by means of genetic modification.

BRIEF SUMMARY OF THE INVENTION

Aspects of the invention are directed to increasing ethanol production by a microorganism through redirecting carbon flux and eliminating the pathways for alternate end-products. In some embodiments, the present invention allows more ethanol to be produced for the same amount of substrate, allowing more profit to be gained from the same substrate, and thus requires less cell mass in exchange for higher fermentation end-products, such as ethanol.

In one embodiment, the invention relates to a recombinant microorganism capable of fermenting biomass and producing ethanol. In some embodiments, the microorganism is a prokaryote.

As recently as 2010 it was published that *C. thermocellum* contains a pyruvate kinase gene. (Roberts S B, Gowen, C M, Brooks, J P, and Fong, S S, Genome-scale metabolic analysis of *Clostridium thermocellum* for bioethanol production. *BMC Systems Biology.* 2010. 4:31). However, contrary to this assertion, the present invention demonstrates that endogenous pyruvate kinase activity is either not present, or is sub-optimal in *C. thermocellum*.

In one embodiment, the invention relates to a recombinant prokaryotic microorganism comprising a heterologous nucleic acid encoding pyruvate kinase wherein the polynucleotide has a nucleotide sequence at least about 80% identical to the nucleotide sequence of SEQ ID NO: 1, and a genetic modification that leads to the down-regulation of an enzyme in a lactic acid and/or acetic acid pathway wherein the polynucleotide encoding for the down-regulated enzyme has a nucleotide sequence at least about 80% identical to the nucleotide sequence of SEQ ID NOs: 3, 5, 7 or 53.

In one embodiment, the invention relates to a recombinant prokaryotic microorganism comprising a heterologous nucleic acid encoding pyruvate kinase wherein the polynucleotide has a nucleotide sequence at least about 80% identical to the nucleotide sequence of SEQ ID NO: 1, and a genetic modification that leads to the down-regulation of an enzyme in a pathway for the conversion of phosphoenolpyruvate to pyruvate wherein the polynucleotide encoding for the down-regulated enzyme has a nucleotide sequence at least about 80% identical to the nucleotide sequence of SEQ ID NOs: 9, 11, 13, 15, 17, or 51.

In one embodiment, the invention relates to a recombinant prokaryotic microorganism comprising a heterologous nucleic acid encoding pyruvate kinase wherein the polynucleotide has a nucleotide sequence at least about 80% identical to the nucleotide sequence of SEQ ID NO: 1; a genetic modification that leads to the down-regulation of an enzyme in a lactic acid or acetic acid pathway wherein the polynucleotide encoding for the down-regulated enzyme has a nucleotide sequence at least about 80% identical to the nucleotide sequence of SEQ ID NOs: 3, 5, 7, or 53; and a genetic modification that leads to the down-regulation of an enzyme in a pathway for conversion of phosphoenolpyruvate to pyruvate wherein the polynucleotide encoding for the down-regulated enzyme has a nucleotide sequence at least about 80% identical to the nucleotide sequences of SEQ ID NOs: 9, 11, 13, 15, 17, or 51.

In one embodiment, the invention relates to a recombinant prokaryotic microorganism comprising a heterologous nucleic acid encoding pyruvate formate lyase wherein the polynucleotide has a nucleotide sequence at least about 80% identical to the nucleotide sequence of SEQ ID NO: 19, and activating enzymes wherein the polynucleotides encoding for them have a nucleotide sequence at least about 80% identical to the nucleotide sequences of SEQ ID NO: 21.

In one embodiment, the invention relates to a recombinant prokaryotic microorganism comprising a heterologous nucleic acid encoding pyruvate formate lyase wherein the polynucleotide has a nucleotide sequence at least about 80% identical to the nucleotide sequence of SEQ ID NO: 19, PFL-activating enzymes wherein the polynucleotides encoding for them have a nucleotide sequence at least about 80% identical to the nucleotide sequences of SEQ ID NO: 21, and a genetic modification that leads to the down-regulation of an enzyme in a pyruvate metabolism pathway wherein the polynucleotide encoding for the down-regulated enzyme has a nucleotide sequence at least about 80% identical to the nucleotide sequences of SEQ ID NOs: 23, 25, 27, 29, 31, 33, 35, 37, 39, or 41. In some embodiments, the enzyme in the pathway is pyruvate oxidoreductase or NADH-dependent reduced ferredoxin:NADP+ oxidoreductase.

In one embodiment, the invention relates to a recombinant prokaryotic microorganism comprising a heterologous nucleic acid encoding pyruvate formate lyase wherein the polynucleotide has a nucleotide sequence at least about 80% identical to the nucleotide sequence of SEQ ID NO: 19, PFL-activating enzymes wherein the polynucleotides encoding for them have a nucleotide sequence at least about 80% identical to the nucleotide sequences of SEQ ID NO: 21, and a polynucleotide encoding for the enzyme has a nucleotide sequence at least about 80% identical to the nucleotide sequences of SEQ ID NOs: 43, 45, or 47 or at least about 80% identical to the polypeptide sequences of 49 and 50. In some embodiments, the recombinant prokaryotic microorganism further comprises a genetic modification that leads to the down-regulation of an enzyme in a lactic acid or acetic acid pathway wherein the polynucleotide encoding for the down-regulated enzyme has a nucleotide sequence at least about 80% identical to the nucleotide sequence of SEQ ID NOs: 3, 5, 7, or 53.

In one embodiment, the invention relates to a recombinant prokaryotic microorganism comprising a heterologous nucleic acid encoding pyruvate formate lyase wherein the polynucleotide has a nucleotide sequence at least about 80% identical to the nucleotide sequence of SEQ ID NO: 19; PFL-activating enzymes wherein the polynucleotides encoding for them have a nucleotide sequence at least about 80% identical to the nucleotide sequences of SEQ ID NO: 21; a genetic modification that leads to the down-regulation of an enzyme in a pyruvate metabolism pathway wherein the polynucleotide encoding for the down-regulated enzyme has a nucleotide sequence at least about 80% identical to the nucleotide sequences of SEQ ID NOs: 23, 25, 27, 29, 31, 33, 35, 37, 39, or 41; and a genetic modification that leads to the down-regulation of an enzyme in a lactic acid and/or acetic acid pathway wherein the polynucleotide encoding for the down-regulated enzyme has a nucleotide sequence at least about 80% identical to the nucleotide sequence of SEQ ID NOs: 3, 5, 7, or 53.

In one embodiment, the invention relates to a recombinant prokaryotic microorganism comprising a heterologous nucleic acid encoding pyruvate kinase wherein the polynucleotide has a nucleotide sequence at least about 80% identical to the nucleotide sequence of SEQ ID NO: 1; a genetic modification that leads to the down-regulation of an enzyme in a lactic acid or acetic acid pathway wherein the polynucleotide encoding for the down-regulated enzyme has a nucleotide sequence at least about 80% identical to the nucleotide sequence of SEQ ID NOs: 3 or 53; a genetic modification that leads to the down-regulation of an enzyme in a pathway for conversion of phosphoenolpyruvate to pyruvate wherein the polynucleotide encoding for the down-regulated enzyme has a nucleotide sequence at least about 80% identical to the nucleotide sequences of SEQ ID NO: 13, and a heterologous nucleic acid encoding a bifunctional acetaldehyde-alcohol dehydrogenase wherein the polynucleotide has a nucleotide sequence at least about 80% identical to the nucleotide sequence of SEQ ID NO: 67.

BRIEF DESCRIPTION OF THE DRAWINGS/FIGURES

FIG. 1 depicts a simplified metabolic pathway from cellobiose to ethanol in *T. saccharolyticum* (A) and *C. thermocellum* (B). Only reduced nicotinamide cofactors are shown; the oxidized forms are implied. The cofactors involved in acetate and lactate production are not shown. The multiple steps from cellobiose to PEP are represented by a dotted line, but all other arrows represent single biochemical reactions. Abbreviations are PEP=phosphoenolpyruvate, Pyr=pyruvate, Oxa=oxaloacetate, Mal=malate, Ac-CoA=acetyl-CoA, Aceald=acetaldehyde, Etoh=ethanol, Ac-P=acetyl phosphate, Fdred=reduced ferredoxin, Fdox=oxidized ferredoxin. The names of the genes encoding the enzymes that catalyze each step are shown in italics.

Figure 5:
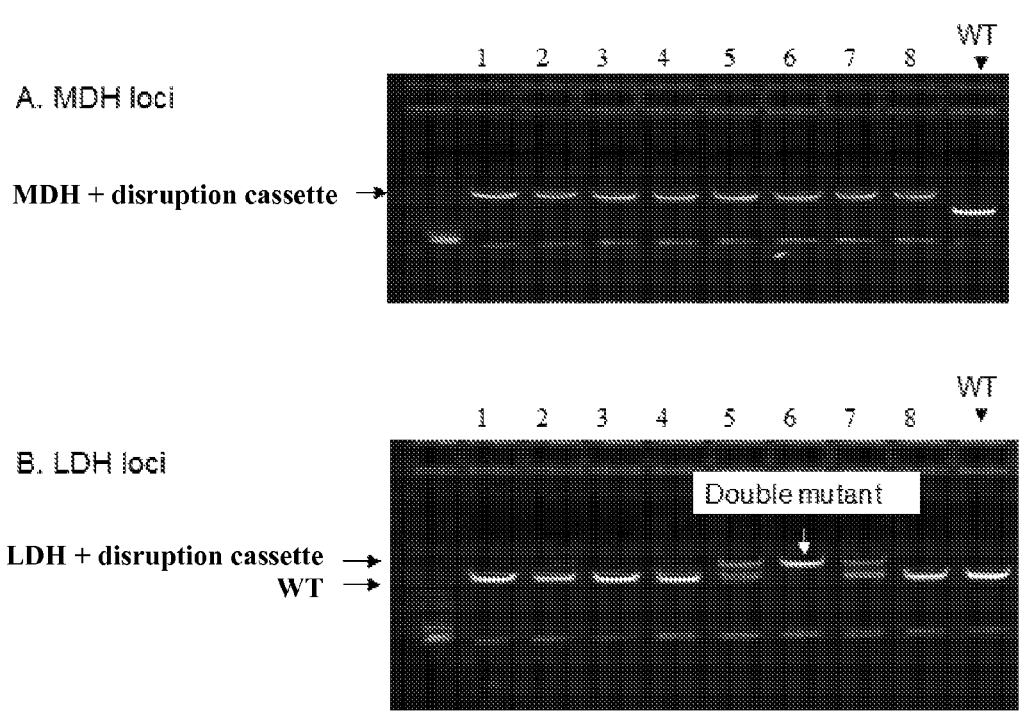

FIG. 5, in Part A, depicts an electrophoretic gel containing DNA samples from the mdh locus. The results of the assay indicate that all 8 strains contain a disruption cassette at the mdh locus, signified by an increased size of the PCR product. Part B depicts the status of the ldh locus in the same eight strains. The gel image demonstrates that the strain represented in lane 6 has a disruption cassette inserted at the ldh locus, disrupting the ldh gene. Strains represented in lanes 5 and 7 are a mixed culture of mutant and wild type cells, while the remainder are just wild type at the ldh locus. Thus, the strain represented in lane 6 has a disruption cassette at both the ldh and mdh loci.

Figure 6:
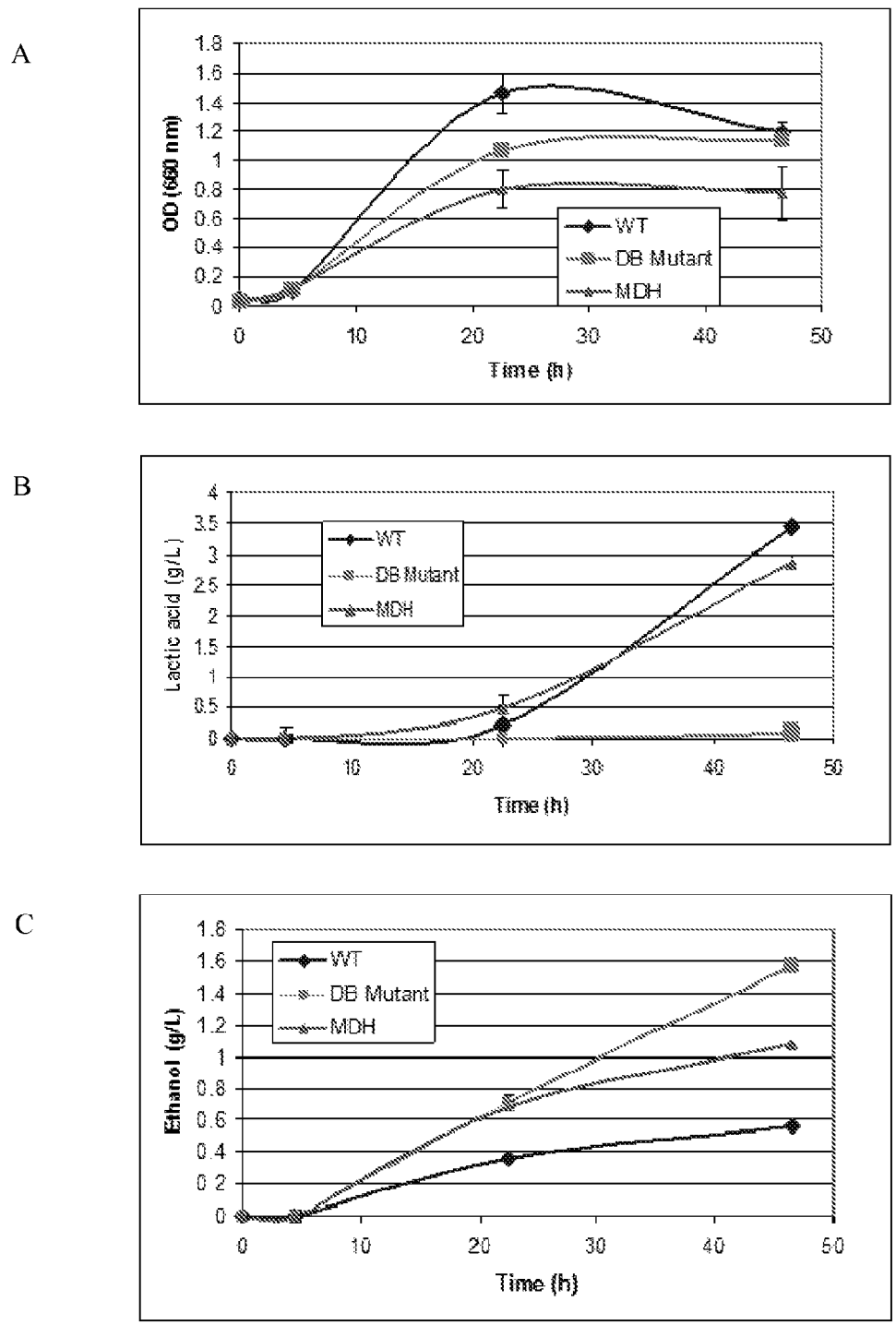

FIG. 6, in part A, shows the growth as a measure of time, measured by optical density (OD), in wild type strains, mdh mutant strains, and mdh, ldh double mutant strains. Part B depicts the lactic acid production as a function of time in wild type strains, mdh mutant strains, and mdh, ldh double mutant strains. Part C depicts the ethanol production as a measure of time in wild type strains, mdh mutant strains, and mdh, ldh double mutant strains.

DETAILED DESCRIPTION OF THE INVENTION

Definitions

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The embodiment(s) described, and references in the specification to "one embodiment", "an embodiment", "an example embodiment", etc., indicate that the embodiment(s) described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

The description of "a" or "an" item herein may refer to a single item or multiple items. It is understood that wherever embodiments are described herein with the language "comprising," otherwise analogous embodiments described in terms of "consisting of" and/or "consisting essentially of" are also provided. Thus, for example, reference to "a polynucleotide" includes a plurality of such polynucleotides and reference to "the microorganism" includes reference to one or more microorganisms, and so forth.

The term "heterologous" is used in reference to a polynucleotide or a gene not normally found in the host organism. "Heterologous" includes up-regulated endogenous genes. "Heterologous" also includes a native coding region, or portion thereof, that is reintroduced into the source organism in a form that is different from the corresponding native gene, e.g., not in its natural location in the organism's genome. A heterologous gene may include a native coding region that is a portion of a chimeric gene including a non-native regulatory region that is reintroduced into the native host or modifications to the native regulatory sequences that affect the expression level of the gene. Foreign genes can comprise native genes inserted into a non-native organism, or chimeric genes. A heterologous polynucleotide, gene, polypeptide, or an enzyme may be derived from any source, e.g., eukaryotes, prokaryotes, viruses, or synthetic polynucleotide fragments, and includes up-regulated endogenous genes.

The terms "gene(s)" or "polynucleotide" or "nucleic acid" or "polynucleotide sequence(s)" are intended to include nucleic acid molecules, e.g., polynucleotides which include an open reading frame encoding a polypeptide, and can further include non-coding regulatory sequences, and introns. In addition, the terms are intended to include one or more genes that map to a functional locus. Also, the terms are intended to include a specific gene for a selected purpose. The gene may be endogenous to the host cell or may be recombinantly introduced into the host cell, e.g., as a plasmid maintained episomally or a plasmid (or fragment thereof) that is stably integrated into the genome. In addition to the plasmid form, a gene may, for example, be in the form of linear DNA or RNA. The term "gene" is also intended to cover multiple copies of a particular gene, e.g., all of the DNA sequences in a cell encoding a particular gene product.

The term "expression" is intended to include the expression of a gene at least at the level of mRNA production, generally subsequently translated into a protein product.

As used herein, an "expression vector" is a vector capable of directing the expression of genes to which it is operably linked.

In some embodiments, the microorganisms contain enzymes involved in cellulose digestion, metabolism and/or hydrolysis. A "cellulolytic enzyme" can be any enzyme involved in cellulose digestion, metabolism, and/or hydrolysis. The term "cellulase" refers to a class of enzymes produced chiefly by fungi, bacteria, and protozoans that catalyze cellulolysis (i.e. the hydrolysis) of cellulose. However, there are also cellulases produced by other types of organisms such as plants and animals. Several different kinds of cellulases are known, which differ structurally and mechanistically. There are general types of cellulases based on the type of reaction catalyzed: endocellulase breaks internal bonds to disrupt the crystalline structure of cellulose and expose individual cellulose polysaccharide chains; exocellulase cleaves 2-4 units from the ends of the exposed chains produced by endocellulase, resulting in the tetrasaccharides or disaccharide such as cellobiose. There are two main types of exocellulases (or cellobiohydrolases, abbreviate CBH)—one type working processively from the reducing end, and one type working processively from the non-reducing end of cellulose; cellobiase or beta-glucosidase hydrolyses the exocellulase product into individual monosaccharides; oxidative cellulases that depolymerize cellulose by radical reactions, as for instance cellobiose dehydrogenase (acceptor); cellulose phosphorylases that depolymerize cellulose using phosphates instead of water. In the most familiar case of cellulase activity, the enzyme complex breaks down cellulose to beta-glucose. A "cellulase" can be any enzyme involved in cellulose digestion, metabolism and/or hydrolysis, including, for example, an endoglucanase, glucosidase, cellobiohydrolase, xylanase, glucanase, xylosidase, xylan esterase, arabinofuranosidase, galactosidase, cellobiose phosphorylase, cellodextrin phosphorylase, mannanase, mannosidase, xyloglucanase, endoxylanase, glucuronidase, acetylxylanesterase, arabinofuranohydrolase, swollenin, glucuronyl esterase, expansin, pectinase, and feruoyl esterase protein.

A "plasmid" or "vector" refers to an extrachromosomal element often carrying one or more genes, and is usually in the form of a circular double-stranded DNA molecule. Plasmids and vectors may also contain additional genetic elements such as autonomously replicating sequences, genome integrating sequences, phage or nucleotide sequences. They may also be linear, circular, or supercoiled, of a single- or double-stranded DNA or RNA, derived from any source. Plasmids and vectors may be constructed by known techniques in which a number of nucleotide sequences have been joined or recombined into a unique construction. Plasmids and vectors generally also include a promoter fragment and DNA sequence for a selected gene product along with appropriate 3' untranslated sequence. Generally, the plasmids of the present invention are stable and self-replicating.

As used herein, the term "anaerobic" refers to an organism, biochemical reaction or process that is active or occurs under conditions of an absence of oxygen.

"Anaerobic conditions" are defined as conditions under which the oxygen concentration in the fermentation medium is too low for the microorganism to use as a terminal electron acceptor. Anaerobic conditions may be achieved by sparging a fermentation medium with an inert gas such as nitrogen until oxygen is no longer available to the microorganism as a terminal electron acceptor. Alternatively, anaerobic conditions may be achieved by the microorganism consuming the available oxygen of the fermentation until oxygen is unavailable to the microorganism as a terminal electron acceptor.

"Aerobic metabolism" refers to a biochemical process in which oxygen is used as a terminal electron acceptor to make energy, typically in the form of ATP, from carbohydrates. Aerobic metabolism typically occurs, for example, via glycolysis and the TCA cycle, wherein a single glucose molecule is metabolized completely into carbon dioxide in the presence of oxygen.

In contrast, "anaerobic metabolism" refers to a biochemical process in which oxygen is not the final acceptor of electrons generated. Anaerobic metabolism can be divided into anaerobic respiration, in which compounds other than oxygen serve as the terminal electron acceptor, and substrate level phosphorylation, in which no exogenous electron acceptor is used and products of an intermediate oxidation state are generated via a "fermentative pathway."

In "fermentative pathways", the amount of NAD(P)H generated by glycolysis is balanced by the consumption of the same amount of NAD(P)H in subsequent steps. For example, in one of the fermentative pathways of certain yeast strains, NAD(P)H generated through glycolysis donates its electrons to acetaldehyde, yielding ethanol. Fermentative pathways are usually active under anaerobic conditions but may also occur under aerobic conditions, under conditions where NADH is not fully oxidized via the respiratory chain.

As used herein, the term "flux" is the rate of flow of molecules through a metabolic pathway, akin to the flow of material in a process.

As used herein, the term "end-product" refers to a chemical compound that is not or cannot be used by a cell, and so is excreted or allowed to diffuse into the extracellular environment. Common examples of end-products from anaerobic fermentation include, but are not limited to, ethanol, acetic acid, formic acid, lactic acid, hydrogen and carbon dioxide.

As used herein, a "pathway" is a group of biochemical reactions that together can convert one compound into another compound in a multi-step process. A product of the first step in a pathway may be a substrate for the second step, and a product of the second step may be a substrate for the third, and so on. Pathways of the present invention include, but are not limited to, the lactate production pathway, the ethanol production pathway, and the acetate production pathway.

The term "recombination" or "recombinant" refers to the physical exchange of DNA between two identical (homologous), or nearly identical, DNA molecules. Recombination is used for targeted gene deletion to modify the sequence of a gene. The term "recombinant microorganism" and "recombinant host cell" are used interchangeably herein and refer to microorganisms that have been genetically modified to express or over-express endogenous polynucleotides, or to express heterologous polynucleotides, such as those included in a vector, or which have a modification in expression of an endogenous gene. By "modification" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the modification.

In one aspect of the invention, genes or particular polynucleotide sequences are partially, substantially, or completely deleted, silenced, inactivated, or down-regulated in order to inactivate the enzymatic activity they encode. Complete deletions provide maximum stability because there is no opportunity for a reverse mutation to restore function. Alternatively, genes can be partially, substantially, or completely deleted, silenced, inactivated, or down-regulated by insertion or substitution of nucleic acid sequences that disrupt the function and/or expression of the gene.

As used herein, the term "down-regulate" includes the deletion or mutation of a genetic sequence, or insertion of a disrupting genetic element, coding or non-coding, such that the production of a gene product is lessened by the deletion, mutation, or insertion. "Delete" or "Deletion" as used herein refers to a removal of a genetic element such that a corresponding gene is completely prevented from being expressed. In some embodiments, deletion refers to a complete gene deletion. Down-regulation can also occur by causing the repression of genetic elements by chemical or other environmental means, for example by engineering a chemically-responsive promoter element to control the expression of a desired gene product.

As used herein, the term "up-regulate" includes the insertion, reintroduction, mutation or increased expression of a genetic sequence, such that the production of a gene product is increased by the insertion, reintroduction, or mutation. "Insert" or "Insertion" as used herein refers to an introduction of a genetic element such that a corresponding gene is expressed. Up-regulation can also occur by causing the increased expression of genetic elements through an alteration of the associated regulatory sequence.

As used herein, the term "lactic acid pathway" refers to the biochemical pathway that converts carbon-containing substrates, such as pyruvate, from glycolysis into the production of lactic acid. Components of the pathway consist of all substrates, cofactors, byproducts, end-products, and enzymes in the pathway.

As used herein, the term "acetic acid pathway" refers to the biochemical pathway that converts carbon-containing substrates, such as pyruvate, from glycolysis into the production of acetic acid or other compounds. Components of the pathway consist of all substrates, cofactors, byproducts, intermediates, end-products, and enzymes in the pathway.

As used herein, the term "ethanol pathway" refers to the canonical pathway of ethanol production from pyruvate generated by glycolysis. Components of the pathway consist of all substrates, cofactors, byproducts, intermediates, end-products, and enzymes in the pathway.

As used herein, the term "glycolysis" or "glycolytic pathway" refers to the canonical pathway of basic metabolism in which a sugar such as glucose is broken down into more oxidized products, generating energy and/or compounds required for cell growth. The pathway consists of all substrates, cofactors, byproducts, end-products, and enzymes in the pathway.

As used herein, the term "pyruvate kinase" is intended to include the enzymes capable of converting phosphoenolpyruvate (PEP) to pyruvate. Pyruvate kinase includes those enzymes that correspond to Enzyme Commission Number (EC) EC 2.7.1.40 and exemplified by SEQ ID NO:1 and SEQ ID NO: 2.

As used herein, the term "lactate dehydrogenase" or "LDH" is intended to include the enzymes capable of converting pyruvate to lactate. LDH includes those enzymes that correspond to EC 1.1.1.27 and EC 1.1.1.28 and exemplified by SEQ ID NOs: 3-4 and SEQ ID NOs: 53-54.

As used herein, the term "phosphotransacetylase" or "PTA" is intended to include the enzymes capable of converting acetyl-CoA to acetylphosphate. PTA includes those enzymes that correspond to EC 2.3.1.8 and exemplified by SEQ ID NO: 5 and SEQ ID NO: 6.

As used herein, the term "acetate kinase" or "ACK" is intended to include the enzymes capable of converting acetylphosphate to acetate. ACK includes those enzymes that correspond to EC 2.7.2.1 and exemplified by SEQ ID NO: 7 and SEQ ID NO: 8.

As used herein, the term "pyruvate-phosphate dikinase" or "PPDK" is intended to include the enzymes capable of converting pyruvate to PEP. PPDK includes those enzymes that correspond to EC 2.7.9.1 and exemplified by SEQ ID NOs: 9-12.

As used herein, the term "phosphoenolpyruvate carboxykinase" or "PEPCK" is intended to include the enzymes capable of converting PEP to oxaloacetate. PEPCK includes those enzymes that correspond to EC 4.1.1.31, EC 4.1.1.32, EC 4.1.1.38, and EC 4.1.1.49 and exemplified by SEQ ID NO: 13 and SEQ ID NO: 14.

As used herein, the term "malic enzyme" is intended to include the enzymes capable of converting malate to pyruvate. Malic enzyme includes those enzymes that correspond to EC 1.1.1.38, EC 1.1.1.39, and EC 1.1.1.40 and exemplified by SEQ ID NO: 15 and SEQ ID NO: 16.

As used herein, the term "malate dehydrogenase" or "MDH" is intended to include the enzymes capable of converting oxaloacetate to malate. MDH includes those enzymes that correspond to EC 1.1.1.37, EC 1.1.1.82, EC 1.1.1.299, EC 1.5.4, EC 1.1.3.3, and EC 1.1.99.7, and exemplified by SEQ ID NOs: 17-18 and SEQ ID NO: 51-52.

As used herein, the term "pyruvate formate lyase" or "PFL" is intended to include the enzymes capable of converting pyruvate to formate and acetyl-CoA. PFL includes those enzymes that correspond to EC 2.3.1.54 and exemplified by SEQ ID NO: 19 and SEQ ID NO: 20.

As used herein, the term "PFL-activating enzymes" is intended to include those enzymes capable of aiding in the activation of PFL. PFL-activating enzymes include those enzymes that correspond to EC 1.97.1.4 and exemplified by SEQ ID NO: 21 and SEQ ID NO: 22.

As used herein, the term "pyruvate oxidoreductase" or "POR" is intended to include those enzymes capable of converting pyruvate and oxidized ferredoxin to acetyl CoA and reduced ferredoxin. POR includes those enzymes that correspond to EC 1.2.7.1 and exemplified by SEQ ID NOs: 23-38.

As used herein, the term "NADH-dependent reduced ferredoxin:NADP+ oxidoreductase" or "NfnAB" is intended to include any enzyme that "couples the exergonic reduction of NADP+ with reduced ferredoxin and the endergonic reduction of NADP+ with NADH in a reversible reaction." Wang S, Huang H, Moll J, Thauer R K. NADP+ reduction with reduced ferredoxin and NADP+ reduction with NADH are coupled via an electron-bifurcating enzyme complex in *Clostridium kluyveri*. *J. Bacteriol.* 2010 October; 192(19): 5115-23. NfnAB includes those enzymes that are exemplified by SEQ ID NOs: 39-42.

As used herein, the term "formate dehydrogenase" is intended to include those enzymes capable of converting formate to bicarbonate (carbon dioxide). Formate dehydrogenase includes those enzymes that correspond to EC 1.2.1.43 (NAD+-specific) and EC 1.2.1.2 (NADP+-specific) and exemplified by SEQ ID NOs: 43-50.

As used herein, the term "alcohol dehydrogenase" or "ADH" is intended to include the enzymes that catalyze the conversion of ethanol into acetaldehyde. Very commonly, the same enzyme catalyzes the reverse reaction from acetaldehyde to ethanol, which is the direction most relevant to fermentation. Alcohol dehydrogenase includes those enzymes that correspond to EC 1.1.1.1 and EC 1.1.1.2 and exemplified by the enzymes disclosed in GenBank Accession # U49975.

As used herein, the term "acetaldehyde dehydrogenase" or "ALDH" is intended to include the enzymes that catalyze the conversion of acetaldehyde into acetyl-CoA. Very commonly, the same enzyme catalyzes the reverse reaction from acetyl-CoA to acetaldehyde, which is the direction most relevant to fermentation. Acetaldehyde dehydrogenase includes those enzymes that correspond to EC 1.2.1.4 and EC 1.2.1.10.

Figure 1:
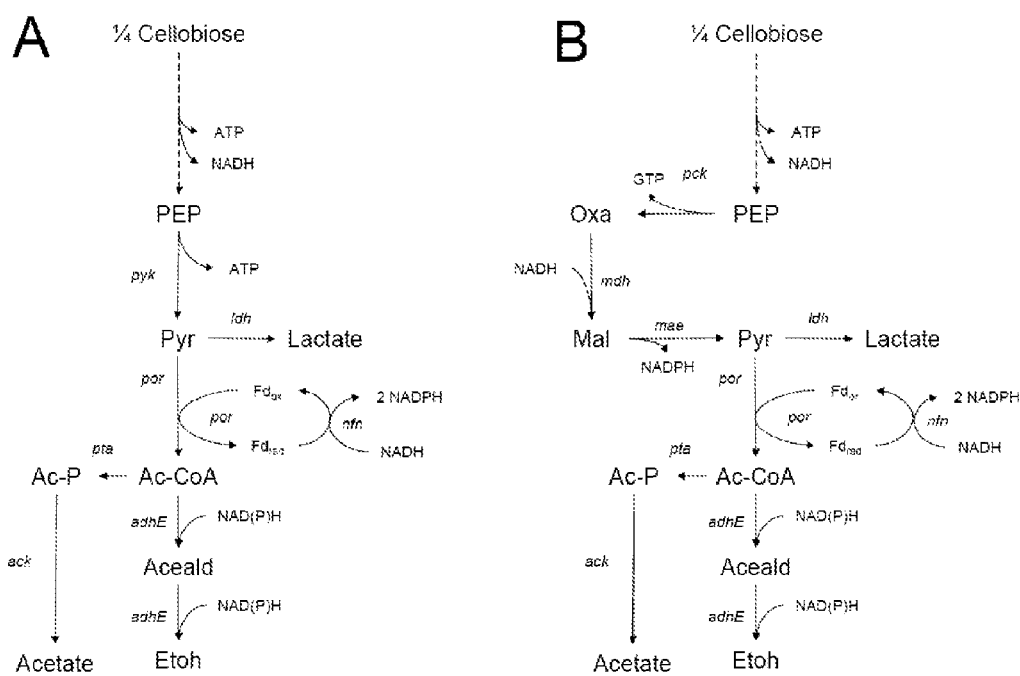

As used herein, the term "bifunctional" is intended to include enzymes that catalyze more than one biochemical reaction step. Specific examples of a bifunctional enzyme used herein are enzymes (AdhE and AdhB) that catalyze both the alcohol dehydrogenase and acetaldehyde dehydrogenase reactions (FIG. 1) and those enzymes encoded by SEQ ID NO: 67 and SEQ ID NO: 68 (bifunctional acetaldehyde-alcohol dehydrogenase from *T. saccharolyticum*). Bifunctional acetaldehyde-alcohol dehydrogenase includes those enzymatic reactions that correspond to EC 1.2.1.4, EC 1.2.1.10, EC 1.1.1.2 and EC 1.1.1.1.

The term "feedstock" is defined as a raw material or mixture of raw materials supplied to a microorganism or fermentation process from which other products can be made. For example, a carbon source, such as biomass or the carbon compounds derived from biomass are a feedstock for a microorganism that produces a product in a fermentation process. A feedstock can contain nutrients other than a carbon source.

Biomass can include any type of biomass known in the art or described herein. The terms "lignocellulosic material," "lignocellulosic substrate," and "cellulosic biomass" mean any type of carbon containing feed stock selected from the group consisting of woody biomass, such as recycled wood pulp fiber, sawdust, hardwood, softwood, grasses, sugar-processing residues, agricultural wastes, such as but not limited to rice straw, rice hulls, barley straw, corn cobs, cereal straw, wheat straw, canola straw, oat straw, oat hulls, corn fiber, stover, succulents, agave, or any combination thereof.

The term "yield" is defined as the amount of product obtained per unit weight of raw material and may be expressed as g product per g substrate (g/g). Yield may be expressed as a percentage of the theoretical yield. "Theoretical yield" is defined as the maximum amount of product that can be generated per a given amount of substrate as dictated by the stoichiometry of the metabolic pathway used to make the product. For example, the theoretical yield for one typical conversion of glucose to ethanol is 0.51 g EtOH per 1 g glucose. As such, a yield of 4.8 g ethanol from 10 g of glucose would be expressed as 94% of theoretical or 94% theoretical yield.

The term "titer" is defined as the strength of a solution or the concentration of a substance in solution. For example, the titer of a product in a fermentation broth is described as g of product in solution per liter of fermentation broth (g/L) or as g/kg broth.

"Bacteria", or "eubacteria", refers to a domain of pro-karyotic organisms. Bacteria include Gram-positive (gram+) bacteria and Gram-negative (gram-) bacteria.

In some embodiments of the invention, the host cell is a prokaryotic microorganism. In some embodiments, the host cell is a bacterium. In some embodiments, the host cell is able to digest and ferment cellulose. In some embodiments, the host cell is a thermophilic bacterium. In some embodiments, the microorganism is from the genus *Clostridium*. In some embodiments the microorganism is from the genus *Caldicellulosiruptor*. In some embodiments, the bacterium is *Clostridium thermocellum*. In some embodiments, the bacterium is *Clostridium cellulolyticum*. In some embodiments, the bacterium is *Clostridium clariflavum*. In some embodiments, the bacterium is *Clostridium phytofermentans*. In some embodiments, the bacterium is *Clostridium acetobutylicum*. In some embodiments, the bacterium is *Caldicellulosiruptor bescii*. In some embodiments, the bacterium is *Caldicellulosiruptor saccharolyticus*.

In some embodiments, the host cell is a thermotolerant host cell. Thermotolerant host cells can be particularly useful in simultaneous saccharification and fermentation processes by allowing externally produced cellulases and ethanol-producing host cells to perform optimally in similar temperature ranges.

In some embodiments, the host cells of the invention are cultured at a temperature above 25° C., above 27° C., above 30° C., above 33° C., above 35° C., above 37° C., above 40° C., above 43° C., above 45° C., or above 47° C.

In some embodiments, the host cells of the invention contain genetic constructs that lead to the down-regulation to one or more genes encoding a polypeptide at least 80%, at least 85%, at least 90%, at least 95%, at least 96%, at least 97%, at least 98%, at least 99%, or 100% identical to one or more of the polypeptides encoded by SEQ ID NOS: 1-54, 57, 60, 67, 68.

In some embodiments, the host cells of the invention contain genetic constructs that lead to the expression or up-regulation of one or more genes encoding a polypeptide at least 80%, at least 85%, at least 90%, at least 95%, at least 96%, at least 97%, at least 98%, at least 99%, or 100% identical to one or more of the polypeptides encoded by SEQ ID NOS: 1-8, 13-54, 57, 60, 67, 68.

In some embodiments, the host cells of the invention are subjected to adaptation to improve their performance. In some embodiments, the host cells are adapted for faster growth by culturing them repeatedly on a growth medium or in a continuous culture device such as a chemostat.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences.

As known in the art, "similarity" between two polypeptides is determined by comparing the amino acid sequence and conserved amino acid substitutes thereto of the polypeptide to the sequence of a second polypeptide.

"Identity" and "similarity" can be readily calculated by known methods, including but not limited to those described in: Computational Molecular Biology (Lesk, A. M., ed.) Oxford University Press, NY (1988); Biocomputing: Informatics and Genome Projects (Smith, D. W., ed.) Academic Press, NY (1993); Computer Analysis of Sequence Data, Part I (Griffin, A. M., and Griffin, H. G., eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid sequences or fragments thereof (isolated polynucleotides of the present invention) encode polypeptides that are at least about 70% to 75% identical to the amino acid sequences reported herein, at least about 80%, 85%, or 90% identical to the amino acid sequences reported herein, or at least about 95%, 96%, 97%, 98%, 99%, or 100% identical to the amino acid sequences reported herein. Suitable nucleic acid fragments are at least about 70%, 75%, or 80% identical to the nucleic acid sequences reported herein, at least about 80%, 85%, or 90% identical to the nucleic acid sequences reported herein, or at least about 95%, 96%, 97%, 98%, 99%, or 100% identical to the nucleic acid sequences reported herein. Suitable nucleic acid fragments not only have the above identities/similarities but typically encode a polypeptide having at least 50 amino acids, at least 100 amino acids, at least 150 amino acids, at least 200 amino acids, or at least 250 amino acids.

Codon Optimization

In some embodiments of the present invention, exogenous genes may be codon-optimized in order to express the polypeptide they encode most efficiently in the host cell. Methods of codon optimization are well known in the art.

(Welch, M., Villalobos, A., Gustafsson, C., Minshull, J. Designing genes for successful protein expression. *Methods Enzymol.* 2011. 498:43-66.

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The Codon Adaptation Index is described in more detail in Sharp et al., "The Codon Adaptation Index: a Measure of Directional Synonymous Codon Usage Bias, and Its Potential Applications." *Nucleic Acids Research* 1987. 15: 1281-1295, which is incorporated by reference herein in its entirety.

A codon optimized sequence may be further modified for expression in a particular organism, depending on that organism's biological constraints. For example, large runs of "As" or "Ts" (e.g., runs greater than 3, 4, 5, 6, 7, 8, 9, or 10 consecutive bases) can effect transcription negatively. Therefore, it can be useful to remove a run by, for example, replacing at least one nucleotide in the run with another nucleotide. Furthermore, specific restriction enzyme sites may be removed for molecular cloning purposes by replacing at least one nucleotide in the restriction site with another nucleotide. Examples of such restriction enzyme sites include PacI, AscI, BamHI, BglII, EcoRI and XhoI. Additionally, the DNA sequence can be checked for direct repeats, inverted repeats and mirror repeats with lengths of about 5, 6, 7, 8, 9 or 10 bases or longer. Runs of "As" or "Ts", restriction sites and/or repeats can be modified by replacing at least one codon within the sequence with the "second best" codons, i.e., the codon that occurs at the second highest frequency for a particular amino acid within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six triplets each, whereas tryptophan and methionine are coded for by just one triplet. This degeneracy allows for DNA base composition to vary over a wide range without altering the amino acid sequence of the proteins encoded by the DNA.

TABLE 1

The Standard Genetic Code

| | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC |
| | TTA Leu (L) | TCA Ser (S) | TAA Ter | TGA Ter |
| | TTG Leu (L) | TCG Ser (S) | TAG Ter | TGG Trp (W) |

TABLE 1-continued

The Standard Genetic Code

| | T | C | A | G |
|---|---|---|---|---|
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| A | ATT Ile (L) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | ATG Met (M) | ACG Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Redirection of Carbon Flux

One aspect of the present invention relates to a recombinant microorganism comprising a heterologous nucleic acid sequence encoding a pyruvate kinase and a genetic modification that leads to the down-regulation of an enzyme in an acetic acid and/or lactic acid pathway. In some embodiments, the host organism lacks an endogenous pyruvate kinase. In other embodiments, endogenous pyruvate kinase may be supplemented by up-regulation of the endogenous enzyme or the expression of one or more additional copies of the pyruvate kinase by introducing the copies into a host cell of the invention. Alternately, in other embodiments of the invention, a gene encoding PEP synthase (EC 2.7.9.2), PEP phosphatase (EC 3.1.3.60), or a PEP phosphotransferase (EC 2.7.3.9, EC 2.7.1.12) can be expressed in place or in addition to a pyruvate kinase.

In some embodiments, the enzyme in the acetic acid pathway or lactic acid pathway is selected from the group encoded by a lactate dehydrogenase polynucleotide, a phosphotransacetylase polynucleotide, or an acetate kinase polynucleotide. In some embodiments, the microorganism is from the genus *Clostridium*. In some embodiments the microorganism is the bacterium *Clostridium thermocellum*. The redirected flux can then be optimized by growth-coupled selection. Specifically, continuous culture or serial dilution cultures can be performed to select for cells that grow faster and, by necessity, produce ethanol faster. Methods for selection of microorganisms are known in the art and described, for example, in U.S. Appl. Pub. Nos. 2011/0189744 and 2011/0059485 which are incorporated herein by reference.

In some aspects, this invention relates to a recombinant microorganism comprising a heterologous nucleic acid sequence encoding a pyruvate kinase and a genetic modification that leads to the down-regulation of an enzyme in a pathway which converts phosphoenolpyruvate (PEP) to pyruvate. In some embodiments, the enzyme that is down-regulated is encoded by a polynucleotide selected from the group consisting of a pyruvate-phosphate dikinase polynucleotide, a phosphoenolpyruvate carboxykinase-encoding polynucleotide, a malate dehydrogenase-encoding polynucleotide, or a malic enzyme-encoding polynucleotide. In some embodiments, the down-regulated enzyme is encoded by the nucleic acid sequence of SEQ ID NOs: 9-18 and SEQ ID NOs: 51-52.

One aspect of this invention relates to a recombinant microorganism comprising a heterologous nucleic acid sequence comprising a pyruvate kinase, a genetic modification that leads to the down-regulation of an enzyme in an acetic acid and/or a lactic acid pathway, and a genetic modification that leads to the down-regulation of an enzyme in a pathway for the conversion of phosphoenolpyruvate to pyruvate through methods known in the art or described herein. In some embodiments, the enzyme in the acetic acid pathway or lactic acid pathway is from the group encoded by a lactate dehydrogenase polynucleotide, a phosphotransacetylase polynucleotide, or an acetate kinase polynucleotide. In some embodiments the enzyme in the phosphoenolpyruvate to pyruvate pathway is from the group encoded by a pyruvate-phosphate dikinase polynucleotide, a phosphoenolpyruvate carboxykinase polynucleotide, a malate dehydrogenase polynucleotide, or a malic enzyme polynucleotide.

In some embodiments, the present invention relates to a microorganism comprising a heterologous nucleic acid sequence encoding a pyruvate formate lyase enzyme and heterologous nucleic acids encoding PFL-activating enzymes. In other embodiments, in organisms that already possess these enzymes, the genes can be up-regulated or one or more additional copies of the desired genes can be introduced to give higher expression of the desired enzymes. In another embodiment, the present invention relates to a microorganism comprising a heterologous nucleic acid sequence encoding a pyruvate formate lyase enzyme, heterologous nucleic acids encoding PFL-activating enzymes, and a genetic modification that leads to the down-regulation of the enzymes pyruvate oxidoreductase or NADH-dependent reduced ferredexin:NADP+ oxidoreductase through methods known in the art, e.g., (Berrios-Rivera 2002, Hatrongjit 2010, Popov 1994, and U.S. Pat. Nos. 7,709,261 and 7,256,016) or described herein.

In one embodiment, the invention relates to a microorganism comprising a heterologous nucleic acid sequence encoding a pyruvate formate lyase, heterologous nucleic acids encoding PFL-activating enzymes, a genetic modification that leads to the down-regulation of the enzymes pyruvate oxidoreductase or NADH-dependent reduced ferredoxin:NADP+ oxidoreductase. In some embodiments, the microorganism is from the genus *Clostridium*. In some embodiments the microorganism is the bacterium *Clostridium thermocellum*.

In another embodiment, the invention relates to a microorganism comprising a heterologous nucleic acid sequence encoding a pyruvate formate lyase, heterologous nucleic acids encoding PFL-activating enzymes, and a genetic modification that leads to the down-regulation of an enzyme in an ethanol pathway through methods known in the art or described herein.

In another embodiment, the invention relates to a microorganism comprising a heterologous nucleic acid sequence encoding a pyruvate formate lyase or the up-regulation of endogenous pyruvate formate lyase, heterologous nucleic acids encoding PFL-activating enzymes, and a heterologous nucleic acid sequence encoding formate dehydrogenase. In other embodiments, endogenous formate dehydrogenase may be supplemented by up-regulation of the endogenous enzyme or the expression of one or more additional copies of the formate dehydrogenase by introducing the copies into a host cell of the invention.

In some embodiments, the microorganism further comprises a genetic modification that leads to the down-regulation of an enzyme in an acetic acid and/or lactic acid pathway through methods known in the art or described herein. In some embodiments, the enzyme in the acetic acid pathway or lactic acid pathway is from the group encoded by a lactate dehydrogenase polynucleotide, a phosphotransacetylase polynucleotide, or an acetate kinase polynucleotide.

One embodiment of the present invention relates to a recombinant microorganism comprising a genetic modification that leads to the down-regulation of the enzyme encoding malate dehydrogenase through methods known in the art or described herein. One embodiment of the invention relates to a recombinant microorganism comprising a genetic modification that leads to the down-regulation of the enzyme encoding lactate dehydrogenase through methods known in the art or described herein. Another embodiment of the present invention relates to a recombinant microorganism comprising a genetic modification that leads to the down-regulation of the enzyme encoding malate dehydrogenase and a genetic modification that leads to the down-regulation of the enzyme encoding lactate dehydrogenase through methods known in the art or described herein. In some embodiments, the microorganism is from the genus *Clostridium*. In some embodiments the microorganism is the bacterium *Clostridium* cellulolyticum.

One embodiment relates to a recombinant prokaryotic microorganism comprising a genetic modification that leads to the down-regulation of an enzyme encoding malate dehydrogenase wherein said microorganism in capable of producing ethanol at a higher rate than an otherwise identical microorganism in which the enzyme encoding malate dehydrogenase is not down-regulated. In some embodiments, the microorganism is from the genus *Clostridium*. In some embodiments the microorganism is the bacterium *Clostridium cellulolyticum*. In some embodiments, the organism contains genetic modifications that lead to the down regulation of malate dehydrogenase and lactate dehydrogenase.

In some embodiments, the microorganism further comprises a genetic modification that leads to the down-regulation of an enzyme containing phosphotransacetylase. In some embodiments, the microorganism further comprises a bifunctional acetaldehyde-alcohol dehydrogenase. In some embodiments, the bifunctional acetaldehyde-alcohol dehydrogenase is AdhE or AdhB.

In some embodiments, the invention relates to a microorganism comprising a heterologous nucleic acid sequence encoding a pyruvate kinase, a heterologous nucleic acid sequence encoding PEPCK, a heterologous nucleic acid sequence encoding a bifunctional acetaldehyde-alcohol dehydrogenase and additionally comprises a genetic modification that leads to the down-regulation of an enzyme encoding lactate dehydrogenase. In some embodiments, the invention relates to a microorganism comprising a heterologous nucleic acid sequence encoding a pyruvate kinase, a heterologous nucleic acid sequence encoding PEPCK, a heterologous nucleic acid sequence encoding AdhB and additionally comprises a genetic modification that leads to the down-regulation of an enzyme encoding lactate dehydrogenase. In some embodiments, the invention relates to a microorganism comprising a heterologous nucleic acid sequence encoding a pyruvate kinase, a heterologous nucleic acid sequence encoding PEPCK, a heterologous nucleic acid sequence encoding AdhE, and a genetic modification that leads to the down-regulation of an enzyme encoding lactate dehydrogenase. In some embodiments, the invention relates to a microorganism comprising a heterologous nucleic acid sequence encoding a pyruvate kinase, a heterologous nucleic acid sequence encoding PEPCK, a heterologous nucleic acid sequence encoding AdhE, a genetic modification that leads to the down-regulation of an enzyme encoding lactate dehydrogenase, and a genetic modification that leads to the down-regulation of PTA. In some embodiments, the invention relates to a microorganism comprising a heterologous nucleic acid sequence encoding a pyruvate kinase, a heterologous nucleic acid sequence encoding PEPCK, a heterologous nucleic acid sequence encoding AdhB, a heterologous nucleic acid sequence encoding AdhE, and additionally comprises a genetic modification that leads to the down-regulation of an enzyme encoding lactate dehydrogenase. In some embodiments, the AdhB is from *T. pseudethanolicus*. In some embodiments, the pyruvate kinase is from *T. saccharolyticum*. In some embodiments, the AdhE is from *T. saccharolyticum*. In some embodiments, PEPCK is down-regulated in the microorganism.

One embodiment of the present invention relates to a composition comprising a microorganism described herein and a carbon-containing feedstock comprising woody biomass, such as recycled wood pulp fiber, sawdust, hardwood, softwood, grasses, sugar processing residues, agricultural wastes, such as but not limited to rise straw, rice hulls, barley straw, corn cobs, cereal straw, wheat straw, canola straw, oat straw, oat hulls, corn fiber, stover, succulents, agave, or any combination thereof.

Ethanol Production

For a microorganism to produce ethanol most economically, it is desired to produce a high yield. In one embodiment, the only product produced is ethanol. Extra products lead to a reduction in product yield and an increase in capital and operating costs, particularly if the extra products have little or no value. Extra products also require additional capital and operating costs to separate these products from ethanol.

Ethanol production can be measured using any method known in the art. For example, the quantity of ethanol in fermentation samples can be assessed using HPLC analysis. Many ethanol assay kits are commercially available that use, for example, alcohol oxidase enzyme based assays. Methods of determining ethanol production are within the scope of those skilled in the art from the teachings herein.

In some embodiments, the host cell is able to digest and ferment cellulose. In some embodiments, the host cell is a thermophilic bacterium. In some embodiments, the microorganism of the invention is from the genus *Clostridium*. In some embodiments the microorganism is from the genus *Caldicellulosiruptor*. In some embodiments, the bacterium is *Clostridium thermocellum*. In some embodiments, the bacterium is *Clostridium cellulolyticum*. In some embodiments, the bacterium is *Clostridium clariflavum*. In some embodiments, the bacterium is *Clostridium phytofermentans*. In some embodiments, the bacterium is *Clostridium acetobutylicum*. In some embodiments, the bacterium is *Caldicellulosiruptor bescii*. In some embodiments, the bacterium is *Caldicellulosiruptor saccharolyticus*.

In some embodiments of the invention where redirected carbon flux generates increased ethanol production, the ethanol output can be improved by growth-coupled selection. For example, continuous culture or serial dilution cultures can be performed to select for cells that grow faster and/or produce ethanol (or any desired product) more efficiently on a desired feedstock.

One embodiment of the present invention relates to a method of producing ethanol using a microorganism described herein wherein said microorganism is cultured in the presence of a carbon containing feedstock for sufficient time to produce ethanol and, optionally, extracting the ethanol.

Ethanol may be extracted by methods known in the art. See, e.g., U.S. Appl. Pub. No. 2011/0171709, which is incorporated herein by reference.

Another embodiment of the present invention relates to a method of producing ethanol using a co-culture composed of at least two microorganisms in which at least one of the organisms is an organism described herein, and at least one of the organisms is a genetically distinct microorganism. In some embodiments, the genetically distinct microorganism is a yeast or bacterium. In some embodiments the genetically distinct microorganism is any organism from the genus *Issatchenkia, Pichia, Clavispora, Candida, Hansenula, Kluyveromyces, Trichoderma, Thermoascus, Escherichia, Clostridium, Thermoanaerobacter* and *Thermoanaerobacterium*.

In some embodiments, the recombinant microorganism produces about 2 to about 3 times more ethanol than a wildtype, non-recombinant organism; about 1.5 to about 2 times more ethanol than a wildtype, non-recombinant organism; about 1.5 to about 5 times more ethanol than a wildtype, non-recombinant organism; about 1.5 to about 7 times more ethanol than a wildtype, non-recombinant organism; about 1.5 to about 10 times more ethanol than a wildtype, non-recombinant organism; about 1.5 to about 15 times more ethanol than a wildtype, non-recombinant organism; about 1.5 to about 20 times more ethanol than a wildtype, non-recombinant organism; about 1.5 to about 30 times more ethanol than a wildtype, non-recombinant organism; about 1.5 to about 50 times more ethanol than a wildtype, non-recombinant organism; about 1.5 to about 75 times more ethanol than a wildtype, non-recombinant organism; about 1.5 to about 100 times more ethanol than a wildtype, non-recombinant organism.

In some embodiments, the recombinant microorganism produces about 2 to about 3% more ethanol than a wildtype, non-recombinant organism; at least about 1.5 to at least about 2% more ethanol than a wildtype, non-recombinant organism; at least about 1.5 to at least about 5% more ethanol than a wildtype, non-recombinant organism; at least about 1.5 to at least about 7% more ethanol than a wildtype, non-recombinant organism; at least about 1.5 to at least about 10% more ethanol than a wildtype, non-recombinant organism; at least about 1.5 to at least about 15% more ethanol than a wildtype, non-recombinant organism; at least about 1.5 to at least about 20% more ethanol than a wildtype, non-recombinant organism; at least about 1.5 to at least about 30% more ethanol than a wildtype, non-recombinant organism; at least about 1.5 to at least about 50% more ethanol than a wildtype, non-recombinant organism; at least about 1.5 to at least about 75% more ethanol than a wildtype, non-recombinant organism; at least about 1.5 to at least about 100% more ethanol than a wildtype, non-recombinant organism.

In some embodiments, the recombinant microorganism produces about 0.5 g/L ethanol to about 2 g/L ethanol, about 0.5 g/L ethanol to about 3 g/L ethanol, about 0.5 g/L ethanol to about 5 g/L ethanol, about 0.5 g/L ethanol to about 7 g/L ethanol, about 0.5 g/L ethanol to about 10 g/L ethanol, about 0.5 g/L ethanol to about 15 g/L ethanol, about 0.5 g/L ethanol to about 20 g/L ethanol, about 0.5 g/L ethanol to about 30 g/L ethanol, about 0.5 g/L ethanol to about 40 g/L ethanol, about 0.5 g/L ethanol to about 50 g/L ethanol, about 0.5 g/L ethanol to about 75 g/L ethanol, or about 0.5 g/L ethanol to about 99 g/L ethanol per 24 hour incubation on a carbon-containing feed stock.

In some embodiments, the recombinant microorganism produces ethanol at about 55% to about 75% of theoretical yield, about 50% to about 80% of theoretical yield, about 45% to about 85% of theoretical yield, about 40% to about 90% of theoretical yield, about 35% to about 95% of theoretical yield, about 30% to about 99% of theoretical yield, or about 25% to about 99% of theoretical yield.

In some embodiments, methods of producing ethanol can comprise contacting a biomass feedstock with a host cell or co-culture of the invention and additionally contacting the biomass feedstock with externally produced saccharolytic enzymes. Exemplary externally produced saccharolytic enzymes are commercially available and are known to those of skill in the art.

EXAMPLES

Example 1

Insertion of Pyruvate Kinase on a Replicating Plasmid

The gene for pyruvate kinase was introduced into *C. thermocellum* on a replicating plasmid. The gene for pyruvate kinase was amplified by PCR from *T. saccharolyticum* and cloned into plasmid pMU102 (described in Tripathi S A, Olson D G, Argyros D A, Miller B B, Barrett T F, Murphy D M, McCool J D, Warner A K, Rajgarhia V B, Lynd L R, Hogsett D A, Caiazza N C. Development of pyrF-based genetic system for targeted gene deletion in *Clostridium thermocellum* and creation of a pta mutant. *Appl Environ Microbiol.* 2010. 76(19):6591-9.), creating plasmid pMU2106. SEQ ID NO: 55. This plasmid was transformed into *C. thermocellum* WT strain DSM1313 [available from the public repository DSMZ] followed by selection for thiamphenicol resistance. The created strain was designated M1716.

Example 2

Insertion of Pyruvate Kinase into the Genome

The gene for pyruvate kinase was introduced into the chromosome of *C. thermocellum*. The pyruvate kinase gene was amplified by PCR from *T. saccharolyticum* and cloned downstream from the native *C. thermocellum* enolase promoter to generate plasmid pDGO-05. SEQ ID NO: 56 and SEQ ID NO: 57. This plasmid was transformed into strain M1354 (hpt deletion strain) (Argyros, D A, Tripathi S A, Barrett T F, Rogers S R, Feinberg L F, Olson D G, Foden J M, Miller B B, Lynd L R, Hogsett D A, Caiazza N C, High ethanol titers from cellulose using metabolically engineered thermophilic, anaerobic microbes. *Appl. Env. Microbiol.* 2011. 77(23):8288-94; use of hpt deletion strains is also described in U.S. application Ser. No. 13/393,093, which is incorporated herein by reference.), and selected for thiamphenicol and FuDR resistance, resulting in insertion of the pyruvate kinase gene at the ldh locus of *C. thermocellum*. Those cells were then subjected to AZH selection to remove the hpt and antibiotic resistance genes. The resulting strain was designated DS8.

Example 3

Redirection of Carbon Flux by Reducing PEPCK Expression

The expression of PEPCK was reduced dramatically in strain DS8 by altering the start codon from ATG to GTG. The plasmid pYD01 was built for this purpose by yeast-mediated recombination using methods described previous and known in the art. SEQ ID NOs: 58-60. (Shanks R M, Caiazza N C, Hinsa S M, Toutain C M, O'Toole G A. *Saccharomyces cerevisiae*-based molecular tool kit for manipulation of genes from gram-negative bacteria. *Appl Environ Microbiol.* 2006 July; 72(7):5027-36). The plasmid pYD01 contains two fragments from the upstream region of the pckA gene. One of the fragments contains a modified start codon that has been changed to GTG. The cat and hpt genes are positioned between the two fragments. The resulting plasmid was transformed into *C. thermocellum*, and integrants were selected with thiamphenicol selection, then integrants were selected with thiamphenicol plus FuDR. Next, by selecting for resistance to AZH, clones were selected which had undergone recombination between the two copies of the pckA upstream region, thus eliminating the cat and hpt genes. Colonies were then screened for those carrying the GTG mutation by PCR amplification. Once such colony was saved as strain YD01. As shown in the table below, PEPCK activity was greatly reduced in the mutant strain.

TABLE 2

| PEPCK activity is greatly reduced in strain YD01. | |
|---|---|
| | PEPCK specific activity (units/mg protein) |
| WT | 4.14 |
| DS8 | 4.09 |
| YD01 | 0.54 |

Example 4

Redirection of Carbon Flux by Down-Regulating Malic Enzyme

The gene for malic enzyme was down-regulated in strain DS8 from Example 2 by using plasmid pYD02, based on the protocol described by Olson et al. ("Deletion of the Ce148S cellulase from *Clostridium thermocellum*." PNAS 2010. 107(41):17727-32.)

pYD02 was built by yeast mediated recombination. (Shanks R M, Caiazza N C, Hinsa S M, Toutain C M, O'Toole G A. "*Saccharomyces cerevisiae*-based molecular tool kit for manipulation of genes from gram-negative bacteria." Appl Environ Microbiol. 2006 July; 72(7):5027-36). It contains the fused 5' and 3' flanking regions of the gene for malic enzyme (gene number Cthe_0344) and an internal fragment of the same gene separated by the hpt and cat genes. SEQ ID NO: 61. The plasmid was transformed into *C. thermocellum* and the transformants were then selected for FuDR resistance to select for integrants. The integrants were further selected on AZH. Surviving clones had undergone recombination between the 5' flanking region DNA and an identical sequence upstream, thereby eliminating the cat and hpt genes and all of the coding sequence of the gene for malic enzyme. A colony was designated YD02 and saved for future work. SEQ ID NO: 62.

In fermentations in minimal carbon medium +1 g/L yeast extract +5 g/L cellobiose, *C. thermocellum* strains YD01 and YD02 produced more ethanol than their parent strain 1313, as shown in the table of HPLC results below.

TABLE 3

Ethanol production greatly increased in strains YD01 and YD02.

| Strain | Acetate g/L | Lactate g/L | Formate g/L | Ethanol g/L | % of theoretical ethanol yield |
|---|---|---|---|---|---|
| YD01 | 0.86 | 0 | .92 | 1.78 | 70% |
| YD02 | 0.768 | 0 | 1.00 | 1.72 | 67% |
| 1313 (no yeast extract) | 1.25 | 0.02 | .27 | .35 | 14% |

Example 5

Redirection of Carbon Flux by Down-Regulation of PPDK

The gene for pyruvate-phosphate dikinase (PPDK) was deleted to improve ethanol yield. To create a deletion construct, plasmid pMU2051 was created using yeast mediated ligation. SEQ ID NO: 63. This plasmid was transformed into strain M1354($\Delta$hpt) and selected for in liquid medium with thiamphenicol. A serial dilution of the transformation was plated to select for isolated colonies. A single colony was PCR screened to confirm presence of plasmid pMU2051 and inoculated into liquid medium and grown overnight. The following day, cells were plated with thiamphenicol (10 ug/ml) plus FUDR(10 ug/ml), with or without pyruvate. Colonies were observed only on the plate supplemented with pyruvate. Seven colonies were screened by PCR for a merodiploid insertion of the drug marker at the PPDK locus using primers X09712 (CCTCATTTGATAATTGCCTCCTCAT(SEQ ID NO: 70)) and X09713(ATCGCATTTTGCCGTTATGTGCCATTGAA(SEQ ID NO: 71)). A ~4.6 kb band indicated the colony contained only cells where the PPDK gene was replaced with the deletion cassette. A ~3.87 kb band indicated the presence of a wild type PDDK locus. Of the seven colonies, one carried the desired mutation. This colony was dilution plated on minimal medium containing 300 ug/ml 8-azahypoxanthine to remove the marker and create a clean deletion of PPDK. This strain was subsequently saved as strain M1631. SEQ ID NO: 64.

Example 6

Redirection of Carbon Flux by Deletion of Malate Dehydrogenase

Figure 2:
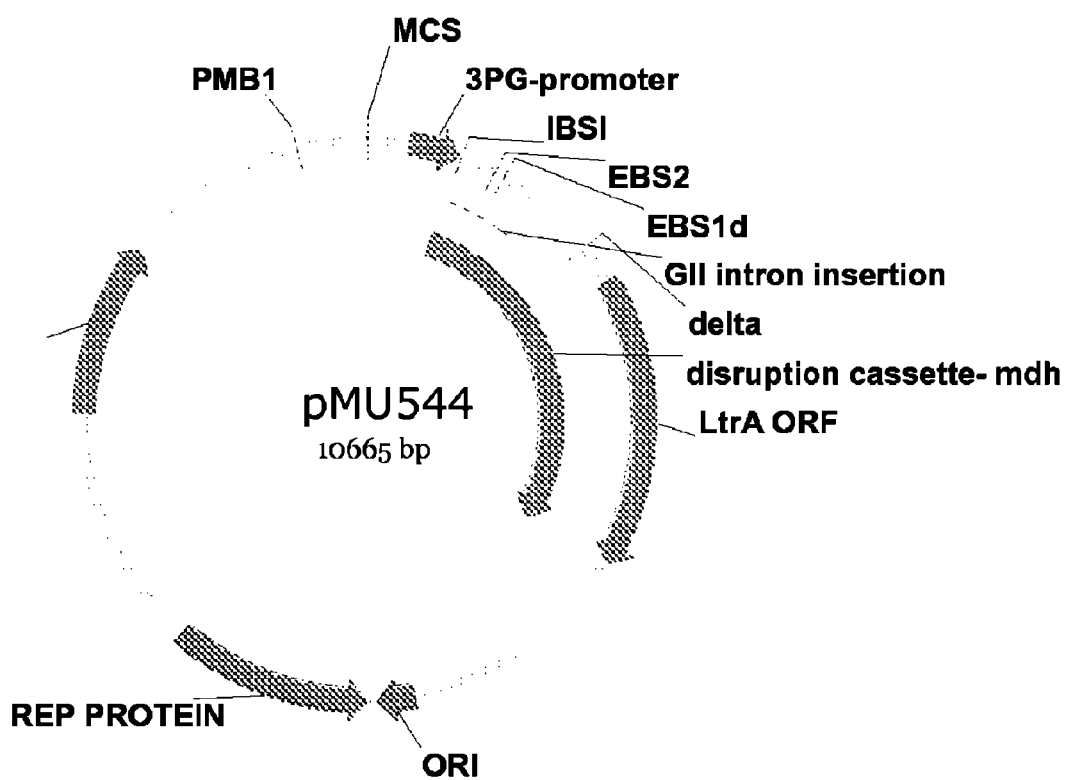
FIG. 2 depicts a gene inactivation plasmid for the malate dehydrogenase gene.
Figure 3:
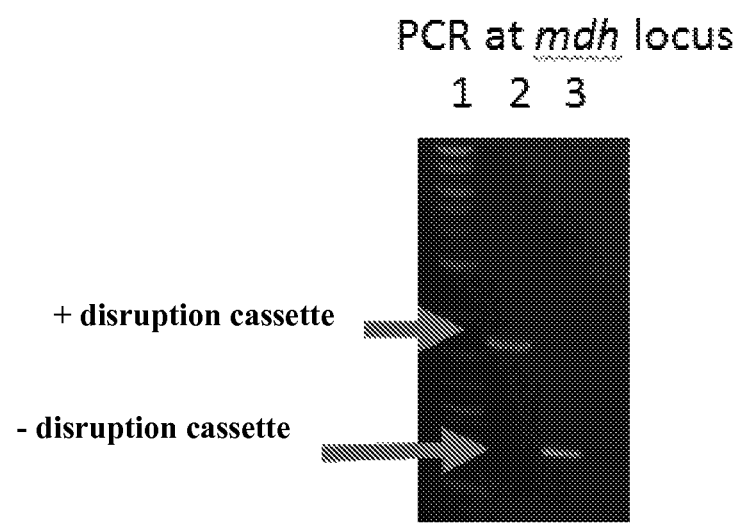
FIG. 3 depicts the shift in size of the mdh locus after the disruption cassette has been inserted into the mdh gene.

Standard cloning methods were used to generate a gene inactivation plasmid aimed at disrupting the malate dehydrogenase ("mdh") gene of *C. cellulolyticum*. The gene inactivation plasmid was created using a disruption cassette. A map of the plasmid can be seen in FIG. 2. The plasmid was transformed into *C. cellulolyticum* and chloramphenicol resistant colonies were screened for insertion at the mdh locus by PCR. FIG. 3 shows the mdh locus in the wild type strain (lane 3) and one of the chloramphenicol resistant clones (lane 2). The shift in size of the band in lane 2 compared to the wild type (lane 3) is evidence that a disruption cassette is inserted into the mdh gene.

Example 7

Figure 4:
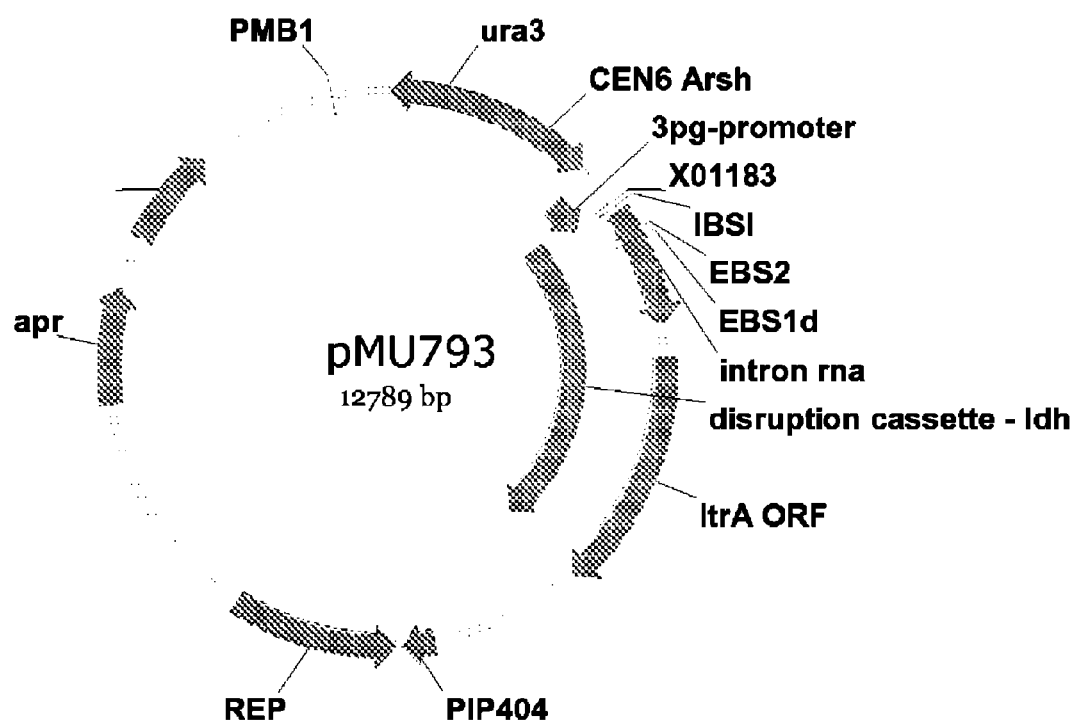
FIG. 4 depicts a gene inactivation plasmid for the lactate dehydrogenase gene.

Redirection of Carbon Flux by Deletion of Malate Dehydrogenase and Lactate Dehydrogenase Standard cloning methods were used to generate a gene inactivation plasmid aimed at disrupting the ldh gene of *C. cellulolyticum*. The gene inactivation plasmid was created using a disruption cassette. A map of the plasmid can be seen in FIG. 4. The above plasmid was transformed into the *C. cellulolyticum* mdh mutant background and 8 erythromycin resistant colonies were screened for insertion at both the mdh and ldh loci by PCR. Part A of the gel image in FIG. 5 shows the mdh locus in which all 8 strains show insertion of the disruption cassette at the mdh locus, signified by an increase size of the PCR product. Part B of the gel image in FIG. 5 shows the status of the ldh locus in the same 8 strains. Of the 8 strains assayed, the gel image below clearly demonstrates that the strain represented in lane 6 has a disruption cassette inserted at the ldh locus. Strains represented in lanes 5 and 7 are a mixed culture of mutant and wild type cells, while the remainder are just wild type at the ldh locus. Thus, the strain represented in lane 6 has a disruption cassette inserted at both the ldh and mdh loci.

Example 8

Ethanol and Lactic Acid Production by mdh and mdh, ldh Mutant Strains

Ethanol and lactic acid production were tested on wild-type, the mdh mutant strain and the mdh, ldh double mutant. As seen in FIG. 6, a fermentation profile was created for the mdh and mdh, ldh mutant strains in comparison to the wildtype, non-recombinant strain. Strains were incubated in media composed of 0.5035 g/L $KH_2PO_4$, 0.6097 g/L $K_2HPO_4$, 1.9820 g/L urea, 0.5083 g/L $MgCl_2*6H_2O$, 0.0441 g/L $CaCl_2*2H_2O$, 0.0011 g/L $FeSO_4$, 6.0491 g/L sodium $\beta$-glycerophosphate*$5H_2O$, 2.9410 g/L sodium citrate tribasic *$2H_2O$, 11.0976 g/L MOPS sodium salt, 1.1063 g/L L-cysteine-HCl*$H_2O$, 5 g/L yeast extract, 0.2% resazurin solution and 15 g/L cellobiose. As can be seen in FIG. 6A, as measured by OD, growth was slightly depressed in both the mdh and mdh, 1 dh mutant cells, with the mdh, ldh mutant ("DB mutant") serving as a partial rescue of growth over the mdh mutant. As can be seen in FIG. 6B, both the wildtype and mdh strains had virtually identical levels of lactic acid production, while there was essentially no lactic acid production in the mdh, ldh mutant. As can be seen in FIG. 6C, both the mutant strains saw an increase in the amount of ethanol produced. The mdh mutant produced almost 2 times as much ethanol as the wildtype strain produced. The mdh, ldh mutant produced almost 3 times as much ethanol as the wildtype strain produced.

Example 9

Heterologous Expression of adhE with Altered Co-factor Specificity in a Strain with Redirected Carbon Flux U.S. Provisional Appl. No. 61/565,261, which is incorporated herein by reference describes bifunctional enzymes that catalyze both the alcohol dehydrogenase and acetaldehyde dehydrogenase reactions. The bifunctional acetaldehyde-alcohol dehydrogenase, encoded by the gene adhE, was PCR amplified from *Thermoanaerobacterium saccharolyticum* strain ALK2 (*T. saccharolyticum* adhE: SEQ ID NOs: 67 and 68). This strain is described in Shaw A J et al., Metabolic engineering of a thermophilic bacterium to produce ethanol at high yield. *Proc Natl Acad Sci USA*. 2008. 105(37):13769-74. The adhE gene was cloned into *Clostridium thermocellum* replicating plasmid pDGO-66 to form plasmid pYD10 (SEQ ID NO: 65). Plasmid pYD10 was transformed into *Clostridium thermocellum* strain YD01 and selected for in liquid medium with thiamphenicol, resulting in strain YD12. This strain was grown in MTC media with 2 g/L yeast extract to test fermentation characteristics. Strain YD 12 produced 6.25 g/L ethanol from 15 g/L cellobiose, and the ethanol yield was 1.55 mole ethanol/mole glucose equivalent, which is equal to 78% of theoretical yield. In another experiment, strain YD12 was grown in medium containing 25 g/L cellobiose. After 72 hours, 24.3 g/L of cellobiose was used and the optical density of the culture was 2.4. The products observed by HPLC are shown in the table below.

TABLE 4

Products observed by HPLC.

| Acetate g/L | Lactate g/L | Formate g/L | Ethanol g/L |
|---|---|---|---|
| 2.2 | 0.2 | 0.6 | 10 |

Other strains of *C. thermocellum* were generated that contained genes encoding bifunctional alcohol dehydrogenase. The adhB gene from *Thermoanaerobacter pseudoethanolicus* was amplified by PCR and cloned between DNA flanking regions matching the hpt gene from *C. thermocellum*, generating plasmid pJLO7 (SEQ ID NO: 69). Insertion of heterologous adhB into the hpt locus of strain YD01 was performed with this plasmid by established methods, generating strain YD06. An additional bifunctional alcohol dehydrogenase was then expressed heterolgously in YD06 by transforming it with the plasmid pYD10 (SEQ ID NO: 65), generating strain YD08. This plasmid carries the adhE gene from *T.saccharolyticum* strain ALK2.

Example 10

Heterologous Expression of adhE with Altered Co-factor Specificity in a Strain with Redirected Carbon Flux and a pta Knockout The plasmid pMU1817 (SEQ ID NO: 66) was constructed to delete the phosphotransacetylase (pta) gene from *Clostridium thermocellum*. It was transformed into strain YD01 and selected for with thiamphenicol (Tm). Cells were plated onto agar medium containing Tm and FUDR and grown for 3 days until colonies appeared. The colonies were then plated onto media with 8-AZH to select clones in which the cat-hpt cassette had been lost by homologous recombination. The resulting strain, called YD05, was grown on MTC media with yeast extract. The ethanol yield was approximately the same as wild type. In order to increase the ethanol yield, the bifunctional acetaldehyde-alcohol dehydrogenase gene adhE from strain ALK2, which is a gene with altered co-factor specificity, was heterologously expressed. Plasmid pYD10 (SEQ ID NO: 65) was transformed into strain YD05, generating strain YD07. This strain, when grown on media containing cellobiose, produced 1.75 mole-ethanol/mole-glucose equivalent, which equals 87.5% of the theoretical yield.

Adaptation: The strains YD01, YD02 and YD12 were evolved for faster growth by serial transfer in MTC medium containing 5 g/liter Avicel or cellobiose for 10+ transfers. Transfers were by done by subculturing at a dilution of 1:10 every 48 to 72 h.

This specification discloses one or more embodiments that incorporate the features of this invention. The disclosed embodiment(s) merely exemplify the invention. The scope of the invention is not limited to the disclosed embodiment(s). The invention is defined by the claims appended hereto.

In the following description, for purposes of explanation, specific numbers, materials and configurations are set forth in order to provide a thorough understanding of the invention. However, it will be apparent to one having ordinary skill in the art that the invention may be practiced without these specific details. In some instances, well-known features may be omitted or simplified so as not to obscure the present invention. All publications referenced in this specification are incorporated by reference in their entirety.

What is claimed is:

1. A recombinant prokaryotic microorganism comprising:
(a) a heterologous nucleic acid encoding a pyruvate kinase (EC 2.7.1.40);
(b) a genetic modification that leads to the inactivation of malic enzyme (EC 1.1.1.38, EC 1.1.1.39, or EC 1.1.1.40) wherein the inactivation results from a deletion of one or more nucleic acids of an endogenous gene encoding malic enzyme or an insertion of one or more nucleic acids into an endogenous gene encoding malic enzyme; and
(c) one or more genetic modifications that leads to the inactivation of one or more enzymes selected from the group consisting of: lactate dehydrogenase (LDH) (EC 1.1.1.27 or EC 1.1.1.28); phosphotransacetylase (PTA) (EC 2.3.1.8); and acetate kinase (ACK) (EC 2.7.2.1), wherein the inactivation results from a deletion of one or more nucleic acids of an endogenous gene encoding the one or more enzymes or an insertion of one or more nucleic acids into the endogenous gene encoding the one or more enzymes.

2. The recombinant prokaryotic microorganism of claim 1, wherein the pyruvate kinase is from a microorganism of the genus *Thermoanaerobacterium*.

3. The recombinant prokaryotic microorganism of claim 1, wherein the pyruvate kinase is from the bacterium *Thermoanaerobacteriuin saccharolyticum*.

4. The recombinant prokaryotic microorganism of claim 1, further comprising:
(d) a heterologous nucleic acid encoding a pyruvate formate lyase (PFL) (EC 2.3.1.54); and
(e) a heterologous nucleic acid encoding a PFL-activating enzyme (EC 1.97.1.4).

5. The recombinant prokaryotic microorganism of claim 4, further comprising:
(f) a genetic modification that leads to the inactivation of the enzymes pyruvate oxidoreductase (EC 1.2.7.1) or NADH-dependent reduced ferredoxin:NADP+oxidoreductase, wherein the inactivation results from the deletion of one or more nucleic acids of an endogenous gene encoding the enzyme or the insertion of one or more nucleic acids into the endogenous gene encoding the enzyme.

6. The recombinant prokaryotic microorganism of claim 4, further comprising:
(g) a heterologous nucleic acid encoding formate dehydrogenase (EC 1.2.1.43 (NAD+-specific) or EC 1.2.1.2 (NADP+-specific).

7. The recombinant prokaryotic microorganism of claim 1, wherein the microorganism is a thermophilic bacterium.

8. The recombinant prokaryotic microorganism of claim 7, wherein the microorganism is a cellulose-digesting bacterium.

9. The recombinant prokaryotic microorganism of claim 8, wherein the microorganism is in the genus *Clostridium*.

10. The recombinant prokaryotic microorganism of claim 9, wherein the microorganism is the bacterium *Clostridium thermocellum*.

11. The recombinant prokaryotic microorganism of claim 1, wherein the microorganism comprises an ethanol producing pathway comprising the following substrate to product conversions: a) phosphoenolpyruvate to pyruvate; b) pyruvate to acetyl-CoA; c) acetyl-CoA to acetaldehyde; and, d) acetaldehyde to ethanol.

12. The recombinant prokaryotic microorganism of claim 1, wherein the microorganism produces ethanol at a higher yield than a microorganism lacking the genetic modifications.

13. The recombinant prokaryotic microorganism of claim 1, wherein the microorganism further comprises a bifunctional acetaldehyde-alcohol dehydrogenase (EC 1.2.1.4, EC 1.2.1.10, EC 1.1.1.2 or EC 1.1.1.1).

14. The recombinant prokaryotic microorganism of claim 13, wherein the bifunctional acetaldehyde-alcohol dehydrogenase is AdhB or AdhE.

15. A composition comprising the recombinant prokaryotic microorganism of claim 1 having faster growth by culturing it repeatedly on a growth medium or in a continuous culture device.

16. A composition comprising the recombinant prokaryotic microorganism of claim 1 and a carbon containing feed stock.

17. The composition of claim 16, wherein the feed stock is selected from the group consisting of woody biomass, grasses, sugar-processing residues, agricultural wastes, and any combination thereof.

18. The composition of claim 17, wherein the feed stock comprises recycled wood pulp fiber, sawdust, hardwood, softwood, rice straw, rice hulls, barley straw, corn cobs, cereal straw, wheat straw, canola straw, oat straw, oat hulls, corn fiber, stover, succulents, agave, cane bagasse, switchgrass, miscanthus, paper sludge, municipal waste or any combination thereof.

19. A co-culture comprising at least two microorganisms wherein (a) one of the microorganisms comprises the recombinant prokaryotic microorganism of claim 1; and, (b) one of the microorganisms is genetically distinct from (a).

20. The co-culture of claim 19, wherein the genetically distinct microorganism is a yeast or bacterium.

21. The co-culture of claim 20, wherein the genetically distinct microorganism is any organism from the genus *Issatchenkia, Pichia, Clavispora, Candida, Hansenula, Kluyveromyces, Trichoderma, Thermoascus, Escherichia, Clostridium, Caldicellulosiruptor, Zymomonas, Thermoanaerobacter* or *Thermoanaerobacterium*.

22. A method of producing ethanol comprising: (a) providing the recombinant prokaryotic microorganism of claim 1; (b) culturing the recombinant prokaryotic microorganism of claim 1 in the presence of a carbon containing feedstock for sufficient time to produce ethanol; and, optionally (c) extracting the ethanol.

\* \* \* \* \*

UNITED STATES PATENT AND TRADEMARK OFFICE
CERTIFICATE OF CORRECTION

PATENT NO. : 9,803,221 B2
APPLICATION NO. : 14/348231
DATED : October 31, 2017
INVENTOR(S) : Deng et al.

Page 1 of 1

It is certified that error appears in the above-identified patent and that said Letters Patent is hereby corrected as shown below:

On the Title Page

Inventor "Aaron Argyros" should read --D. Aaron Argyros--.

In the Claims

Claim 3
Column 193, Line 59, "*Thermoanaerobacteriuin*" should read --*Thermoanaerobacterium*--.

Claim 6
Column 194, Line 45, "(EC 1.2.1.43 (NAD+-specific) or EC 1.2.1.2 (NADP+-specific)" should read --(EC 1.2.1.43 (NAD+-specific) or EC 1.2.1.2 (NADP+-specific))--.

Claim 13
Column 195, Line 2, "1.2.1.10, EC 1.1.1.2or EC 1.1.1.1" should read --1.2.1.10, EC 1.1.1.2 or EC 1.1.1.1--.

Signed and Sealed this
Eighth Day of May, 2018

Andrei Iancu
*Director of the United States Patent and Trademark Office*